United States Patent
Anderson et al.

(10) Patent No.: US 9,764,037 B2
(45) Date of Patent: Sep. 19, 2017

(54) CONJUGATE COMPOUNDS

(71) Applicant: Victoria Link Limited, Wellington (NZ)

(72) Inventors: Regan James Anderson, Lower Hutt (NZ); Benjamin Jason Compton, Lower Hutt (NZ); Colin Malcolm Hayman, Lower Hutt (NZ); Ian Francis Hermans, Wellington (NZ); David Samuel Larsen, Dunedin (NZ); Gavin Frank Painter, Lower Hutt (NZ); Franca Ronchese, Wellington (NZ)

(73) Assignee: Victoria Link Limited, Wellington (NZ)

( * ) Notice: Subject to any disclaimer, the term of this patent is extended or adjusted under 35 U.S.C. 154(b) by 97 days.

(21) Appl. No.: 14/649,902

(22) PCT Filed: Dec. 6, 2013

(86) PCT No.: PCT/NZ2013/000224
§ 371 (c)(1),
(2) Date: Jun. 4, 2015

(87) PCT Pub. No.: WO2014/088432
PCT Pub. Date: Jun. 12, 2014

(65) Prior Publication Data
US 2015/0352219 A1 Dec. 10, 2015

(30) Foreign Application Priority Data
Dec. 6, 2012 (NZ) ........................ 604085

(51) Int. Cl.
| | | |
|---|---|---|
| A61K 38/00 | (2006.01) | |
| A61K 47/48 | (2006.01) | |
| A61K 39/385 | (2006.01) | |
| C07D 405/14 | (2006.01) | |
| C07D 309/12 | (2006.01) | |
| C07D 405/12 | (2006.01) | |
| C07D 495/04 | (2006.01) | |
| A61K 39/00 | (2006.01) | |

(52) U.S. Cl.
CPC ...... *A61K 47/48092* (2013.01); *A61K 39/385* (2013.01); *A61K 47/48246* (2013.01); *C07D 309/12* (2013.01); *C07D 405/12* (2013.01); *C07D 405/14* (2013.01); *C07D 495/04* (2013.01); *A61K 2039/55572* (2013.01); *A61K 2039/6018* (2013.01); *A61K 2039/627* (2013.01)

(58) Field of Classification Search
CPC .. A61K 2039/55572; A61K 2039/6018; A61K 2039/627; A61K 39/385; A61K 47/48092; A61K 47/48246; C07D 309/12; C07D 405/12; C07D 405/14; C07D 495/04
See application file for complete search history.

(56) References Cited

FOREIGN PATENT DOCUMENTS

| | | |
|---|---|---|
| CN | 101918033 A | 12/2010 |
| WO | 2007/051004 A2 | 5/2007 |
| WO | 2008/128062 A1 | 10/2008 |
| WO | WO 2008/128062 A1 * | 10/2008 |
| WO | 2009/060086 A2 | 5/2009 |
| WO | 2014/017928 A1 | 1/2014 |

OTHER PUBLICATIONS

Alexander et al., "(Acyloxy)alkyl Carbamates as Novel Bioreversible Prodrugs for Amines: Increased Permeation through Biological Membranes," *Journal of Medicinal Chemistry* 31:318-322, 1998.
Alexander et al., "Investigation of (Oxodioxolenyl)methyl Carbamates as Nonchiral Bioreversible Prodrug Moieties for Chiral Amines," *Journal of Medicinal Chemistry* 39:480-486, 1996.
Amsberry et al., "Amine Prodrugs Which Utilize Hydroxy Amide Lactonization. I. A Potential Redox-Sensitive Amide Prodrug," *Pharmaceutical Research* 8(3):323-330, 1991.
Amsberry et al., "Amine Prodrugs Which Utilize Hydroxy Amide Lactonization. II. A Potential Esterase-Sensitive Amide Prodrug," *Pharmaceutical Research* 8(4):455-461, 1991.
Atwell et al., "Relationships between Structure and Kinetics of Cyclization of 2-Aminoaryl Amides: Potential Prodrugs of Cyclization-Activated Aromatic Mustards," *Journal of Medicinal Chemistry* 37:371-380, 1994.
Baadsgaard et al., "201. Zur Kenntnis der komplexen Wolframcyanide $K_4[W(CN)_a]$, 2 $H_2O$ und $K_3[W(CN)_a]$, $H_2O$," *Helvetica Chimica Acta* 38(7):1669-1679, 1955, with English Abstract, 12 pages.
Badovinac et al., "$CD8^+$ T cell contraction is controlled by early inflammation," *Nature Immunology* 5(8):809-817, Aug. 2004.
Baek et al., "The 3-Deoxy Analogue of α-GalCer: Disclosing the Role of the 4-Hydroxyl Group for CD 1d-Mediated NKT Cell Activation," *ACS Medicinal Chemistry Letters* 2:544-548, 2011.
Banchet-Cadeddu et al., "The stimulating adventure of KRN 7000," *Organic & Biomolecular Chemistry* 9:3080-3104, 2011.
Bendelac et al., "The Biology of NKT Cells," *Annual Review of Immunology* 25:297-336, 2007.
Bhat et al., "Efficient Syntheses of β-Cyanosugars Using Glycosyl Iodides Derived from Per-O-silylated Mono- and Disaccharides," *Organic Letters* 3(13):2081-2084, 2001.
Brossart et al., "Identification of HLA-A2-Restricted T-Cell Epitopes Derived From the MUC1 Tumor Antigen for Broadly Applicable Vaccine Therapies," *Blood* 93(12):4309-4317, Jun. 1999.
Butler et al., "Reactions of Fatty Acids with Amines. Part 2. Sequential Thermal Reactions of Stearic (Octadecanoic) Acid with Some 1,2- and 1,3-Amino-alcohols and Bis-amines," *Journal of the Chemical Society, Perkin Transactions* 1:373-377, 1978.
Carpino et al., "Reductive Lactonization of Strategically Methylated Quinone Propionic Acid Esters and Amides," *Journal of Organic Chemistry* 54(14):3303-3310, 1989.

(Continued)

*Primary Examiner* — Marcela M Cordero Garcia
(74) *Attorney, Agent, or Firm* — Seed IP Law Group LLP

(57) ABSTRACT

The invention relates to sphingoglycolipid analogs and peptide derivatives thereof, which are useful in treating or preventing diseases or such as those relating to infection, atopic disorders, autoimmune diseases or cancer.

21 Claims, 14 Drawing Sheets

(56) References Cited

OTHER PUBLICATIONS

Chen et al., "Efficient Synthesis of α-C-Galactosyl Ceramide Immunostimulants: Use of Ethylene-Promoted Olefin Cross-Metathesis," *Organic Letters* 6(22):4077-4080, 2004.
Cheng et al., "An improved synthesis of dansylated α-galactosylceramide and its use as a fluorescent probe for the monitoring of glycolipid uptake by cells," *Carbohydrate Research* 346:914-926, 2011.
Davidson et al., "Effect of TA-CIN (HPV 16 L2E6E7) booster immunisation in vulval intraepithelial neoplasia patients previously vaccinated with TA-HPV (vaccinia virus encoding HPV 16/18 E6E7)," *Vaccine* 22:2722-2729, 2004.
Deng et al., "Impact of sugar stereochemistry on natural killer T cell stimulation by bacterial glycolipids," *Organic & Biomolecular Chemistry* 9:7659-7662, 2011.
Dere et al., "The First Synthesis of a Thioglycoside Analogue of the Immunostimulant KRN7000," *Organic Letters* 10(20):4641-4644, 2008.
Drefahl et al., "Stereoselektive Darstellung and konfigurative Zuordnung der diastereomeren DL-3-Amino-1.2-diphenyl-propanole-(1) (zum Mechanismus der Ringschluβreaktion von Aminoalkoholen mit Benzimidsäureester)," *Chemische Berichte* 94(6):1641-1656, 1961, with English Abstract, 17 pages.
Du et al., "Efficient, one-pot syntheses of biologically active α-linked glycolipids," *Chemical Communications* 23:2336-2338, 2007.
Ebensen et al., "A Pegylated Derivative of α-Galactosylceramide Exhibits Improved Biological Properties," *Journal of Immunology* 179:2065-2073, 2007, 11 pages.
Fujii et al., "Activation of Natural Killer T Cells by a α-Galactosylceramide Rapidly Induces the Full Maturation of Dendritic Cells In Vivo and Thereby Acts as an Adjuvant for Combined CD4 and CD8 T Cell Immunity to a Coadministered Protein," *The Journal of Experimental Medicine* 198(2):267-279, Jul. 2003.
Fujii et al., "Prolonged IFN-γ-producing NKT response induced with α-galactosylceramide-loaded DCs," *Nature Immunology* 3(9):867-874, Sep. 2002.
Gangwar et al., "Synthesis of a Novel Esterase-Sensitive Cyclic Prodrug of a Hexapeptide Using an (Acyloxy)alkoxy Promoiety," *Journal of Organic Chemistry* 62:1356-1362, 1997.
Giaccone et al., "A Phase I Study of the Natural Killer T-Cell Ligand α-Galactosylceramide (KRN7000) in Patients with Solid Tumors," *Clinical Cancer Research* 8:3702-3709, Dec. 2002.
Greenwald et al., "Drug Delivery Systems Based on Trimethyl Lock Lactonization: Poly(ethylene glycol) Prodrugs of Amino-Containing Compounds," *Journal of Medicinal Chemistry* 43:475-487, 2000.
Greenwald et al., "Drug Delivery Systems Employing 1,4- or 1,6-Elimination: Poly(ethylene glycol) Prodrugs of Amine-Containing Compounds," *Journal of Medicinal Chemistry* 42:3657-3667, 1999.
Gryko et al., "Thiol-Derivatized Porphyrins for Attachment to Electroactive Surfaces," *Journal of Organic Chemistry* 64:8635-8647, 1999.
Harris et al., "Complex Target-Oriented Synthesis in the Drug Discovery Process: A Case History in the dEpoB Series," *Journal of Organic Chemistry* 64:8434-8456, 1999.
Hermans et al., "NKT Cells Enhance CD4$^+$ and CD8$^+$ T Cell Responses to Soluble Antigen In Vivo Direct Interaction with Dendritic Cells," *The Journal of Immunology* 171:5140-5147, 9 pages.
Hillery et al., "Stereopopulation Control. 9. Rate and Equilibrium Enhancement in the Lactonization of (o-Hydroxyphenyl)acetic Acids," *Journal of Organic Chemistry* 48:3465-3471, 1983.
Hong et al., "The natural killer T-cell ligand α-galactosylceramide prevents autoimmune diabetes in non-obese diabetic mice," *Nature Medicine* 7(9):1052-1056, Sep. 2001.
Howell et al., "Approaches to the preparation of sphinganines," *Tetrahedron* 60:11327-11347, 2004.
Iha et al., "Complex, Degradable Polyester Materials via Ketoxime Ether-Based Functionalization: Amphiphilic, Multifunctional Graft Copolymers and Their Resulting Solution-State Aggregates," *Journal of Polymer Science: Part A: Polymer Chemistry* 48:3553-3563, 2010.
Ingram et al., "Introduction of 2,2,2-Trichloroethyl-Protected Sulfates into Monosaccharides with a Sulfuryl Imidazolium Salt and Application to the Synthesis of Sulfated Carbohydrates," *Angewandte Chemie International Edition* 45:3503-3506, 2006.
Johansen et al., "Synthesis of Carbasugars from Aldonolactones: Ritter-Type Epoxide Opening in the Synthesis of Polyhydroxylated Aminocyclopentanes," *Synthesis* 1:171-177, 1999.
Karbach et al., "Tumor-reactive CD8$^+$ T-cell responses after vaccination with NY-ESO-1 peptide, CpG 7909 and Montanide® ISA-51: association with survival," *International Journal of Cancer* 126:909-918, 2010.
Kawano et al., "CD 1d-Restricted and TCR-Mediated Activation of V$_\alpha$14 NKT Cells by Glycosylceramides," *Science* 278:1626-1629, Nov. 1997.
Kinjo et al., "Invariant natural killer T cells recognize glycolipids from pathogenic Gram-positive bacteria," *Nature Immunology* 12(10):966-975, Oct. 2011.
Lee et al., "Novel synthesis of α-galactosyl-ceramides and confirmation of their powerful NKT cell agonist activity," *Carbohydrate Research* 341:2785-2798, 2006.
Leung et al., "Protease Inhibitors: Current Status and Future Prospects," *Journal of Medicinal Chemistry* 43(3):305-341, Feb. 2000.
Levy et al., "A melanoma multiepitope polypeptide induces specific CD8$^+$ T-cell response," *Cellular Immunology* 250:24-30, 2007.
Li et al., "Identification of a WT1 protein-derived peptide, WT1$_{187}$, as a HLA-A*0206-restricted, WT1-specific CTL epitope," *Microbiology & Immunology* 52:551-558, 2008.
Li et al., "Synthesis and Biological Evaluation of a Water Soluble Phosphate Prodrug of 3-Aminopyridine-2-Carboxaldehyde Thiosemicarbazone (3-AP)," *Bioorganic & Medicinal Chemistry Letters* 8:3159-3164, 1998.
Li et al., "The Vα14 invariant natural killer T cell TCR forces microbial glycolipids and CD1d into a conserved binding mode," *The Journal of Experimental Medicine* 207(11):2383-2393, Oct. 2010.
Liao et al., "Substituted Coumarins as Esterase-Sensitive Prodrug Moieties with Improved Release Rates," *Bioorganic & Medicinal Chemistry Letters* 9:1795-1800, 1999.
Lin et al., "A Continuous Procedure for Preparation of *para*Functionalized Aromatic Thiols using Newman-Kwart Chemistry," *Organic Preparations and Procedures International* 32(6):547-555, 2000.
Lin et al., "Mono and Bis Double Ester Prodrugs of Novel Aminomethyl-THF 1β- Methylcarbapenems," *Bioorganic & Medicinal Chemistry Letters* 7(14):1811-1816, 1997.
Lu et al., "Induction of the Epstein-Barr Virus Latent Membrane Protein 2 Antigen-specific Cytotoxic T Lymphocytes Using Human Leukocyte Antigen Tetramer-based Artificial Antigen-presenting Cells," *Acta Biochimic et Biophysica Sinica* 38(3):157-163, 2006.
Lu et al., "Synthesis and Evaluation of an α-C-Galactosylceramide Analogue that Induces Th1-biased Responses in Human Natural Killer T Cells," *ChemBioChem* 7:1750-1756, 2006.
Luo et al., "A Concise Synthesis of Tetrahydroxy-LCB, α-Galactosyl Ceramide, and 1,4-Dideoxy-1,4-imino-$^L$-ribitol via $_D$-Allosamines as Key Building Blocks," *The Journal of Organic Chemistry* 71:1226-1229, 2006.
Matto et al., "A General and Stereoselective Route to α- or β-Galactosphingolipids via a Common Four-Carbon Building Block," *The Journal of Organic Chemistry* 72:7757-7760, 2007.
Morita et al., "Structure-Activity Relationship of α-Galactosylceramides against B16-Bearing Mice," *The Journal of Medicinal Chemistry* 38:2176-2187, 1995.
Motoki et al., "Immunostimulatory and Antitumor Activities of Monoglycosylceramides Having Various Sugar Moieties," *Biological and Pharmaceutical Bulletin* 18(11):1487-1491, 1995.

(56) References Cited

OTHER PUBLICATIONS

Murata et al., "Total Synthesis of an Immunosuppressive Glycolipid, (2S, 3S, 4R)-1-O-(α-D-Galactosyl)-2-tetracosanoylamino-1,3,4-nonanetriol," *The Journal of Organic Chemistry* 70:2398-2401, 2005.

Nicolaou et al., "Phosphate Prodrugs for Amines Utilizing a Fast Intramolecular Hydroxy Amide Lactonization," *The Journal of Organic Chemistry* 61:8636-8641, 1996.

O'Reilly et al., "Synthesis of α-S-Glycosphingolipids Based on Uronic Acids," *Organic Letters* 13(19):5168-5171, 2011.

Parekh et al., "Glycolipid antigen induces long-term natural killer T cell anergy in mice," *The Journal of Clinical Investigation* 115(9):2572-2583, Sep. 2005.

Park et al., "Synthesis of all stereoisomers of KRN7000, the CD1d-binding NKT cell ligand," *Bioorganic & Medicinal Chemistry Letters* 18:3906-3909, 2008.

Plettenburg et al., "Synthesis of α-Galactosyl Ceramide, a Potent Immunostimulatory Agent," *The Journal of Organic Chemistry* 67:4559-4564, 2002.

Pu et al., "C-Galactosylceramide diastereomers via Sharpless asymmetric epoxidation chemistry," *Tetrahedron* 64:8618-8629, 2008.

Raju et al., "Synthesis and evaluation of 3"- and 4"-deoxy and -fluoro analogs of the immunostimulatory glycolipid, KRN7000," *Bioorganic & Medicinal Chemistry Letters* 19:4122-4125, 2009.

Sakurai et al., "Design and synthesis of functionalized trisaccharides as p53-peptide mimics," *Tetrahedron Letters* 51:3724-3727, 2010.

Schneider et al., "Ritter-Reaction on Steroids: Ring Expansion of Steroid Oxethans into Dihydrooxazines," *Tetrahedron* 41(16):3377-3386, 1985.

Secrist III et al., "Amine Hydrochlorides by Reduction in the Presence of Chloroform," *Journal of Organic Chemistry* 37(2):335-336, 1972.

Silk et al., "Utilizing the adjuvant properties of CD1d-dependent NK T cells in T cell-mediated immunotherapy," *Journal of Clinical Investigation* 114(12):1800-1811, Dec. 2004.

Sullivan et al., "Mechanisms for Glycolipid Antigen-Driven Cytokine Polarization by V α14i NKT Cells," *The Journal of Immunology* 184:141-153, 2010.

Sun et al., "A general synthesis of dioxolenone prodrug moieties," *Tetrahedron Letters* 43:1161-1164, 2002.

Tashiro et al., "RCAI-17, 22, 24-26, 29, 31, 34-36, 38-40, and 88, the analogs of KRN7000 with a sulfonamide linkage: Their synthesis and bioactivity for mouse natural killer T cells to produce Th2-biased cytokines," *Bioorganic & Medicinal Chemistry* 16:8896-8906, 2008.

Tashiro et al., "RCAI-61, the 6'-O-methylated analog of KRN7000: its synthesis and potent bioactivity for mouse lymphocytes to produce interferon-γ in vivo," *Tetrahedron Letters* 49:6827-6830, 2008.

Taylor et al., "Rapid and efficient chemoselective and multiple sulfations of phenols using sulfuryl imidazolium salts," *Tetrahedron Letters* 52:3353-3357, 2011.

Trappeniers et al., "Synthesis and in vitro Evaluation of α-GalCer Epimers," *ChemMedChem* 3:1061-1070, 2008.

Tupin et al., "CD 1d-dependent Activation of NKT Cells Aggravates Atherosclerosis," *The Journal of Experimental Medicine* 199(3):417-422, Jan. 2004.

Turner et al., "Synthesis of Two Metabolites of (+)-Propoxyphene," *Journal of Medicinal Chemistry* 20(8):1065-1068, 1977.

Uchimura et al., "Immunostimulatory Activities of Monoglycosylated α-D-Pyranosylceramides," *Bioorganic & Medicinal Chemistry* 5(12):2245-2249, 1997.

Veerapen et al., "Synthesis and biological activity of α-galactosyl ceramide KRN7000 and galactosyl (α1 → 2) galactosyl ceramide," *Bioorganic & Medicinal Chemistry Letters* 19:4288-4291, 2009.

Wingender et al., "Invariant NKT cells are required for airway inflammation induced by environmental antigens," *The Journal of Experimental Medicine* 208(6):1151-1162, May 2011.

Wipf et al., "Expedient Synthesis of the α-C-Glycoside Analogue of the Immunostimulant Galactosylceramide (KRN7000)," *Organic Letters* 8(15):3375-3378, 2006.

Wu et al., "Avidity of CD1d-ligand-receptor ternary complex contributes to T-helper 1 (Th1) polarization and anticancer efficacy," *Proceedings of the National Academy of Sciences* 108(42): 17275-17280, Oct. 2011.

Zeng et al., "Activation of natural killer T cells in NZB/W mice induces Th1-type immune responses exacerbating lupus," *Journal of Clinical Investigation* 112(8):1211-1222, Oct. 2003.

Zhang et al., "The Total Synthesis of Immunostimulant α-Galactosylceramides from Naturally Configured α-Galactoside Raffinose," *Organic Letters* 13(17):4530-4533, 2011.

Anderson et al., "A self-adjuvanting vaccine induces cytotoxic T lymphocytes that suppress allergy," *Nature Chemical Biology* 10:943-951, 2014.

\* cited by examiner

SEQUENCE LISTING

```
<160> NUMBER OF SEQ ID NOS: 414

<210> SEQ ID NO 1
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 1

Ala Met Leu Gly Thr His Thr Met Glu Val
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 2
```

```
Met Leu Gly Thr His Thr Met Glu Val
1               5
```

<210> SEQ ID NO 3
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 3

```
Glu Ala Ala Gly Ile Gly Ile Leu Thr Val
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 4

```
Ala Ala Gly Ile Gly Ile Leu Thr Val
1               5
```

<210> SEQ ID NO 5
<211> LENGTH: 18
<212> TYPE: PRT
<213> ORGANISM: Artificial Sequence
<220> FEATURE:
<223> OTHER INFORMATION: Synthetic Immunogen

<400> SEQUENCE: 5

```
Ala Ala Asp His Arg Gln Leu Gln Leu Ser Ile Ser Ser Cys Leu Gln
1               5                   10                  15

Gln Leu
```

<210> SEQ ID NO 6
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 6

```
Ala Ala Gly Ile Gly Ile Leu Thr Val Ile Leu Gly Val Leu
1               5                   10
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 7

```
Ala Ala Arg Ala Val Phe Leu Ala Leu
1               5
```

<210> SEQ ID NO 8
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 8

```
Ala Cys Asp Pro His Ser Gly His Phe Val
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 9

Ala Cys Tyr Glu Phe Leu Trp Gly Pro Arg Ala Leu Val Glu Thr Ser
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 10

Ala Asp His Arg Gln Leu Gln Leu Ser Ile Ser Ser Cys Leu Gln Gln
1               5                   10                  15

Leu

<210> SEQ ID NO 11
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 11

Ala Glu Glu Ala Ala Gly Ile Gly Ile Leu Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 12

Ala Glu Glu Ala Ala Gly Ile Gly Ile Leu
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 13

Ala Glu Leu Val His Phe Leu Leu Leu
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic Immunogen
```

```
<400> SEQUENCE: 14

Ala Glu Leu Val His Phe Leu Leu Lys Tyr Arg Ala Arg
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 15

Ala Glu Pro Ile Asn Ile Gln Thr Trp
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 16

Ala Phe Leu Pro Trp His Arg Leu Phe
1               5

<210> SEQ ID NO 17
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 17

Ala Gly Ala Thr Gly Gly Arg Gly Pro Arg Gly Ala Gly Ala
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 18

Ala Leu Cys Arg Trp Gly Leu Leu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 19

Ala Leu Asp Val Tyr Asn Gly Leu Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 20
```

Ala Leu Phe Asp Ile Glu Ser Lys Val
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 21

Ala Leu Gly Gly His Pro Leu Leu Gly Val
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 22

Ala Leu Ile His His Asn Thr His Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 23

Ala Leu Lys Asp Val Glu Glu Arg Val
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 24

Ala Leu Leu Ala Val Gly Ala Thr Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 25

Ala Leu Leu Glu Ile Ala Ser Cys Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 26

```
Ala Leu Asn Phe Pro Gly Ser Gln Lys
1               5
```

<210> SEQ ID NO 27
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 27

```
Ala Leu Pro Tyr Trp Asn Phe Ala Thr Gly
1               5                   10
```

<210> SEQ ID NO 28
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 28

```
Ala Leu Ser Val Met Gly Val Tyr Val
1               5
```

<210> SEQ ID NO 29
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 29

```
Ala Leu Trp Pro Trp Leu Leu Met Ala Thr
1               5                   10
```

<210> SEQ ID NO 30
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 30

```
Ala Leu Trp Pro Trp Leu Leu Met Ala
1               5
```

<210> SEQ ID NO 31
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 31

```
Ala Leu Tyr Val Asp Ser Leu Phe Phe Leu
1               5                   10
```

<210> SEQ ID NO 32
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 32

```
Ala Asn Asp Pro Ile Phe Val Val Leu
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 33

Ala Pro Pro Ala Tyr Glu Lys Leu Ser Ala Glu Gln
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 34

Ala Pro Arg Gly Pro His Gly Gly Ala Ala Ser Gly Leu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 35

Ala Pro Arg Gly Val Arg Met Ala Val
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 36

Ala Arg Gly Pro Glu Ser Arg Leu Leu
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 37

Ala Ser Gly Pro Gly Gly Gly Ala Pro Arg
1               5                   10

<210> SEQ ID NO 38
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 38

Ala Thr Gly Phe Lys Gln Ser Ser Lys Ala Leu Gln Arg Pro Val Ala
1               5                   10                  15
```

Ser

<210> SEQ ID NO 39
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 39

Ala Val Cys Pro Trp Thr Trp Leu Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 40

Ala Trp Ile Ser Lys Pro Pro Gly Val
1               5

<210> SEQ ID NO 41
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 41

Ala Tyr Val Cys Gly Ile Gln Asn Ser Val Ser Ala Asn Arg Ser
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 42

Cys Ala Thr Trp Lys Val Ile Cys Lys Ser Cys Ile Ser Gln Thr Pro
1               5                   10                  15

Gly

<210> SEQ ID NO 43
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 43

Cys Glu Phe His Ala Cys Trp Pro Ala Phe Thr Val Leu Gly Glu
1               5                   10                  15

<210> SEQ ID NO 44
<211> LENGTH: 22
<212> TYPE: PRT
<213> ORGANISM: Artificial Sequence
<220> FEATURE:
<223> OTHER INFORMATION: Synthetic Immunogen

<400> SEQUENCE: 44

```
Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 45
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 45

Cys Met Thr Trp Asn Gln Met Asn Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 46

Cys Gln Trp Gly Arg Leu Trp Gln Leu
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 47

Cys Thr Ala Cys Arg Trp Lys Lys Ala Cys Gln Arg
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 48

Asp Pro Ala Arg Tyr Glu Phe Leu Trp
1               5

<210> SEQ ID NO 49
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 49

Asp Thr Gly Phe Tyr Thr Leu His Val Ile Lys Ser Asp Leu Val Asn
1               5                   10                  15

Glu Glu Ala Thr Gly Gln Phe Arg Val
            20                  25

<210> SEQ ID NO 50
<211> LENGTH: 12
<212> TYPE: PRT
```

```
<213> ORGANISM: Artificial Sequence
<220> FEATURE:
<223> OTHER INFORMATION: Synthetic Immunogen

<400> SEQUENCE: 50

Asp Val Thr Phe Asn Ile Ile Cys Lys Lys Cys Gly
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 51

Glu Ala Ala Gly Ile Gly Ile Leu Thr Val
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 52

Glu Ala Asp Pro Thr Gly His Ser Tyr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 53

Glu Ala Phe Ile Gln Pro Ile Thr Arg
1               5

<210> SEQ ID NO 54
<211> LENGTH: 29
<212> TYPE: PRT
<213> ORGANISM: Artificial Sequence
<220> FEATURE:
<223> OTHER INFORMATION: Synthetic Immunogen

<400> SEQUENCE: 54

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 55
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 55

Glu Glu Ala Ala Gly Ile Gly Ile Leu Thr Val Ile
1               5                   10

<210> SEQ ID NO 56
```

```
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 56

Glu Glu Lys Leu Ile Val Val Leu Phe
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 57

Glu Phe Tyr Leu Ala Met Pro Phe Ala Thr Pro Met
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 58

Glu Gly Asp Cys Ala Pro Glu Glu Lys
1               5

<210> SEQ ID NO 59
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 59

Glu Ile Ile Tyr Pro Asn Ala Ser Leu Leu Ile Gln Asn
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 60

Glu Lys Ile Gln Lys Ala Phe Asp Asp Ile Ala Lys Tyr Phe Ser Lys
1               5                   10                  15

<210> SEQ ID NO 61
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 61

Glu Leu Thr Leu Gly Glu Phe Leu Lys Leu
1               5                   10

<210> SEQ ID NO 62
<211> LENGTH: 9
```

<212> TYPE: PRT
<213> ORGANISM: Artificial Sequence
<220> FEATURE:
<223> OTHER INFORMATION: Synthetic Immunogen

<400> SEQUENCE: 62

Glu Leu Val Arg Arg Ile Leu Ser Arg
1               5

<210> SEQ ID NO 63
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 63

Glu Ser Arg Leu Leu Glu Phe Tyr Leu Ala Met Pro Phe
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 64

Glu Thr Val Ser Glu Gln Ser Asn Val
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 65

Glu Val Asp Pro Ala Ser Asn Thr Tyr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 66

Glu Val Asp Pro Ile Gly His Leu Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 67

Glu Val Asp Pro Ile Gly His Val Tyr
1               5

<210> SEQ ID NO 68
<211> LENGTH: 10
<212> TYPE: PRT

```
<213> ORGANISM: Artificial Sequence
<220> FEATURE:
<223> OTHER INFORMATION: Synthetic Immunogen

<400> SEQUENCE: 68

Glu Val Ile Ser Cys Lys Leu Ile Lys Arg
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 69

Glu Val Tyr Asp Gly Arg Glu His Ser Ala
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 70

Glu Tyr Leu Gln Leu Val Phe Gly Ile
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 71

Glu Tyr Leu Ser Leu Ser Asp Lys Ile
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 72

Glu Tyr Ser Lys Glu Cys Leu Lys Glu Phe
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 73

Glu Tyr Val Ile Lys Val Ser Ala Arg Val Arg Phe
1               5                   10

<210> SEQ ID NO 74
<211> LENGTH: 10
<212> TYPE: PRT
<213> ORGANISM: Artificial Sequence
```

```
<220> FEATURE:
<223> OTHER INFORMATION: Synthetic Immunogen

<400> SEQUENCE: 74

Phe Ile Ala Ser Asn Gly Val Lys Leu Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 75

Phe Ile Asn Asp Glu Ile Phe Val Glu Leu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 76

Phe Leu Asp Glu Phe Met Glu Gly Val
1               5

<210> SEQ ID NO 77
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 77

Phe Leu Glu Gly Asn Glu Val Gly Lys Thr Tyr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 78

Phe Leu Phe Leu Leu Phe Phe Trp Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 79

Phe Leu Ile Ile Trp Gln Asn Thr Met
1               5

<210> SEQ ID NO 80
<211> LENGTH: 21
<212> TYPE: PRT
<213> ORGANISM: Artificial Sequence
<220> FEATURE:
```

<223> OTHER INFORMATION: Synthetic Immunogen

<400> SEQUENCE: 80

Phe Leu Leu His His Ala Phe Val Asp Ser Ile Phe Glu Gln Trp Leu
1               5                   10                  15
Gln Arg His Arg Pro
            20

<210> SEQ ID NO 81
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 81

Phe Leu Leu Leu Lys Tyr Arg Ala Arg Glu Pro Val Thr Lys Ala Glu
1               5                   10                  15

<210> SEQ ID NO 82
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 82

Phe Leu Thr Pro Lys Lys Leu Gln Cys Val
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 83

Phe Leu Trp Gly Pro Arg Ala Leu Val
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 84

Phe Met Asn Lys Phe Ile Tyr Glu Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 85

Phe Met Val Glu Asp Glu Thr Val Leu
1               5

<210> SEQ ID NO 86
<211> LENGTH: 9
<212> TYPE: PRT

```
<213> ORGANISM: Artificial Sequence
<220> FEATURE:
<223> OTHER INFORMATION: Synthetic Immunogen

<400> SEQUENCE: 86

Phe Pro Ser Asp Ser Trp Cys Tyr Phe
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 87

Phe Arg Ser Gly Leu Asp Ser Tyr Val
1               5

<210> SEQ ID NO 88
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 88

Phe Ser Trp Ala Met Asp Leu Asp Pro Lys Gly Ala
1               5                   10

<210> SEQ ID NO 89
<211> LENGTH: 38
<212> TYPE: PRT
<213> ORGANISM: Artificial Sequence
<220> FEATURE:
<223> OTHER INFORMATION: Synthetic Immunogen

<400> SEQUENCE: 89

Gly Ala Arg Gly Pro Glu Ser Arg Leu Leu Glu Phe Tyr Leu Ala Met
1               5                   10                  15

Pro Phe Ala Thr Pro Met Glu Ala Glu Leu Ala Arg Arg Ser Leu Ala
            20                  25                  30

Gln Asp Ala Pro Pro Leu
        35

<210> SEQ ID NO 90
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 90

Gly Asp Asn Gln Ile Met Pro Lys Ala Gly Leu Leu Ile Ile Val
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 91

Gly Glu Leu Ile Gly Ile Leu Asn Ala Ala Lys Val Pro Ala Asp
1               5                   10                  15
```

```
<210> SEQ ID NO 92
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 92

Gly Phe Lys Gln Ser Ser Lys Ala Leu
1               5

<210> SEQ ID NO 93
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 93

Gly Leu Ala Ser Phe Lys Ser Phe Leu Lys
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 94

Gly Leu Cys Thr Leu Val Ala Met Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 95

Gly Leu Pro Pro Asp Val Gln Arg Val
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 96

Gly Leu Tyr Asp Gly Met Glu His Leu Leu
1               5                   10

<210> SEQ ID NO 97
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 97

Gly Arg Ala Met Leu Gly Thr His Thr Met Glu Val Thr Val Tyr
1               5                   10                  15
```

-continued

```
<210> SEQ ID NO 98
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 98

Gly Val Ala Leu Gln Thr Met Lys Gln
1               5

<210> SEQ ID NO 99
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 99

Gly Val Gly Ser Pro Tyr Val Ser Arg Leu Leu Gly Ile Cys Leu
1               5                   10                  15

<210> SEQ ID NO 100
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 100

Ala Lys Phe Val Ala Ala Trp Thr Leu Lys Ala Ala Ala
1               5                   10

<210> SEQ ID NO 101
<211> LENGTH: 19
<212> TYPE: PRT
<213> ORGANISM: Artificial Sequence
<220> FEATURE:
<223> OTHER INFORMATION: Synthetic Immunogen

<400> SEQUENCE: 101

Gly Val Leu Leu Lys Glu Phe Thr Val Ser Gly Asn Ile Leu Thr Ile
1               5                   10                  15

Arg Leu Thr

<210> SEQ ID NO 102
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 102

Gly Val Leu Val Gly Val Ala Leu Ile
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 103

Gly Val Tyr Asp Gly Arg Glu His Thr Val
1               5                   10
```

<210> SEQ ID NO 104
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 104

His Leu Phe Gly Tyr Ser Trp Tyr Lys
1               5

<210> SEQ ID NO 105
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 105

His Leu Ile Arg Val Glu Gly Asn Leu Arg Val Glu
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 106

His Leu Ser Thr Ala Phe Ala Arg Val
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 107

His Leu Tyr Gln Gly Cys Gln Val Val
1               5

<210> SEQ ID NO 108
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 108

His Gln Gln Tyr Phe Tyr Lys Ile Pro Ile Leu Val Ile Asn Lys
1               5                   10                  15

<210> SEQ ID NO 109
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 109

His Thr Met Glu Val Thr Val Tyr His Arg
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 110

Ile Ala Leu Asn Phe Pro Gly Ser Gln Lys
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 111

Ile Gly Arg Ile Ala Glu Cys Ile Leu Gly Met Asn Pro Ser Arg
1               5                   10                  15

<210> SEQ ID NO 112
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 112

Ile Ile Ser Ala Val Val Gly Ile Leu
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 113

Ile Leu Ala Lys Phe Leu His Trp Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 114

Ile Leu Asp Ser Ser Glu Glu Asp Lys
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 115

Ile Leu Asp Thr Ala Gly Arg Glu Glu Tyr
1               5                   10

```
<210> SEQ ID NO 116
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 116

Ile Leu His Asn Gly Ala Tyr Ser Leu
1               5

<210> SEQ ID NO 117
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 117

Ile Leu Ser Arg Asp Ala Ala Pro Leu Pro Arg Pro Gly
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 118

Ile Leu Thr Val Ile Leu Gly Val Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 119

Ile Met Asp Gln Val Pro Phe Phe Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 120

Ile Met Asp Gln Val Pro Phe Ser Val
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 121

Ile Met Ile Gly Val Leu Val Gly Val
1               5

<210> SEQ ID NO 122
```

```
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 122

Ile Asn Lys Thr Ser Gly Pro Lys Arg Gly Lys His Ala Trp Thr His
1               5                   10                  15
Arg Leu Arg Glu
            20

<210> SEQ ID NO 123
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 123

Ile Ser Gly Gly Pro Arg Ile Ser Tyr
1               5

<210> SEQ ID NO 124
<211> LENGTH: 21
<212> TYPE: PRT
<213> ORGANISM: Artificial Sequence
<220> FEATURE:
<223> OTHER INFORMATION: Synthetic Immunogen

<400> SEQUENCE: 124

Ile Ser Pro Asn Ser Val Phe Ser Gln Trp Arg Val Val Cys Asp Ser
1               5                   10                  15
Leu Glu Asp Tyr Asp
            20

<210> SEQ ID NO 125
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 125

Ile Ser Gln Ala Val His Ala Ala His Ala Glu Ile Asn Glu Ala Gly
1               5                   10                  15
Arg

<210> SEQ ID NO 126
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 126

Ile Thr Asp Gln Val Pro Phe Ser Val
1               5

<210> SEQ ID NO 127
<211> LENGTH: 11
<212> TYPE: PRT
<213> ORGANISM: Artificial Sequence
<220> FEATURE:
<223> OTHER INFORMATION: Synthetic Immunogen
```

```
<400> SEQUENCE: 127

Ile Thr Lys Lys Val Ala Asp Leu Val Gly Phe
1               5                   10

<210> SEQ ID NO 128
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 128

Lys Ala Ser Glu Lys Ile Phe Tyr Val
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 129

Lys Ala Val Tyr Asn Phe Ala Thr Met
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 130

Lys Cys Asp Ile Cys Thr Asp Glu Tyr
1               5

<210> SEQ ID NO 131
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 131

Lys Glu Phe Thr Val Ser Gly Asn Ile Leu Thr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 132

Lys Glu Phe Thr Val Ser Gly Asn Ile Leu Thr Ile
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 133
```

```
Lys Glu Leu Glu Gly Ile Leu Leu Leu
1               5
```

<210> SEQ ID NO 134
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 134

```
Lys His Ala Trp Thr His Arg Leu Arg Glu Arg Lys Gln Leu Val Val
1               5                   10                  15

Tyr Glu Glu Ile
            20
```

<210> SEQ ID NO 135
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 135

```
Lys Ile Phe Gly Ser Leu Ala Phe Leu
1               5
```

<210> SEQ ID NO 136
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 136

```
Lys Ile Phe Ser Glu Val Thr Leu Lys
1               5
```

<210> SEQ ID NO 137
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 137

```
Lys Ile Phe Tyr Val Tyr Met Lys Arg Lys Tyr Glu Ala Met
1               5                   10
```

<210> SEQ ID NO 138
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 138

```
Lys Ile Phe Tyr Val Tyr Met Lys Arg Lys Tyr Glu Ala Met Thr
1               5                   10                  15
```

<210> SEQ ID NO 139
<211> LENGTH: 10
<212> TYPE: PRT
<213> ORGANISM: Artificial Sequence
<220> FEATURE:
<223> OTHER INFORMATION: Synthetic Immunogen

```
<400> SEQUENCE: 139

Lys Ile Leu Asp Ala Val Val Ala Gln Lys
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 140

Lys Ile Asn Lys Asn Pro Lys Tyr Lys
1               5

<210> SEQ ID NO 141
<211> LENGTH: 31
<212> TYPE: PRT
<213> ORGANISM: Artificial Sequence
<220> FEATURE:
<223> OTHER INFORMATION: Synthetic Immunogen

<400> SEQUENCE: 141

Lys Ile Ser Gln Ala Val His Ala Ala His Ala Glu Ile Asn Glu Ala
1               5                   10                  15

Gly Arg Glu Ser Ile Ile Asn Phe Glu Lys Leu Thr Glu Trp Thr
            20                  25                  30

<210> SEQ ID NO 142
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 142

Lys Lys Leu Leu Thr Gln His Phe Val Gln Glu Asn Tyr Leu Glu Tyr
1               5                   10                  15

<210> SEQ ID NO 143
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 143

Lys Met Asp Ala Glu His Pro Glu Leu
1               5

<210> SEQ ID NO 144
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 144

Lys Asn Cys Glu Pro Val Val Pro Asn Ala Pro Pro Ala Tyr Glu Lys
1               5                   10                  15

Leu Ser Ala Glu
            20

<210> SEQ ID NO 145
```

```
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 145

Lys Arg Tyr Phe Lys Leu Ser His Leu Gln Met His Ser Arg Lys His
1               5                   10                  15

<210> SEQ ID NO 146
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 146

Lys Ser Ser Glu Lys Ile Val Tyr Val Tyr Met Lys Leu Asn Tyr Glu
1               5                   10                  15

Val Met Thr Lys
            20

<210> SEQ ID NO 147
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 147

Lys Thr Trp Gly Gln Tyr Trp Gln Val
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 148

Lys Val Ala Glu Leu Val His Phe Leu
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 149

Lys Val His Pro Val Ile Trp Ser Leu
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 150

Lys Val Leu Glu Tyr Val Ile Lys Val
1               5
```

```
<210> SEQ ID NO 151
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 151

Lys Tyr Asp Cys Phe Leu His Pro Phe
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 152

Lys Tyr Val Gly Ile Glu Arg Glu Met
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 153

Leu Ala Ala Leu Pro His Ser Cys Leu
1               5

<210> SEQ ID NO 154
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 154

Leu Ala Ala Gln Glu Arg Arg Val Pro Arg
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 155

Leu Ala Gly Ile Gly Ile Leu Thr Val
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 156

Leu Ala Met Pro Phe Ala Thr Pro Met
1               5
```

```
<210> SEQ ID NO 157
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 157

Leu Gly Phe Lys Val Thr Leu Pro Pro Phe Met Arg Ser Lys Arg Ala
1               5                   10                  15

Ala Asp Phe His
            20

<210> SEQ ID NO 158
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 158

Leu Gly Pro Gly Arg Pro Tyr Arg
1               5

<210> SEQ ID NO 159
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 159

Leu His His Ala Phe Val Asp Ser Ile Phe
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 160

Leu Ile Tyr Arg Arg Arg Leu Met Lys
1               5

<210> SEQ ID NO 161
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 161

Leu Lys Glu Phe Thr Val Ser Gly Asn Ile Leu Thr Ile Arg Leu
1               5                   10                  15

<210> SEQ ID NO 162
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 162

Leu Lys Leu Ser Gly Val Val Arg Leu
1               5
```

```
<210> SEQ ID NO 163
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 163

Leu Leu Ala Asn Gly Arg Met Pro Thr Val Leu Gln Cys Val Asn
1               5                   10                  15

<210> SEQ ID NO 164
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 164

Leu Leu Asp Gly Thr Ala Thr Leu Arg Leu
1               5                   10

<210> SEQ ID NO 165
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 165

Leu Leu Glu Phe Tyr Leu Ala Met Pro Phe Ala Thr Pro Met
1               5                   10

<210> SEQ ID NO 166
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 166

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 167
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 167

Leu Leu Phe Gly Leu Ala Leu Ile Glu Val
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 168
```

```
Leu Leu Gly Ala Thr Cys Met Phe Val
1               5
```

<210> SEQ ID NO 169
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 169

```
Leu Leu Gly Pro Gly Arg Pro Tyr Arg
1               5
```

<210> SEQ ID NO 170
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 170

```
Leu Leu Gly Arg Asn Ser Phe Glu Val
1               5
```

<210> SEQ ID NO 171
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 171

```
Leu Leu Lys Tyr Arg Ala Arg Glu Pro Val Thr Lys Ala Glu
1               5                   10
```

<210> SEQ ID NO 172
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 172

```
Leu Leu Leu Asp Asp Leu Leu Val Ser Ile
1               5                   10
```

<210> SEQ ID NO 173
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 173

```
Leu Leu Leu Leu Thr Val Leu Thr Val
1               5
```

<210> SEQ ID NO 174
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 174

```
Leu Leu Trp Ser Phe Gln Thr Ser Ala
```

```
1               5
```

<210> SEQ ID NO 175
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 175

```
Leu Leu Tyr Lys Leu Ala Asp Leu Ile
1               5
```

<210> SEQ ID NO 176
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 176

```
Leu Met Leu Gln Asn Ala Leu Thr Thr Met
1               5                   10
```

<210> SEQ ID NO 177
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 177

```
Leu Pro Ala Val Val Gly Leu Ser Pro Gly Glu Gln Glu Tyr
1               5                   10
```

<210> SEQ ID NO 178
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 178

```
Leu Pro His Ser Ser Ser His Trp Leu
1               5
```

<210> SEQ ID NO 179
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 179

```
Leu Pro Arg Trp Pro Pro Pro Gln Leu
1               5
```

<210> SEQ ID NO 180
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 180

```
Leu Pro Ser Ser Ala Asp Val Glu Phe
1               5
```

```
<210> SEQ ID NO 181
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 181

Leu Ser His Leu Gln Met His Ser Arg Lys His
1               5                   10

<210> SEQ ID NO 182
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 182

Leu Ser Arg Leu Ser Asn Arg Leu Leu
1               5

<210> SEQ ID NO 183
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 183

Leu Thr Asp Leu Gln Pro Tyr Met Arg Gln Phe Val Ala His Leu
1               5                   10                  15

<210> SEQ ID NO 184
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 184

Leu Trp Trp Val Asn Asn Gln Ser Leu Pro Val Ser Pro
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 185

Leu Tyr Ala Thr Val Ile His Asp Ile
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 186

Leu Tyr Ser Ala Cys Phe Trp Trp Leu
1               5
```

<210> SEQ ID NO 187
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 187

Leu Tyr Val Asp Ser Leu Phe Phe Leu
1               5

<210> SEQ ID NO 188
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 188

Met Glu Val Asp Pro Ile Gly His Leu Tyr
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 189

Met Ile Ala Val Phe Leu Pro Ile Val
1               5

<210> SEQ ID NO 190
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 190

Met Ile Phe Glu Lys His Gly Phe Arg Arg Thr Thr Pro Pro
1               5                   10

<210> SEQ ID NO 191
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 191

Met Lys Leu Asn Tyr Glu Val Met Thr Lys Leu Gly Phe Lys Val Thr
1               5                   10                  15

Leu Pro Pro Phe
            20

<210> SEQ ID NO 192
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 192

Met Leu Ala Val Ile Ser Cys Ala Val

```
<210> SEQ ID NO 193
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 193

Met Leu Leu Ala Val Leu Tyr Cys Leu
1               5

<210> SEQ ID NO 194
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 194

Met Leu Met Ala Gln Glu Ala Leu Ala Phe Leu
1               5                   10

<210> SEQ ID NO 195
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 195

Met Pro Phe Ala Thr Pro Met Glu Ala
1               5

<210> SEQ ID NO 196
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 196

Met Pro Arg Glu Asp Ala His Phe Ile Tyr Gly Tyr Pro Lys Lys Gly
1               5                   10                  15

His Gly His Ser
            20

<210> SEQ ID NO 197
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 197

Met Ser Leu Gln Arg Gln Phe Leu Arg
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 198
```

Met Val Lys Ile Ser Gly Gly Pro Arg
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 199

Asn Leu Val Pro Met Val Ala Thr Val
1               5

<210> SEQ ID NO 200
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 200

Asn Pro Pro Ser Met Val Ala Ala Gly Ser Val Val Ala Ala Val
1               5                   10                  15

<210> SEQ ID NO 201
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 201

Asn Ser Ile Val Lys Ser Ile Thr Val Ser Ala Ser Gly
1               5                   10

<210> SEQ ID NO 202
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 202

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 203
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 203

Asn Ser Gln Pro Val Trp Leu Cys Leu
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 204

Asn Thr Tyr Ala Ser Pro Arg Phe Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 205

Asn Tyr Ala Arg Thr Glu Asp Phe Phe
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 206

Asn Tyr Lys Arg Cys Phe Pro Val Ile
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 207

Asn Tyr Asn Asn Phe Tyr Arg Phe Leu
1               5

<210> SEQ ID NO 208
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 208

Pro Asp Thr Arg Pro Ala Pro Gly Ser Thr Ala Pro Pro Ala His Gly
1               5                   10                  15

Val Thr Ser Ala
            20

<210> SEQ ID NO 209
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 209

Pro Phe Ala Thr Pro Met Glu Ala Glu Leu Ala Arg Arg
1               5                   10

<210> SEQ ID NO 210
<211> LENGTH: 12
<212> TYPE: PRT
<213> ORGANISM: Artificial Sequence
```

```
<220> FEATURE:
<223> OTHER INFORMATION: Synthetic Immunogen

<400> SEQUENCE: 210

Pro Gly Ser Thr Ala Pro Pro Ala His Gly Val Thr
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 211

Pro Gly Thr Arg Val Arg Ala Met Ala Ile Tyr Lys Gln
1               5                   10

<210> SEQ ID NO 212
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 212

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 213
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 213

Pro Leu Leu Glu Asn Val Ile Ser Lys
1               5

<210> SEQ ID NO 214
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 214

Pro Leu Pro Pro Ala Arg Asn Gly Gly Leu
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 215

Pro Leu Gln Pro Glu Gln Leu Gln Val
1               5

<210> SEQ ID NO 216
<211> LENGTH: 9
```

```
<212> TYPE: PRT
<213> ORGANISM: Artificial Sequence
<220> FEATURE:
<223> OTHER INFORMATION: Synthetic Immunogen

<400> SEQUENCE: 216

Pro Leu Thr Ser Ile Ile Ser Ala Val
1               5

<210> SEQ ID NO 217
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 217

Pro Arg Ala Leu Ala Glu Thr Ser Tyr Val Lys Val Leu Glu Tyr
1               5                   10                  15

<210> SEQ ID NO 218
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 218

Pro Val Thr Trp Arg Arg Ala Pro Ala
1               5

<210> SEQ ID NO 219
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 219

Pro Tyr Tyr Phe Ala Ala Glu Leu Pro Pro Arg Asn Leu Pro Glu Pro
1               5                   10                  15

<210> SEQ ID NO 220
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 220

Gln Cys Ser Gly Asn Phe Met Gly Phe
1               5

<210> SEQ ID NO 221
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 221

Gln Cys Thr Glu Val Arg Ala Asp Thr Arg Pro Trp Ser Gly Pro
1               5                   10                  15

<210> SEQ ID NO 222
<211> LENGTH: 20
<212> TYPE: PRT
```

-continued

```
<213> ORGANISM: Artificial Sequence
<220> FEATURE:
<223> OTHER INFORMATION: Synthetic Immunogen

<400> SEQUENCE: 222

Gln Gly Ala Met Leu Ala Ala Gln Glu Arg Arg Val Pro Arg Ala Ala
1               5                   10                  15

Glu Val Pro Arg
            20

<210> SEQ ID NO 223
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 223

Gln Gly Gln His Phe Leu Gln Lys Val
1               5

<210> SEQ ID NO 224
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 224

Gln Leu Ala Val Ser Val Ile Leu Arg Val
1               5                   10

<210> SEQ ID NO 225
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 225

Gln Asn Ile Leu Leu Ser Asn Ala Pro Leu Gly Pro Gln Phe Pro
1               5                   10                  15

<210> SEQ ID NO 226
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 226

Gln Gln Ile Thr Lys Thr Glu Val
1               5

<210> SEQ ID NO 227
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 227

Gln Arg Pro Tyr Gly Tyr Asp Gln Ile Met
1               5                   10

<210> SEQ ID NO 228
```

```
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 228

Gln Tyr Ser Trp Phe Val Asn Gly Thr Phe
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 229

Arg Ala Gly Leu Gln Val Arg Lys Asn Lys
1               5                   10

<210> SEQ ID NO 230
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 230

Arg Glu Pro Phe Thr Lys Ala Glu Met Leu Gly Ser Val Ile Arg
1               5                   10                  15

<210> SEQ ID NO 231
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 231

Arg Glu Pro Val Thr Lys Ala Glu Met Leu
1               5                   10

<210> SEQ ID NO 232
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 232

Arg Ile Ala Glu Cys Ile Leu Gly Met
1               5

<210> SEQ ID NO 233
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 233

Arg Lys Val Ala Glu Leu Val His Phe Leu Leu Leu Lys Tyr Arg
1               5                   10                  15

<210> SEQ ID NO 234
<211> LENGTH: 16
```

```
<212> TYPE: PRT
<213> ORGANISM: Artificial Sequence
<220> FEATURE:
<223> OTHER INFORMATION: Synthetic Immunogen

<400> SEQUENCE: 234

Arg Lys Val Ala Glu Leu Val His Phe Leu Leu Leu Lys Tyr Arg Ala
1               5                   10                  15

<210> SEQ ID NO 235
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 235

Arg Leu Leu Glu Phe Tyr Leu Ala Met Pro Phe Ala
1               5                   10

<210> SEQ ID NO 236
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 236

Arg Leu Leu Gln Glu Thr Glu Leu Val
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 237

Arg Leu Met Lys Gln Asp Phe Ser Val
1               5

<210> SEQ ID NO 238
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 238

Arg Leu Pro Arg Ile Phe Cys Ser Cys
1               5

<210> SEQ ID NO 239
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 239

Arg Leu Ser Ser Cys Val Pro Val Ala
1               5

<210> SEQ ID NO 240
<211> LENGTH: 9
<212> TYPE: PRT
```

<213> ORGANISM: Artificial Sequence
<220> FEATURE:
<223> OTHER INFORMATION: Synthetic Immunogen

<400> SEQUENCE: 240

Arg Leu Val Asp Asp Phe Leu Leu Val
1               5

<210> SEQ ID NO 241
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 241

Arg Met Pro Glu Ala Ala Pro Pro Val
1               5

<210> SEQ ID NO 242
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 242

Arg Met Pro Thr Val Leu Gln Cys Val Asn Val Ser Val Val Ser
1               5                   10                  15

<210> SEQ ID NO 243
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 243

Arg Asn Gly Tyr Arg Ala Leu Met Asp Lys Ser
1               5                   10

<210> SEQ ID NO 244
<211> LENGTH: 23
<212> TYPE: PRT
<213> ORGANISM: Artificial Sequence
<220> FEATURE:
<223> OTHER INFORMATION: Synthetic Immunogen

<400> SEQUENCE: 244

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 245
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 245

Arg Pro Gly Leu Leu Gly Ala Ser Val Leu Gly Leu Asp Asp Ile
1               5                   10                  15

<210> SEQ ID NO 246

```
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 246

Arg Pro His Val Pro Glu Ser Ala Phe
1               5

<210> SEQ ID NO 247
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 247

Arg Gln Lys Arg Ile Leu Val Asn Leu
1               5

<210> SEQ ID NO 248
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 248

Arg Ser Asp Ser Gly Gln Gln Ala Arg Tyr
1               5                   10

<210> SEQ ID NO 249
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 249

Arg Thr Lys Gln Leu Tyr Pro Glu Trp
1               5

<210> SEQ ID NO 250
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 250

Arg Val Ile Lys Asn Ser Ile Arg Leu Thr Leu
1               5                   10

<210> SEQ ID NO 251
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 251

Arg Val Arg Phe Phe Phe Pro Ser Leu
1               5

<210> SEQ ID NO 252
<211> LENGTH: 9
```

```
<212> TYPE: PRT
<213> ORGANISM: Artificial Sequence
<220> FEATURE:
<223> OTHER INFORMATION: Synthetic Immunogen

<400> SEQUENCE: 252

Arg Tyr Gln Leu Asp Pro Lys Phe Ile
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 253

Ser Ala Phe Pro Thr Thr Ile Asn Phe
1               5

<210> SEQ ID NO 254
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 254

Ser Ala Trp Ile Ser Lys Pro Pro Gly Val
1               5                   10

<210> SEQ ID NO 255
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 255

Ser Ala Tyr Gly Glu Pro Arg Lys Leu
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 256

Ser Glu Ile Trp Arg Asp Ile Asp Phe
1               5

<210> SEQ ID NO 257
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 257

Ser Glu Leu Phe Arg Ser Gly Leu Asp Ser Tyr
1               5                   10

<210> SEQ ID NO 258
<211> LENGTH: 9
<212> TYPE: PRT
```

<213> ORGANISM: Artificial Sequence
<220> FEATURE:
<223> OTHER INFORMATION: Synthetic Immunogen

<400> SEQUENCE: 258

Ser Glu Ser Ile Lys Lys Lys Val Leu
1               5

<210> SEQ ID NO 259
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 259

Ser Glu Ser Leu Lys Met Ile Phe
1               5

<210> SEQ ID NO 260
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 260

Ser Phe Ser Tyr Thr Leu Leu Ser Leu
1               5

<210> SEQ ID NO 261
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 261

Ser His Glu Thr Val Ile Ile Glu Leu
1               5

<210> SEQ ID NO 262
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 262

Ser Ile Ile Asn Phe Glu Lys Leu
1               5

<210> SEQ ID NO 263
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 263

Ser Leu Ala Asp Thr Asn Ser Leu Ala Val
1               5                   10

<210> SEQ ID NO 264
<211> LENGTH: 10
<212> TYPE: PRT
<213> ORGANISM: Artificial Sequence

```
<220> FEATURE:
<223> OTHER INFORMATION: Synthetic Immunogen

<400> SEQUENCE: 264

Ser Leu Phe Glu Gly Ile Asp Ile Tyr Thr
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 265

Ser Leu Phe Pro Asn Ser Pro Lys Trp Thr Ser Lys
1               5                   10

<210> SEQ ID NO 266
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 266

Ser Leu Phe Arg Ala Val Ile Thr Lys
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 267

Ser Leu Gly Trp Leu Phe Leu Leu Leu
1               5

<210> SEQ ID NO 268
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 268

Ser Leu Leu Met Trp Ile Thr Gln Cys
1               5

<210> SEQ ID NO 269
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 269

Ser Leu Leu Met Trp Ile Thr Gln Cys Phe Leu Pro Val Phe
1               5                   10

<210> SEQ ID NO 270
<211> LENGTH: 9
<212> TYPE: PRT
<213> ORGANISM: Artificial Sequence
<220> FEATURE:
```

<223> OTHER INFORMATION: Synthetic Immunogen

<400> SEQUENCE: 270

Ser Leu Leu Gln His Leu Ile Gly Leu
1               5

<210> SEQ ID NO 271
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 271

Ser Leu Pro Tyr Trp Asn Phe Ala Thr Gly
1               5                   10

<210> SEQ ID NO 272
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 272

Ser Leu Ser Lys Ile Leu Asp Thr Val
1               5

<210> SEQ ID NO 273
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 273

Ser Leu Tyr Lys Phe Ser Pro Phe Pro Leu
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 274

Ser Leu Tyr Ser Phe Pro Glu Pro Glu Ala
1               5                   10

<210> SEQ ID NO 275
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 275

Ser Asn Asp Gly Pro Thr Leu Ile
1               5

<210> SEQ ID NO 276
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 276

Ser Pro Arg Trp Trp Pro Thr Cys Leu
1               5

<210> SEQ ID NO 277
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 277

Ser Pro Ser Ser Asn Arg Ile Arg Asn Thr
1               5                   10

<210> SEQ ID NO 278
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 278

Ser Gln Lys Thr Tyr Gln Gly Ser Tyr
1               5

<210> SEQ ID NO 279
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 279

Ser Arg Phe Gly Gly Ala Val Val Arg
1               5

<210> SEQ ID NO 280
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 280

Ser Ser Ala Leu Leu Ser Ile Phe Gln Ser Ser Pro Glu
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 281

Ser Ser Asp Tyr Val Ile Pro Ile Gly Thr Tyr
1               5                   10

<210> SEQ ID NO 282
<211> LENGTH: 9
<212> TYPE: PRT
<213> ORGANISM: Artificial Sequence
<220> FEATURE:
<223> OTHER INFORMATION: Synthetic Immunogen
```

```
<400> SEQUENCE: 282

Ser Ser Lys Ala Leu Gln Arg Pro Val
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 283

Ser Ser Pro Gly Cys Gln Pro Pro Ala
1               5

<210> SEQ ID NO 284
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 284

Ser Thr Ala Pro Pro Val His Asn Val
1               5

<210> SEQ ID NO 285
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 285

Ser Val Ala Ser Thr Ile Thr Gly Val
1               5

<210> SEQ ID NO 286
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 286

Ser Val Asp Tyr Phe Phe Val Trp Leu
1               5

<210> SEQ ID NO 287
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 287

Ser Val Ser Glu Ser Asp Thr Ile Arg Ser Ile Ser Ile Ala Ser
1               5                   10                  15

<210> SEQ ID NO 288
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 288
```

```
Ser Val Tyr Asp Phe Phe Val Trp Leu
1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 289

Ser Tyr Leu Asp Ser Gly Ile His Phe
1               5

<210> SEQ ID NO 290
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 290

Ser Tyr Leu Gln Asp Ser Asp Pro Asp Ser Phe Gln Asp
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 291

Thr Phe Pro Asp Leu Glu Ser Glu Phe
1               5

<210> SEQ ID NO 292
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 292

Thr Gly Arg Ala Met Leu Gly Thr His Thr Met Glu Val Thr Val Tyr
1               5                   10                  15

His

<210> SEQ ID NO 293
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 293

Thr Leu Asp Ser Gln Val Met Ser Leu
1               5

<210> SEQ ID NO 294
<211> LENGTH: 10
<212> TYPE: PRT
<213> ORGANISM: Artificial Sequence
<220> FEATURE:
<223> OTHER INFORMATION: Synthetic Immunogen
```

<400> SEQUENCE: 294

Thr Leu Asp Trp Leu Leu Gln Thr Pro Lys
1               5                   10

<210> SEQ ID NO 295
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 295

Thr Leu Glu Glu Ile Thr Gly Tyr Leu
1               5

<210> SEQ ID NO 296
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 296

Thr Leu Met Ser Ala Met Thr Asn Leu
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 297

Thr Leu Asn Asp Glu Cys Trp Pro Ala
1               5

<210> SEQ ID NO 298
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 298

Thr Leu Pro Gly Tyr Pro Pro His Val
1               5

<210> SEQ ID NO 299
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 299

Thr Leu Tyr Gln Asp Asp Thr Leu Thr Leu Gln Ala Ala Gly
1               5                   10

<210> SEQ ID NO 300
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 300

```
Thr Met Lys Gln Ile Cys Lys Lys Glu Ile Arg Arg Leu His Gln Tyr
1               5                   10                  15

<210> SEQ ID NO 301
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 301

Thr Met Asn Gly Ser Lys Ser Pro Val
1               5

<210> SEQ ID NO 302
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 302

Thr Pro Arg Leu Pro Ser Ser Ala Asp Val Glu Phe
1               5                   10

<210> SEQ ID NO 303
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 303

Thr Ser Cys Ile Leu Glu Ser Leu Phe Arg Ala Val Ile Thr Lys
1               5                   10                  15

<210> SEQ ID NO 304
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 304

Thr Ser Glu Lys Arg Pro Phe Met Cys Ala Tyr
1               5                   10

<210> SEQ ID NO 305
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 305

Thr Ser Tyr Val Lys Val Leu His His Met Val Lys Ile Ser Gly
1               5                   10                  15

<210> SEQ ID NO 306
<211> LENGTH: 18
<212> TYPE: PRT
<213> ORGANISM: Artificial Sequence
<220> FEATURE:
<223> OTHER INFORMATION: Synthetic Immunogen

<400> SEQUENCE: 306
```

Thr Thr Glu Trp Val Glu Thr Thr Ala Arg Glu Leu Pro Ile Pro Glu
1               5                   10                  15

Pro Glu

<210> SEQ ID NO 307
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 307

Thr Val Ser Gly Asn Ile Leu Thr Ile Arg
1               5                   10

<210> SEQ ID NO 308
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 308

Thr Tyr Ala Cys Phe Val Ser Asn Leu
1               5

<210> SEQ ID NO 309
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 309

Thr Tyr Leu Pro Thr Asn Ala Ser Leu
1               5

<210> SEQ ID NO 310
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 310

Thr Tyr Tyr Arg Pro Gly Val Asn Leu Ser Leu Ser Cys
1               5                   10

<210> SEQ ID NO 311
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 311

Val Ala Glu Leu Val His Phe Leu Leu
1               5

<210> SEQ ID NO 312
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 312

Val Phe Gly Ile Glu Leu Met Glu Val Asp Pro Ile Gly His Leu
1               5                   10                  15

<210> SEQ ID NO 313
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 313

Val Gly Gln Asp Val Ser Val Leu Phe Arg Val Thr Gly Ala Leu Gln
1               5                   10                  15

<210> SEQ ID NO 314
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 314

Val Ile Phe Ser Lys Ala Ser Ser Ser Leu Gln Leu
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 315

Val Ile Ser Asn Asp Val Cys Ala Gln Val
1               5                   10

<210> SEQ ID NO 316
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 316

Val Leu Asp Gly Leu Asp Val Leu Leu
1               5

<210> SEQ ID NO 317
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 317

Val Leu Phe Tyr Leu Gly Gln Tyr
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 318

```
Val Leu His Trp Asp Pro Glu Thr Val
1               5
```

<210> SEQ ID NO 319
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 319

```
Val Leu Leu Lys Glu Phe Thr Val Ser Gly
1               5                   10
```

<210> SEQ ID NO 320
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 320

```
Val Leu Leu Gln Ala Gly Ser Leu His Ala
1               5                   10
```

<210> SEQ ID NO 321
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 321

```
Val Leu Pro Asp Val Phe Ile Arg Cys Val
1               5                   10
```

<210> SEQ ID NO 322
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 322

```
Val Leu Pro Asp Val Phe Ile Arg Cys
1               5
```

<210> SEQ ID NO 323
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 323

```
Val Leu Arg Glu Asn Thr Ser Pro Lys
1               5
```

<210> SEQ ID NO 324
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 324

```
Val Leu Tyr Arg Tyr Gly Ser Phe Ser Val
```

```
1               5              10

<210> SEQ ID NO 325
<211> LENGTH: 26
<212> TYPE: PRT
<213> ORGANISM: Artificial Sequence
<220> FEATURE:
<223> OTHER INFORMATION: Synthetic Immunogen

<400> SEQUENCE: 325

Val Pro Gly Val Leu Leu Lys Glu Phe Thr Val Ser Gly Asn Ile Leu
1               5                  10                  15

Thr Ile Arg Leu Thr Ala Ala Asp His Arg
            20                  25

<210> SEQ ID NO 326
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 326

Val Pro Leu Asp Cys Val Leu Tyr Arg Tyr
1               5                  10

<210> SEQ ID NO 327
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 327

Val Arg Ile Gly His Leu Tyr Ile Leu
1               5

<210> SEQ ID NO 328
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 328

Val Ser Ser Phe Phe Ser Tyr Thr Leu
1               5

<210> SEQ ID NO 329
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 329

Val Val Leu Gly Val Val Phe Gly Ile
1               5

<210> SEQ ID NO 330
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 330
```

```
Val Val Pro Cys Glu Pro Pro Glu Val
1               5

<210> SEQ ID NO 331
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 331

Val Val Val Gly Ala Val Gly Val Gly
1               5

<210> SEQ ID NO 332
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 332

Val Tyr Phe Phe Leu Pro Asp His Leu
1               5

<210> SEQ ID NO 333
<211> LENGTH: 18
<212> TYPE: PRT
<213> ORGANISM: Artificial Sequence
<220> FEATURE:
<223> OTHER INFORMATION: Synthetic Immunogen

<400> SEQUENCE: 333

Trp Glu Lys Met Lys Ala Ser Glu Lys Ile Phe Tyr Val Tyr Met Lys
1               5                   10                  15

Arg Lys

<210> SEQ ID NO 334
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 334

Trp Leu Pro Phe Gly Phe Ile Leu Ile
1               5

<210> SEQ ID NO 335
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 335

Trp Asn Arg Gln Leu Tyr Pro Glu Trp Thr Glu Ala Gln Arg Leu Asp
1               5                   10                  15

<210> SEQ ID NO 336
<211> LENGTH: 9
<212> TYPE: PRT
<213> ORGANISM: Artificial Sequence
<220> FEATURE:
<223> OTHER INFORMATION: Synthetic Immunogen
```

```
<400> SEQUENCE: 336

Trp Gln Tyr Phe Phe Pro Val Ile Phe
1               5

<210> SEQ ID NO 337
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 337

Trp Arg Arg Ala Pro Ala Pro Gly Ala
1               5

<210> SEQ ID NO 338
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 338

Tyr Ala Cys Phe Val Ser Asn Leu Ala Thr Gly Arg Asn Asn Ser
1               5                   10                  15

<210> SEQ ID NO 339
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 339

Tyr Phe Ser Lys Lys Glu Trp Glu Lys Met Lys Ser Ser Glu Lys Ile
1               5                   10                  15

Val Tyr Val Tyr
            20

<210> SEQ ID NO 340
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 340

Tyr Leu Glu Pro Gly Pro Val Thr Ala
1               5

<210> SEQ ID NO 341
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 341

Tyr Leu Glu Pro Gly Pro Val Thr Val
1               5

<210> SEQ ID NO 342
<211> LENGTH: 10
<212> TYPE: PRT
<213> ORGANISM: Artificial Sequence
<220> FEATURE:
```

```
<223> OTHER INFORMATION: Synthetic Immunogen

<400> SEQUENCE: 342

Tyr Leu Asn Asp His Leu Glu Pro Trp Ile
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 343

Tyr Leu Gln Leu Val Phe Gly Ile Glu Val
1               5                   10

<210> SEQ ID NO 344
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 344

Tyr Leu Ser Gly Ala Asn Leu Asn Leu
1               5

<210> SEQ ID NO 345
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 345

Tyr Leu Val Pro Gln Gln Gly Phe Phe Cys
1               5                   10

<210> SEQ ID NO 346
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 346

Tyr Met Asp Gly Thr Met Ser Gln Val
1               5

<210> SEQ ID NO 347
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 347

Tyr Met Ile Met Val Lys Cys Trp Met Ile
1               5                   10

<210> SEQ ID NO 348
<211> LENGTH: 8
<212> TYPE: PRT
<213> ORGANISM: Artificial Sequence
<220> FEATURE:
<223> OTHER INFORMATION: Synthetic Immunogen
```

<400> SEQUENCE: 348

Tyr Arg Pro Arg Pro Arg Arg Tyr
1               5

<210> SEQ ID NO 349
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 349

Tyr Ser Val Tyr Phe Asn Leu Pro Ala Asp Thr Ile Tyr Thr Asn
1               5                   10                  15

<210> SEQ ID NO 350
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 350

Tyr Ser Trp Arg Ile Asn Gly Ile Pro Gln Gln His Thr Gln Val
1               5                   10                  15

<210> SEQ ID NO 351
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 351

Tyr Val Asp Phe Arg Glu Tyr Glu Tyr Tyr
1               5                   10

<210> SEQ ID NO 352
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 352

Tyr Tyr Trp Pro Arg Pro Arg Arg Tyr
1               5

<210> SEQ ID NO 353
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 353

Ile Met Asp Gln Val Pro Phe Phe Ser
1               5

<210> SEQ ID NO 354
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 354

Ser Val Asp Tyr Phe Phe Val Trp Leu
1               5

<210> SEQ ID NO 355
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 355

Ala Leu Phe Asp Ile Glu Ser Lys Val
1               5

<210> SEQ ID NO 356
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 356

Asn Leu Val Pro Met Val Ala Thr Val
1               5

<210> SEQ ID NO 357
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 357

Gly Leu Cys Thr Leu Val Ala Met Leu
1               5

<210> SEQ ID NO 358
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 358

Ser Val Ala Ser Thr Ile Thr Gly Val
1               5

<210> SEQ ID NO 359
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 359

Val Met Ala Gly Asp Ile Tyr Ser Val
1               5

<210> SEQ ID NO 360
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 360
```

```
Ala Leu Ala Asp Gly Val Gln Lys Val
1               5

<210> SEQ ID NO 361
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 361

Leu Leu Gly Ala Thr Cys Met Phe Val
1               5

<210> SEQ ID NO 362
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 362

Ser Val Phe Ala Gly Val Val Gly Val
1               5

<210> SEQ ID NO 363
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 363

Ala Leu Phe Asp Gly Asp Pro His Leu
1               5

<210> SEQ ID NO 364
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 364

Tyr Val Asp Pro Val Ile Thr Ser Ile
1               5

<210> SEQ ID NO 365
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 365

Ser Thr Ala Pro Pro Val His Asn Val
1               5

<210> SEQ ID NO 366
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 366
```

```
Leu Ala Ala Leu Pro His Ser Cys Leu
1               5
```

<210> SEQ ID NO 367
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 367

```
Ser Gln Asp Asp Ile Lys Gly Ile Gln Lys Leu Tyr Gly Lys Arg Ser
1               5                   10                  15
```

<210> SEQ ID NO 368
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 368

```
Phe Leu Pro Ser Asp Phe Phe Pro Ser Val
1               5                   10
```

<210> SEQ ID NO 369
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 369

```
Phe Leu Pro Ser Asp Phe Phe Pro Ser Val
1               5                   10
```

<210> SEQ ID NO 370
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 370

```
Thr Leu Gly Glu Phe Leu Lys Leu Asp Arg Glu Arg Ala Lys Asn
1               5                   10                  15
```

<210> SEQ ID NO 371
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 371

```
Thr Phe Ser Tyr Val Asp Pro Val Ile Thr Ser Ile Ser Pro Lys Tyr
1               5                   10                  15

Gly Met Glu Thr
            20
```

<210> SEQ ID NO 372
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 372

Ala Met Thr Gln Leu Leu Ala Gly Val
1               5

<210> SEQ ID NO 373
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 373

Lys Val Phe Ala Gly Ile Pro Thr Val
1               5

<210> SEQ ID NO 374
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 374

Ala Ile Ile Asp Gly Val Glu Ser Val
1               5

<210> SEQ ID NO 375
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 375

Gly Leu Trp His His Gln Thr Glu Val
1               5

<210> SEQ ID NO 376
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 376

Asn Leu Asp Thr Leu Met Thr Tyr Val
1               5

<210> SEQ ID NO 377
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 377

Lys Ile Gln Glu Ile Leu Thr Gln Val
1               5

<210> SEQ ID NO 378
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 378
```

```
Leu Thr Phe Gly Asp Val Val Ala Val
1               5

<210> SEQ ID NO 379
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 379

Thr Met Leu Ala Arg Leu Ala Ser Ala
1               5

<210> SEQ ID NO 380
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 380

Ile Met Asp Gln Val Pro Phe Ser Val
1               5

<210> SEQ ID NO 381
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 381

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

<210> SEQ ID NO 382
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 382

Leu Pro Gln Leu Cys Thr Glu Leu Gln Thr Thr Ile
1               5                   10

<210> SEQ ID NO 383
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 383

His Asp Ile Ile Leu Glu Cys Val Tyr Cys Lys Gln Gln Leu Leu Arg
1               5                   10                  15

Arg Glu Val Tyr
            20

<210> SEQ ID NO 384
<211> LENGTH: 25
<212> TYPE: PRT
```

<213> ORGANISM: Artificial Sequence
<220> FEATURE:
<223> OTHER INFORMATION: Synthetic Immunogen

<400> SEQUENCE: 384

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 385
<211> LENGTH: 26
<212> TYPE: PRT
<213> ORGANISM: Artificial Sequence
<220> FEATURE:
<223> OTHER INFORMATION: Synthetic Immunogen

<400> SEQUENCE: 385

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 386
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 386

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25

<210> SEQ ID NO 387
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 387

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 388
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 388

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 389
<211> LENGTH: 32

```
<212> TYPE: PRT
<213> ORGANISM: Artificial Sequence
<220> FEATURE:
<223> OTHER INFORMATION: Synthetic Immunogen

<400> SEQUENCE: 389

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 390
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 390

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 391
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 391

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 392
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 392

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 393
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 393

Gly Gln Ala Glu Pro Asp Arg Ala His Tyr Asn Ile Val Thr Phe Cys
1               5                   10                  15
```

```
Cys Lys Cys Asp Ser Thr Leu Arg Leu Cys Val Gln Ser Thr His Val
            20                  25                  30

Asp Ile Arg
        35

<210> SEQ ID NO 394
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 394

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35

<210> SEQ ID NO 395
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 395

Ala Leu Pro Phe Gly Phe Ile Leu Val
1               5

<210> SEQ ID NO 396
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 396

Thr Leu Ala Asp Phe Asp Pro Arg Val
1               5

<210> SEQ ID NO 397
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 397

Ile Met Asp Gln Val Pro Phe Ser Val
1               5

<210> SEQ ID NO 398
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 398

Ser Ile Met Thr Tyr Asp Phe His Gly Ala
1               5                   10
```

```
<210> SEQ ID NO 399
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 399

Ala Gln Tyr Ile Lys Ala Asn Ser Lys Phe Ile Gly Ile Thr Glu Leu
1               5                   10                  15

<210> SEQ ID NO 400
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 400

Phe Leu Tyr Asp Asp Asn Gln Arg Val
1               5

<210> SEQ ID NO 401
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 401

Tyr Leu Ile Glu Leu Ile Asp Arg Val
1               5

<210> SEQ ID NO 402
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 402

Asn Leu Met Glu Gln Pro Ile Lys Val
1               5

<210> SEQ ID NO 403
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 403

Phe Leu Ala Glu Asp Ala Leu Asn Thr Val
1               5                   10

<210> SEQ ID NO 404
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 404

Ala Leu Met Glu Gln Gln His Tyr Val
1               5

<210> SEQ ID NO 405
```

<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 405

Ile Leu Asp Asp Ile Gly His Gly Val
1               5

<210> SEQ ID NO 406
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 406

Lys Leu Asp Val Gly Asn Ala Glu Val
1               5

<210> SEQ ID NO 407
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 407

Thr Phe Glu Phe Thr Ser Phe Phe Tyr
1               5

<210> SEQ ID NO 408
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 408

Ser Trp Pro Asp Gly Ala Glu Leu Pro Phe
1               5                   10

<210> SEQ ID NO 409
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 409

Gly Ile Leu Gly Phe Val Phe Thr Leu
1               5

<210> SEQ ID NO 410
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 410

Gly Ile Leu Gly Phe Val Phe Thr Leu
1               5

<210> SEQ ID NO 411
<211> LENGTH: 23

```
<212> TYPE: PRT
<213> ORGANISM: Artificial Sequence
<220> FEATURE:
<223> OTHER INFORMATION: Synthetic Immunogen

<400> SEQUENCE: 411

Ser Val Tyr Asp Phe Phe Val Trp Leu Lys Phe Phe His Arg Thr Cys
1               5                   10                  15

Lys Cys Thr Gly Asn Phe Ala
            20

<210> SEQ ID NO 412
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 412

Asp Leu Ala Gln Met Phe Phe Cys Phe Lys Glu Leu Glu Gly Trp
1               5                   10                  15

<210> SEQ ID NO 413
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 413

Ala Val Gly Ala Leu Glu Gly Pro Arg Asn Gln Asp Trp Leu Gly Val
1               5                   10                  15

Pro Arg Gln Leu
            20

<210> SEQ ID NO 414
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 414

Arg Ala His Tyr Asn Ile Val Thr Phe
1               5
```

CONJUGATE COMPOUNDS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 191184_401USPC_SEQUENCE_LISTING.txt. The text file is 88.8 KB, was created on Jun. 4, 2015, and is being submitted electronically via EFS-Web.

FIELD OF INVENTION

This invention relates generally to certain sphingoglycolipid analogues and peptide derivatives thereof, compositions comprising these compounds, including pharmaceutical compositions and adjuvant compositions, processes for preparing the compounds, and methods of treating or preventing diseases or conditions using such compounds, especially diseases or conditions relating to cancer, infection, atopic disorders, autoimmune disease or diabetes.

BACKGROUND

Invariant natural killer T-cells (NKT) are a subset of T-cells that are implicated in a broad range of diseases. In some circumstances they can enhance the response to infection (Kinjo, Illarionov et al. 2011) and cancer (Wu, Lin et al. 2011) but also possess the ability to suppress autoimmune disease (Hong, Wilson et al. 2001) and type II diabetes. Activation of NKT cells can also lead to undesirable immune responses as related to allergy, (Wingender, Rogers et al. 2011) autoimmunity (Zeng, Liu et al. 2003) and atherosclerosis (Tupin, Nicoletti et al. 2004).

Unlike conventional T-cells that are restricted by major histocompatibility complex (MHC) molecules that present peptide antigens, NKT cells are uniquely restricted by CD1d proteins (Bendelac, Savage et al. 2007). CD1d proteins belong to the CD1 family that contains five members, CD1a-e. Like MHC molecules, the CD1 family members all contain an antigen binding region that is flanked by two anti-parallel α-helices that sit above a β-sheet. Unlike MHC molecules, the binding region of the CD1 proteins contain two large hydrophobic binding pockets that are suited to bind lipid antigens rather than peptide-based antigens (Li, Girardi et al. 2010). α-Galactosylceramide (α-GalCer) is the most studied NKT cell antigen and potently activates human and mouse NKT cells (Kawano, Cui et al. 1997). In animal studies, α-GalCer is reported to be useful in the treatment of a number of diseases including cancer, (Morita, Motoki et al. 1995; Motoki, Morita et al. 1995) and autoimmune disease (Hong, Wilson et al. 2001). The compound has also been shown to function as a potent vaccine adjuvant in the treatment and prophylaxis of cancer and infectious disease (Silk, Hermans et al. 2004). This adjuvant activity has been attributed to stimulatory interactions between activated NKT cells and dendritic cells (DCs), the most potent antigen-presenting cells in the body. As a consequence, the DCs are rendered capable of promoting strong adaptive immune responses (Fujii, Shimizu et al. 2003; Hermans, Silk et al. 2003).

There is considerable interest in therapeutic vaccines for the treatment of cancer. The aim is to stimulate clonal expansion of T cells within a host that are capable of recognising and killing tumour cells, leaving normal tissues intact. This specificity relies on recognition of unique, tumour-derived, protein fragments presented by major histocompatibility complex (MHC) molecules on the tumour cell surface. Vaccines used in this context typically involve injection of the defined tumour-associated "tumour antigens", or their peptide fragments, together with immune adjuvants capable of driving an immune response. In the absence of such adjuvants, the opposite outcome may ensue, with the tumour antigens actually being "tolerated" by the immune system rather than provoking tumour rejection. Advances in this therapy are therefore dependent on appropriate combinations of antigen and adjuvant (Speiser and Romero 2010).

When incorporated into a vaccine, α-GalCer must first be acquired by antigen-presenting cells in the host, and then presented to NKT cells within the local environment (Fujii, Shimizu et al. 2003; Hermans, Silk et al. 2003). This process brings the two cell-types into close association, permitting stimulatory signals to be passed from NKT cell to antigen-presenting cell.

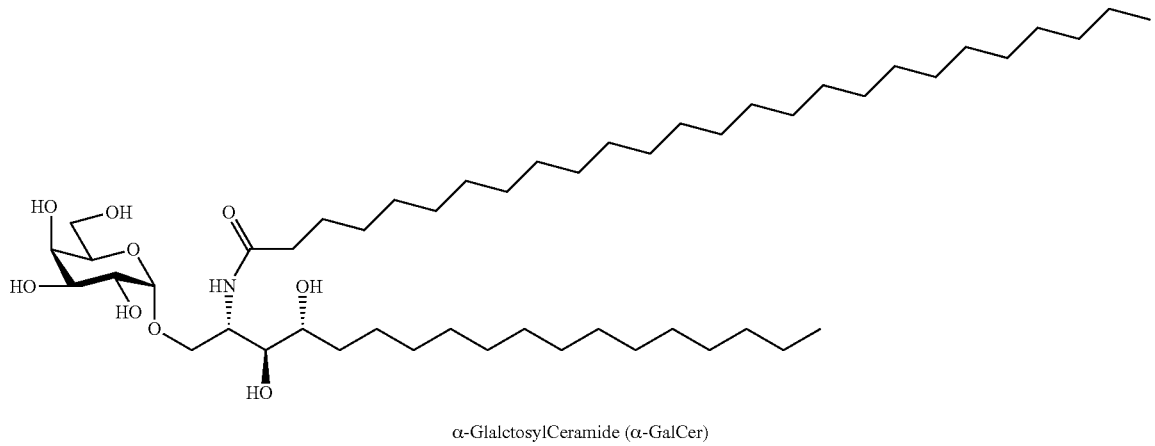

α-GlalctosylCeramide (α-GalCer)

Importantly, if the same antigen-presenting cells acquire the defined antigens of the vaccine, the stimulatory signals received through interaction with NKT cells can be translated directly into a superior capacity to provoke clonal proliferation of antigen-specific T cells with capacity to kill (Hermans, Silk et al. 2003; Semmling, Lukacs-Kornek et al. 2010). One way to achieve this is to load antigen-presenting cells ex vivo with antigenic material and NKT cell ligands (Petersen, Sika-Paotonu et al. 2010). Although a promising approach, in the clinic this requires leukapheresis and the ex vivo culturing of peripheral blood mononuclear cells (PBMC) over 7 days in a highly controlled sterile facility to generate sufficient antigen-presenting cells, which is a cumbersome and costly process. An alternative is to target antigen-presenting cells in vivo, with covalent attachment of antigen to NKT cell ligand ensuring entry into the same cell. Although used successfully with other immune adjuvant compounds, including the covalent attachment of a TLR2 agonist to MUC1 peptides (Cai, Huang et al. 2011), the approach has not been regarded as easily applicable to α-GalCer because the chemical attachment of peptide will result in a conjugate with significantly diminished, or no, capacity to stimulate NKT cells. In particular, the specific lipid moieties of α-GalCer are required for optimal binding into the A and F pockets of CD1d, and the polar head-group is required to be positioned appropriately for interaction with the T-cell receptor of the NKT cell (Borg, Wun et al. 2007), placing particularly tight constraints on the whole glycolipid structure for activity.

Although α-GalCer has considerable biological activity it does have limitations such as poor solubility, (Ebensen, Link et al. 2007) lack of efficacy in human clinical trials, (Giaccone, Punt et al. 2002) promotion of T-cell anergy (Parekh, Wilson et al. 2005) and the generation of both Th1 and Th2 cytokines that may contribute to mixed results in model studies.

It is an object of the invention to provide novel compounds or vaccines useful as agents for treating diseases or conditions relating to cancer, infection, autoimmune disease, atopic disorders or cancer, or to at least provide a useful alternative.

STATEMENTS OF INVENTION

In a first aspect, the invention provides a compound of formula (I):

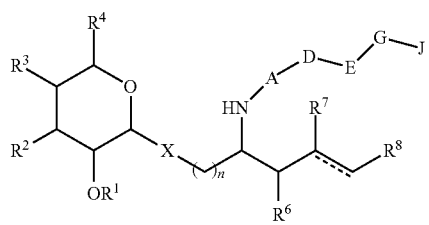
(I)

wherein:
A is a self-immolative linker group;
D is selected from the group consisting of:

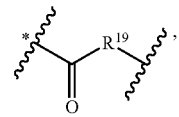
D1

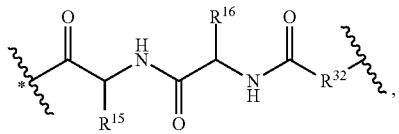
D2

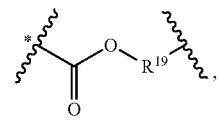
D3

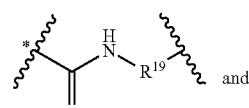
D4

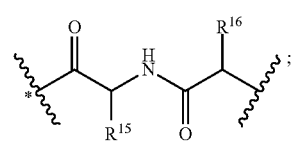
D5 wherein * denotes a point of attachment of group D to group A;

$R^{15}$ is a side chain of one of the following amino acids: L-lysine, L-citrulline, L-arginine, L-glutamine or L-threonine;

$R^{16}$ is a side chain of a hydrophobic amino acid;

$R^{19}$ is an alkylene group;

$R^{32}$ is an alkylene group or an O-alkylene group wherein the O is attached to the carbonyl group of D2;

E is selected from the group consisting of:

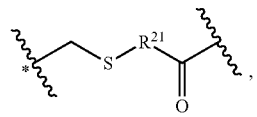
E1

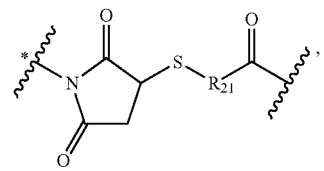
E2

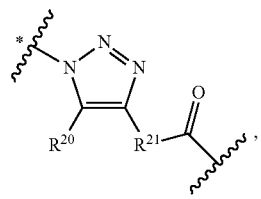
E3

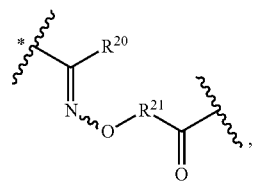
E4

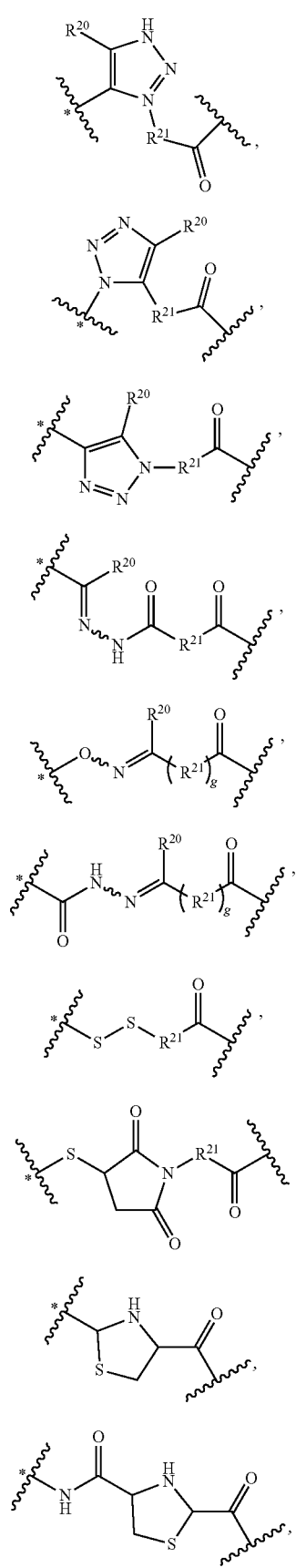

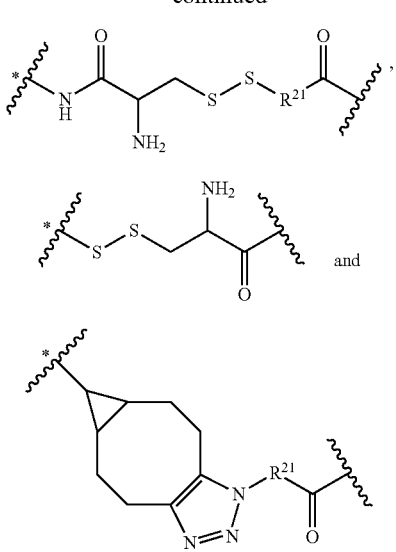

wherein * denotes a point of attachment of group E to group D;
$R^{20}$ is H or lower alkyl;
$R^{21}$ is an alkylene group;
g is 0 when $R^{20}$ is H or g is 1 when $R^{20}$ is lower alkyl;
provided that E is E18 only when D is D1, D2 or D3 and provided that E is E1, E2, E3, E4, E5, E6, E7, E8, E9, E10, E11, E12, E13, E15, E20, E21, E93, E94 or E96 only when D is D1, D2, D3 or D4; and provided that E is E91, E92 or E95 only when D is D5 and provided that E is E97 only when D is D2;
G is absent or G is an amino acid sequence of up to 6 amino acids, attached through its N-terminus to group E and through its C-terminus to group J;
J is a peptidic antigen, optionally substituted at its N and/or C-termini with up to 6 amino acids selected from the group of natural flanking residues for the antigen, and optionally terminated with $NH_2$ at the C-terminus so as to provide a C-terminal amide, and attached to group G through its N-terminus or, wherein G is absent, attached to group E through its N-terminus;
$R^1$ is H or glycosyl, provided that if $R^1$ is glycosyl then $R^2$ and $R^3$ are both OH and $R^4$ is $CH_2OH$;
$R^2$ is selected from the group consisting of H, OH, F and $OR^{10}$; provided that if $R^2$ is H, F or $OR^{10}$, then $R^1$ is H, $R^3$ is OH and $R^4$ is $CH_2OH$;
$R^3$ is selected from the group consisting of H, OH, F and $OR^{10}$; provided that if $R^3$ is H, F or $OR^{10}$, then $R^1$ is H, $R^2$ is OH and $R^4$ is $CH_2OH$;
$R^4$ is $CH_3$, $CH_2OH$, $CH_2OCOR^{11}$, $CH_2OR^{10}$, $CH_2OR^{11}$, $CH_2OSO_3H$, $CH_2SH$, $CH_2SR^{11}$, $CH_2SOR^{11}$, $CH_2SO_2R^{11}$, $CH_2PO_3H_2$, $CH_2OP(O)(OH)_2$, $CH_2OP(O)(OH)(OR^{11})$, $CH_2OP(O)(OR^{11})_2$, $CO_2H$, $CH_2NHCOR^{11}$, $CH_2NHCO_2R^{11}$, $CH_2NHCONH_2$, $CH_2NHCONHR^{11}$, $CH_2NHCON(R^{11})_2$, $CH_2N(R^{11})_2$, $CH_2NHSO_2R^{11}$; provided that if $R^4$ is other than $CH_2OH$, then $R^1$ is H and $R^2$ and $R^3$ are OH;
$R^6$ is $OR^{12}$, OH or H;
$R^7$ is $OR^{12}$, OH or H; provided that at least one of $R^6$ and $R^7$ is $OR^{12}$; wherein when $R^6$ is $OR^{12}$, $R^7$ is H, $R^8$ is $C_1$-$C_{15}$ alkyl and X is O, ----- denotes an optional double bond linking the carbon adjacent to $R^7$ with the carbon adjacent to $R^8$;

$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;
$R^{10}$ is glycosyl;
$R^{11}$ is lower alkyl, lower alkenyl or aralkyl;
$R^{12}$ is $C_8$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;
X is O, $CH_2$ or S;
n is 1 when X is O or S; or n is 0 or 1 when X is $CH_2$;
wherein where X is $CH_2$ then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$ or $CH_2OR^{11}$; and:
either $R^6$ is OH and $R^7$ is $OR^{12}$ and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is $OR^{12}$ and $R^7$ is H, and $R^8$ is $C_{13}H_{27}$ and the stereochemistry at carbon atoms 2 and 3 is (2S, 3S);
wherein where X is S then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$, $CH_2OR^{11}$ or $CO_2H$; and:
either $R^6$ is OH and $R^7$ is $OR^{12}$ and the stereochemistry at carbon atoms 2, 3 and 4 is (2S, 3S, 4R); or $R^6$ is $OR^{12}$ and $R^7$ is H and the stereochemistry at the carbon atoms 2 and 3 is (2S, 3S);
or a pharmaceutically acceptable salt thereof.

Preferably, the compound of formula (I) is a compound of formula (Ia):

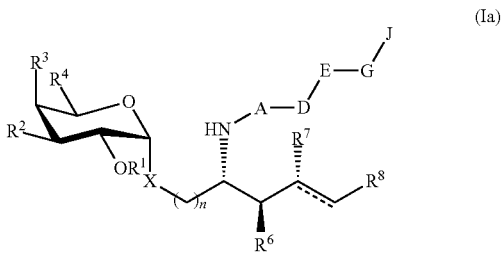

(Ia)

wherein X, $R^1$, $R^2$, $R^3$, $R^4$, $R^6$, $R^7$, $R^8$, $R^{10}$, $R^{11}$, $R^{12}$, $R^{15}$, $R^{16}$, $R^{19}$, $R^{20}$, $R^{21}$, $R^{32}$, n, g, A, D, E, G and J are all as defined above for formula (I);
or a pharmaceutically acceptable salt thereof.

Preferably the compound of formula (I) is a compound of formula (Ib):

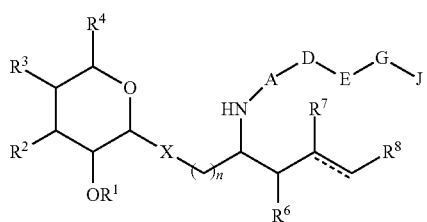
(Ib)

wherein:
A is a self-immolative linker group;
D is selected from the group consisting of:

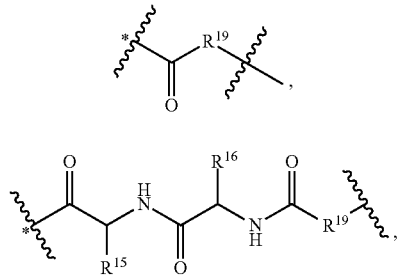
D1

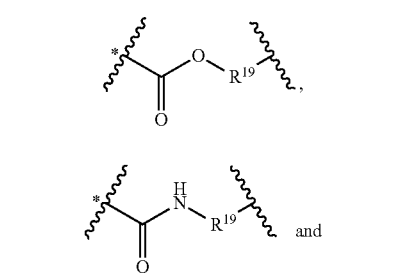
D2

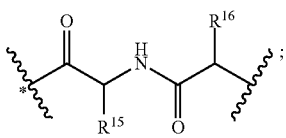
D3

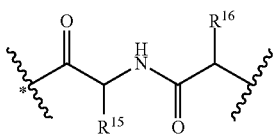
D4
and

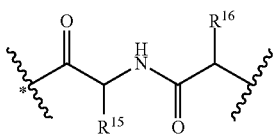
D5 wherein * denotes a point of attachment of group D to group A;
$R^{15}$ is a side chain of one of the following amino acids: L-lysine, L-citrulline, L-arginine, L-glutamine or L-threonine;
$R^{16}$ is a side chain of a hydrophobic amino acid;
$R^{19}$ is an alkylene group;
E is selected from the group consisting of:

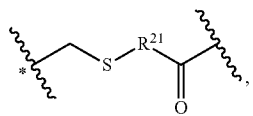
E1

-continued

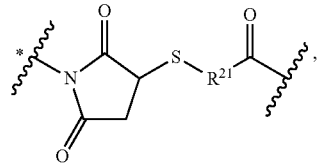
E2

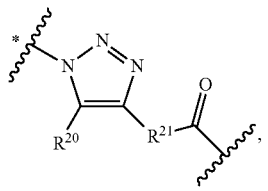
E3

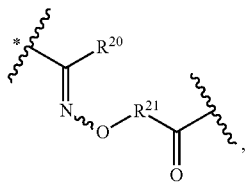
E4

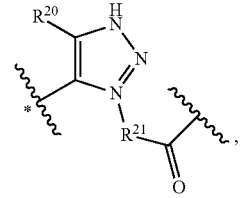
E5

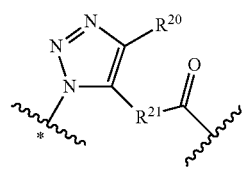
E6

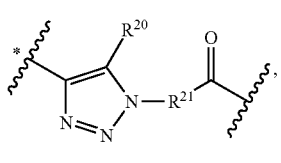
E7

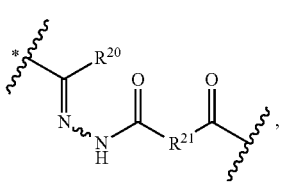
E8

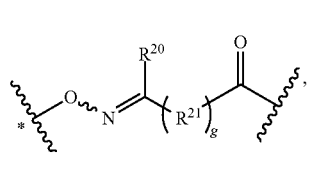
E9

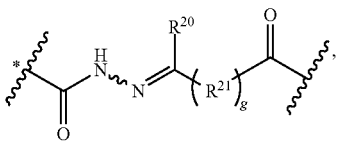
E10

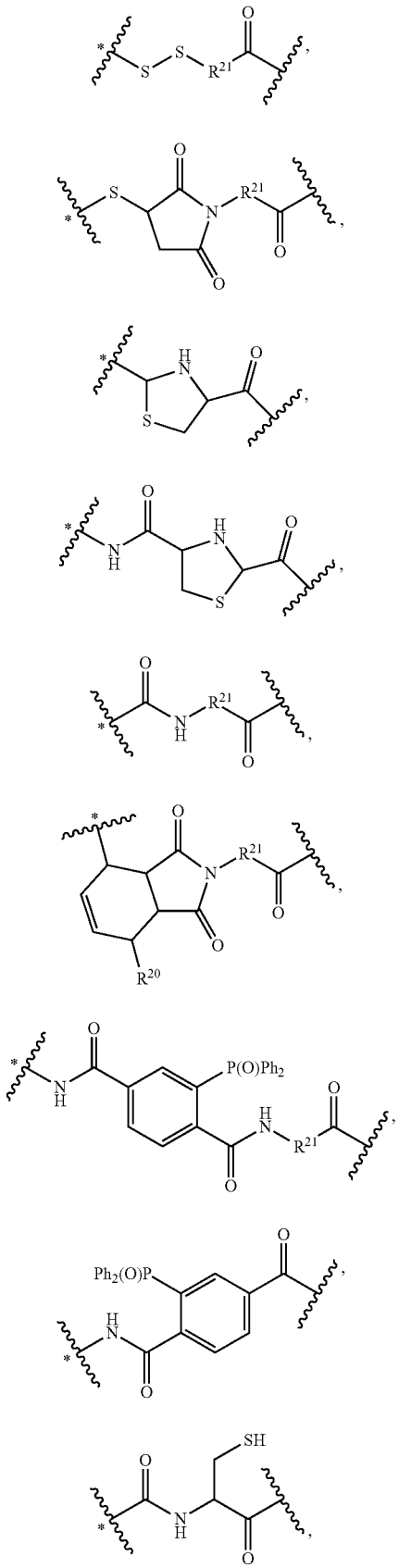
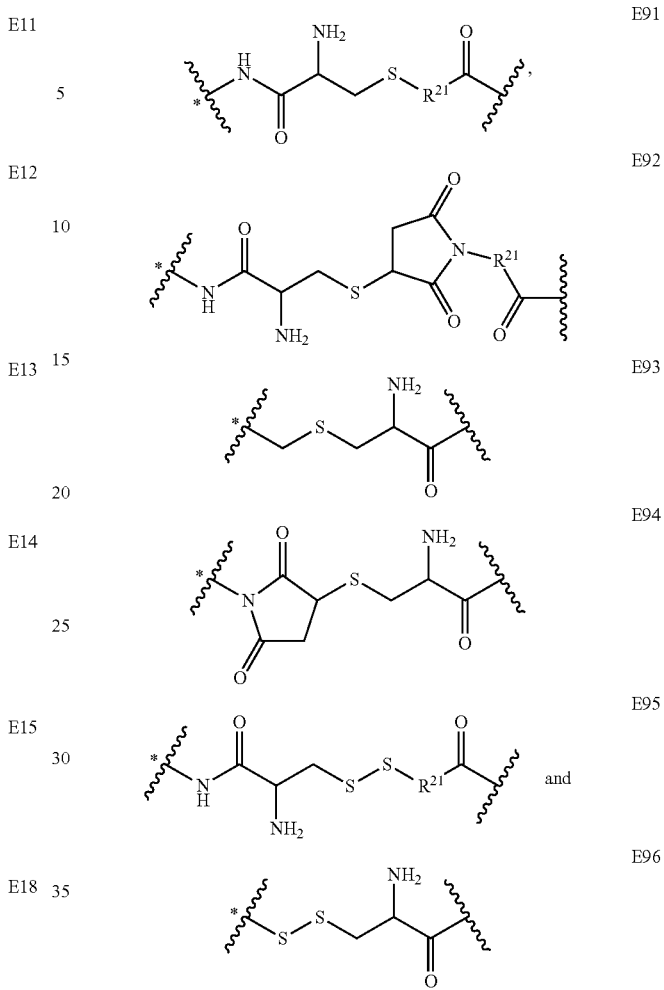

wherein * denotes a point of attachment of group E to group D;
R²⁰ is H or lower alkyl;
R²¹ is an alkylene group;
g is 0 when R²⁰ is H or g is 1 when R²⁰ is lower alkyl;
provided that E is E18 only when D is D1, D2 or D3 and provided that E is E1, E2, E3, E4, E5, E6, E7, E8, E9, E10, E11, E12, E13, E15, E20, E21, E93, E94 or E96 only when D is D1, D2, D3 or D4; and provided that E is E91, E92 or E95 only when D is D5;
G is absent or G is an amino acid sequence of up to 6 amino acids, attached through its N-terminus to group E and through its C-terminus to group J;
J is a peptidic antigen, optionally substituted at its N and/or C-termini with up to 6 amino acids selected from the group of natural flanking residues for the antigen, and optionally terminated with NH₂ at the C-terminus so as to provide a C-terminal amide, and attached to group G through its N-terminus or, wherein G is absent, attached to group E through its N-terminus;
R¹ is H or glycosyl, provided that if R¹ is glycosyl then R² and R³ are both OH and R⁴ is CH₂OH;
R² is selected from the group consisting of H, OH, F and OR¹⁰; provided that if R² is H, F or OR¹⁰, then R¹ is H, R³ is OH and R⁴ is CH₂OH;
R³ is selected from the group consisting of H, OH, F and OR¹⁰; provided that if R³ is H, F or OR¹⁰, then R¹ is H, R² is OH and R⁴ is CH₂OH;

$R^4$ is $CH_3$, $CH_2OH$, $CH_2OCOR^{11}$, $CH_2OR^{10}$, $CH_2OR^{11}$, $CH_2OSO_3H$, $CH_2SH$, $CH_2SR^{11}$, $CH_2SOR^{11}$, $CH_2SO_2R^{11}$, $CH_2PO_3H_2$, $CH_2OP(O)(OH)_2$, $CH_2OP(O)(OH)(OR^{11})$, $CH_2OP(O)(OR)_2$, $CO_2H$, $CH_2NHCOR^{11}$, $CH_2NHCO_2R^{11}$, $CH_2NHCONH_2$, $CH_2NHCONHR^{11}$, $CH_2NHCON(R^{11})_2$, $CH_2N(R^{11})_2$, $CH_2NHSO_2R^{11}$; provided that if $R^4$ is other than $CH_2OH$, then $R^1$ is H and $R^2$ and $R^3$ are OH;

$R^6$ is $OR^{12}$, OH or H;

$R^7$ is $OR^{12}$, OH or H; provided that at least one of $R^6$ and $R^7$ is $OR^{12}$; wherein when $R^8$ is $OR^{12}$, $R^7$ is H, $R^8$ is $C_1$-$C_{15}$ alkyl and X is O, ---------- denotes an optional double bond linking the carbon adjacent to $R^7$ with the carbon adjacent to $R^8$;

$R^8$ is H or $C_1$-$C_5$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{11}$ is lower alkyl, lower alkenyl or aralkyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

X is O, $CH_2$ or S;

n is 1 when X is O or S; or n is 0 or 1 when X is $CH_2$;

wherein where X is $CH_2$ then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$ or $CH_2OR^{11}$; and:

either $R^6$ is OH and $R^7$ is $OR^{12}$ and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is $OR^{12}$ and $R^7$ is H, and $R^8$ is $C_{13}H_{27}$ and the stereochemistry at carbon atoms 2 and 3 is (2S, 3S);

wherein where X is S then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$, $CH_2OR^{11}$ or $CO_2H$; and:

either $R^6$ is OH and $R^7$ is $OR^{12}$ and the stereochemistry at carbon atoms 2, 3 and 4 is (2S, 3S, 4R); or $R^6$ is $OR^{12}$ and $R^7$ is H and the stereochemistry at the carbon atoms 2 and 3 is (2S, 3S);

or a pharmaceutically acceptable salt thereof.

In another aspect, the invention provides a compound of formula (II):

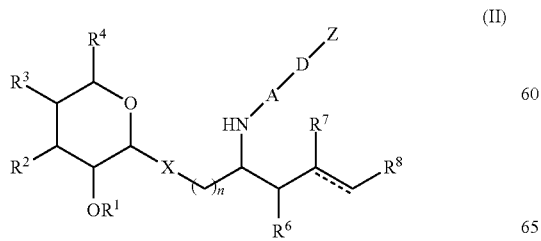

(II)

wherein A, D, X, $R^1$, $R^2$, $R^3$, $R^4$, $R^6$, $R^7$, $R^8$, $R^{10}$, $R^{11}$, $R^{12}$, $R^{15}$, $R^{16}$, $R^{32}$, and n are all as defined above for formula (I);

Z is selected from the group consisting of:

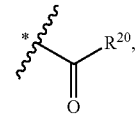 Z1

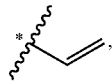 Z2

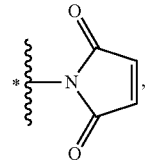 Z3

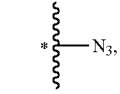 Z4

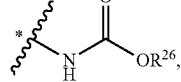 Z5

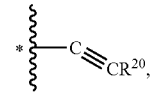 Z7

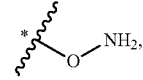 Z8

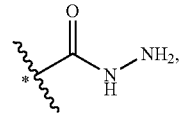 Z9

 Z10

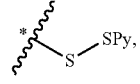 Z11

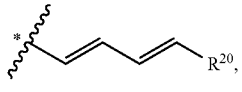 Z12

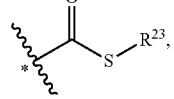 Z13

-continued

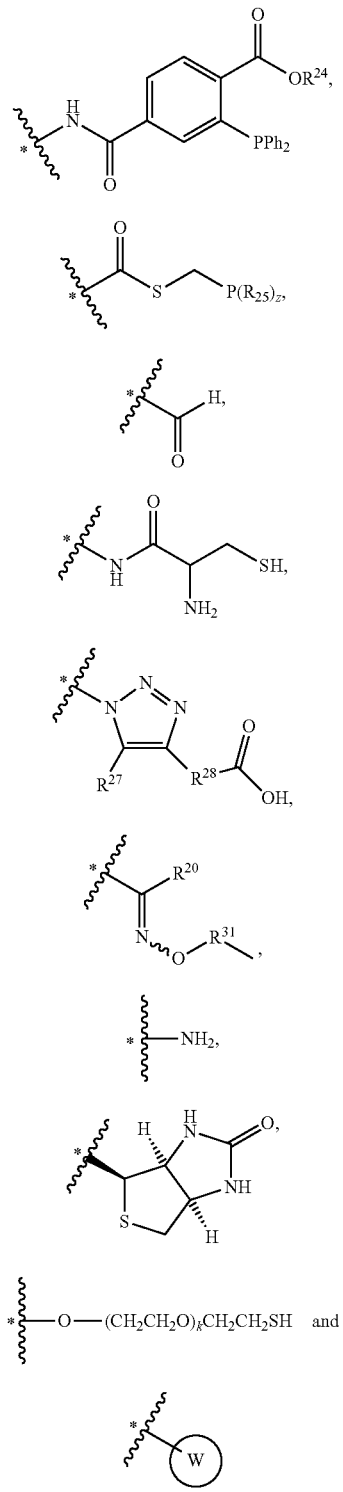

wherein * denotes a point of attachment of group Z to group D, except as defined for Z23;
$R^{20}$ is as defined above for formula (I);
$R^{23}$ is aryl, aralkyl or optionally substituted alkyl;
$R^{24}$ is lower alkyl;
$R^{25}$ is p-$C_8H_4L$ wherein L is H, methoxy, COOH, C(O)NHCH$_2$COOH or CH$_2$CH$_2$NMe$_2$;
$R^{26}$ is aralkyl;
$R^{27}$ is H or lower alkyl;
$R^{28}$ is alkylene;
$R^{31}$ is $(CH_2CH_2O)_k$
k is an integer from 2 to 100;
W is an optionally substituted cyclooctynyl ring; or W is a fused bicyclic or tricyclic ring system comprising an optionally substituted cyclooctynyl ring fused to one or more aryl groups or one or more cycloalkyl groups; wherein the cyclooctynyl ring optionally contains a N atom within the ring, which N atom is optionally substituted with an acyl group; and wherein the cyclooctynyl ring is optionally substituted with one or more substituents selected from the group consisting of halogen, hydroxyl, alkoxy and aralkyl wherein the aryl part of this group is optionally substituted with a carboxylic acid; and wherein * or one of the optional substituents comprises a point of attachment of Z23 to group D;
provided that Z is Z1, Z2, Z3, Z4, Z7, Z8, Z9, Z10, Z11, Z13, Z15, Z16, Z17 or Z18 only when D is D1, D2, D3 or D4 and provided that Z is Z12 only when D is D1, D2 or D3 and provided that Z is Z5 or Z20 only when D is D5, and provided that Z is Z21, Z22 or Z23 only when D is D2;
or a pharmaceutically acceptable salt thereof.

Preferably, the compound of formula (II) is a compound of formula (IIa):

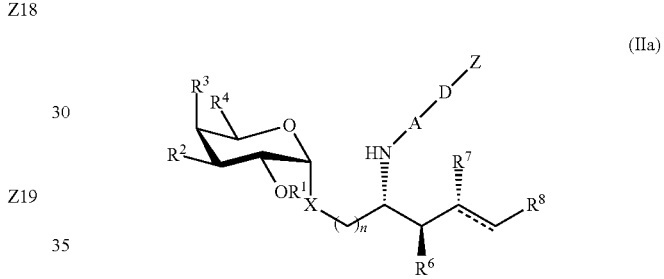

(IIa)

wherein A, D, X, Z, $R^1$, $R^2$, $R^3$, $R^4$, $R^6$, $R^7$, $R^8$, $R^{10}$, $R^{11}$, $R^{12}$, $R^{15}$, $R^{16}$, $R^{19}$, $R^{20}$, $R^{21}$, $R^{23}$, $R^{24}$, $R^{25}$, $R^{26}$, $R^{27}$, $R^{28}$, $R^{31}$, W, k and n are all as defined above for formula (II);
or a pharmaceutically acceptable salt thereof.

Preferably, the compound of formula (II) is a compound of formula (IIb):

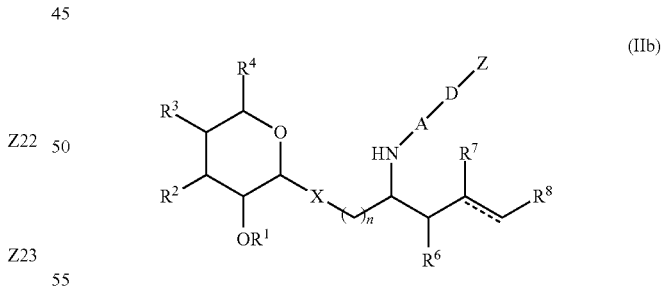

(IIb)

wherein A, D, X, $R^1$, $R^2$, $R^3$, $R^4$, $R^6$, $R^7$, $R^8$, $R^{10}$, $R^{11}$, $R^{12}$, $R^{15}$, $R^{16}$, $R^{19}$ and n are all as defined above for formula (Ib);
Z is selected from the group consisting of:

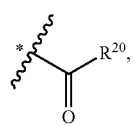

Z1

-continued

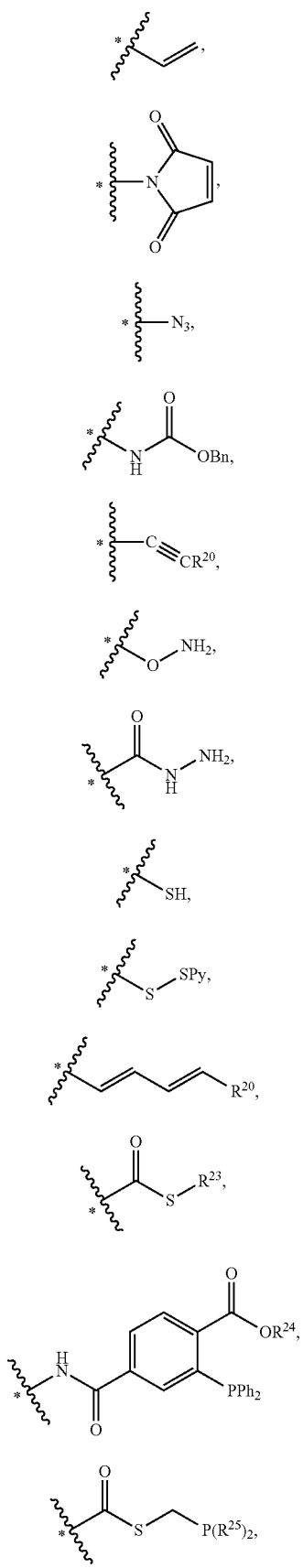

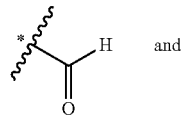

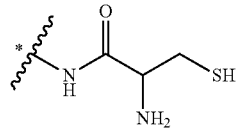

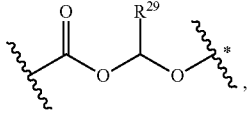

wherein * denotes a point of attachment of group Z to group D;

$R^{20}$ is as defined above for formula (I);

$R^{23}$ is aryl, aralkyl or optionally substituted alkyl;

$R^{24}$ is lower alkyl;

$R^{25}$ is p-$C_6H_4$L wherein L is H, methoxy, COOH, C(O)NHCH$_2$COOH or CH$_2$CH$_2$NMe$_2$;

provided that Z is Z1, Z2, Z3, Z4, Z7, Z8, Z9, Z10, Z11, Z13, Z15 or Z16 only when D is D1, D2, D3 or D4 and provided that Z is Z12 only when D is D1, D2 or D3 and provided that Z is Z5 only when D is D5;

or a pharmaceutically acceptable salt thereof.

Preferably A is selected from the group consisting of:

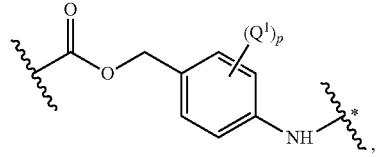

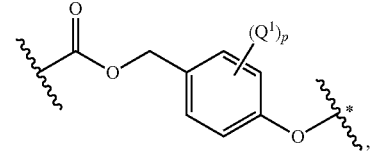

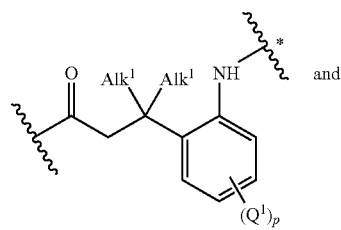

-continued

A5

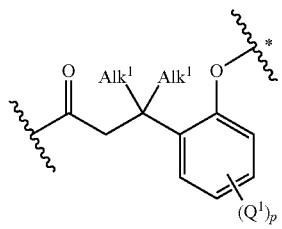

wherein * denotes a point of attachment of group A to group D;
each $Q^1$, the same or different, is independently selected from the group consisting of H, alkyl, alkoxy, halogen, nitro, aryl; or, together with the ring to which it is attached, forms a fused bicyclic aryl group;
p is an integer from 1 to 4;
$Alk^1$ is $C_1$-$C_4$ straight chain alkyl; and
$R^{29}$ is H or lower alkyl;
provided that A is A1 only when D is D1 and provided that A is A2 only when D is D2, D3 or D5 and provided that A is A3 only when D is D1, D3 or D4 and provided that A is A4 only when D is D2, D3 or D5 and provided that A is A5 only when D is D1, D3 or D4.

More preferably, A is A1 or A2. Still more preferably, A is A1 wherein $R^{29}$ is H, or A is A2 wherein $Q^1$ is H.

Preferably, $Q^1$ in A2 or A3 is H. More preferably $Q^1$ in A2 or A3 is H and p is 4.

Alternatively preferably, $Q^1$ in A2 or A3 is Me or OMe and p is 2, wherein the Me or OMe groups are situated ortho- to the heteroatom on the aromatic ring.

Preferably D is D1.
Alternatively preferably D is D2.
Alternatively preferably D is D3.
Alternatively preferably D is D4.
Alternatively preferably D is D5.
Preferably $R^{15}$ is selected from the group consisting of:

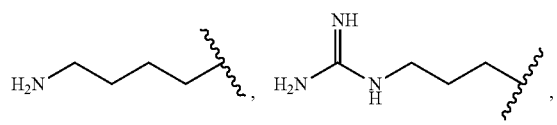

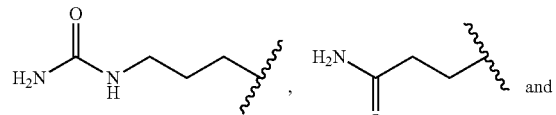

More preferably $R^{15}$ is selected from the group consisting of:

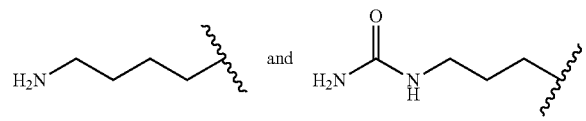 [SMILES: *CCCCN ; *CCCNC(N)=O]

Preferably $R^{16}$ is a side chain of one of the following amino acids: L-phenylalanine, L-valine, L-leucine, L-isoleucine, L-norleucine, L-methionine, L-tryptophan or L-tyrosine; that is, preferably $R^{16}$ is selected from the group consisting of:

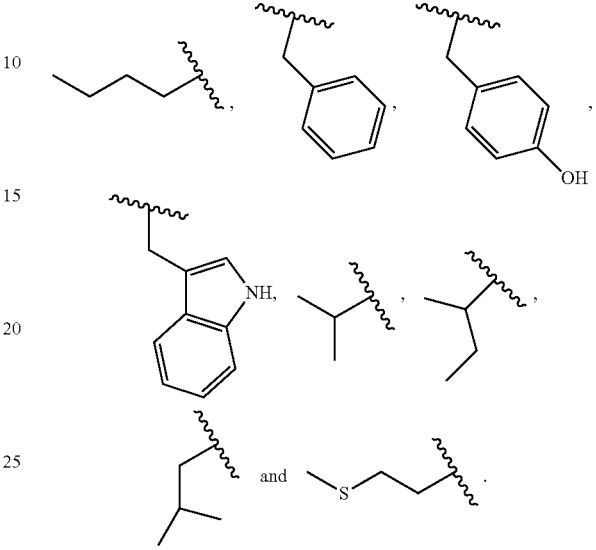

More preferably $R^{16}$ is selected from the group consisting of:

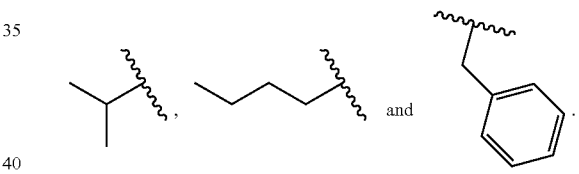

Preferably E is any one of E1 to E8, E93 or E94. More preferably E is any one of E1 to E4, E93 or E94.

Preferably E is E3 wherein $R^{20}$ is H. Alternatively preferably E is E4 wherein $R^{20}$ is methyl.

Alternatively preferably E is E7 wherein $R^{20}$ is H.
Alternatively preferably E is E97.
Preferably E is E97 when D is D2, wherein $R^{32}$ is O-alkylene, preferably $OCH_2$.
Most preferably E is:

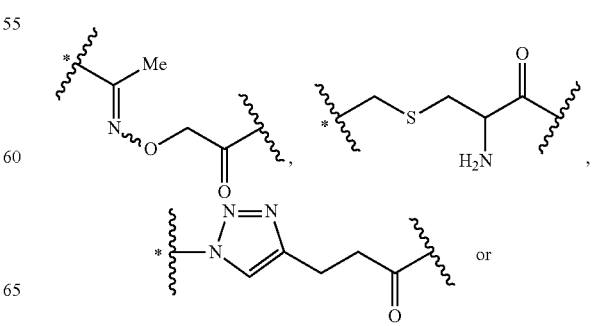

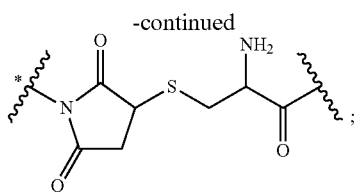

wherein * denotes a point of attachment of group E to group D.

Preferably Z is Z23, Z22, Z21, Z20, Z19, Z18, Z4, Z3 or Z1. Most preferably Z is Z4.

Preferably W is a cyclooctynyl ring fused to a cycloalkyl ring, preferably a cyclopropyl ring.

Preferably Z23 is

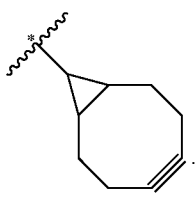 [SMILES: *C1C2CCC#CCCC12]

Preferably k is an integer from 10 to 32. More preferably k is an integer from 19 to 32. More preferably k is 10.

Preferably G is

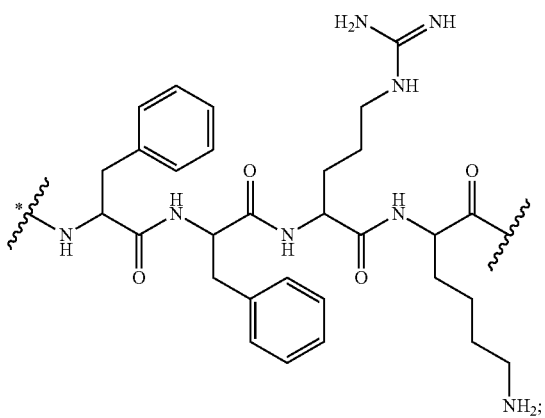 [SMILES: *NC(Cc1ccccc1)C(=O)NC(Cc1ccccc1)C(=O)NC(CCCNC(=N)N)C(=O)NC(CCCCN)C(*)=O]

wherein * denotes a point of attachment of group G to group E.

Alternatively preferably G is absent.

Preferably J is a peptide that contains within its sequence one or more epitopes that bind to MHC molecules and induce T cell responses.

More preferably J is selected from the group consisting of: AMLGTHTMEV (SEQ ID NO:1), MLGTHTMEV (SEQ ID NO:2), EAAGIGILTV (SEQ ID NO:3), AAGIGILTV (SEQ ID NO:4), AADHRQLQLSISSCLQQL (SEQ ID NO:5), AAGIGILTVILGVL (SEQ ID NO:6), AARAVFLAL (SEQ ID NO:7), ACDPHSGHFV (SEQ ID NO:8), ACYEFLWGPRALVETS (SEQ ID NO:9), ADHRQLQLSISSCLQQL (SEQ ID NO:10), AEEAAGIGILT (SEQ ID NO:11), AEEAAGIGIL (SEQ ID NO:12), AELVHFLLL (SEQ ID NO:13), AELVHFLLLKYRAR (SEQ ID NO:14), AEPINIQTW (SEQ ID NO:15), AFLPWHRLF (SEQ ID NO:16), AGATGGRGPRGAGA (SEQ ID NO:17), ALCRWGLLL (SEQ ID NO:18), ALDVYNGLL (SEQ ID NO:19), ALFDIESKV (SEQ ID NO:20), ALGGHPLLGV (SEQ ID NO:21), ALIHHNTHL (SEQ ID NO:22), ALKDVEERV (SEQ ID NO:23), ALLAVGATK (SEQ ID NO:24), ALLEIASCL (SEQ ID NO:25), ALNFPGSQK (SEQ ID NO:26), ALPYWNFATG (SEQ ID NO:27), ALSVMGVYV (SEQ ID NO:28), ALWPWLLMAT (SEQ ID NO:29), ALWPWLLMA (SEQ ID NO:30), ALYVDSLFFL (SEQ ID NO:31), ANDPIFWL (SEQ ID NO:32), APPAYEKLSAEQ (SEQ ID NO:33), APRGPHGGAASGL (SEQ ID NO:34), APRGVRMAV (SEQ ID NO:35), ARGPESRLL (SEQ ID NO:36), ASGPGGGAPR (SEQ ID NO:37), ATGFKQSSKALQRPVAS (SEQ ID NO:38), AVCPWTWLR (SEQ ID NO:39), AWISKPPGV (SEQ ID NO:40), AYVCGIQNSVSANRS (SEQ ID NO:41), CATWKVICKSCISQTPG (SEQ ID NO:42), CEFHACWPAFTVLGE (SEQ ID NO:43), CLSRRPWKRSWSAGSCPGMPHL (SEQ ID NO:44), CMTWNQMNL (SEQ ID NO:45), CQWGRLWQL (SEQ ID NO:46), CTACRWKKACQR (SEQ ID NO:47), DPARYEFLW (SEQ ID NO:48), DTGFYTLHVIKSDLVNEEATGQFRV (SEQ ID NO:49), DVTFNIICKKCG (SEQ ID NO:50), EAAGIGILTV (SEQ ID NO:51), EADPTGHSY (SEQ ID NO:52), EAFIQPITR (SEQ ID NO:53), EDLTVKIGDFGLATEKSRWSGSHQFEQLS (SEQ ID NO:54), EEAAGIGILTVI (SEQ ID NO:55), EEKLIWLF (SEQ ID NO:56), EFYLAMPFATPM (SEQ ID NO:57), EGDCAPEEK (SEQ ID NO:58), EIIYPNASLLIQN (SEQ ID NO:59), EKIQKAFDDIAKYFSK (SEQ ID NO:60), ELTLGEFLKL (SEQ ID NO:61), ELVRRILSR (SEQ ID NO:62), ESRLLEFYLAMPF (SEQ ID NO:63), ETVSEQSNV (SEQ ID NO:64), EVDPASNTY (SEQ ID NO:65), EVDPIGHLY (SEQ ID NO:66), EVDPIGHVY (SEQ ID NO:67), EVISCKLIKR (SEQ ID NO:68), EVYDGREHSA (SEQ ID NO:69), EYLQLVFGI (SEQ ID NO:70), EYLSLSDKI (SEQ ID NO:71), EYSKECLKEF (SEQ ID NO:72), EYVIKVSARVRF (SEQ ID NO:73), FIASNGVKLV (SEQ ID NO:74), FINDEIFVEL (SEQ ID NO:75), FLDEFMEGV (SEQ ID NO:76), FLEGNEVGKTY (SEQ ID NO:77), FLFLLFFWL (SEQ ID NO:78), FLIIWQNTM (SEQ ID NO:79), FLLHHAFVDSIFEQWLQRHRP (SEQ ID NO:80), FLLLKYRAREPVTKAE (SEQ ID NO:81), FLTPKKLQCV (SEQ ID NO:82), FLWGPRALV (SEQ ID NO:83), FMNKFIYEI (SEQ ID NO:84), FMVEDETVL (SEQ ID NO:85), FPSDSWCYF (SEQ ID NO:86), FRSGLDSYV (SEQ ID NO:87), FSWAMDLDPKGA (SEQ ID NO:88), GARGPESRLLEFYLAMPFATPMEAELARRSLAQDAPPL (SEQ ID NO:89), GDNQIMPKAGLLIIV (SEQ ID NO:90), GELIGILNAAKVPAD (SEQ ID NO:91), GFKQSSKAL (SEQ ID NO:92), GLASFKSFLK (SEQ ID NO:93), GLCTLVAML (SEQ ID NO:94), GLPPDVQRV (SEQ ID NO:95), GLYDGMEHLI (SEQ ID NO:96), GRAMLGTHTMEVTVY (SEQ ID NO:97), GVALQTMKQ (SEQ ID NO:98), GVGSPYVSRLLGICL (SEQ ID NO:99), AKFVAAWTLKAAA (SEQ ID NO:100), GVLLKEFTVSGNILTIRLT (SEQ ID NO:101), GVLVGVALI (SEQ ID NO:102), GVYDGREHTV (SEQ ID NO:103), HLFGYSWYK (SEQ ID NO:104), HLIRVEGNLRVE (SEQ ID NO:105), HLSTAFARV (SEQ ID NO:106), HLYQGCQW (SEQ ID NO:107), HQQYFYKIPILVINK (SEQ ID NO:108), HTMEVTVYHR (SEQ ID NO:109), IALNFPGSQK (SEQ ID NO:110), IGRIAECILGMNPSR (SEQ ID NO:111), IISAVVGIL (SEQ ID NO:112), ILAKFLHWL (SEQ ID NO:113), ILDSSEEDK (SEQ ID NO:114), ILDTAGREEY (SEQ ID NO:115), ILHNGAYSL (SEQ ID NO:116), ILSRDAAPLPRPG (SEQ ID NO:117), ILTVILGVL (SEQ ID NO:118), IMDQVPFFS (SEQ ID NO:119), IMDQVPFSV (SEQ ID NO:120), IMI- GVLVGV (SEQ ID NO:121), INKTSGPKRGKHAVVTHRLRE (SEQ ID NO:122), ISGGPRISY (SEQ ID NO:123), ISPNSVFSQWRVVCDSLEDYD (SEQ ID NO:124), ISQAVHAAHAEINEAGR (SEQ ID NO:125), ITDQVPFSV (SEQ ID NO:126), ITKKVADLVGF (SEQ ID NO:127), KASEKIFYV (SEQ ID NO:128), KAVYNFATM (SEQ ID NO:129), KCDICTDEY (SEQ ID NO:130), KEFTVSGNILT (SEQ ID NO:131), KEFTVSGNILTI (SEQ ID NO:132), KELEGILLL (SEQ ID NO:133), KHAWTHRLRERKQLVVYEEI (SEQ ID NO:134), KIFGSLAFL (SEQ ID NO:135), KIFSEVTLK (SEQ ID NO:136), KIFYVYMKRKYEAM (SEQ ID NO:137), KIFYVYMKRKYEAMT (SEQ ID NO:138), KILDAVVAQK (SEQ ID NO:139), KINKNPKYK (SEQ ID NO:140), KISQAVHAAHAEINEAGRESIINFEKLTEWT (SEQ ID NO:141), KKLLTQHFVQENYLEY (SEQ ID NO:142), KMDAEHPEL (SEQ ID NO:143), KNCEPWPNAPPAYEKLSAE (SEQ ID NO:144), KRYFKLSHLQMHSRKH (SEQ ID NO:145), KSSEKIVYVYMKLNYEVMTK (SEQ ID NO:146), KTWGQYWQV (SEQ ID NO:147), KVAELVHFL (SEQ ID NO:148), KVHPVIWSL (SEQ ID NO:149), KVLEYVIKV (SEQ ID NO:150), KYDCFLHPF (SEQ ID NO:151), KYVGIEREM (SEQ ID NO:152), LAALPHSCL (SEQ ID NO:153), LAAQERRVPR (SEQ ID NO:154), LAGIGILTV (SEQ ID NO:155), LAMPFATPM (SEQ ID NO:156), LGFKVTLPPFMRSKRAADFH (SEQ ID NO:157), LGPGRPYR (SEQ ID NO:158), LHHAFVDSIF (SEQ ID NO:159), LIYRRRLMK (SEQ ID NO:160), LKEFTVSGNILTIRL (SEQ ID NO:161), LKLSGVVRL (SEQ ID NO:162), LLANGRMPTVLQCVN (SEQ ID NO:163), LLDGTATLRL (SEQ ID NO:164), LLEFYLAMPFATPM (SEQ ID NO:165), LLEFYLAMPFATPMEAELARRSLAQ (SEQ ID NO:166), LLFGLALIEV (SEQ ID NO:167), LLGATCMFV (SEQ ID NO:168), LLGPGRPYR (SEQ ID NO:169), LLGRNSFEV (SEQ ID NO:170), LLKYRAREPVTKAE (SEQ ID NO:171), LLLDDLLVSI (SEQ ID NO:172), LLLLTVLTV (SEQ ID NO:173), LLWSFQTSA (SEQ ID NO:174), LLYKLADLI (SEQ ID NO:175), LMLQNALTTM (SEQ ID NO:176), LPAVVGLSPGEQEY (SEQ ID NO:177), LPHSSSHWL (SEQ ID NO:178), LPRWPPPQL (SEQ ID NO:179), LPSSADVEF (SEQ ID NO:180), LSHLQMHSRKH (SEQ ID NO:181), LSRLSNRLL (SEQ ID NO:182), LTDLQPYMRQFVAHL (SEQ ID NO:183), LWWVNNQSLPVSP (SEQ ID NO:184), LYATVIHDI (SEQ ID NO:185), LYSACFWWL (SEQ ID NO:186), LYVDSLFFL (SEQ ID NO:187), MEVDPIGHLY (SEQ ID NO:188), MIAVFLPIV (SEQ ID NO:189), MIFEKHGFRRTTPP (SEQ ID NO:190), MKLNYEVMTKLGFKVTLPPF (SEQ ID NO:191), MLAVISCAV (SEQ ID NO:192), MLLAVLYCL (SEQ ID NO:193), MLMAQEALAFL (SEQ ID NO:194), MPFATPMEA (SEQ ID NO:195), MPREDAHFIYGYPKKGHGHS (SEQ ID NO:196), MSLQRQFLR (SEQ ID NO:197), MVKISGGPR (SEQ ID NO:198), NLVPMVATV (SEQ ID NO:199), NPPSMVAAGSWAAV (SEQ ID NO:200), NSIVKSITVSASG (SEQ ID NO:201), NSNHVASGAGEAAIETQSSSSEEIV (SEQ ID NO:202), NSQPVWLCL (SEQ ID NO:203), NTYASPRFK (SEQ ID NO:204), NYARTEDFF (SEQ ID NO:205), NYKRCFPVI (SEQ ID NO:206), NYNNFYRFL (SEQ ID NO:207), PDTRPAPGSTAPPAHGVTSA (SEQ ID NO:208), PFATPMEAELARR (SEQ ID NO:209), PGSTAPPAHGVT (SEQ ID NO:210), PGTRVRAMAIYKQ (SEQ ID NO:211), PGVLLKEFTVSGNILTIRLTAADHR (SEQ ID NO:212), PLLENVISK (SEQ ID NO:213), PLPPARNGGL (SEQ ID NO:214), PLQPEQLQV (SEQ ID NO:215), PLTSIISAV (SEQ ID NO:216), PRALAETSYVKVLEY (SEQ ID NO:217), PVTWRRAPA (SEQ ID NO:218), PYYFAAELPPRNLPEP (SEQ ID NO:219), QCSGNFMGF (SEQ ID NO:220), QCTEVRADTRPWSGP (SEQ ID NO:221), QGAMLAAQERRVPRAAEVPR (SEQ ID NO:222), QGQHFLQKV (SEQ ID NO:223), QLAVSVILRV (SEQ ID NO:224), QNILLSNAPLGPQFP (SEQ ID NO:225), QQITKTEV (SEQ ID NO:226), QRPYGYDQIM (SEQ ID NO:227), QYSWFVNGTF (SEQ ID NO:228), RAGLQVRKNK (SEQ ID NO:229), REPFTKAEMLGSVIR (SEQ ID NO:230), REPVTKAEML (SEQ ID NO:231), RIAECILGM (SEQ ID NO:232), RKVAELVHFLLLKYR (SEQ ID NO:233), RKVAELVHFLLLKYRA (SEQ ID NO:234), RLLEFYLAMPFA (SEQ ID NO:235), RLLQETELV (SEQ ID NO:236), RLMKQDFSV (SEQ ID NO:237), RLPRIFCSC (SEQ ID NO:238), RLSSCVPVA (SEQ ID NO:239), RLVDDFLLV (SEQ ID NO:240), RMPEAAPPV (SEQ ID NO:241), RMPTVLQCVNSVVS (SEQ ID NO:242), RNGYRALMDKS (SEQ ID NO:243), RNGYRALMDKSLHVGTQCALTRR (SEQ ID NO:244), RPGLLGASVLGLDDI (SEQ ID NO:245), RPHVPESAF (SEQ ID NO:246), RQKRILVNL (SEQ ID NO:247), RSDSGQQARY (SEQ ID NO:248), RTKQLYPEW (SEQ ID NO:249), RVIKNSIRLTL (SEQ ID NO:250), RVRFFFPSL (SEQ ID NO:251), RYQLDPKFI (SEQ ID NO:252), SAFPTTINF (SEQ ID NO:253), SAWISKPPGV (SEQ ID NO:254), SAYGEPRKL (SEQ ID NO:255), SEIWRDIDF (SEQ ID NO:256), SELFRSGLDSY (SEQ ID NO:257), SESIKKKVL (SEQ ID NO:258), SESLKMIF (SEQ ID NO:259), SFSYTLLSL (SEQ ID NO:260), SHETVIIEL (SEQ ID NO:261), SIINFEKL (SEQ ID NO:262), SLADTNSLAV (SEQ ID NO:263), SLFEGIDIYT (SEQ ID NO:264), SLFPNSPKWTSK (SEQ ID NO:265), SLFRAVITK (SEQ ID NO:266), SLGWLFLLL (SEQ ID NO:267), SLLMWITQC (SEQ ID NO:268), SLLMWITQCFLPVF (SEQ ID NO:269), SLLQHLIGL (SEQ ID NO:270), SLPYWNFATG (SEQ ID NO:271), SLSKILDTV (SEQ ID NO:272), SLYKFSPFPL (SEQ ID NO:273), SLYSFPEPEA (SEQ ID NO:274), SNDGPTLI (SEQ ID NO:275), SPRWWPTCL (SEQ ID NO:276), SPSSNRIRNT (SEQ ID NO:277), SQKTYQGSY (SEQ ID NO:278), SRFGGAVVR (SEQ ID NO:279), SSALLSIFQSSPE (SEQ ID NO:280), SSDYVIPIGTY (SEQ ID NO:281), SSKALQRPV (SEQ ID NO:282), SSPGCQPPA (SEQ ID NO:283), STAPPVHNV (SEQ ID NO:284), SVASTITGV (SEQ ID NO:285), SVDYFFVWL (SEQ ID NO:286), SVSESDTIRSISIAS (SEQ ID NO:287), SVYDFFVWL (SEQ ID NO:288), SYLDSGIHF (SEQ ID NO:289), SYLQDSDPDSFQD (SEQ ID NO:290), TFPDLESEF (SEQ ID NO:291), TGRAMLGTHTMEVTVYH (SEQ ID NO:292), TLDSQVMSL (SEQ ID NO:293), TLDWLLQTPK (SEQ ID NO:294), TLEEITGYL (SEQ ID NO:295), TLMSAMTNL (SEQ ID NO:296), TLNDECWPA (SEQ ID NO:297), TLPGYPPHV (SEQ ID NO:298), TLYQDDTLTLQAAG (SEQ ID NO:299), TMKQICKKEIRRLHQY (SEQ ID NO:300), TMNGSKSPV (SEQ ID NO:301), TPRLPSSADVEF (SEQ ID NO:302), TSCILESLFRAVITK (SEQ ID NO:303), TSEKRPFMCAY (SEQ ID NO:304), TSYVKVLHHMVKISG (SEQ ID NO:305), TTEWVETTARELPIPEPE (SEQ ID NO:306), TVSGNILTIR (SEQ ID NO:307), TYACFVSNL (SEQ ID NO:308), TYLPTNASL (SEQ ID NO:309), TYYRPGVNLSLSC (SEQ ID NO:310), VAELVHFLL (SEQ ID NO:311), VFGIELMEVDPIGHL (SEQ ID NO:312), VGQDVSVLFRVTGALQ (SEQ ID NO:313), VIFSKASSSLQL (SEQ ID NO:314), VISNDVCAQV (SEQ ID NO:315), VLDGLDVLL (SEQ ID NO:316), VLFYLGQY (SEQ ID NO:317), VLHWDPETV (SEQ ID NO:318), VLLKEFTVSG (SEQ ID NO:319), VLLQAGSLHA (SEQ ID NO:320), VLPDVFIRCV (SEQ ID NO:321), VLPDVFIRC (SEQ ID NO:322), VLRENTSPK (SEQ ID NO:323), VLYRYGSFSV (SEQ ID NO:324), VPGVLLKEFTVSGNILTIRLTAADHR (SEQ ID NO:325), VPLDCVLYRY (SEQ ID NO:326), VRIGHLYIL (SEQ ID NO:327), VSSFFSYTL (SEQ ID NO:328), VVLGWFGI (SEQ ID NO:329), WPCEPPEV (SEQ ID NO:330), VWGAVGVG (SEQ ID NO:331), VYFFLPDHL (SEQ ID NO:332), WEKMKASEKIFYVYMKRK (SEQ ID NO:333), WLPFGFILI (SEQ ID NO:334), WNRQLYPEVVTEAQRLD (SEQ ID NO:335), WQYFFPVIF (SEQ ID NO:336), WRRAPAPGA (SEQ ID NO:337), YACFVSNLATGRNNS (SEQ ID NO:338), YFSKKEWEKMKSSEKIVYVY (SEQ ID NO:339), YLEPGPVTA (SEQ ID NO:340), YLEPGPVTV (SEQ ID NO:341), YLNDHLEPWI (SEQ ID NO:342), YLQLVFGIEV (SEQ ID NO:343), YLSGANLNL (SEQ ID NO:344), YLVPQQGFFC (SEQ ID NO:345), YMDGTMSQV (SEQ ID NO:346), YMIMVKCWMI (SEQ ID NO:347), YRPRPRRY (SEQ ID NO:348), YSVYFNLPADTIYTN (SEQ ID NO:349), YSWRINGIPQQHTQV (SEQ ID NO:350), YVDFREYEYY (SEQ ID NO:351), YYWPRPRRY (SEQ ID NO:352), IMDQVPFFS (SEQ ID NO:353), SVDYFFVWL (SEQ ID NO:354), ALFDIESKV (SEQ ID NO:355), NLVPMVATV (SEQ ID NO:356) and GLCTLVAML (SEQ ID NO:357), SVASTITGV (SEQ ID NO:358), VMAGDIYSV (SEQ ID NO:359), ALADGVQKV (SEQ ID NO:360), LLGATCMFV (SEQ ID NO:361), SVFAGWGV (SEQ ID NO:362), ALFDGDPHL (SEQ ID NO:363), YVDPVITSI (SEQ ID NO:364), STAPPVHNV (SEQ ID NO:365), LAALPHSCL (SEQ ID NO:366), SQDDIKGIQKLYGKRS (SEQ ID NO:367), FLPSDFFPSV (SEQ ID NO:368)

FLPSDFFPSV (SEQ ID NO:369), TLGEFLKLDRERAKN (SEQ ID NO:370), TFSYVDPVITSISPKYGMET (SEQ ID NO:371), AMTQLLAGV (SEQ ID NO:372), KVFAGIPTV (SEQ ID NO:373), AIIDGVESV (SEQ ID NO:374), GLWHHQTEV (SEQ ID NO:375), NLDTLMTYV (SEQ ID NO:376), KIQEILTQV (SEQ ID NO:377), LTFGDWAV (SEQ ID NO:378), TMLARLASA (SEQ ID NO:379), IMDQVPFSV (SEQ ID NO:380), MHQKRTAMFQDPQERPRKLPQLCTELQTTIHD (SEQ ID NO:381), LPQLCTELQTTI (SEQ ID NO:382), HDIILECVYCKQQLLRREVY (SEQ ID NO:383), KQQLLRREVYDFAFRDLCIVYRDGN (SEQ ID NO:384), RDLCIVYRDGNPYAVCDKCLKFYSKI (SEQ ID NO:385), DKCLKFYSKISEYRHYCYSLYGTTL (SEQ ID NO:386), HYCYSLYGTTLEQQYNKPLCDLLIR (SEQ ID NO:387), YGTTLEQQYNKPLCDLLIRCINCQKPLCPEEK (SEQ ID NO:388), RCINCQKPLCPEEKQRHLDKKQRFHNIRGRWT (SEQ ID NO:389), DKKQRFHNIRGRWTGRCMSCCRSSRTRRETQL (SEQ ID NO:390), MHGDTPTLHEYMLDLQPETTDLYCYEQLNDSSEEE (SEQ ID NO:391), LYCYEQLNDSSEEEDEIDGPAGQAEPDRAHYNIVT (SEQ ID NO:392), GQAEPDRAHYNIVTFCCKCDSTLRLCVQSTHVDIR (SEQ ID NO:393), TLRLCVQSTHVDIRTLEDLLMGTLGIVCPICSQKP (SEQ ID NO:394), ALPFGFILV (SEQ ID NO:395), TLADFDPRV (SEQ ID NO:396), IMDQVPFSV (SEQ ID NO:397), SIMTYDFHGA (SEQ ID NO:398), AQYIKANSKFIGITEL (SEQ ID NO:399), FLYDDNQRV (SEQ ID NO:400), YLIELIDRV (SEQ ID NO:401), NLMEQPIKV (SEQ ID NO:402), FLAEDALNTV (SEQ ID NO:403), ALMEQQHYV (SEQ ID NO:404), ILDDIGHGV (SEQ ID NO:405), KLDVGNAEV (SEQ ID NO:406), TFEFTSFFY (SEQ ID NO:407), SWPDGAELPF (SEQ ID NO:408), GILGFVFTL (SEQ ID NO:409), ILRGSVAHK (SEQ ID NO:410) SVYDFFVWLKFFHRTCKCTGNFA (SEQ ID NO:411), DLAQMFFCFKELEGW (SEQ ID NO:412), AVGALEGPRNQDWLGVPRQL (SEQ ID NO:413) and RAHYNIVTF (SEQ ID NO:414).

Still more preferably J is selected from the group consisting of: IMDQVPFSV (SEQ ID NO: 120), YLEPGPVTV (SEQ ID NO: 341), LAGIGILTV (SEQ ID NO: 155), YMDGTMSQV (SEQ ID NO: 346), SIINFEKL (SEQ ID NO: 262), ISQAVHAAHAEINEAGR (SEQ ID NO: 125), KISQAVHAAHAEINEAGRESIINFEKLTEWT (SEQ ID NO: 141), KAVYNFATM (SEQ ID NO: 129), MLMAQEALAFL (SEQ ID NO: 194), SLLMWITQC (SEQ ID NO: 268), GARGPESRLLEFYLAMPFATPMEAELARRSLAQDAPPL (SEQ ID NO: 89), VPGVLLKEFTVSGNILTIRLTAADHR (SEQ ID NO: 325), ESRLLEFYLAMPF (SEQ ID NO: 63), SLLMWITQCFLPVF (SEQ ID NO: 269), ILHNGAYSL (SEQ ID NO: 116), GVGSPYVSRLLGICL (SEQ ID NO: 99), AKFVAAWTLKAAA (SEQ ID NO: 100), IMDQVPFFS (SEQ ID NO: 119), SVDYFFVWL (SEQ ID NO: 286), ALFDIESKV (SEQ ID NO: 20), NLVPMVATV (SEQ ID NO: 199) and GLCTLVAML (SEQ ID NO: 94).

Alternatively more preferably J is selected from the group consisting of: SVASTITGV (SEQ ID NO: 285), VMAGDIYSV (SEQ ID NO: 359), ALADGVQKV (SEQ ID NO: 360), LLGATCMFV (SEQ ID NO: 168), SVFAGVVGV (SEQ ID NO: 362), ALFDGDPHL (SEQ ID NO: 363), YVDPVITSI (SEQ ID NO: 364), STAPPVHNV (SEQ ID NO: 284, LAALPHSCL (SEQ ID NO: 153), SQDDIKGIQKLYGKRS (SEQ ID NO: 367), FLPSDFFPSV (SEQ ID NO: 368), FLPSDFFPSV (SEQ ID NO: 368), TLGEFLKLDRERAKN (SEQ ID NO: 370), TFSYVDPVITSISPKYG-MET (SEQ ID NO: 371), AMTQLLAGV (SEQ ID NO: 372), KVFAGIPTV (SEQ ID NO: 373), AIIDGVESV (SEQ ID NO: 374), GLWHHQTEV (SEQ ID NO: 375), NLDTLMTYV (SEQ ID NO: 376), KIQEILTQV (SEQ ID NO: 377), LTFGDVVAV (SEQ ID NO: 378), TMLARLASA (SEQ ID NO: 379), IMDQVPFSV (SEQ ID NO: 120), MHQKRTAMFQDPQERPRKLPQLCTELQTTIHD (SEQ ID NO: 381), LPQLCTELQTTI (SEQ ID NO: 382), HDIILECVYCKQQLLRREVY (SEQ ID NQ: 383), KQQLLRREVYDFAFRDLCIVYRDGN (SEQ ID NO: 384), RDLCIVYRDGNPYAVCDKCLKFYSKI (SEQ ID NO: 385), DKCLKFYSKISEYRHYCYSLYGTTL (SEQ ID NO: 386), HYCYSLYGTTLEQQYNKPLCDLLIR (SEQ ID NO: 387), YGTTLEQQYNKPLCDLLIRCINCQKPLCPEEK (SEQ ID NO: 388), RCINCQKPLCPEEKQRHLDKKQRFHNIRGRWT (SEQ ID NO: 389), DKKQRFHNIRGRWTGRCMSCCRSSRTRRETQL (SEQ ID NO: 390), MHGDTPTLHEYMLDLQPETTDLYCYEQLNDSSEEE (SEQ ID NO: 391), LYCYEQLNDSSEEEDEIDGPAGQAEPDRAHYNIVT (SEQ ID NO: 392), GQAEPDRAHYNIVTFCCKCDSTLRLCVQSTHVDIR (SEQ ID NO: 393), TLRLCVQSTHVDIRTLEDLLMGTLGIVCPICSQKP (SEQ ID NO: 394), ALPFGFILV (SEQ ID NO: 395, TLADFDPRV (SEQ ID NO: 396), IMDQVPFSV (SEQ ID NO: 120), SIMTYDFHGA (SEQ ID NO: 398), FLYDDNQRV (SEQ ID NO: 400), YLIELIDRV (SEQ ID NO: 401), NLMEQPIKV (SEQ ID NO: 402), FLAEDALNTV (SEQ ID NO: 403, ALMEQQHYV (SEQ ID NO: 404), ILDDIGHGV (SEQ ID NO: 405), and KLDVGNAEV (SEQ ID NO: 406).

Preferably Z is any one of Z1 to Z5. Still more preferably Z is Z1. Still more preferably Z is Z1 wherein $R^{20}$ is methyl.

Preferably the stereochemistry of the 6-membered sugar ring of formula (I) or formula (II) is α-D-galacto.

Preferably X is O.

Preferably $R^{23}$ is 2-sulfoethyl.

Preferably $R^{12}$ is $C_{28}$ acyl. Alternatively preferably $R^{12}$ is $C_{11}$ acyl.

Preferably $R^8$ is $C_{10}$ to $C_{14}$ alkyl, most preferably $C_{13}$ alkyl.

Preferably, n in formula (I) or formula (II) is 1, the stereochemistry of the 6-membered sugar ring of formula (I) or formula (II) is α-D-galacto, $R^6$ is OH and $R^7$ is $OR^{12}$. It is further preferred that n in formula (I) or formula (II) is 1, the stereochemistry of the 6-membered sugar ring of formula (I) or formula (II) is α-D-galacto, $R^6$ is OH, $R^7$ is $OR^{12}$ and the stereochemistry at carbon atoms 2, 3 and 4 is (2S, 3S, 4R).

Alternatively preferably, n in formula (I) or formula (II) is 0, X is $CH_2$, the stereochemistry of the 6-membered sugar ring of formula (I) or formula (II) is α-D-galacto, $R^6$ is OH and $R^7$ is $OR^{12}$. It is further preferred that n in formula (I) or formula (II) is 0, the stereochemistry of the 6-membered sugar ring of formula (I) or formula (II) is α-D-galacto, $R^6$ is OH, $R^7$ is $OR^{12}$ and the stereochemistry at carbon atoms 2, 3 and 4 is (2S, 3S, 4R).

Preferably, in formula (I) or formula (II) when X is O, $R^6$ is $OR^{12}$, $R^7$ is H, $R^8$ is $C_1$-$C_{15}$ alkyl and ---------- is a double bond linking the carbon adjacent to $R^7$ with the carbon adjacent to $R^8$, then the stereochemistry at the carbon atoms 2, 3 is (2S, 3S).

Preferably $R^1$ is H.

It is also preferred that $R^2$ is OH. More preferably $R^1$ is H and $R^2$ is OH.

Preferably $R^3$ is OH.

Preferably $R^4$ is $CH_2OH$. It is also preferred that $R^4$ is $CH_2OH$ and $R^1$ is H. It is further preferred that $R^4$ is $CH_2OH$, $R^2$ is OH and $R^1$ is H. More preferably $R^4$ is $CH_2OH$, $R^1$ is H and $R^2$ and $R^3$ are both OH.

Preferably $R^6$ is OH. Alternatively it is preferred that $R^6$ is $OR^{12}$.

Preferably $R^7$ is $OR^{12}$. More preferably $R^7$ is $OR^{12}$ and $R^6$ is OH. Still more preferably $R^7$ is $OR^{12}$, $R^6$ is OH and X is O.

Alternatively it is preferred that $R^7$ is OH. More preferably $R^6$ is $OR^{12}$ and $R^7$ is OH.

Alternatively it is preferred that $R^6$ and $R^7$ are both $OR^{12}$.

Alternatively it is preferred that $R^7$ is H and $R^6$ is $OR^{12}$.

Preferably $R^8$ is $C_1$-$C_{15}$ alkyl. More preferably $R^8$ is $C_1$-$C_{15}$ alkyl having a straight or branched carbon chain containing no double bonds, triple bonds, oxygen atoms or aryl groups. Preferably $R^8$ is $C_{13}$ alkyl. Still more preferably $R^8$ is $C_{13}$ alkyl having a straight carbon chain containing no double bonds, triple bonds, oxygen atoms or aryl groups. Alternatively preferably $R^8$ is $C_5$ alkyl. More preferably $R^8$ is $C_5$ alkyl having a straight carbon chain containing no double bonds, triple bonds, oxygen atoms or aryl groups. Still more preferably $R^8$ is $C_1$-$C_{15}$ alkyl, $R^7$ is $OR^{12}$ and $R^6$ is OH. Still more preferably $R^8$ is $C_1$-$C_{15}$ alkyl, $R^7$ is $OR^{12}$, $R^6$ is OH and X is O.

Preferably $R^{11}$ is alkyl, more preferably lower alkyl.

Preferably $R^{12}$ is acyl having a straight carbon chain from 6 to 30 carbon atoms long. More preferably $R^{12}$ is $C_{26}$ acyl. More preferably $R^{12}$ is $C_{26}$ acyl having a straight carbon chain containing no double bonds, triple bonds, oxygen atoms, aryl groups and which is unsubstituted. More preferably X is O and $R^{12}$ is acyl having a straight carbon chain from 6 to 30 carbon atoms long.

Alternatively preferably $R^{12}$ is acyl having a straight carbon chain from 6 to 30 carbon atoms long and having an optionally substituted chain terminating aryl group. More preferably $R^{12}$ is $C_{11}$ acyl having an optionally substituted chain terminating aryl group. Still more preferably the optionally substituted aryl group is phenyl, optionally substituted with a halogen, e.g. a fluorine, e.g. the optionally substituted aryl group is p-fluorophenyl. More preferably X is O and $R^{12}$ is acyl having a straight carbon chain from 6 to 30 carbon atoms long and having an optionally substituted chain terminating aryl group.

Preferably $R^{26}$ is benzyl.

Preferably any halogen in the compound of formula (I) or (II) is fluorine.

Preferably the compound of formula (I) is a compound selected from the group consisting of:

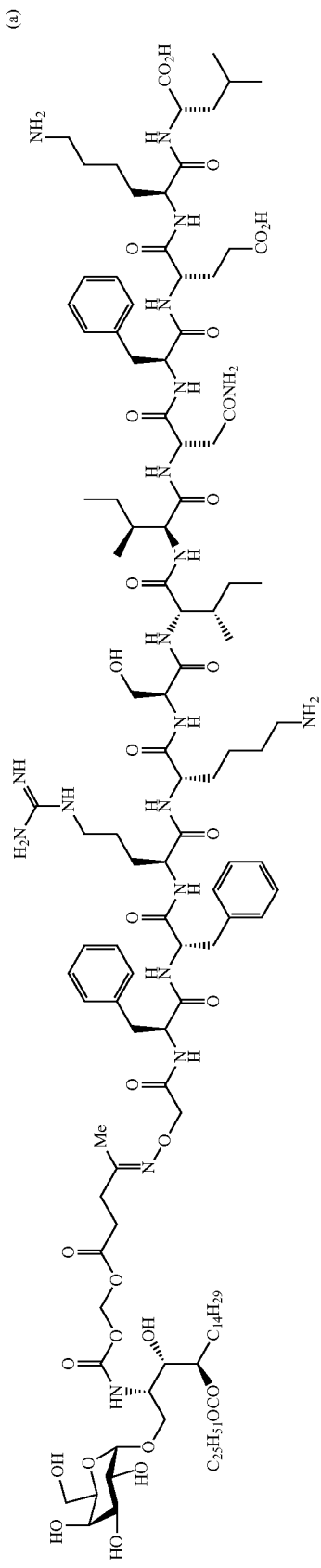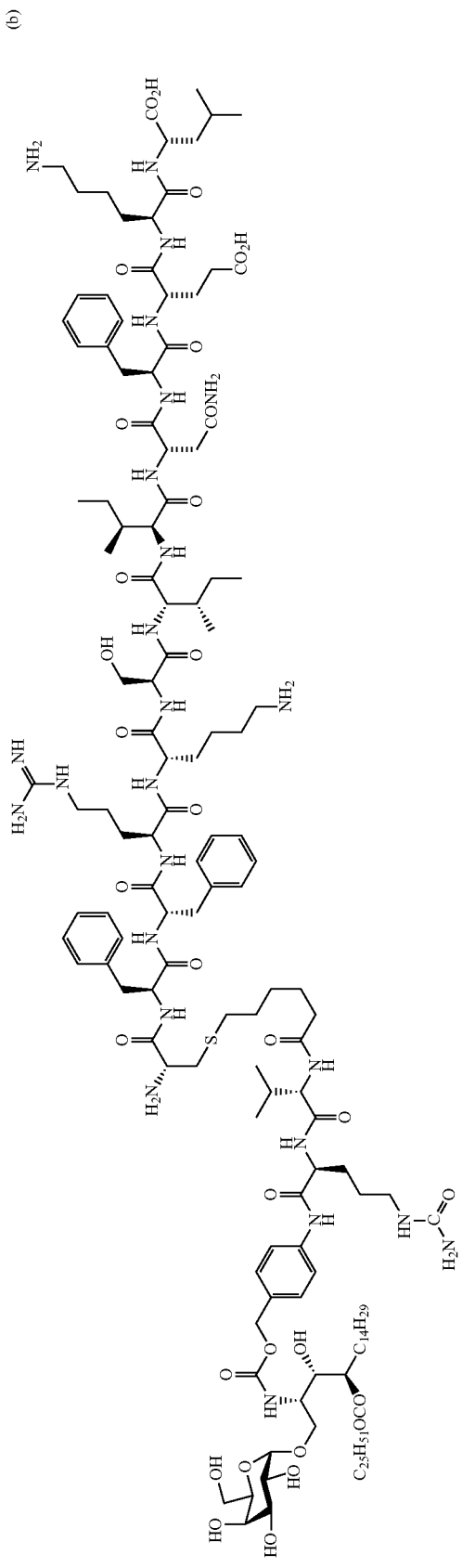

(c)
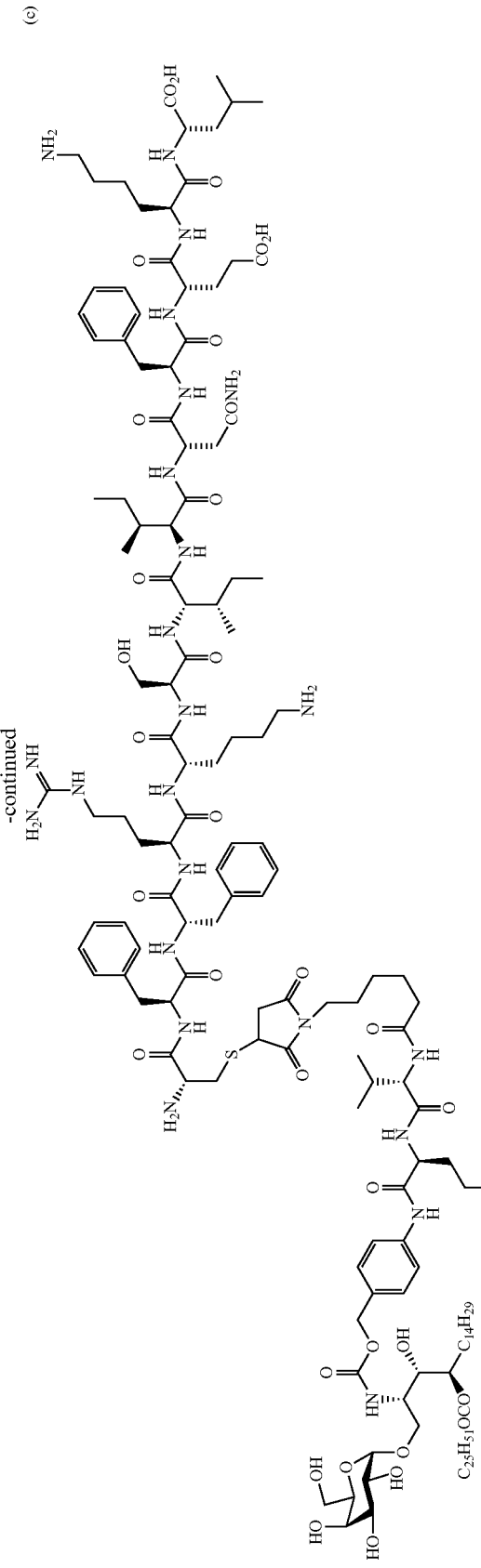
(d)
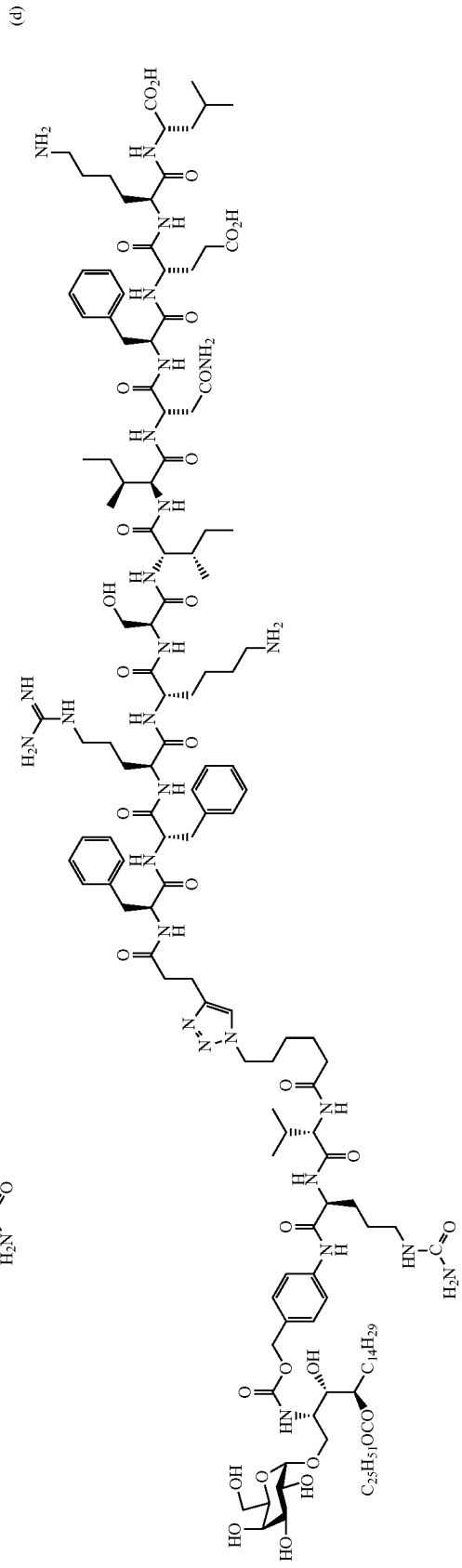

(e)
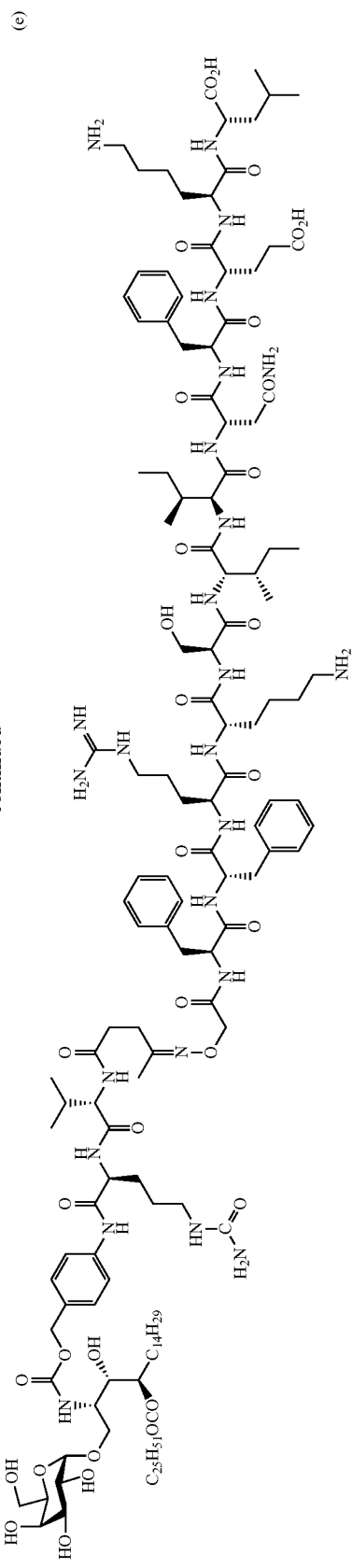
(f)
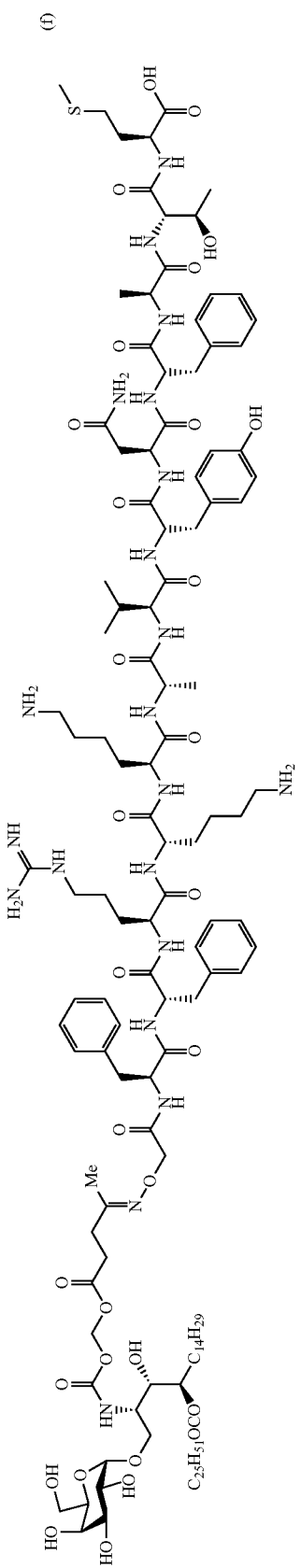

-continued
(g)
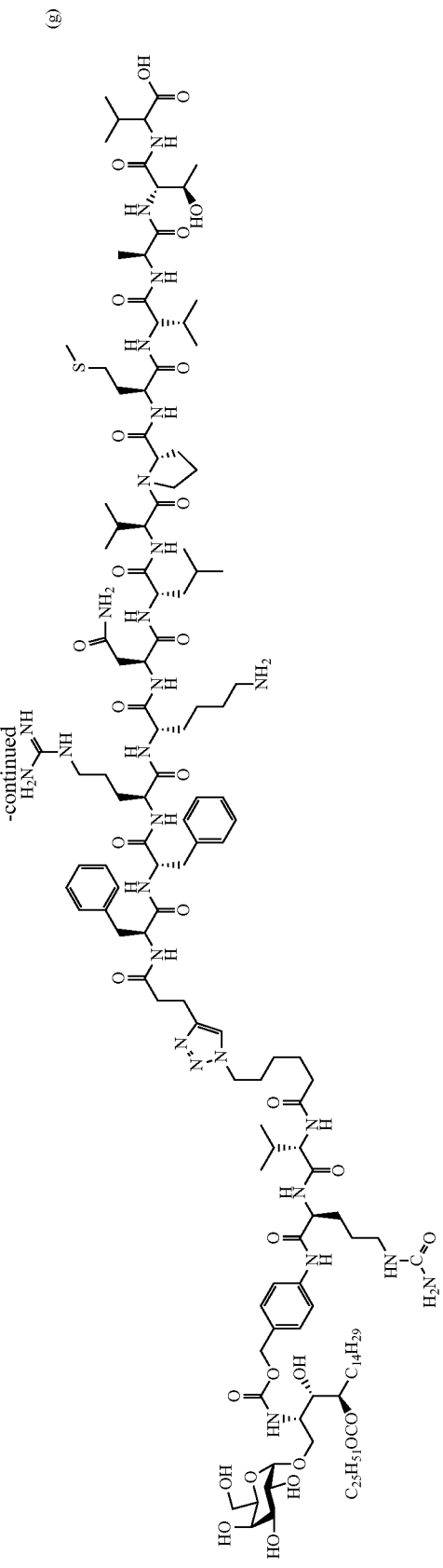
(h)
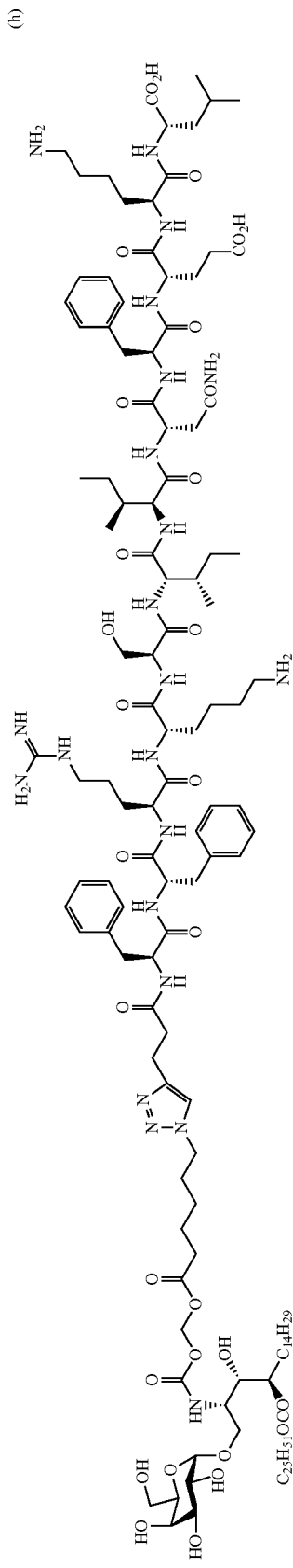

(i)
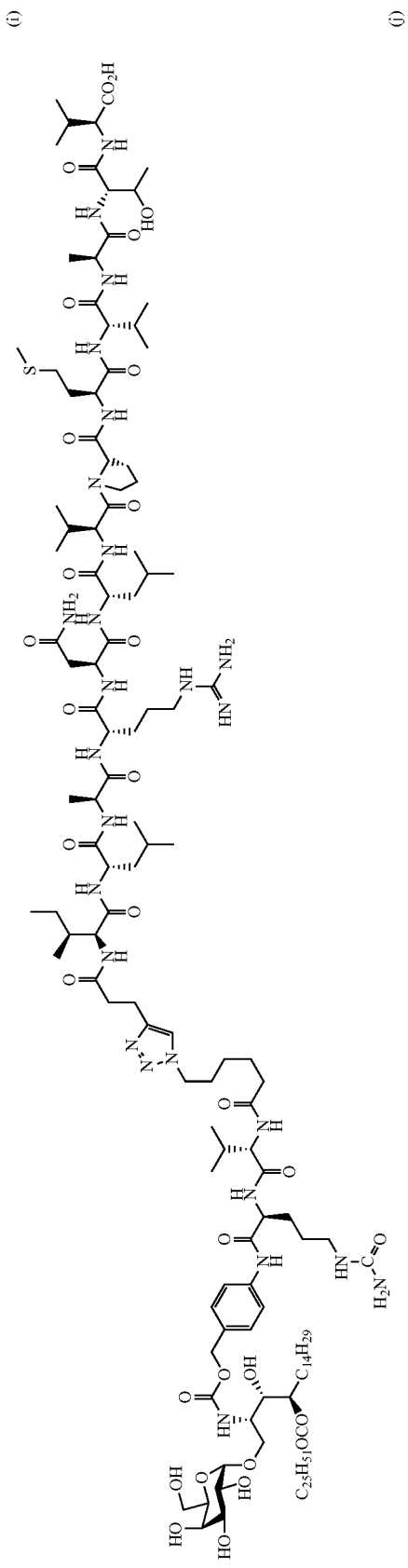
(j)
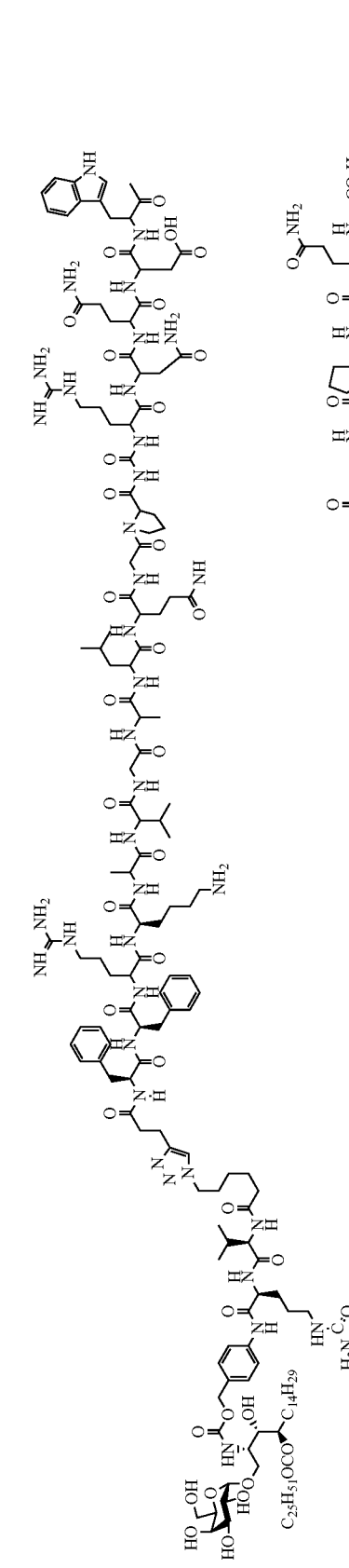

(k)
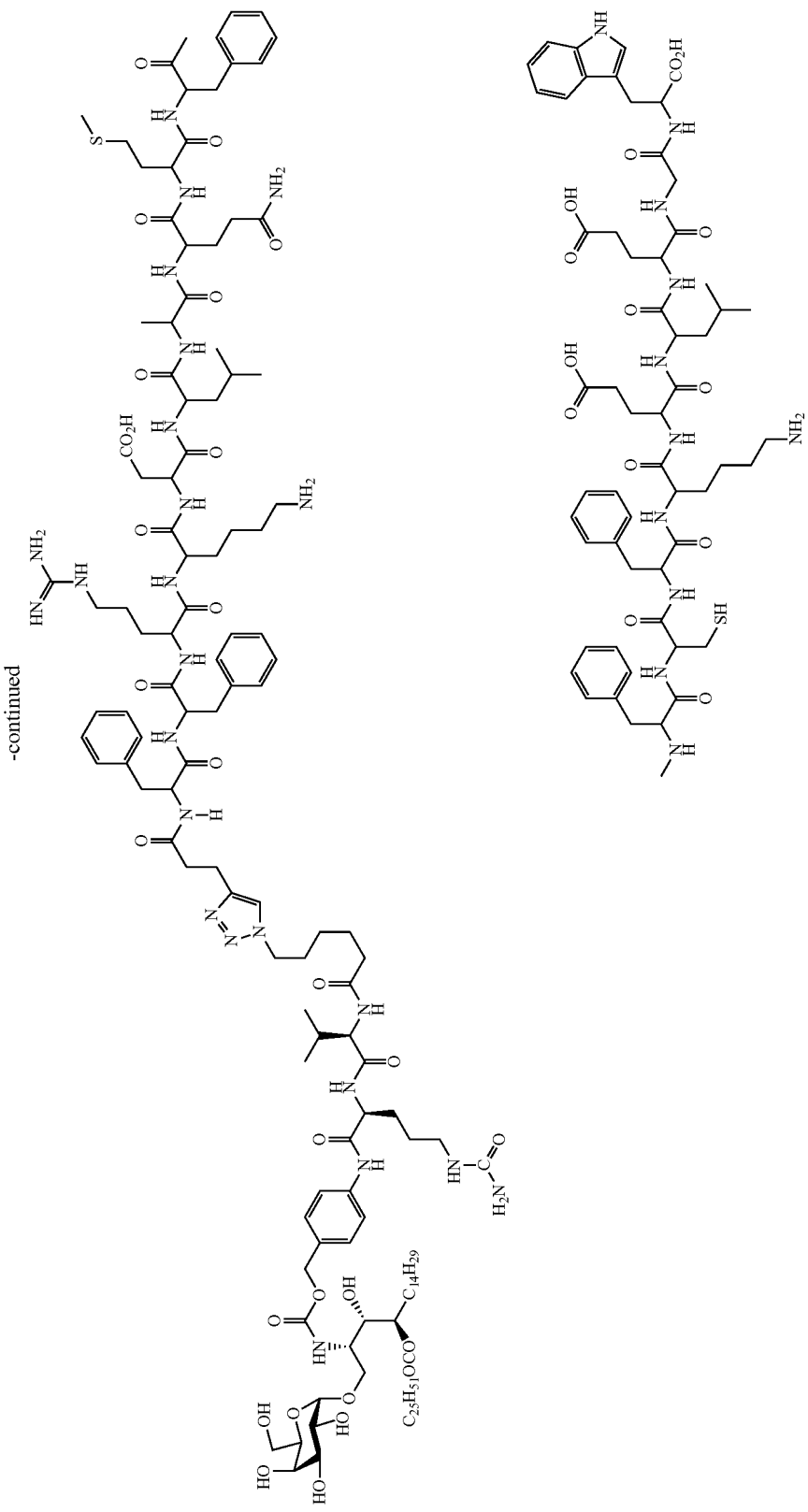

-continued
(I)
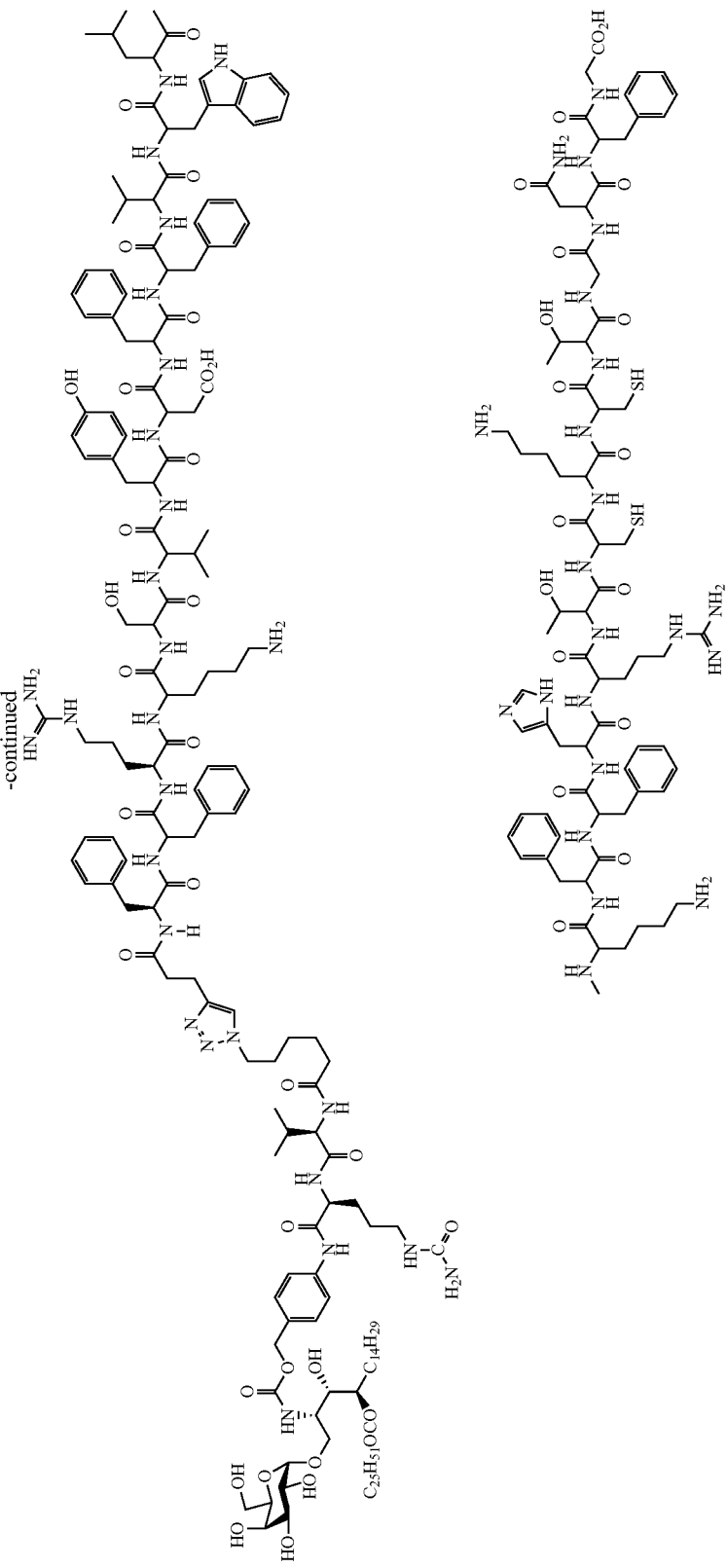

(m)
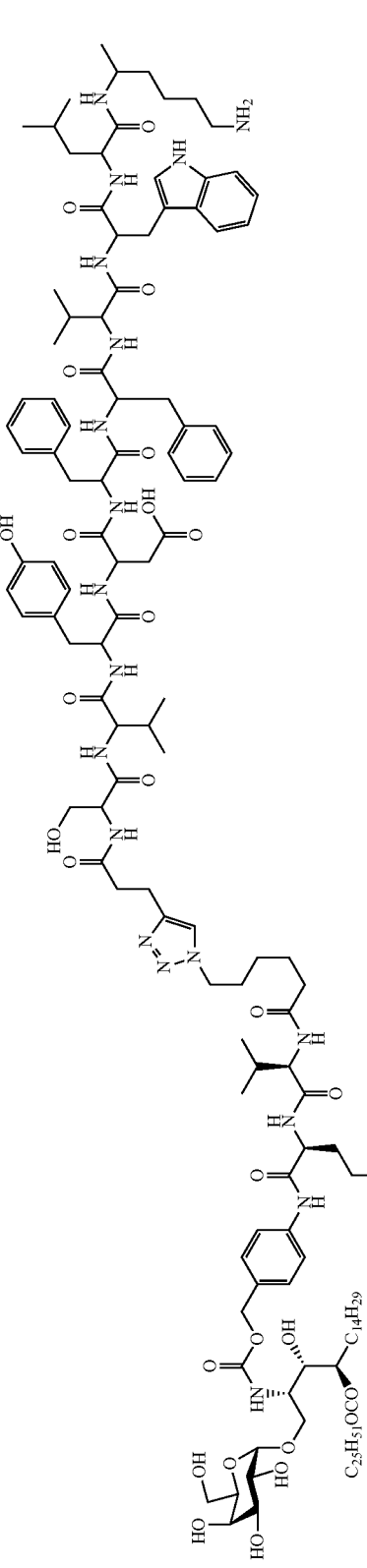
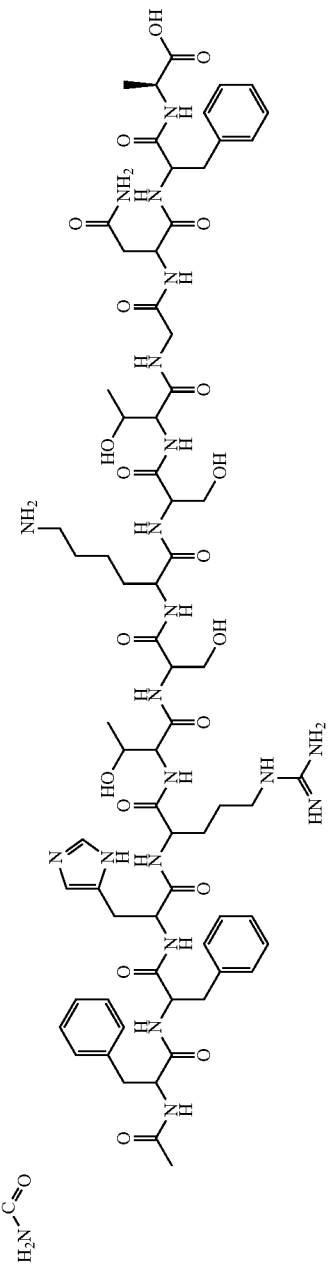

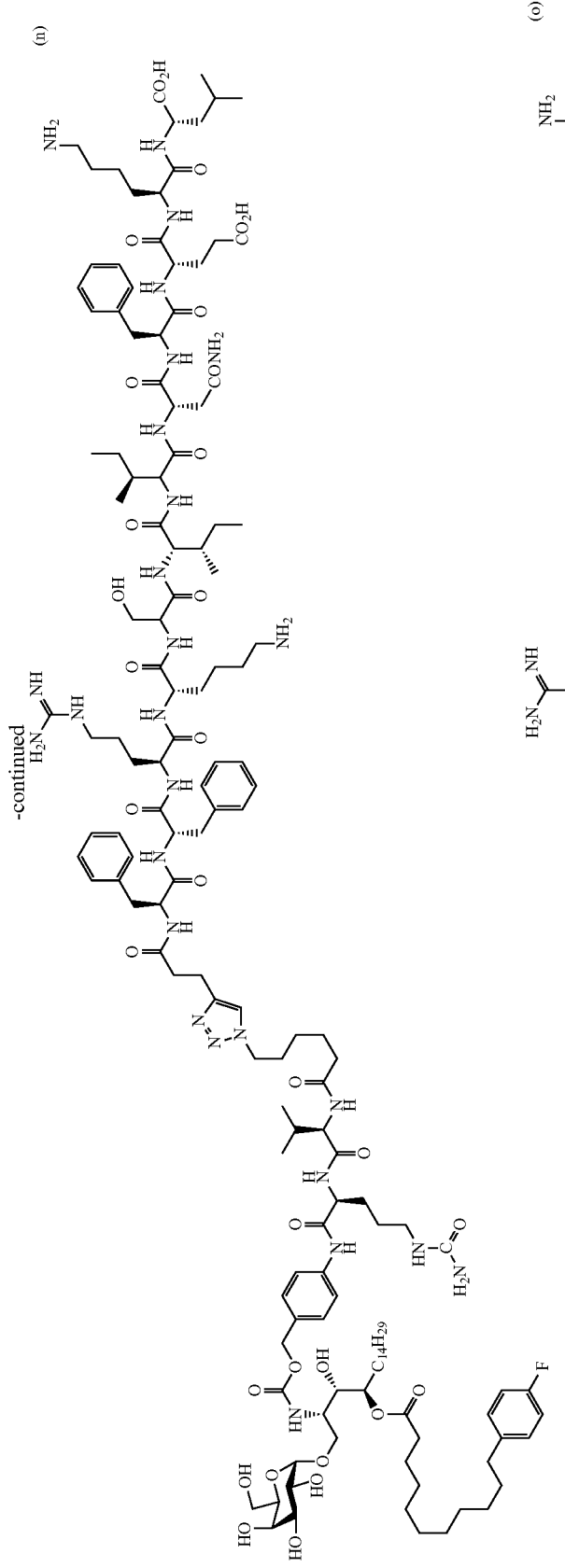

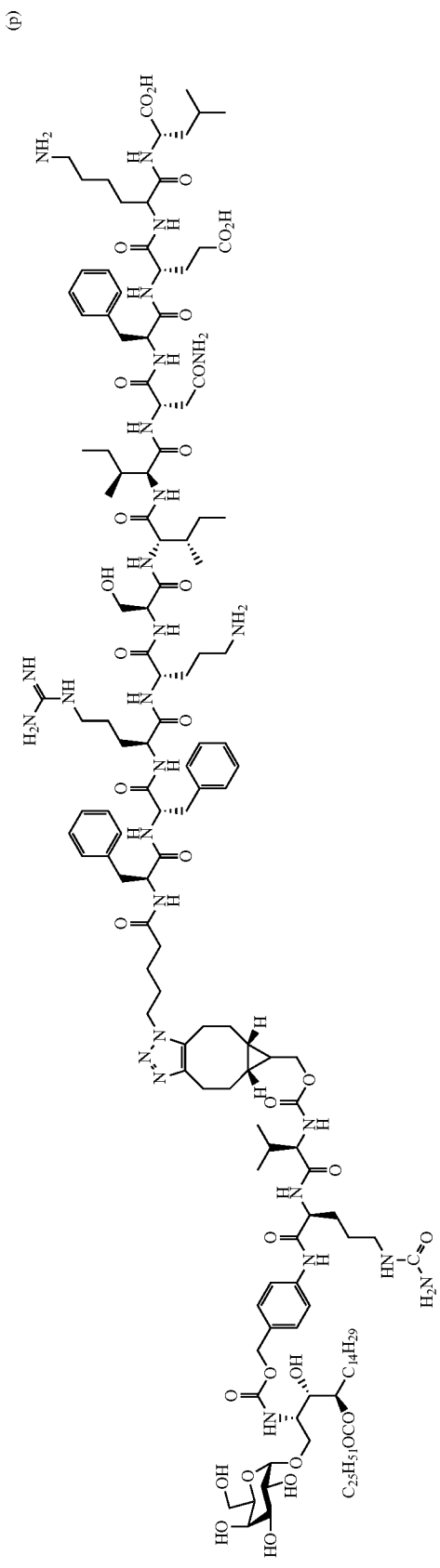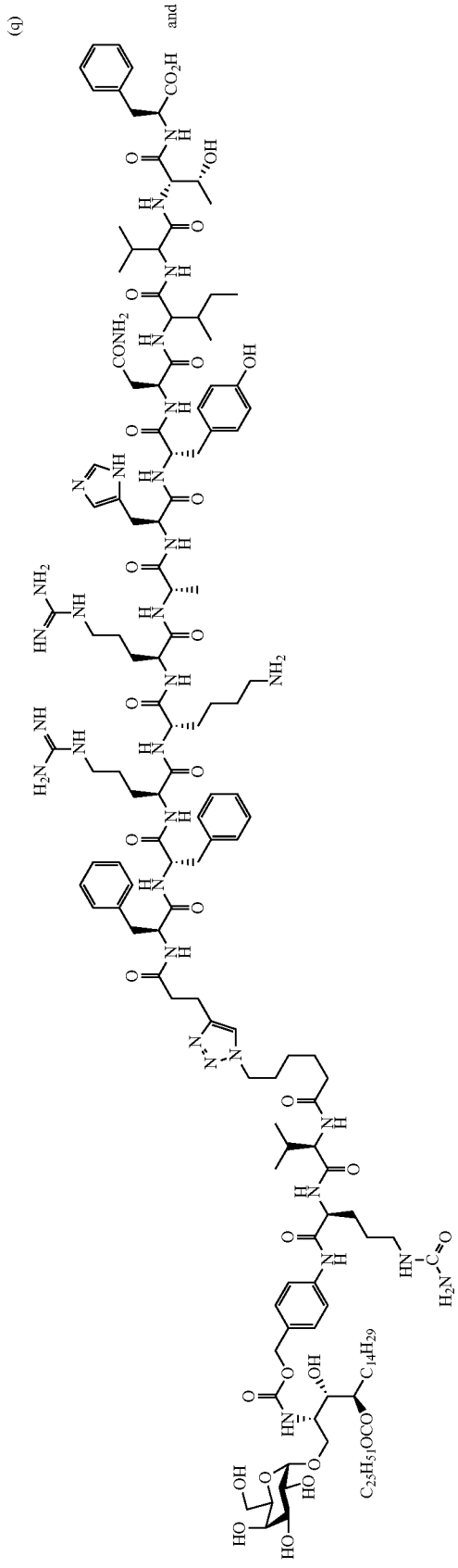

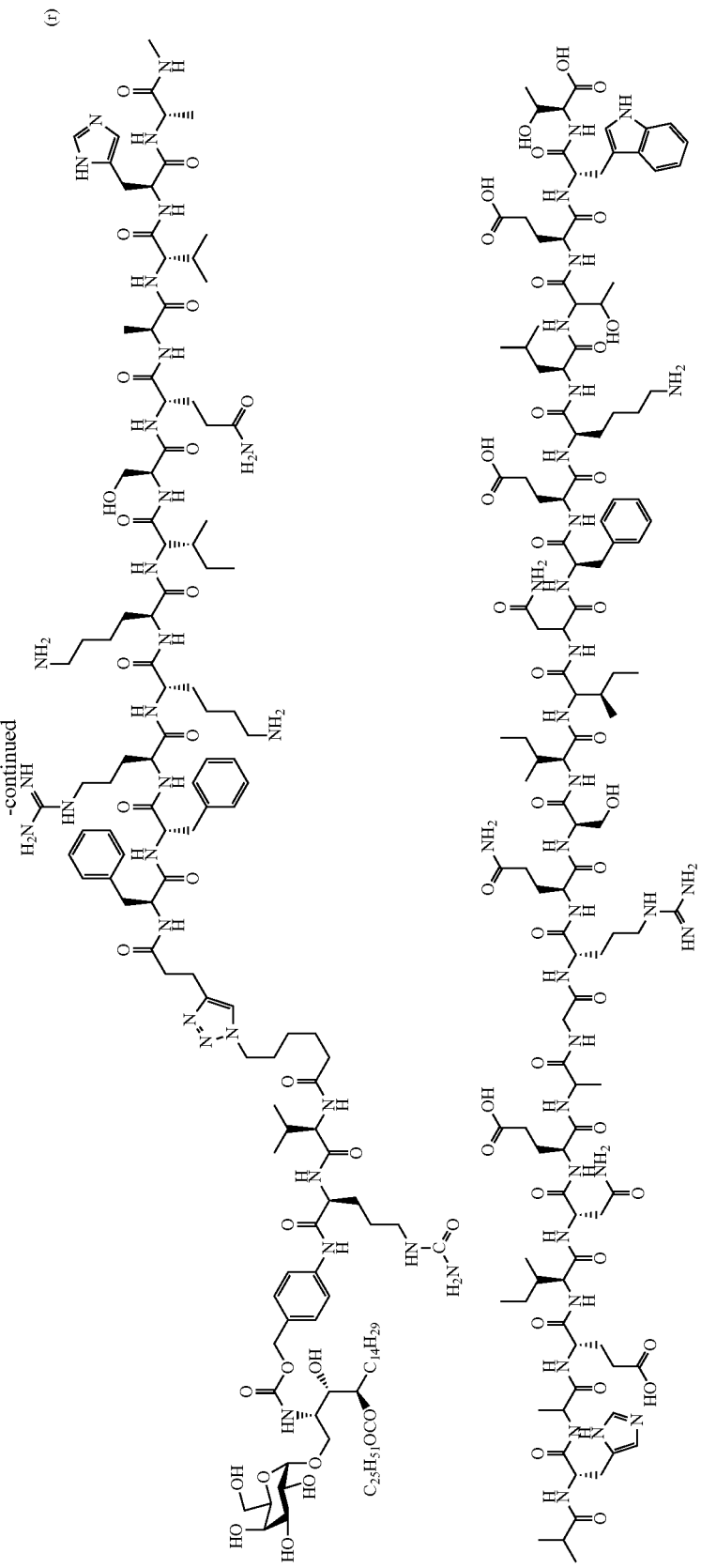

or a pharmaceutically acceptable salt thereof.
Preferably the compound of formula (II) is a compound selected from the group consisting of:
(aa)
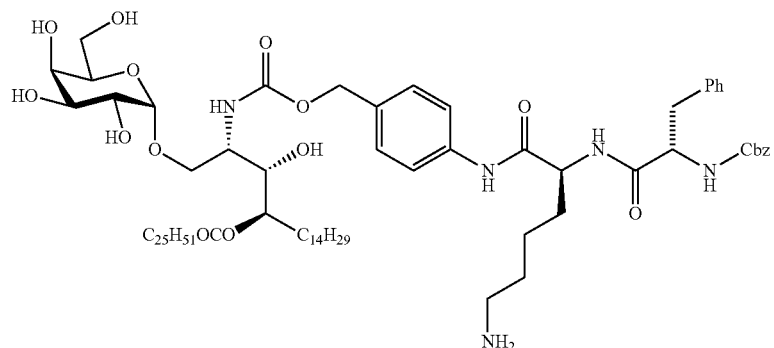
(bb)
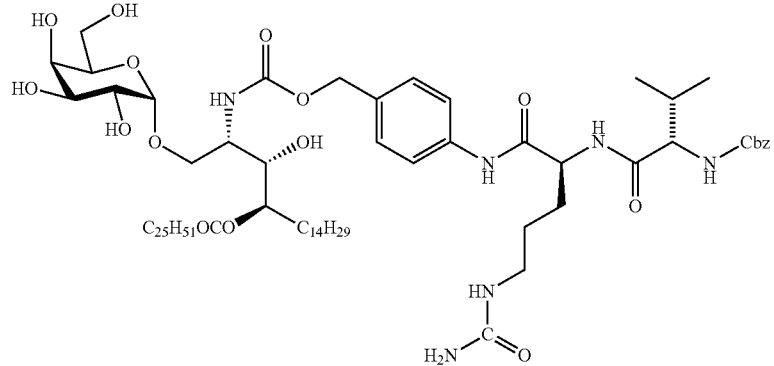
(cc)
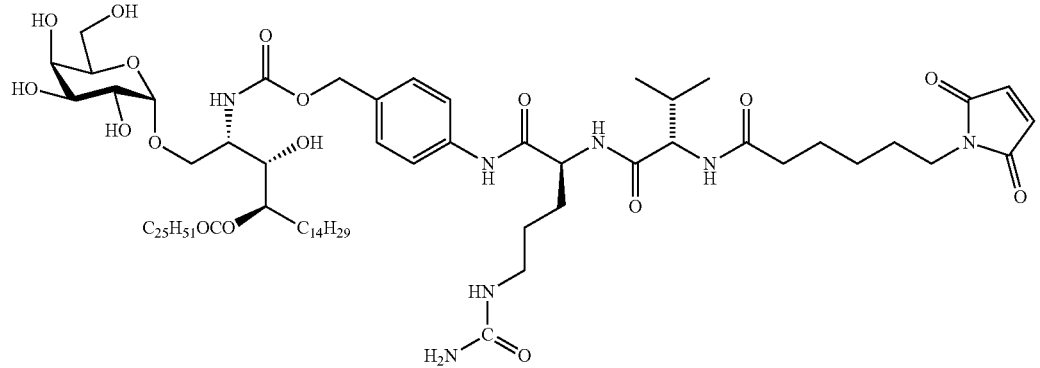
(dd)
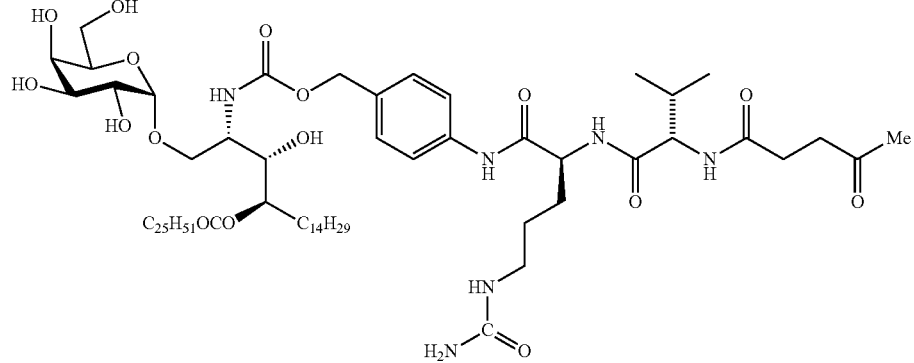

(ee)
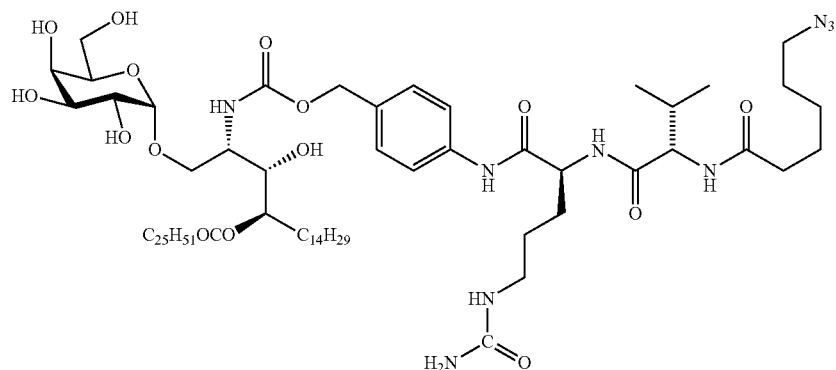
(ff)
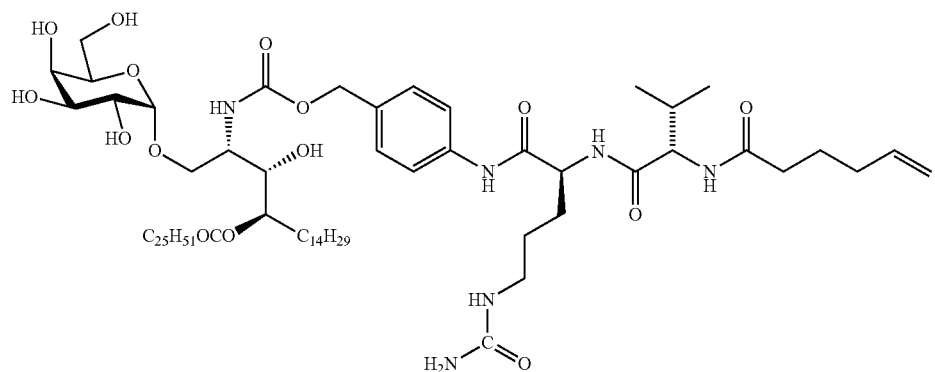
(gg)
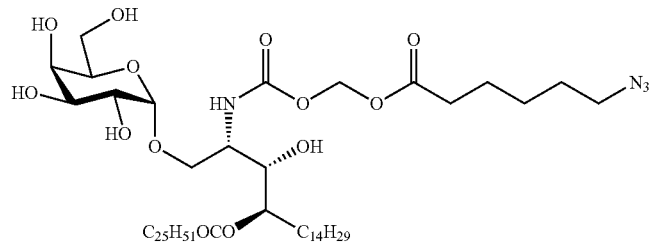
(hh)
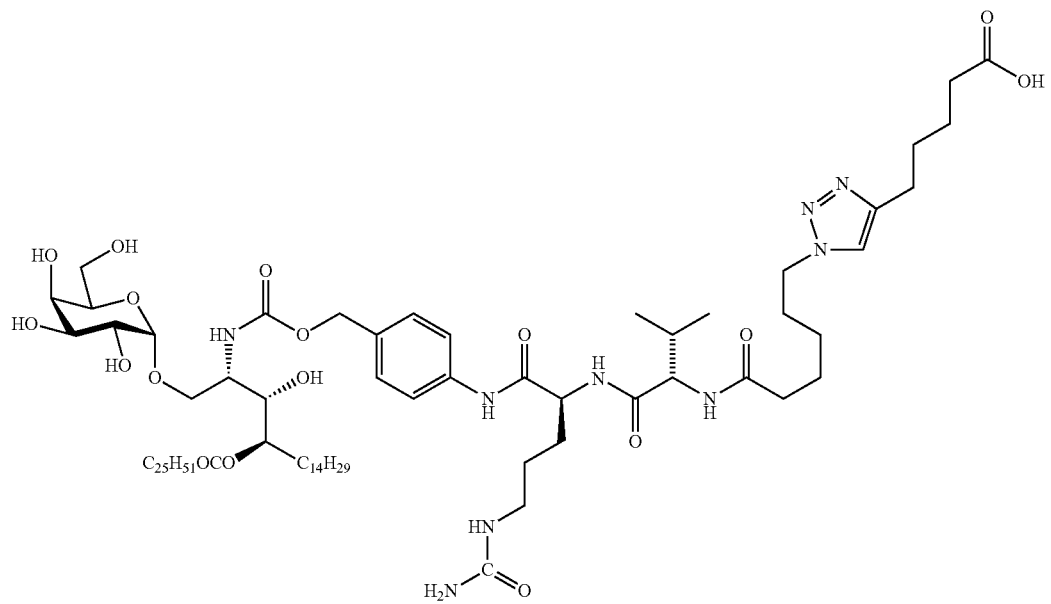

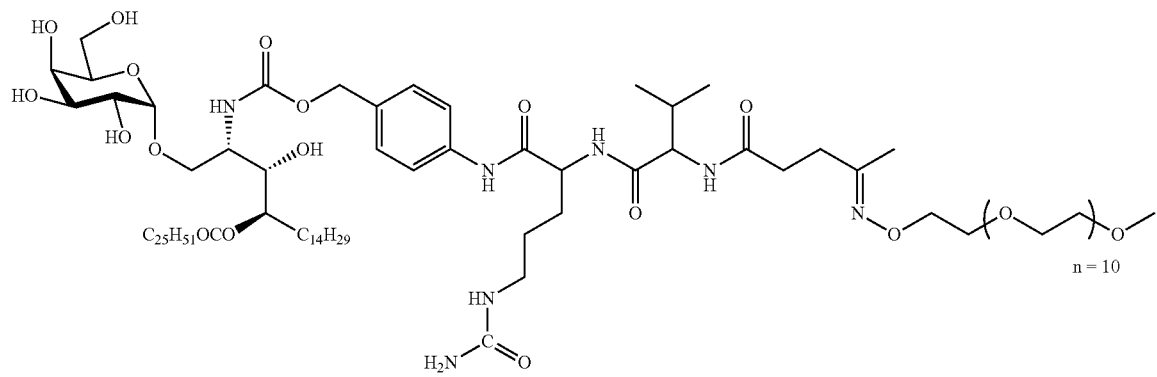
(ii)
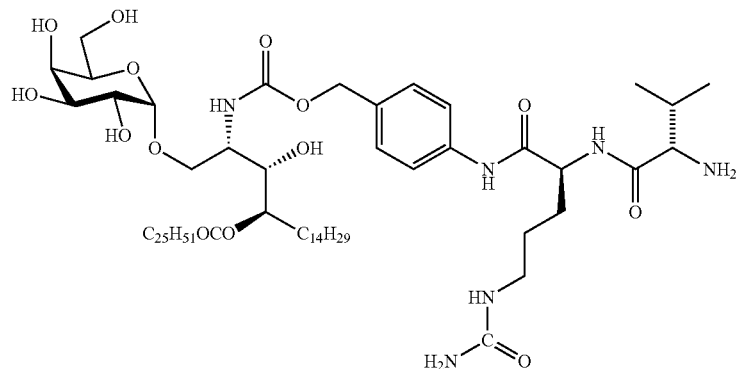
(jj)
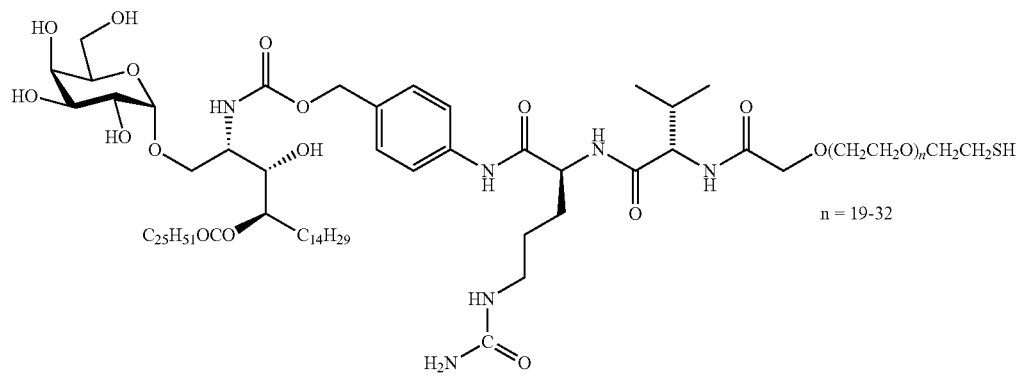
(kk)
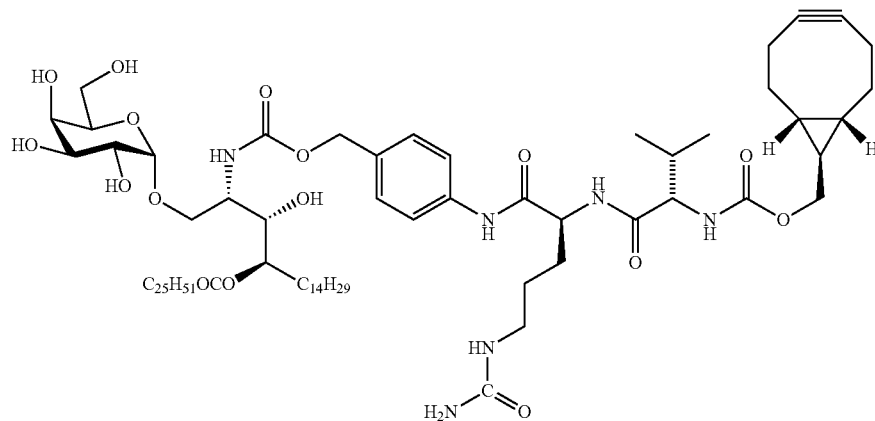
(ll)

(mm)
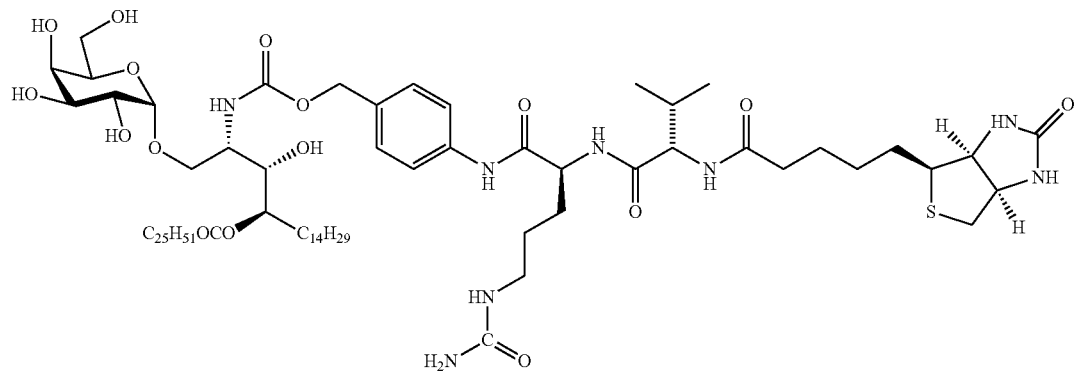
(nn)
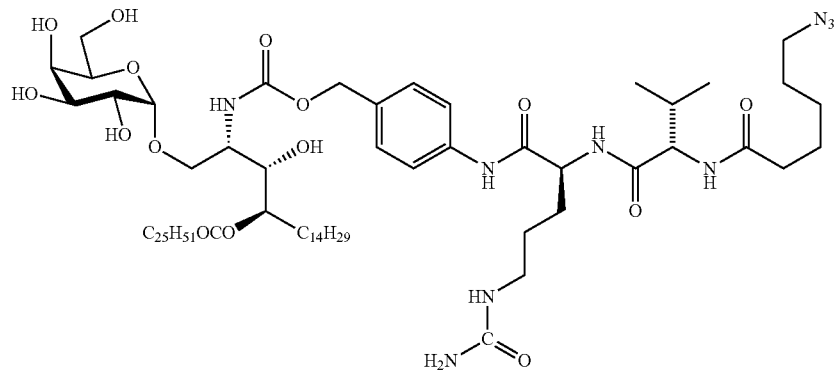
(oo)
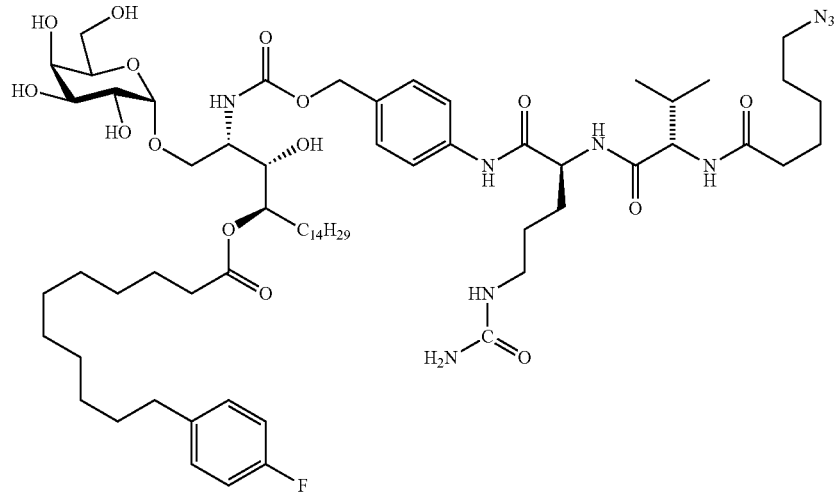
(pp)
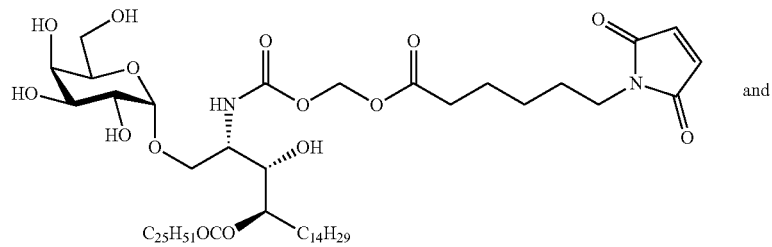
and (qq)

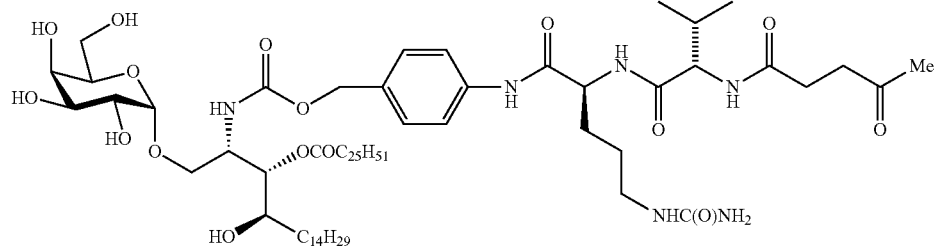

or a pharmaceutically acceptable salt thereof.

In another aspect the invention provides a pharmaceutical composition comprising a pharmaceutically effective amount of a compound of formula (I) or formula (II) and optionally a pharmaceutically acceptable carrier.

In another aspect the invention provides an immunogenic composition comprising a compound of formula (I) or formula (II) and a pharmaceutically acceptable diluent and optionally an antigen.

In another aspect the invention provides a vaccine comprising a compound of formula (I) or formula (II) and a pharmaceutically acceptable diluent and optionally an antigen.

In another aspect the invention provides a compound of formula (I) or (II), and optionally an antigen, for use in the preparation of a vaccine.

The antigen may be, or may be a combination of, a bacterium such as *Bacillus* Calmette-Guérin (BCG), a virus, a protein or peptide. Examples of suitable antigens include, but are not limited to, Wilms' Tumor 1 (WT1), (Li, Oka et al. 2008) tumor-associated antigen MUC1, (Brossart, Heinrich et al. 1999) latent membrane protein 2 (LMP2), (Lu, Liang et al. 2006) HPV E6E7, (Davidson, Faulkner et al. 2004) NY-ESO-1 (Karbach, Gnjatic et al. 2010), tyrosinase-related protein (Trp)-2 (Noppen, Levy et al. 2000; Chang 2006), survivin (Schmitz, Diestelkoetter et al. 2000; Friedrichs, Siegel et al. 2006; Ciesielski, Kozbor et al. 2008), MART-1 (Bettinotti, Kim et al. 1998; Jager, Hohn et al. 2002), CEA691 (Huarte, Sarobe et al. 2002) and glycoprotein 100 (gp100) (Levy, Pitcovski et al. 2007), helper epitopes (Alexander, Sidney et al 1994), Topoisomerase II α, Integrin 38 subunit precursor, Abl-binding protein C3, TACE/ADAM 17, Junction plakoglobin, EDDR1 and BAP31 (Berinstein, Karkada et al 2012).

In still another aspect the invention provides a compound of formula (I) or formula (II) in combination with at least one other compound, e.g. a second drug compound, e.g. an anti-bacterial agent or an anti-cancer agent such as Vemurafenib (PLX4032), Imatinib or Carfilzomib.

In yet another aspect the invention provides the use of a compound of formula (I) or formula (II) as a medicament.

In another aspect the invention provides the use of a compound of formula (I) or formula (II) for treating or preventing an infectious disease, an atopic disorder, an autoimmune disease, diabetes or cancer.

In another aspect the invention provides the use of a pharmaceutical composition comprising a pharmaceutically effective amount of a compound of formula (I) or formula (II), for treating or preventing an infectious disease, an atopic disorder, an autoimmune disease, diabetes or cancer.

In another aspect the invention provides a compound of formula (I) or formula (II) for use in the manufacture of a medicament.

In another aspect the invention provides a pharmaceutical composition for treating or preventing an infectious disease, an atopic disorder, an autoimmune disease, diabetes or cancer, comprising a compound of formula (I) or formula (II).

In another aspect the invention provides the use of a compound of formula (I) or formula (II) in the manufacture of a medicament for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering a pharmaceutically effective amount of a compound of formula (I) or formula (II) to a patient requiring treatment.

In another aspect the invention provides a method of treating or preventing an infectious disease, an atopic disorder, an autoimmune disease, diabetes or cancer comprising sequential administration of pharmaceutically effective amounts of one or more compounds of formula (I) or formula (II) to a patient requiring treatment. The compounds of formula (I) or (II) may be formulated as a vaccine, for separate, sequential administration. The sequential administration may include two or more administration steps, preferably wherein the compounds of formula (I) or (II) are administered 1 to 90 days apart, preferably 14 to 28 days apart. The sequential administration may include administering the same compound of formula (I) or (II) two or more times. Alternatively, the sequential administration may include administering differing compounds of formula (I) or (II) two or more times. Alternatively, the sequential administration may include administering a compound of formula (I) or (II) one or more times, and administering α-galactosylceramide one or more times.

In another aspect the invention provides the use of a compound of formula (I) or formula (II) in combination with at least one other compound, e.g. a second drug compound, e.g. an anti-bacterial agent or an anti-cancer agent such as Vemurafenib (PLX4032), Imatinib or Carfilzomib for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering to a patient a pharmaceutically effective amount of a compound of formula (I) or formula (II) in combination with at least one other compound, e.g. a second drug compound, e.g. an anti-bacterial agent or an anti-cancer agent such as Vemurafenib (PLX4032), Imatinib or Carfilzomib. The compound of formula (I) or formula (II) and the other compound may be administered separately, simultaneously or sequentially.

The diseases or conditions include cancer, e.g. melanoma, prostate, breast, lung, glioma, lymphoma, colon, head and neck and nasopharyngeal carcinoma (NPV); infectious diseases, e.g. HIV; bacterial infections; atopic diseases, e.g. asthma; or autoimmune diseases.

In another aspect the invention provides a method of treating or preventing asthma comprising administering a pharmaceutically effective amount of a compound of formula (I) or formula (II) to a patient requiring treatment.

In another aspect the invention provides a vaccine for preventing asthma comprising administering a pharmaceutically effective amount of a compound of formula (I) or formula (II).

In another aspect the invention provides a method of modifying an immune response in a patient, comprising administering a compound of formula (I) or formula (II), and optionally an antigen, to the patient.

Preferably the patient is a human.

Preferably the compound is a compound of formula (I). The compound of formula (I) may be selected from the group consisting of compounds (a) to (r), as defined above.

Alternatively preferably the compound is a compound of formula (II). The compound of formula (II) may be selected from the group consisting of compounds (aa) to (qq), as defined above.

Compounds of formula (I) and formula (II) are described herein as "compounds of the invention". A compound of the invention includes a compound in any form, e.g. in free form or in the form of a salt or a solvate.

It will be appreciated that any of the sub-scopes disclosed herein, e.g. with respect to X, $R^1$, $R^2$, $R^3$, $R^4$, $R^6$, $R^7$, $R^8$, $R^{10}$, $R^{11}$, $R^{12}$, $R^{15}$, $R^{16}$, $R^{19}$, $R^{20}$, $R^{21}$, $R^{23}$, $R^{24}$, $R^{25}$, $R^{26}$, $R^{27}$, $R^{28}$, $R^{29}$, $R^{31}$, $R^{32}$, n, k, g, W, $Alk^1$, $Q^1$, Z, A, D, E, G and J may be combined with any of the other sub-scopes disclosed herein to produce further sub-scopes.

DETAILED DESCRIPTION

Definitions

The term "cancer" and like terms refer to a disease or condition in a patient that is typically characterized by abnormal or unregulated cell growth. Cancer and cancer pathology can be associated, for example, with metastasis, interference with the normal functioning of neighbouring cells, release of cytokines or other secretory products at abnormal levels, cell proliferation, tumour formation or growth, suppression or aggravation of inflammatory or immunological response, neoplasia, premalignancy, malignancy, invasion of surrounding or distant tissues or organs, such as lymph nodes, etc. Particular cancers are described in detail herein. Examples include lung, glioma, lymphoma, colon, head and neck and nasopharyngeal carcinoma (NPV), melanoma, chronic myelogenous leukemia (CML), myeloma, prostate, breast, glioblastoma, renal cell carcinoma, hepatic cancers.

"Infections" and like terms refer to diseases or conditions of a patient comprising internal and/or external growth or establishment of microbes. Microbes include all living forms too small to be seen by eye, including bacteria, viruses, fungi, and protozoa. Included are aerobic and anaerobic bacteria, and gram positive and gram negative bacteria such as cocci, bacilli, spirochetes, and mycobacteria. Particular infectious disorders are described in detail herein. Examples include bacterial or viral infections, e.g. HIV.

"Atopic disorders" and like terms refer to a disease or condition of a patient that is typically characterized by an abnormal or up-regulated immune response, for example, an IgE-mediated immune response, and/or Th2-cell immune response. This can include hypersensitivity reactions (e.g., Type I hypersensitivity), in particular, as associated with allergic rhinitis, allergic conjunctivitis, atopic dermatitis, and allergic (e.g. extrinsic) asthma. Typically, atopic disorders are associated with one or more of rhinorrhea, sneezing, nasal congestion (upper respiratory tract), wheezing, dyspnea (lower respiratory tract), itching (e.g., eyes, skin), nasal turbinate edema, sinus pain on palpation, conjunctival hyperemia and edema, skin lichenification, stridor, hypotension, and anaphylaxis. Particular atopic disorders are described in detail herein.

The term "patient" includes human and non-human animals. Non-human animals include, but are not limited to birds and mammals, in particular, mice, rabbits, cats, dogs, pigs, sheep, goats, cows, horses, and possums.

"Treatment" and like terms refer to methods and compositions to prevent, cure, or ameliorate a medical disease, disorder, or condition, and/or reduce at least a symptom of such disease or disorder. In particular, this includes methods and compositions to prevent or delay onset of a medical disease, disorder, or condition; to cure, correct, reduce, slow, or ameliorate the physical or developmental effects of a medical disease, disorder, or condition; and/or to prevent, end, reduce, or ameliorate the pain or suffering caused by the medical disease, disorder, or condition.

The term "amino acid" includes both natural and non-natural amino acids.

The term "antigen" refers to a molecule that contains one or more epitopes (linear, overlapping, conformational or a combination of these) that, upon exposure to a subject, will induce an immune response that is specific for that antigen.

The term "self-immolative linker" means any chemical group that, by covalent attachment, bridges a second and a third chemical group, wherein the covalent bond between the self-immolative linker and the second chemical group is metabolically cleavable in vivo and wherein, upon cleavage of this covalent bond in vivo, the self-immolative linker is detached from the third chemical group through spontaneous chemical bond rearrangements. At least one, preferably both, of the second and third chemical groups is a biologically active, e.g. pharmaceutically active, agent or prodrug thereof. Most preferably, each of the second and third chemical groups is independently an immune stimulant (e.g. pattern recognition receptor agonist, TLR agonist or NKT-cell agonist), an antigen (e.g. peptide, protein or carbohydrate) or a targeting group (e.g. antibody or glycan). In some examples, upon detachment of the self-immolative linker from the second chemical group, the self-immolative linker fragments and detaches from the third chemical group. Examples of self-immolative linkers are described in Philip L. Carl, Prasun K. Chakravarty, John A. Katzenellenbogen, Journal of Medicinal Chemistry, 1981, Vol. 24, No. 5, pg 479; and Simplicio et al., Molecules, 2008, vol. 13, pg 519. The covalent bond between the self-immolative linker and the second chemical group may be cleaved by, for example, an esterase, a peptidase, a phosphatase, a phospholipase or a hydrolase, or by way of a redox or pH-dependent process.

The term "alkyl" means any saturated hydrocarbon radical having up to 30 carbon atoms and includes any $C_1$-$C_{25}$, $C_1$-$C_{20}$, $C1$-$C_{15}$, $C1$-$C_{10}$, or $C_1$-$C_6$ alkyl group, and is intended to include cyclic (including fused bicyclic) alkyl groups (sometimes referred to herein as "cycloalkyl"), straight-chain and branched-chain alkyl groups, and straight or branched chain alkyl groups substituted with cyclic alkyl groups. Examples of alkyl groups include: methyl group, ethyl group, n-propyl group, iso-propyl group, cyclopropyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, cyclohexyl group, cyclooctyl group, and 1-methyl-2-ethylpropyl group.

The term "alkylene" means a diradical corresponding to an alkyl group. Examples of alkylene groups include methylene group, cyclohexylene group, ethylene group. An alkylene group can incorporate one or more cyclic alkylene group(s) in the alkylene chain, for example, "alkylene" can include a cyclohexylene group attached to a methylene group. Any alkylene group may be optionally substituted with one or more substituents selected from the group consisting of hydroxyl, halogen, e.g. fluorine, alkyl, e.g. methyl, and aryl.

Any alkylene may optionally include one or more arylene moieties within the alkylene chain, for example, a phenylene group may be included within an alkylene chain.

The term "lower alkyl" means any saturated hydrocarbon radical having from 1 to 6 carbon atoms and is intended to include both straight- and branched-chain alkyl groups.

Any alkyl group may optionally be substituted with one or more substituents selected from the group consisting of $SO_3H$ (or a salt thereof), hydroxy and halogen, e.g. fluorine.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_5$ alkenyl group, and is intended to include both straight- and branched-chain alkenyl groups. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "lower alkenyl" means any hydrocarbon radical having at least one double bond, and having from 2 to 6 carbon atoms, and is intended to include both straight- and branched-chain alkenyl groups.

Any alkenyl group may optionally be substituted with one or more substituents selected from the group consisting of alkoxy, hydroxy and halogen, e.g. fluorine.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "arylene" means a diradical corresponding to an aryl group. Examples include phenylene group.

The term "aralkyl" means an aryl group which is attached to an alkylene moiety, where aryl and alkylene are as defined above. Examples include benzyl group.

Any aryl or aralkyl group may optionally be substituted with one or more substituents selected from the group consisting of alkyl, halogen, cyano, dialkylamino, amide (both N-linked and C-linked: —NHC(O)R and —C(O)NHR), nitro, alkoxy, acyloxy and thioalkyl.

The term "alkoxy" means an OR group, where R is alkyl as defined above. The term "lower alkoxy" means an OR group, where R is "lower alkyl" as defined above.

The term "acyl" means C(=O)R' group, where R' is alkyl as defined above.

The term "acyloxy" means OR" group, where R" is acyl as defined above.

The term "glycosyl" means a radical derived from a cyclic monosaccharide, disaccharide or oligosaccharide by removal of the hemiacetal hydroxy group. Examples include α-D-glucopyranosyl, α-D-galactopyranosyl, β-D-galactopyranosyl, α-D-2-deoxy-2-acetamidogalactopyranosyl.

The term "amide" includes both N-linked (—NHC(O)R) and C-linked (—C(O)NHR) amides.

The term "pharmaceutically acceptable salt" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

For the purposes of the invention, any reference to the disclosed compounds includes all possible formulations, configurations, and conformations, for example, in free form (e.g. as a free acid or base), in the form of salts or hydrates, in the form of isomers (e.g. cis/trans isomers), stereoisomers such as enantiomers, diastereomers and epimers, in the form of mixtures of enantiomers or diastereomers, in the form of racemates or racemic mixtures, or in the form of individual enantiomers or diastereomers. Specific forms of the compounds are described in detail herein.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

The Compounds of the Invention

The compounds of the invention, particularly those exemplified, are useful as pharmaceuticals, particularly for the treatment or prevention of diseases or conditions relating to cancer, infection, atopic disorders or autoimmune disease. The compounds of the invention are also useful as vaccine adjuvants or simple vaccines. For example, a compound of the invention may be formulated in a vaccine together with one or more antigens.

The compounds of the invention are useful in both free base form and in the form of salts and/or solvates.

The carbon atoms of the acyclic moiety of the compounds of formula (I) and formula (II) are numbered as shown below. This is the numbering used herein to denote these carbon atoms.

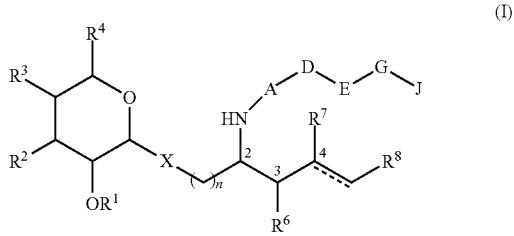

It has been found that compounds of formula (I) and (II) of the invention (e.g. the compounds shown as formula (I') in Scheme 1) are useful as simple synthetic vaccines or vaccine adjuvants. Without wishing to be bound by theory, the applicants propose that such compounds are chemically stable, but can be cleaved enzymatically or at specific sites in vivo. The compounds of formula (I) constitute antigen-adjuvant conjugates (AAC) that can serve as precursors to amines (I'') (e.g. CN089) and antigen-containing component. The antigen component may then be further processed by the antigen-presenting cell and ultimately loaded and displayed by major histocompatibility complex (MHC) molecules. The amines (I'') may in turn undergo O→N acyl-migration, leading to amides (III) (e.g. α-GalCer).

Advantageously, this approach provides for the incorporation of a range of "trigger" groups to allow control of the rate of release of amides (III) (such as α-GalCer) and peptide antigens.

Scheme 1

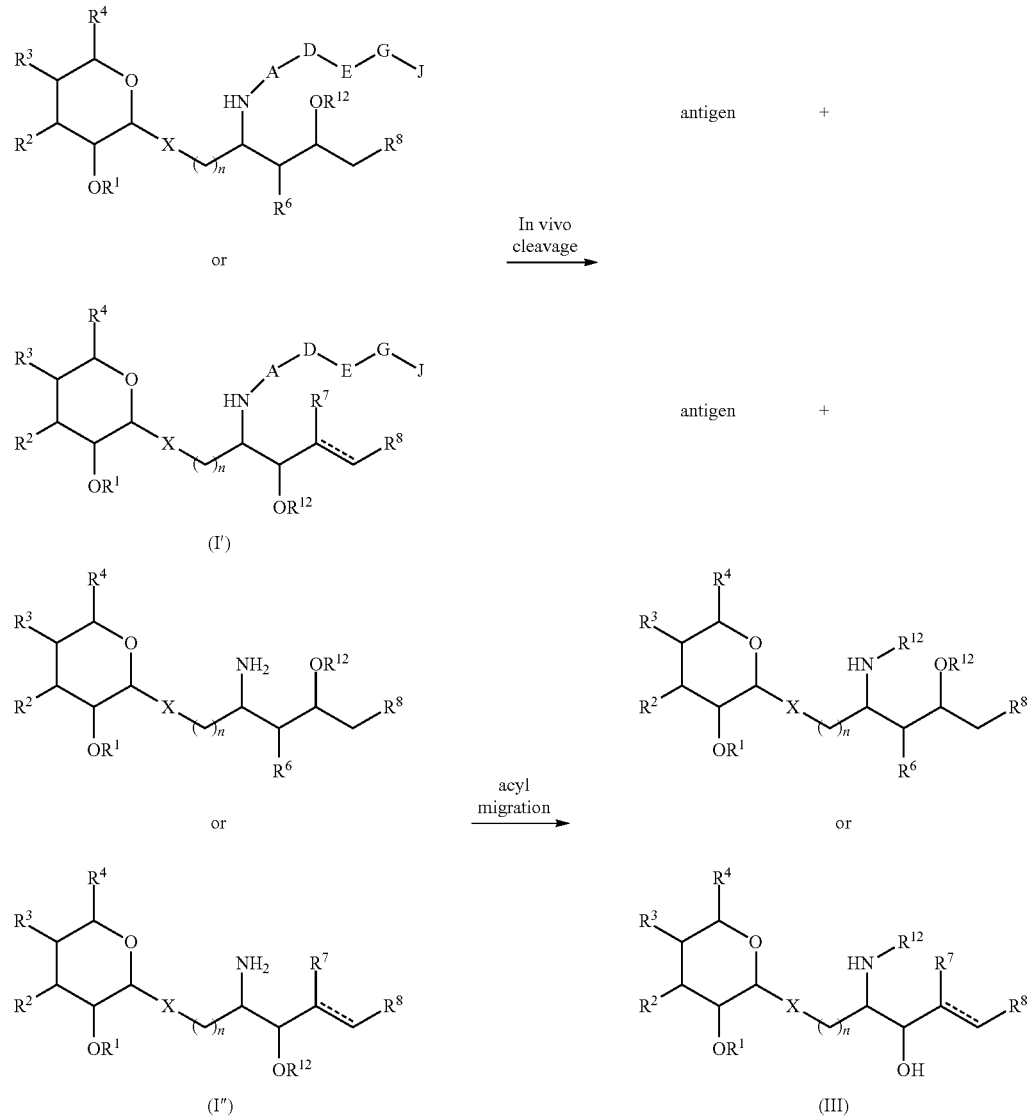

In a further embodiment of the invention, compounds (I″) can be chemically modified to produce a series of prodrug compounds, which are compounds of formula (I) and (II) of the invention (e.g. compounds (a) to (r) and (aa) to (qq) as shown above and those shown in Schemes 2 and 4.
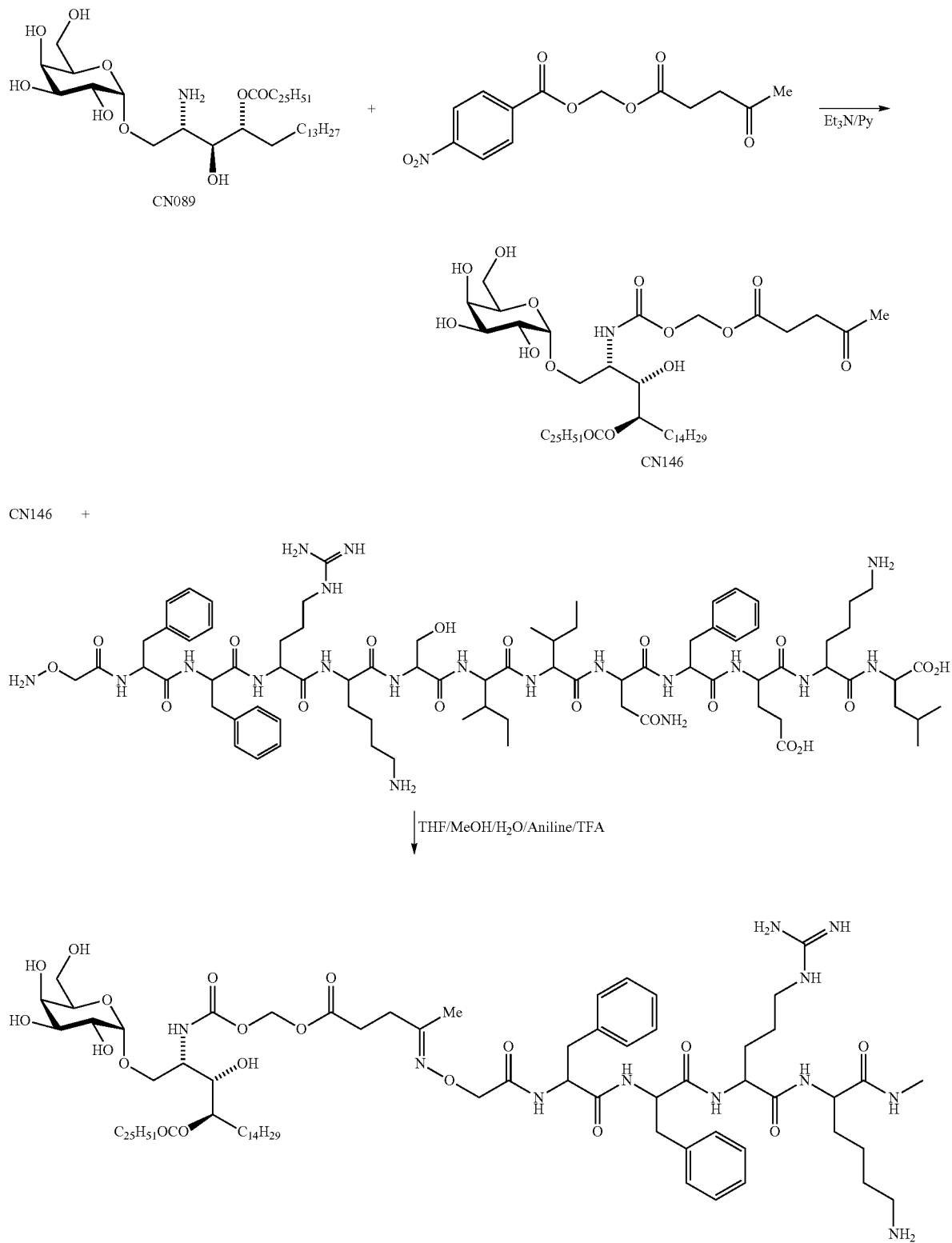
Scheme 2

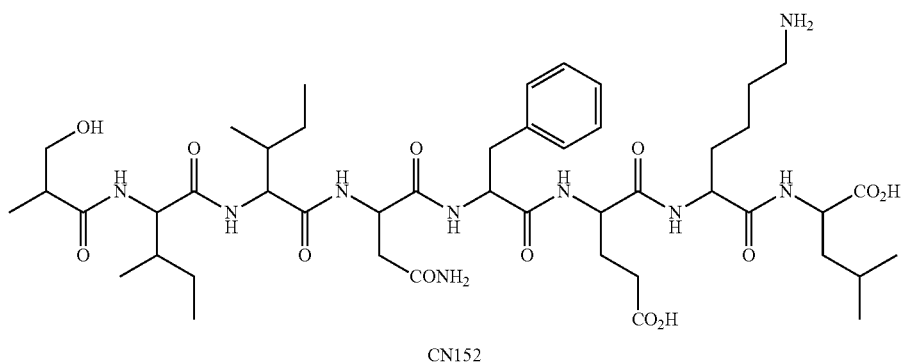
Scheme 3
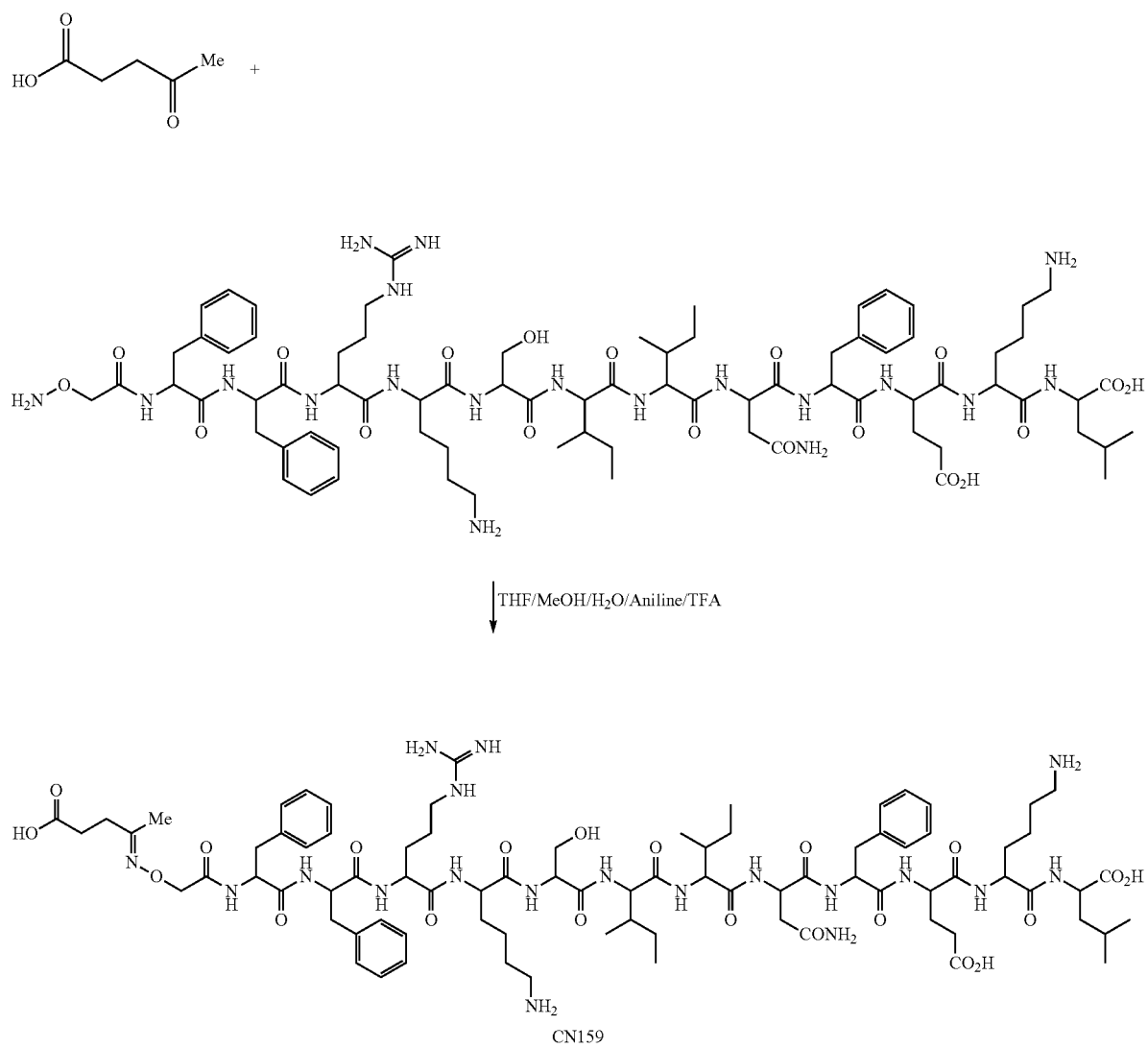

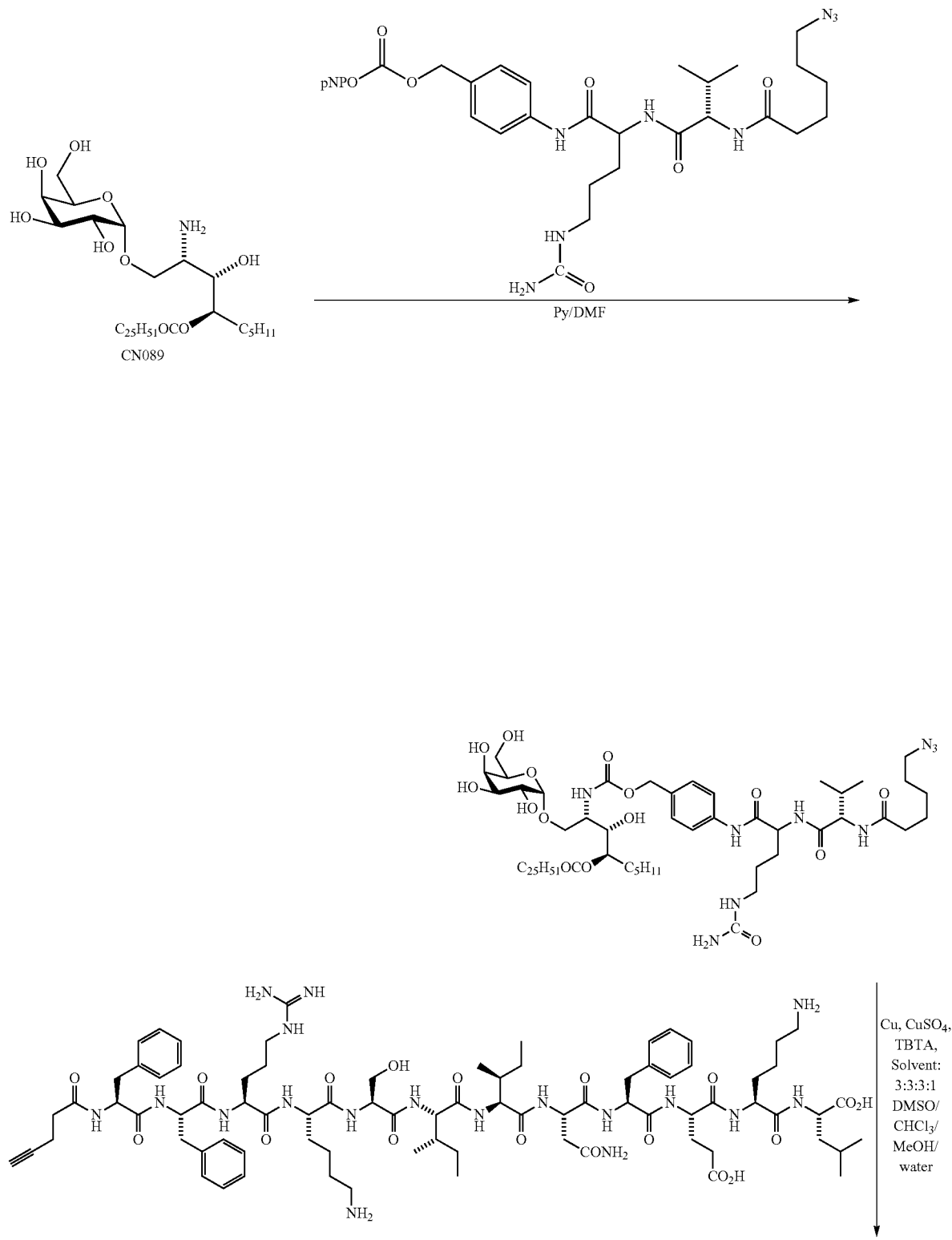
Scheme 4

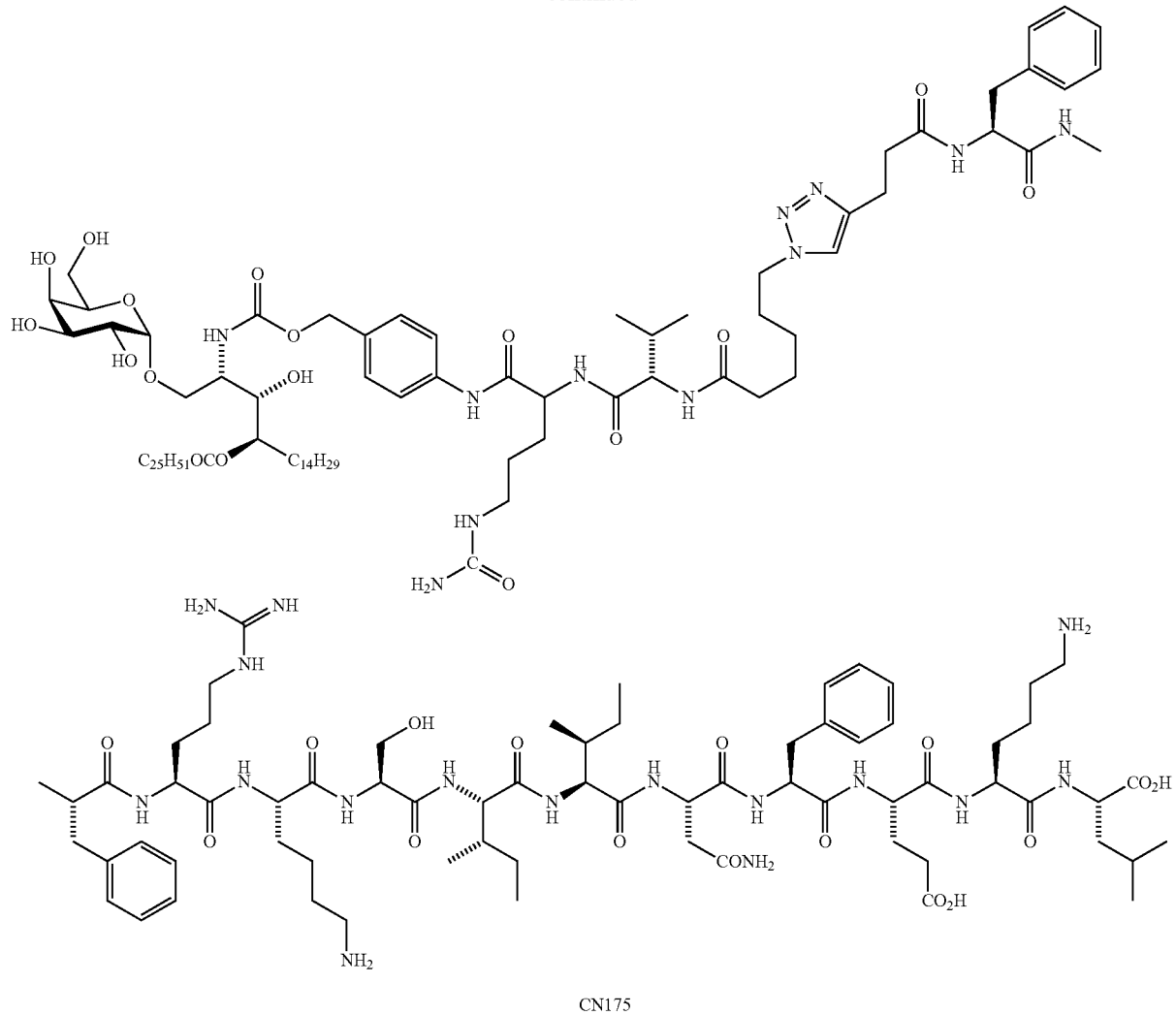

CN175

When injected into mice CN152 or CN175 potently activates DCs in an NKT cell-dependent manner, as defined by increased expression of the activation marker CD86 on the surface of splenic DCs (FIG. 1). Without wishing to be bound by theory, the applicants hypothesise that the observed activity is due to reversion of CN152 or CN175 to α-GalCer by the action of esterases and/or proteases followed by O→N acyl-migration.

Advantageously, vaccination of mice with CN152 is immunologically superior to vaccination with the individual components (α-GalCer and peptide). For example, vaccination with CN152 (which contains the peptide SIINFEKL— an epitope of chicken ovalbumin protein that binds the MHC molecule H-2K$^b$) results in a larger population of peptide-specific T cells (defined as Vα2$^+$ CD45.1$^+$ cells by flow cytometry) as compared with vaccination with admixed α-GalCer and SIINFEKL peptide, or α-GalCer and the same peptide with the N-terminal substitution required for linkage (CN159). The increased activity is dependent on a sub-set of splenic antigen-presenting cells known as langerin$^+$ CD8α$^+$ DCs (FIG. 2).

The increase in peptide-specific T cells for the conjugate compounds of the invention translates into a much stronger vaccine as evidenced by the superior capacity of the induced T cells to kill peptide-bearing target cells in vivo. This activity is dependent on NKT cells and CD1d, as cytotoxicity is not seen in animals genetically deficient in CD1d expression (FIG. 3).

A conjugate compound of the invention containing chemical features from both CN152 (i.e. the oxime linkage) and CN175 (the para-aminobenzyl linker group), CN174, also possesses potent cytotoxicity in an in vivo assay (FIG. 4).

Although less potent than CN175, a conjugate compound of the invention containing both oxime and acyloxycarbamate functional groups also induces a larger population of T cell response as compared to admixed controls (FIG. 5).

The exhaustion of NKT cells by α-GalCer is well documented (Parekh, Wilson et al. 2005). Therefore it is observed that re-administration of α-GalCer following earlier vaccinations that contained free α-GalCer results in no measurable activation of DCs. However, it is surprising that administration of α-GalCer following vaccination with CN152, CN165 or CN166 does lead to some DC activation (FIGS. 6 and 7).

Advantageously, this indicates that the compounds of the invention, such as CN152 or prodrug compounds such as CN165 or CN166, do not, unlike α-GalCer, completely exhaust NKT cells. A pool of responding cells remains, making it possible to include a "boosting step" when using conjugate compounds of the invention such as CN152 in vaccination protocols. Indeed, repeated administration of either CN152 or CN175 induces further T cell expansion (FIG. 8) whereas the same is not observed for repeated administration of α-GalCer with the long peptide KISQAVHAAHAEINEAGRESIINFEKLTEWT ("ISQ-SI-INFEKL") (SEQ ID NO: 141).

Vaccination of mice with CN152 or CN175 after priming with α-GalCer+peptide also leads to a T cell response (FIG. 9). This is most surprising since it would be expected that the NKT cells would be exhausted at this point (14 days post α-GalCer prime) and the T cell response observed for the conjugates (i.e. CN152 and CN175) is CD1d dependent (FIG. 3).

The increased T cell response observed with the conjugate compounds of the invention as compared to admixed administration also translates into an increased anti-tumour effect as a therapy for the murine model for melanoma, B16-OVA (FIG. 10).

The increased cytotoxicity observed for the conjugate compounds of the invention is not limited to the CD8 epitope SIINFEKL (SEQ ID NO: 262), as evidenced by CN178, which contains the CD8 epitope from lymphochoriomengitis virus glycoprotein ("gp33"; KAVYNFATM (SEQ ID NO: 129)) and can induce a potent T cytotoxic response as compared to admixed controls, including the N-terminal substituted peptide (lev-FFRK-gp33, which is prepared as described in Scheme 3 for CN 153, and in which amino acids 5-13 comprise SEQ ID NO: 129) (FIG. 11).

A significant T cell response, in terms of cytotoxicity, can also be observed for a vaccine containing a modified peptide sequence from the tumour-associated antigen gp100 [gp100$_{25-33(27P)}$]. In particular, CN197 induces superior cytotoxicity as compared to admixed controls (FIG. 12).

Allergen-specific CD4$^+$ T cells promote allergic asthma by stimulating IgE antibody production and recruiting leukocytes into the airways. In contrast, allergen-specific CD8$^+$ T cells that have differentiated into cytotoxic T lymphocytes (CTLs) can play a protective role (Enomoto, Hyde el al. 2012). However, these approaches generally require the adoptive transfer of allergen-specific CD8$^+$ T cells, as common vaccination strategies with whole allergens would run the risk of exacerbating disease through activation of the allergen-specific CD4$^+$ T cells that are central to the development of the allergic response (Wills-Karp, 1999). In models of airway inflammation using ovalbumin as a model allergen, vaccination of sensitized mice with CN152 one week before challenge is sufficient to significantly suppress leukocyte infiltration into the lungs, whereas vaccination with α-GalCer and peptide ("unconjugated", FIG. 13) is not. The conjugate compound of the invention CN178, which contains an irrelevant antigen, also does not significantly prevent leukocyte infiltration, although it does have some impact on infiltration of eosinophils (FIG. 13).

Also, compound CN188, containing an immunodominant HLA-A2-binding epitope from cytomegalovirus (NLVPMVATV (SEQ ID NO: 199) (i.e. α-GalCer-NLV-conjugate), is superior to admixed peptide antigen and α-GalCer in the expansion of peptide-specific human CD8 T cells from a cytomegalovirus sero-positive donor in an in vitro assay (FIG. 14).

Other Aspects

The compounds of the invention may be administered to a patient by a variety of routes, including orally, parenterally, by inhalation spray, topically, rectally, nasally, buccally, intravenously, intra-muscularly, intra-dermally, subcutaneously or via an implanted reservoir, preferably intravenously. The amount of compound to be administered will vary widely according to the nature of the patient and the nature and extent of the disorder to be treated. Typically the dosage for an adult human will be in the range 50-15000 μg/m². The specific dosage required for any particular patient will depend upon a variety of factors, including the patient's age, body weight, general health, sex, etc.

For oral administration the compounds of the invention can be formulated into solid or liquid preparations, for example tablets, capsules, powders, solutions, suspensions and dispersions. Such preparations are well known in the art as are other oral dosage regimes not listed here. In the tablet

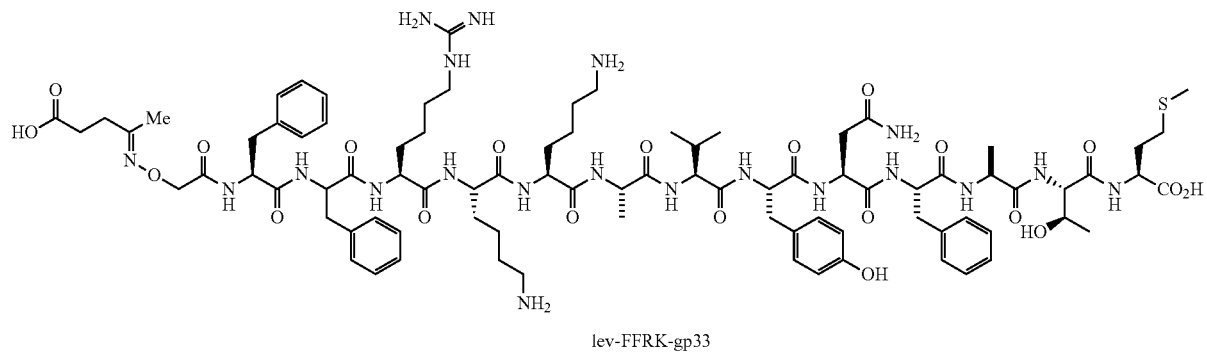

lev-FFRK-gp33 form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried corn-starch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant. In one preferred embodiment, the compounds are administered by intravenous injection, where the diluent comprises an aqueous solution of sucrose, L-histidine and a pharmaceutically acceptable surfactant, e.g. Tween 20.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Synthesis of the Compounds of the Invention

The applicant has surprisingly found that, in the synthesis of α-GalCer, hydrogenolytic deprotection of compound 1 with $Pd(OH)_2$ leads to the isolation of significant quantities of CN089 (Scheme 5). In particular, when 1 is subjected to $Pd(OH)_2$-catalyzed hydrogenolysis in 3:7 $CHCl_3$/MeOH at 35° C., in addition to the expected product, a more polar compound is isolated in 17% yield. This compound is determined to be amine CN089, an isomer of α-GalCer in which the $C_{26}$-acyl chain has undergone a 1,3 N→O migration. The location of the acyl group on O4 of the side-chain is established using 2D-NMR techniques. Although intramolecular N→O migrations of acyl groups are known in the literature they are usually promoted in strongly acidic media (Baadsgaard and Treadwell 1955; Drefahl and Hörhold 1961; Butler, O'Regan et al. 1978; Schneider, Hackler et al. 1985; Johansen, Kornø et al. 1999). Without wishing to be bound by theory, the applicant hypothesises that, in the present case, it would appear that a certain amount of HCl is produced from the solvent $CHCl_3$ under the hydrogenolytic conditions, leading to the observed migration.

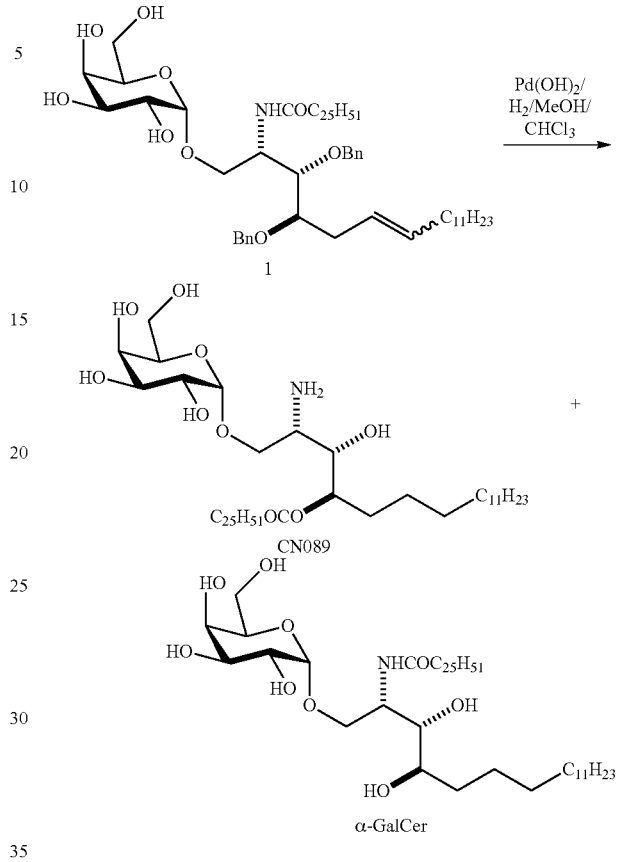

Scheme 5

Alternative conditions for the formation of CN089 (Scheme 6) are as follows: when α-GalCer is heated in 1,4-dioxane with aq HCl, N→O migration of the $C_{26}$-acyl chain is effected and CN089 is isolated in 65-70% yield after chromatography.

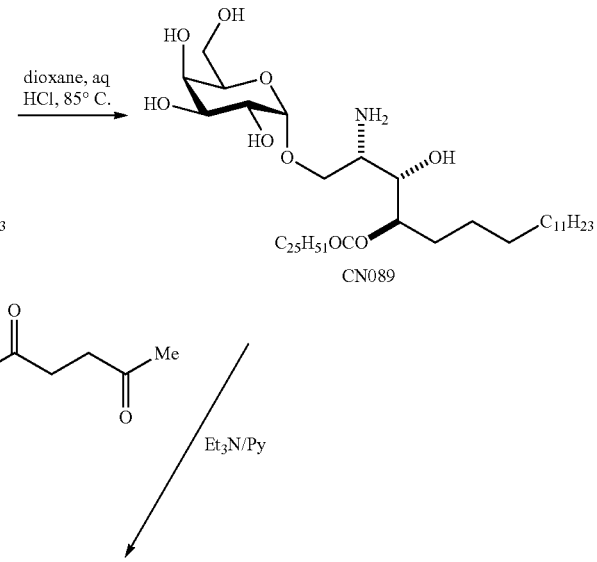

Scheme 6

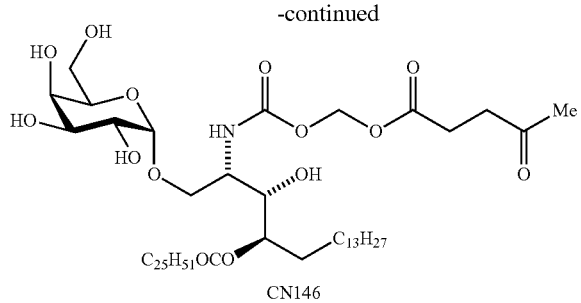

CN146

The overall synthetic strategy for the compounds of the invention therefore includes the isomerization of α-GalCer or its congeners (which are compounds of formula (III) as shown above in Scheme 1) under acidic conditions to give compounds with a free amino group where the fatty acid has migrated to an O-atom on the sphingosine chain (compounds of formula (I″) as shown in Scheme 1) followed by subsequent functionalisation of the free amine to give compounds of formula (I) or formula (II) of the invention. Certain targets may not be accessible by this approach. An alternative strategy, shown in Scheme 8, involves the synthesis of N-protected intermediates 6 followed by acylation of the sphingosine chain hydroxyl group(s) with $R^{12}$ to give compounds 7. After various functional group transformations, the N-protecting group is cleaved to give compounds of formula (I″), which are converted to compounds of formula (I) or formula (II) in the usual manner.

Compounds (I″) are prepared according to the following general procedures:

General Method (1) for the Synthesis of Compounds of Formula (I″)

(wherein $R^4$ is Me, $CH_2OH$, $CH_2OR^{10}$, $CH_2OR^{11}$, $CO_2H$; $R^6$ is OH and $R^7$ is $OR^{12}$, or $R^6$ is H and $R^7$ is $OR^{12}$, or $R^6$=$OR^{12}$ and $R^7$=H.)

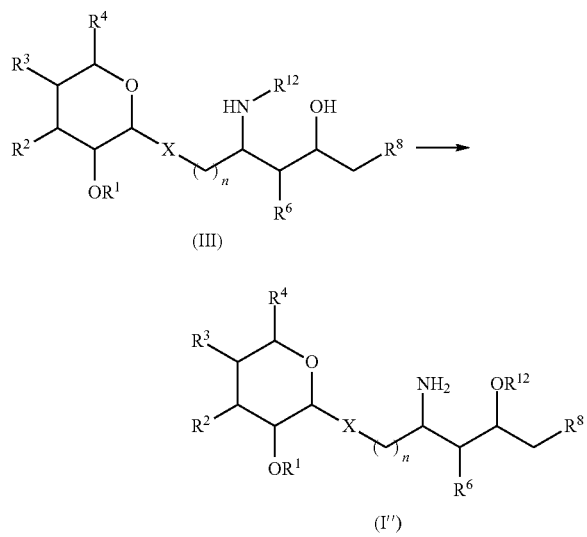

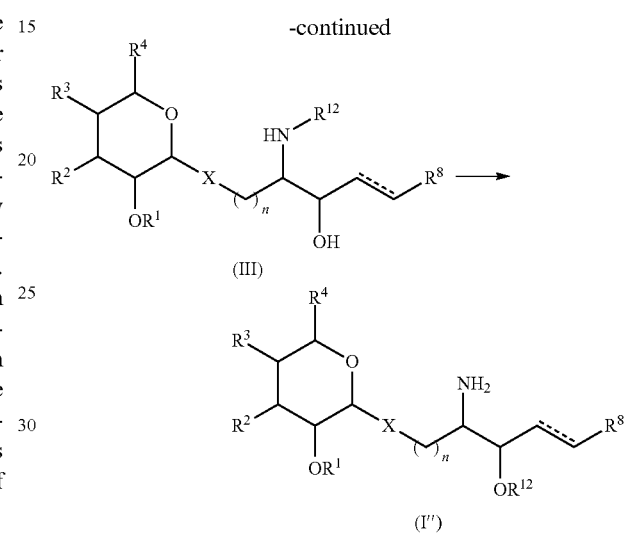

Starting materials of formula (III) (wherein $R^4$ is Me, $CH_2OH$, $CH_2OR^{10}$, $CH_2OR^{11}$ or $CO_2H$; and $R^6$ is OH and $R^7$ is OH, or $R^6$ is H and $R^7$ is OH, or $R^6$ is OH and $R^7$ is H) are synthesized according to literature methods referenced herein, and in some cases, by combining elements of two or more literature methods. (For a recent review of α-GalCer analogues synthesized, see Banchet-Cadeddu et al (Banchet-Cadeddu, Henon et al. 2011)). For example, a key step in all syntheses of α-GalCer is the coupling of a suitably protected donor with a suitably functionalized acceptor in a glycosylation reaction. A wide variety of donors have been used in the synthesis of α-GalCer analogues, which allows variation of groups $R^1$-$R^4$ and the stereochemistry of these groups. Methods for the synthesis of donors where $R^1$ is glycosyl, (Veerapen, Brigl et al. 2009) $R^2$ or $R^3$ is O-glycosyl, (Kawano, Cui et al. 1997) $R^2$ or $R^3$ is either H or F, (Raju, Castillo et al. 2009) $R^4$ is Me, (Tashiro, Nakagawa et al. 2008) $CH_2OR^{10}$, (Uchimura, Shimizu et al. 1997) $CH_2OR^{11}$, (Tashiro, Nakagawa et al. 2008) or $CO_2H$, (Deng, Mattner et al. 2011) have been reported. An equally large variety of acceptors have also been employed. For example, all 8 stereoisomers of a protected phytosphingosine acceptor have been synthesized in an approach that also allows modification of the group $R^8$ (Park, Lee et al. 2008; Baek, Seo et al. 2011). Furthermore, 3-deoxy (Baek, Seo et al. 2011) and 4-deoxy phytosphingosine (Morita, Motoki et al. 1995; Howell, So et al. 2004; Du, Kulkarni et al. 2007) derivatives have also been described. Combination of these acceptors with various donors leads to protected α-GalCer derivatives which are transformed, by literature methods referenced above, to the unprotected α-GalCer analogues, which comprise the starting materials (III) (where X is O) in the present General Method 1. For starting materials (III) in which X is $CH_2$ and $R^7$ is OH, syntheses have been described (Chen, Schmieg et al. 2004; Lu, Song et al. 2006; Wipf and Pierce 2006; Pu and Franck 2008). Variation of the group $R^4$ is available by adapting the protecting group chemistry used on intermediates XI and XII in the reported procedures.

For starting materials (III) where X is $CH_2$ and $R^7$ is H, these are synthesized according to reported methods (Chen, Schmieg et al. 2004) using sphingosine as the starting material in place of phytosphingosine. For starting materials (III) in which X is S, syntheses have been described (Dere and Zhu 2008; O'Reilly and Murphy 2011).

The starting material (III) (~5 mM) is stirred in a suitable solvent (e.g. 10:1 1,4-dioxane-water) with acid (eg 1 M HCl, TFA) at an appropriate temperature (60-100° C.) until the reaction is judged to be ~75% complete (TLC). The solvents are removed and the crude residue is purified by column chromatography on silica gel.

Alternative General Method (2) for Synthesis of Compounds of Formula (I'').

(wherein X is O; $R^1$ is H; $R^2$ and $R^3$ are OH; $R^4$ is Me, $CH_2OH$, $CH_2OCOR^{11}$, $CH_2SH$, $CH_2SR^{11}$, $CH_2SOR^{11}$, $CH_2SO_2R^{11}$, $CH_2NHCOR^{11}$, $CH_2NHCO_2R^{11}$, $CH_2NHCONH_2$, $CH_2NHCONHR^{11}$, $CH_2NHCON(R^{11})_2$, $CH_2NHSO_2R^{11}$, $CH_2PO_3H_2$, $CH_2OSO_3H$ or $CH_2OPO_3H$; $R^6$ is $OR^{12}$ and $R^7$ is OH, or $R^6$ is OH and $R^7$ is $OR^{12}$, or $R^6$ and $R^7$ are $OR^{12}$, or $R^6$ is H and $R^7$ is $OR^{12}$, or $R^6$ is $OR^{12}$ and $R^7$ is H.)

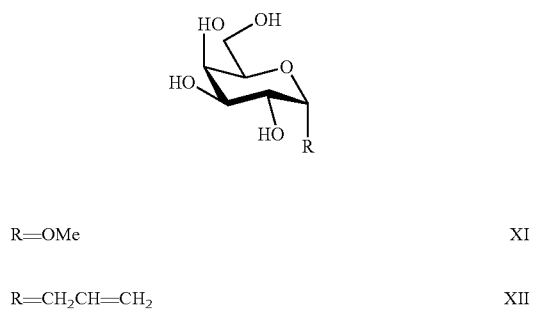

R=OMe      XI

R=$CH_2CH=CH_2$      XII

Scheme 8

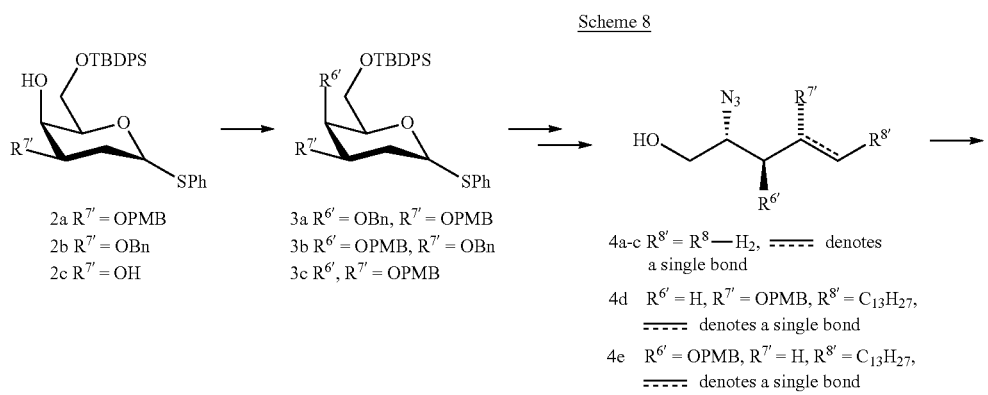

2a $R^{7'}$ = OPMB
2b $R^{7'}$ = OBn
2c $R^{7'}$ = OH

3a $R^{6'}$ = OBn, $R^{7'}$ = OPMB
3b $R^{6'}$ = OPMB, $R^{7'}$ = OBn
3c $R^{6'}, R^{7'}$ = OPMB 4a-c $R^{8'}$ = $R^8$—$H_2$, ----- denotes a single bond
4d $R^{6'}$ = H, $R^{7'}$ = OPMB, $R^{8'}$ = $C_{13}H_{27}$, ----- denotes a single bond
4e $R^{6'}$ = OPMB, $R^{7'}$ = H, $R^{8'}$ = $C_{13}H_{27}$, ----- denotes a single bond

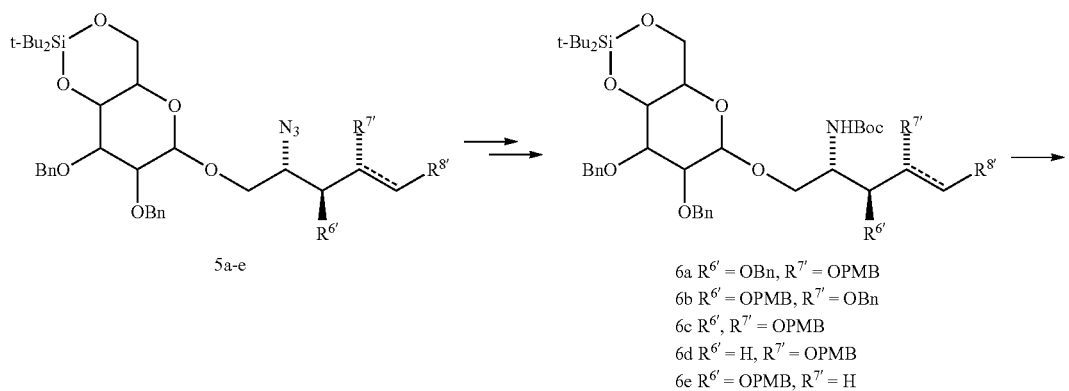

5a-e

6a $R^{6'}$ = OBn, $R^{7'}$ = OPMB
6b $R^{6'}$ = OPMB, $R^{7'}$ = OBn
6c $R^{6'}, R^{7'}$ = OPMB
6d $R^{6'}$ = H, $R^{7'}$ = OPMB
6e $R^{6'}$ = OPMB, $R^{7'}$ = H

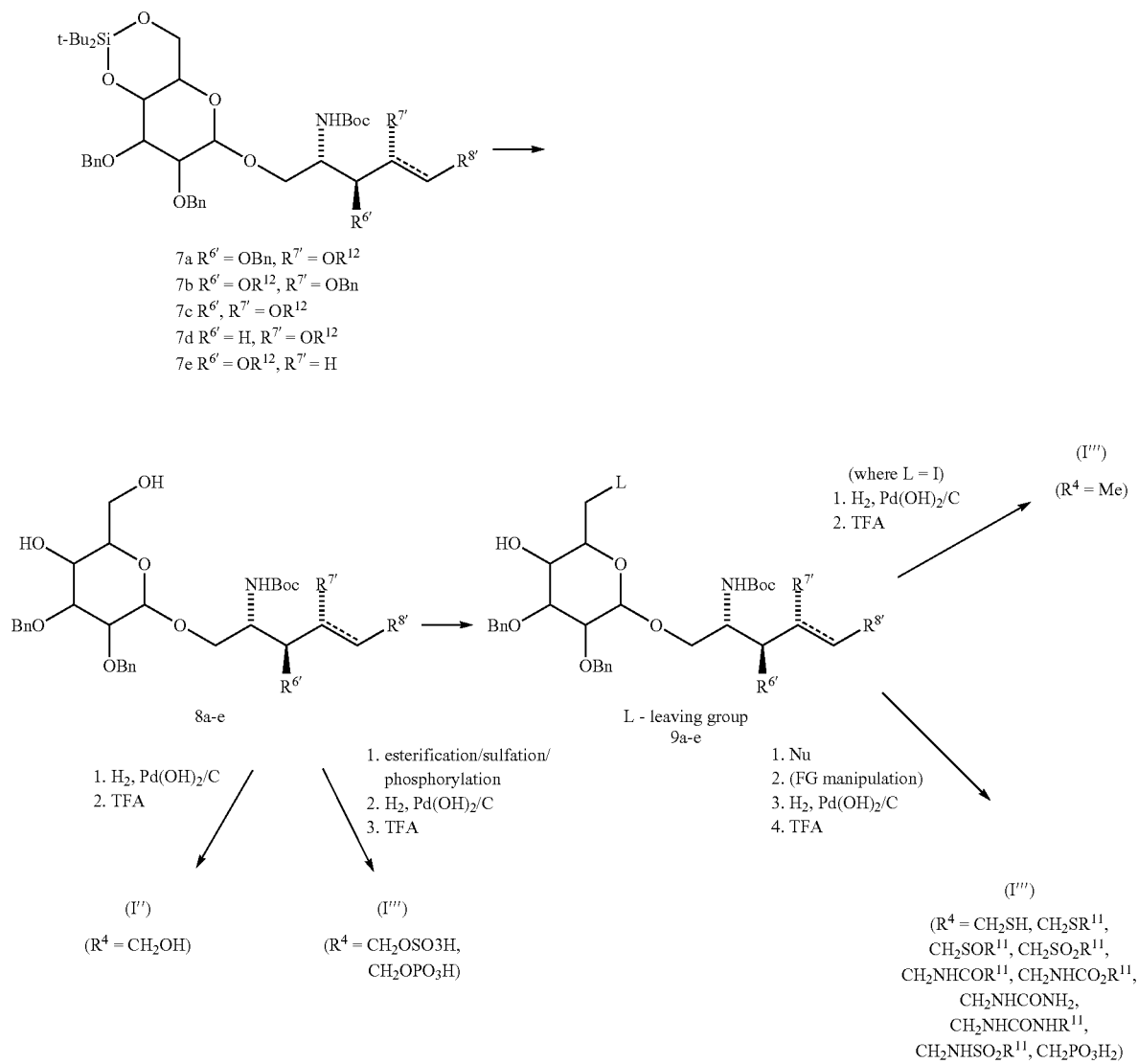

The free hydroxyl groups of compound 2α-c (Sakurai and Kahne 2010) (Scheme 6) are either benzylated or p-methoxybenzylated using NaH as base in THF or DMF. The products 3α-c are converted to acceptors 4α-c following reported procedures for the corresponding dibenzyl compounds (Plettenburg, Bodmer-Narkevitch et al. 2002; Lee, Farrand et al. 2006). PMB ether 4d is obtained from D-ribo-phytosphingosine as reported for the corresponding Bn ether (Trappeniers, Goormans et al. 2008; Baek, Seo et al. 2011). PMB ether 4e is obtained from sphingosine by a) conversion of the amino group to an azide with trifluoromethanesulfonyl azide; b) TBDPS-protection of the primary hydroxyl group; c) PMB-protection of the secondary hydroxyl group; d) desilylation. Glycosylation is effected using an appropriately protected glycosyl trichloroacetimidate donor (1.5 equiv) and TMSOTf (0.1 equiv) as activator in dry THF/ether. Appropriate protecting groups include benzyl and di-tert-butylsilylene. The azido group of 5a-e is reduced under Staudinger conditions (PMe$_3$, THF then aq NaOH) followed by amine-protection with Boc$_2$O in CH$_2$Cl$_2$. The PMB groups of 6a-e are cleaved with either CAN or DDQ in CH$_2$Cl$_2$-water and the free hydroxyl groups esterified with the appropriate carboxylic acid (R$^{12}$OH) in the presence of DCC, DMAP to give esters 7a-e. Cleavage of the di-tert-butylsilyl group with TBAF gives intermediates 8a-e which may be treated in various ways to provide compounds of formula (I″) with a variety of different R$^4$ groups. For example, hydrogenolysis followed by N-Boc deprotection gives compounds of formula (I″) where R$^4$ is CH$_2$OH. Alternatively, the primary hydroxyl group of 8 may be esterified, sulfated or phosphorylated, and subsequently deprotected in a similar fashion, to give compounds of formula (I″) where R$^4$ is CH$_2$OCOR$^{11}$, CH$_2$OSO$_3$H or CH$_2$OPO$_3$H$_2$. Conversion of the primary hydroxyl group of 8 to a leaving group (eg, iodide, tosylate, compounds 9a-e) followed by nucleophilic displacement gives access into thioethers and related derivatives, amides, carbamates, ureas, N-sulfonates and phosphonates which, after removal of protecting groups, leads to further compounds of formula (I″).

Amines (I'') are further transformed into compounds of formula (II) (as shown below in General Method 3) according to the following general procedures:

General Method (3) for Synthesis of Compounds of Formula (II)

Scheme 9

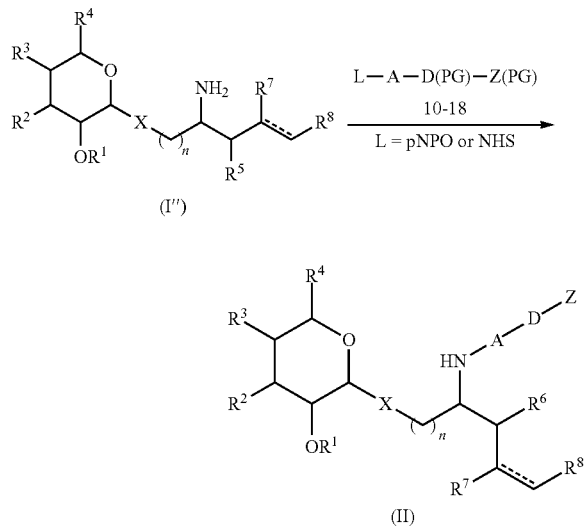

pNPO = 4-nitrophenoxy
NHS = N-hydroxysuccinimide

For the preparation of compounds of formula (II) (Scheme 9), a mixture of amine (I'') (0.05-0.1 M), activated carbonate or ester 10-18 (where D(PG) may be D as defined herein for formula (I) and (II) or a protected form of D, and where Z(PG) may be Z as defined herein for formula (II) or a protected form of Z) (1.05-2 equiv) and NEt$_3$ (0-10 equiv) are stirred in a suitable solvent (e.g. pyridine, pyridine-CHCl$_3$, CHCl$_3$-MeOH, DMF, DMSO) at ambient temperature until the reaction is essentially complete (TLC). Diethylamine may be added to quench excess reagent. After concentration of the mixture, the residue is purified by column chromatography on silica gel and/or C18 silica gel. Any protecting groups in D(PG) and/or Z(PG) are subsequently removed, by standard methods, (Isidro-Llobet, Alvarez et al. 2009). The deprotected products are purified by chromatography on silica gel and/or C18 silica gel.

Scheme 9a

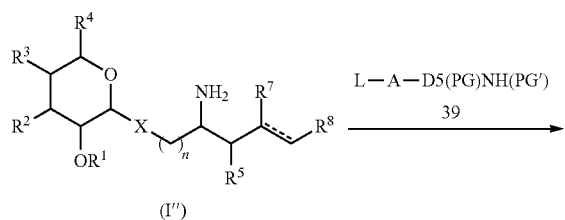

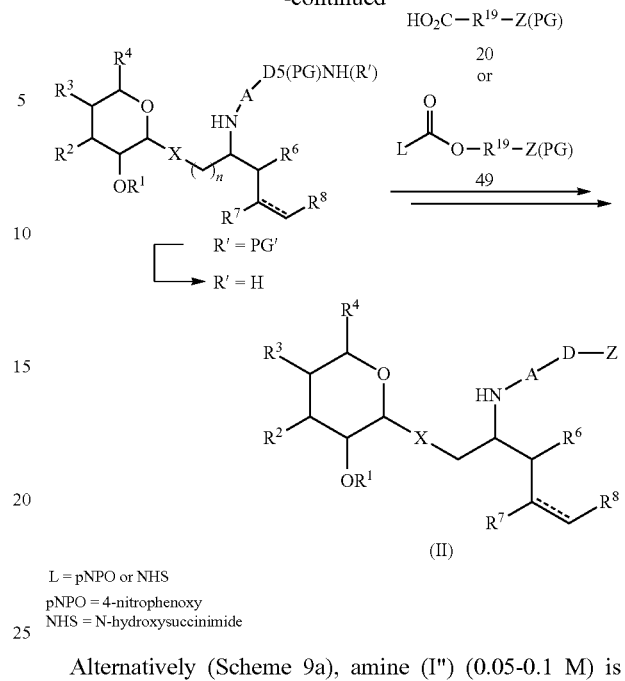

L = pNPO or NHS
pNPO = 4-nitrophenoxy
NHS = N-hydroxysuccinimide

Alternatively (Scheme 9a), amine (I'') (0.05-0.1 M) is reacted with activated carbonate or ester 39 (Dubowchik, Firestone et al. 2002) (where PG' is defined as an amine protecting group, e.g. Fmoc, Boc, Alloc, preferably Fmoc) under similar conditions to the reaction shown in Scheme 9). PG' is removed by standard methods, (Isidro-Llobet, Alvarez et al. 2009), e.g. piperidine/DMF for removal of the Fmoc group, and the resulting amine is coupled with a reagent containing the component Z(PG), where Z(PG) may be Z as defined herein for formula (II) or a protected form of Z. The reagent may be a) a carboxylic acid (20), in which case standard peptide coupling activators (e.g. HBTU, HATU) are employed; or b) an activated ester (e.g. NHS ester, pNP ester, mixed carbonic anhydride) which is derived from carboxylic acid 20 by standard methods; or c) an activated carbonate 49 (preferably pNP carbonate) which is derived from the corresponding alcohol. Any protecting groups in D(PG) and/or Z(PG) are subsequently removed, by standard methods, (Isidro-Llobet, Alvarez et al. 2009). The deprotected products are purified by chromatography on silica gel and/or C18 silica gel.

General Method (4) for Synthesis of Reagents 10

Scheme 10

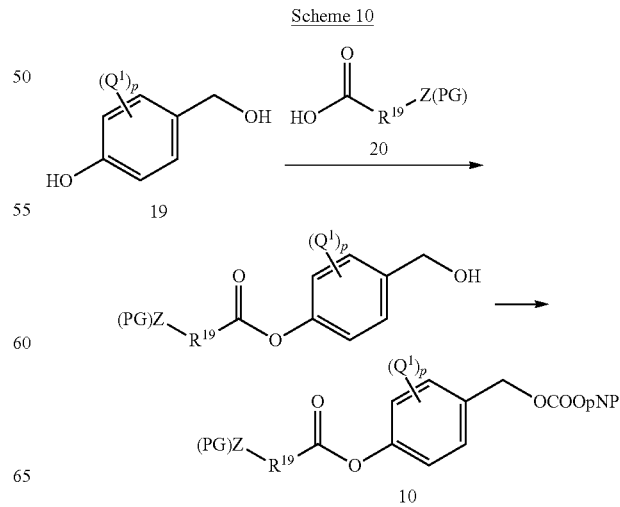

Esters 10 (where Z(PG) may be Z as defined herein for formula (II) or a protected form of Z) are synthesized by the reaction of 4-hydroxybenzylic alcohols 19 with carboxylic acids or their activated esters in accordance with or by adapting literature procedures (Greenwald, Pendri et al. 1999). In some cases, it may be advantageous to use a protected form of 19, eg, 4-hydroxybenzyl THP ether or 4-hydroxybenzaldehyde. The benzylic alcohol products are subsequently converted to the corresponding p-nitrophenyl carbonates 10 by reaction with bis(p-nitrophenyl carbonate) and Hünig's base in DMF (Dubowchik, Firestone et al. 2002). Benzylic alcohols 19 are commercially available or obtained by simple derivatisation of commercially available 4-hydroxybenzyl alcohols. Acids 20 are commercially available, or accessed by standard chemical transformations of common starting materials (e.g. terminal alkenoic acids, hydroxyalkanoic acids, haloalkanoic acids, aminoalkanoic acids, alkanedioic acids), or by following literature methods: (Iha, van Horn et al. 2010) for Z=Z8; (Hudlicky, Koszyk et al. 1980) for Z=Z12; (Saxon and Bertozzi 2000) for Z=Z14; (Tam, Soellner et al. 2007) for Z=Z15. Acids 20 containing a keto group (Z=Z1), may also be accessed by coupling of 2-metallated alkenyl reagents with haloalkanoic esters (Hatakeyama, Nakagawa et al. 2009), followed by ozonolysis of the double bond. In certain cases, groups Z in 20 may be used in protected form Z(PG) (eg, phthalimides for Z8 and Z9, thioester or disulfide for Z10, acetal or alkene for Z16, Tbeoc-Thz for Z17 (Fang, Wang et al. 2012).

General Method (5) for Synthesis of Reagents 11 solution is transferred to a solution of the amine 21 in $CH_2Cl_2$/MeOH. The reaction is generally complete within 2 h at room temperature. An alternative method involves reaction of 21 with the NHS ester of 20 in a polar aprotic solvent (eg, DMF, NMP) (Dubowchik, Firestone et al. 2002). Amines 21 may also be reacted with activated carbonates 49 (preferably pNP carbonate) derived from the corresponding alcohol, to give carbamate products. The hydroxyl group of the resulting amide or carbamate products is subsequently converted to the corresponding p-nitrophenyl carbonates 11 by reaction with bis(p-nitrophenyl carbonate) and Hünig's base in DMF (Dubowchik, Firestone et al. 2002).

General Method (6) for Synthesis of Carbonate and Carbamate Reagents 12-15

Scheme 12

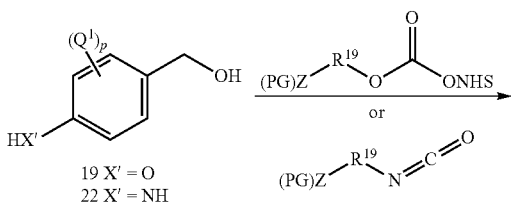

Scheme 11

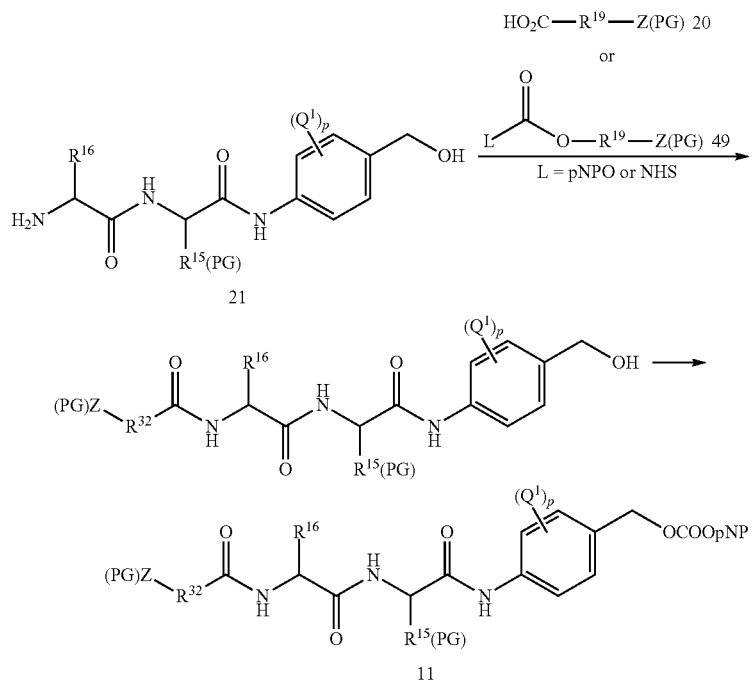

-continued

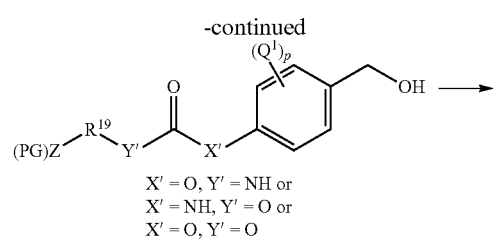

Dipeptides 11 (where $R^{15}$(PG) may be $R^{15}$ as defined herein for formula (I) or a protected form of $R^{15}$ and where Z(PG) may be Z as defined herein for formula (II) or a protected form of Z) are prepared by reaction of amines 21 (Dubowchik, Firestone et al. 2002) with the appropriate acid 20 using the chloroformate method (Chaudhary, Girgis et al. 2003) to give amide products. Briefly, 20 (1.3 equiv) is dissolved in solvent (eg, in $CH_2Cl_2$, THF, ether) and treated at 0° C. with $NEt_3$ (1.4 equiv) followed by isobutyl chloroformate (1.25 equiv) and, after ~30 min, the resulting -continued

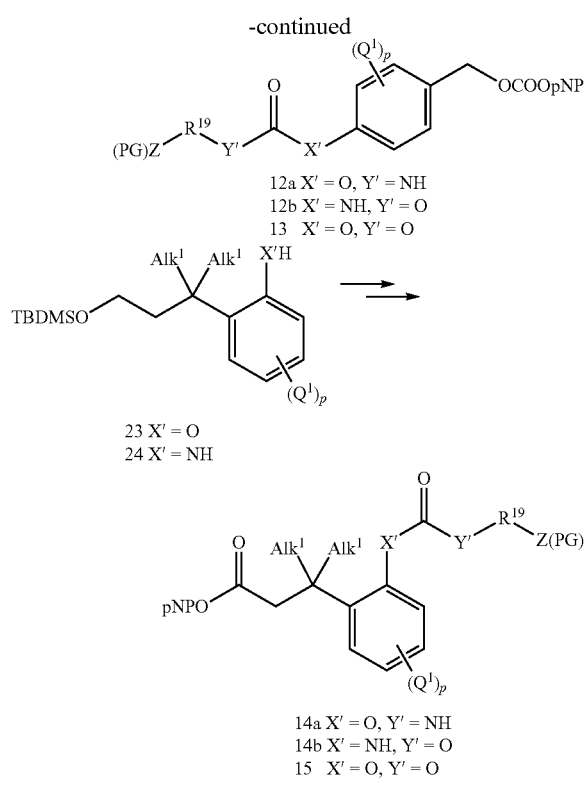

12a X' = O, Y' = NH
12b X' = NH, Y' = O
13  X' = O, Y' = O

23 X' = O
24 X' = NH

14a X' = O, Y' = NH
14b X' = NH, Y' = O
15  X' = O, Y' = O

Carbamates 12 and carbonates 13 (where Z(PG) may be Z as defined herein for formula (II) or a protected form of Z) are prepared by reaction of 4-hydroxybenzylic alcohols 19 or 4-aminobenzylic alcohols 22 with isocyanates or activated NHS carbonates as reported (Greenwald, Pendri et al. 1999). In some cases, it may be advantageous to use a protected form of 19, eg, 4-hydroxybenzyl THP ether or 4-hydroxybenzaldehyde. The benzylic alcohol products are subsequently converted to the corresponding p-nitrophenyl carbonates 12, 13 by reaction with bis(p-nitrophenyl carbonate) and Hünig's base in DMF (Dubowchik, Firestone et al. 2002).

Carbamates 14 and carbonates 15 are prepared in a similar manner, from phenols 23 or anilines 24, with standard manipulations for conversion of the silyl ether group into an active ester (see General Methods 8 and 9).

General Method (7) for Synthesis of Reagents 16

Scheme 13

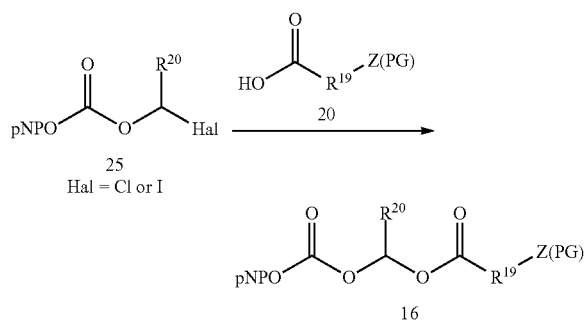

25
Hal = Cl or I

16

Esters 16 (where Z(PG) may be Z as defined herein for formula (II) or a protected form of Z) are prepared by reaction of α-haloalkyl 4-nitrophenyl carbonates 25, eg, iodomethyl 4-nitrophenyl carbonate (Gangwar, Pauletti et al. 1997) or α-chloroethyl 4-nitrophenyl carbonate) (Alexander, Cargill et al. 1988), with a carboxylic acid 20, either in the presence of $Ag_2O$ or $Cs_2CO_3$, or as the preformed salt, in an anhydrous solvent (e.g. MeCN, toluene, dioxane, DMF), at a temperature between 20 and 80° C.

General Method (8) for Synthesis of Reagents 17

Scheme 14

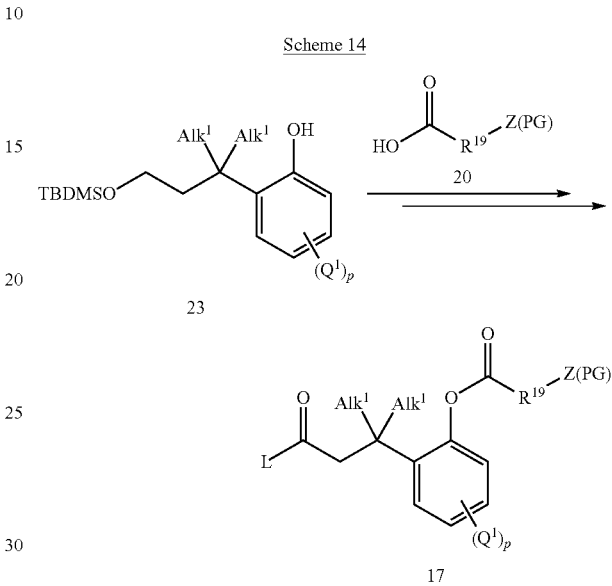

17

L = pNPO or NHS
(pNP = 4-nitrophenyl, NHS = N-hydroxysuccinimide)

Esters 17 (where Z(PG) may be Z as defined herein for formula (II) or a protected form of Z) are synthesised from phenols 23 in accordance with or by adapting literature procedures, (Carpino, Tnriolo et al. 1989; Amsberry and Borchardt 1991; Amsberry, Gerstenberger et al. 1991; Nicolaou, Yuan et al. 1996; Greenwald, Choe et al. 2000).

General Method (9) for Synthesis of Reagents 18

Scheme 15

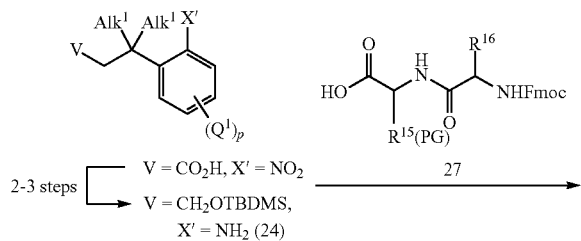

Dipeptides 18 (where Z(PG) may be Z as defined herein for formula (II) or a protected form of Z) are synthesised from o-nitrophenylacetic acid esters 26 (Scheme 15), obtained from commercial sources, or by known procedures, or by Arndt-Eistert homologation of the corresponding 6-nitrobenzoic acid esters (Atwell, Sykes et al. 1994)). The esters 26 are gem-dialkylated with an alkyl iodide and a suitable base (e.g. NaH, KO$^t$Bu, n-BuLi), optionally in the presence of 18-crown-6. The dialkylated product is, via the acid chloride, subjected to Arndt-Eistert homologation (CH$_2$N$_2$; then heat or Ag(II)). The carboxyl group is reduced to the alcohol oxidation level to prevent premature lactamization and the resulting alcohol is protected as the TBDMS ether. After reduction of the nitro group, the resulting amine 24 is coupled with dipeptides 27 (Dubowchik, Firestone et al. 2002). Fmoc cleavage is followed by amide or carbamate formation (see General Method 5). Finally, desilylation, oxidation and activation of the resulting carboxylic acid by standard methods gives reagents 18.

General Method (10) for Coupling of Antigen to Compounds of Formula (II) by Thiolene Ligation where Z is Z2, Z10 or Z17

Z is Z2: The compound of formula (II) and peptide-thiol 28a or N-terminal cysteinyl peptide 28b are dissolved in an appropriate solvent. Suitable solvent systems may include chloroform, THF, methanol, DMF, DMSO, tert-butanol, water, or mixtures thereof. After purging with Ar, the mixture is stirred in the presence of a radical initiator under photochemical conditions (Campos, Killops et al. 2008), or alternatively, under thermal conditions (Dondoni 2008). After completion of the reaction, the product is purified by chromatography on the appropriate solid phase (e.g. silica gel, C4, and/or C18 silica).

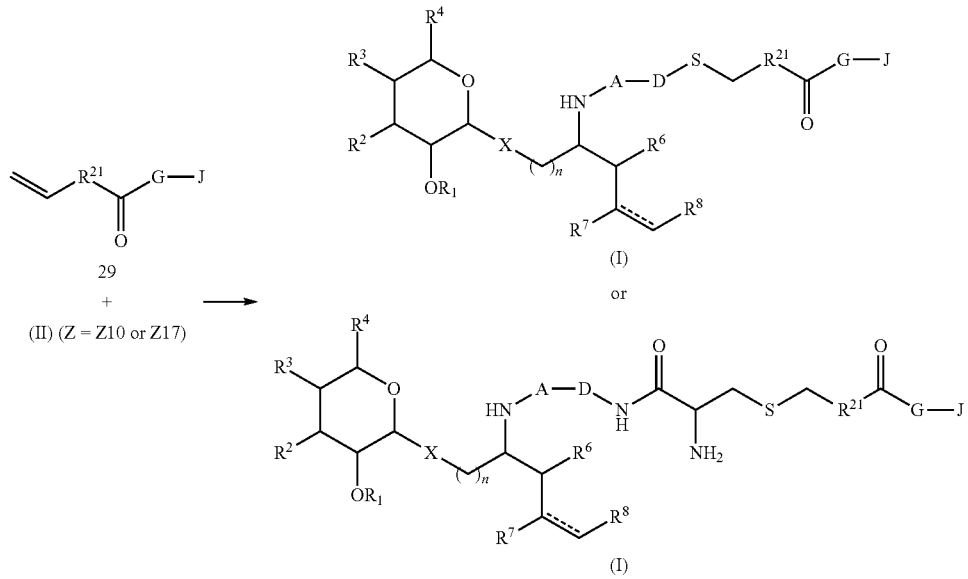

Scheme 17

Z is Z10 or Z17: The compound of formula (II) is reacted with N-terminal alkenoyl peptide 29 under the conditions described above.

General Method (11) for Coupling of Antigen to Compounds of Formula (II) by Azide-Alkyne Cycloaddition where Z is Z4, Z7 or Z23

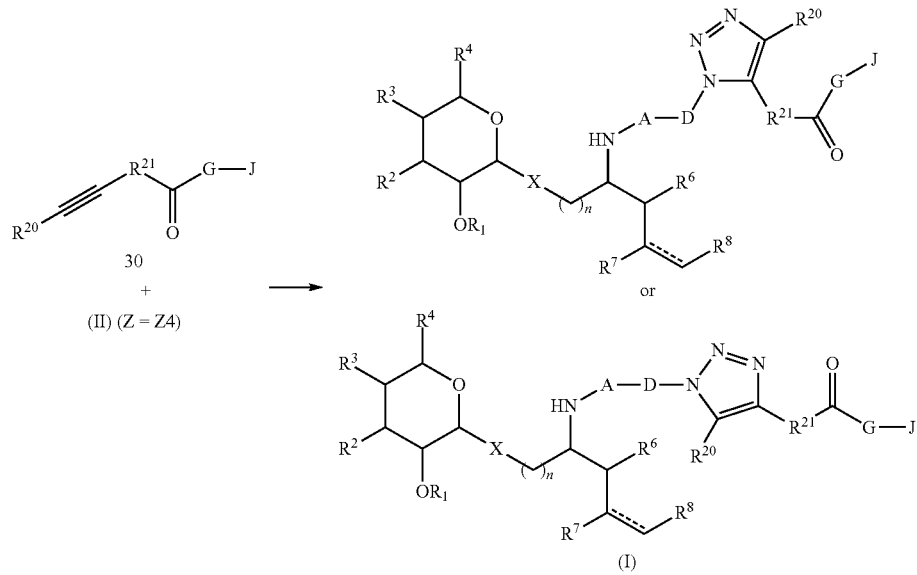

Scheme 18

Z is Z4: The compound of formula (II) and N-terminal alkynoyl peptide 30 are stirred with copper (II) sulfate (up to 0.1 mM), a coordinating ligand (e.g. TBTA, THPTA or Bim(Py)$_2$, preferably TBTA) (Presolski, Hong et al. 2010) and a reducing agent (e.g., copper metal, ascorbic acid or TCEP, preferably copper metal) in a deoxygenated aqueous-organic solvent system (Rostovtsev, Green et al. 2002). Suitable organic solvents may include chloroform, THF, methanol, DMF, DMSO, tert-butanol, or mixtures thereof. After completion of the reaction, the crude product may be isolated from the catalyst by precipitation into aq EDTA (pH 7.7) and separation of the pellet by centrifugation. Alternatively, pentamethylcyclopentadienyl ruthenium catalysts may be employed to provide regioisomeric products (Zhang, Chen et al. 2005; Majireck and Weinreb 2006). The product is purified by chromatography on the appropriate solid phase (e.g. silica gel, C4, and/or C18 silica).

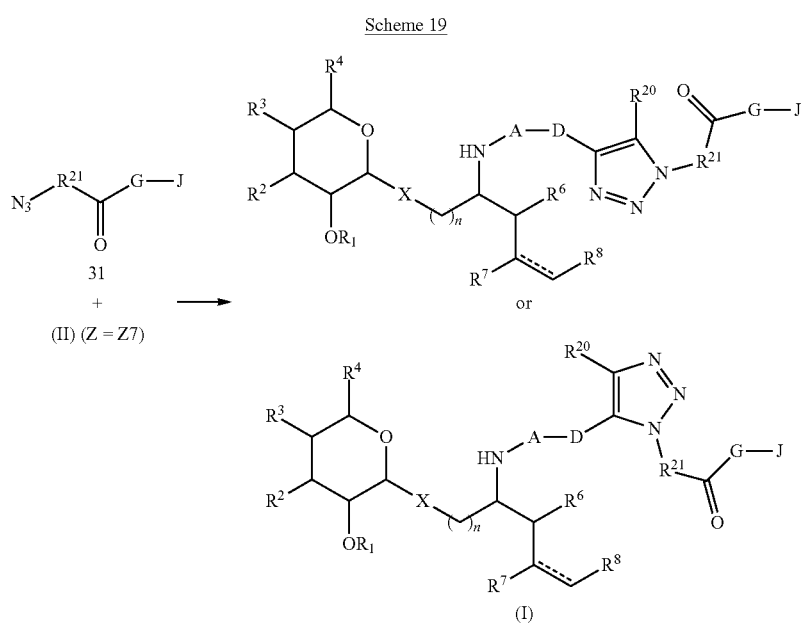

Scheme 19

Z is Z7: The compound of formula (II) is reacted with azido-functionalized peptide 31 under the conditions described above.

Z is Z23: The compound of formula (II) is mixed with azido-functionalized peptide 31 in an appropriate solvent at rt. After completion of the reaction, the solvent is removed and the product is purified by chromatography on the appropriate solid phase (e.g. silica gel, C4, and/or C18 silica).

General Method (12) for Coupling of Antigen to Compounds of Formula (II) by Thiol-Maleimide Conjugate Addition where Z is Z3, Z10 or Z17

Scheme 20

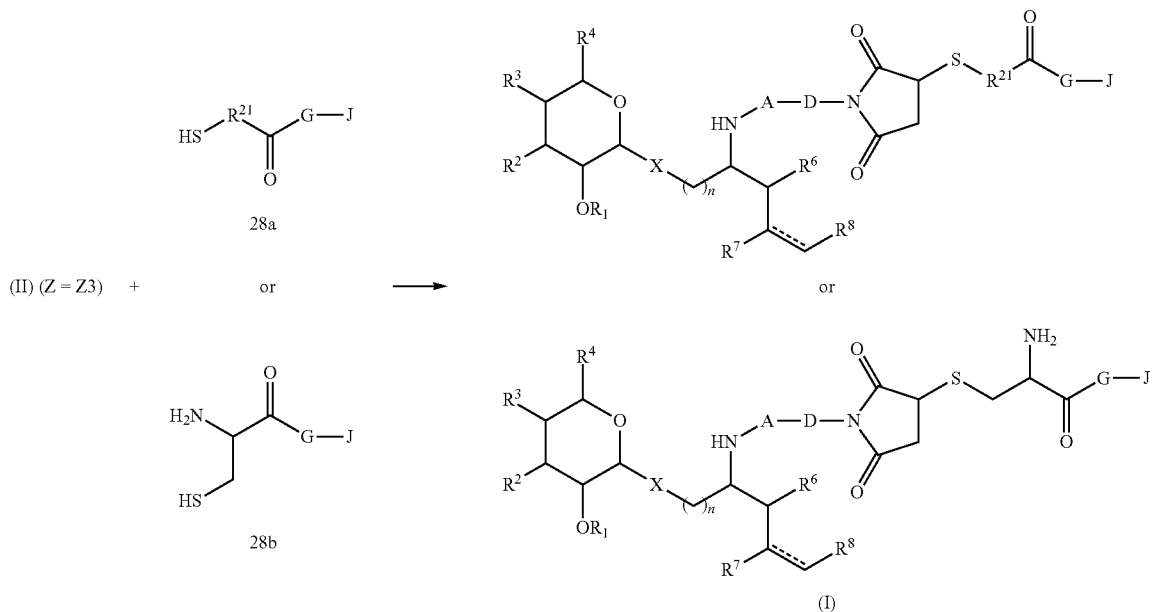

Z is Z3: The compound of formula (II) and peptide-thiol 28a or N-terminal cysteinyl peptide 28b are dissolved in an appropriate solvent system, optionally in the presence of excess TCEP to ensure the thiol remains in the reduced state. Suitable solvents may include chloroform, THF, methanol, DMF, DMSO, tert-butanol, water, or mixtures thereof. The mixture is stirred at 4° C. to rt. After completion of the reaction, the product is purified by chromatography on the appropriate solid phase (e.g. silica gel, C4, and/or C18 silica).

Scheme 21

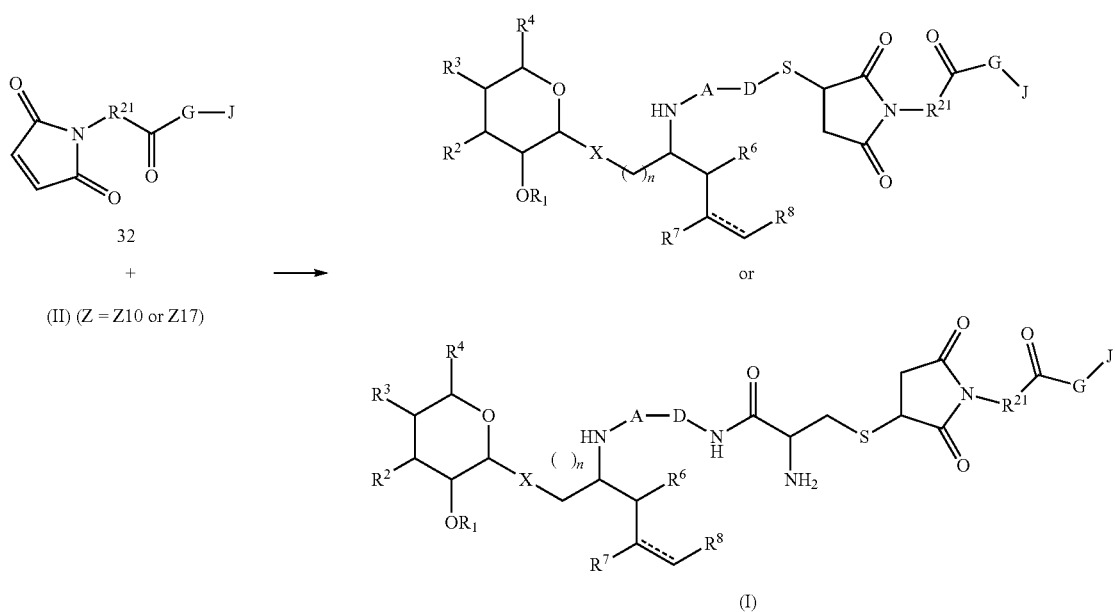

Z is Z10 or Z17: The compound of formula (II) is reacted with maleimido-functionalized peptide 32 under the conditions described above.

General Method (13) for Coupling of Antigen to Compounds of Formula (II) by Oxime or Hydrazone Formation where Z is Z1, Z8 or Z9

Scheme 22

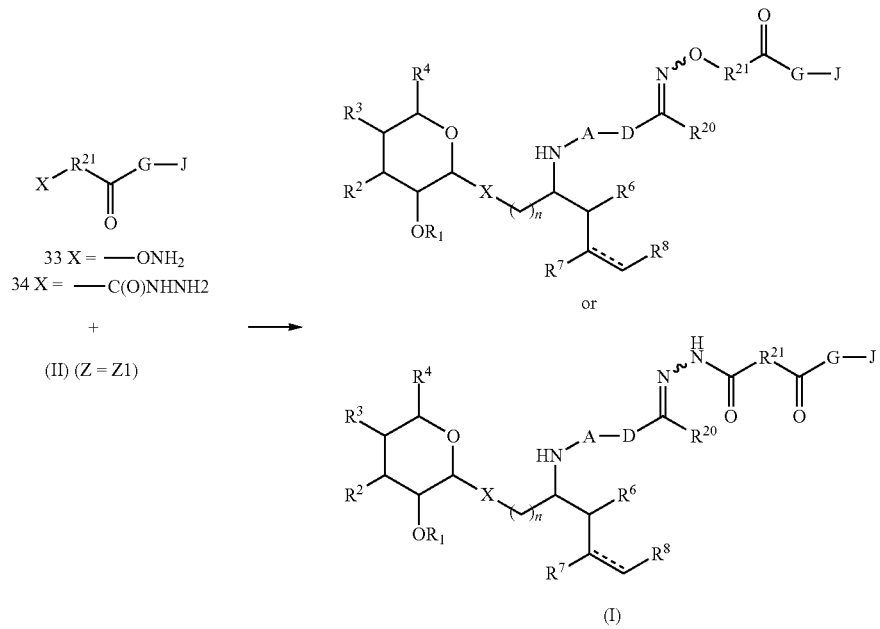

Z is Z1: The compound of formula (II) and either aminooxy-functionalised peptide 33 or hydrazide derivative 34 are stirred at room temperature in the minimum amount of an aqueous-organic solvent system required for dissolution of both components. Suitable organic solvents may include chloroform, THF, methanol, DMF, DMSO, tert-butanol, or mixtures thereof. Anilinium acetate (Dirksen, Hackeng et al. 2006) or anilinium trifluoroacetate (up to 200 mM) may be incorporated as both buffer (pH 3.5-5.0) and catalyst for the reaction. After completion of the reaction, the product is purified by chromatography on the appropriate solid phase (i.e. silica gel, C4, and/or C18 silica).

Z is Z8 or Z9: The compound of formula (II) and aldehydo-functionalized peptide 35, obtained by periodate treatment of the precursor N-terminal serine peptide (Geoghegan and Stroh 1992), or keto-functionalized peptide 36 are reacted under the conditions described above.

Scheme 23

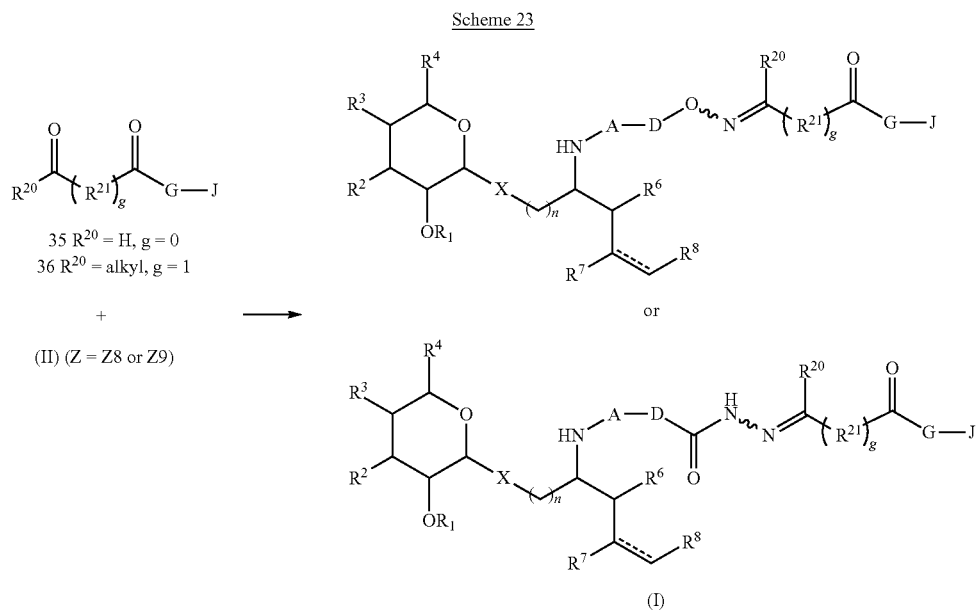

General Method (14) for Coupling of Antigen to Compounds of Formula (II) by Disulfide Exchange where Z is Z10 or Z11

Scheme 24

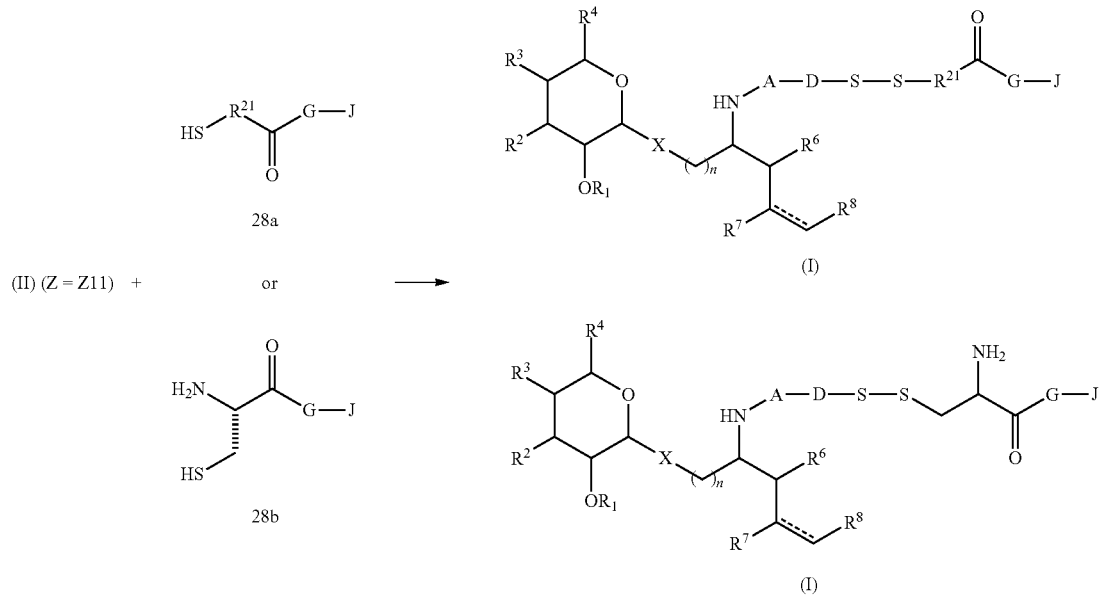

Z is Z11: The compound of formula (II) (prepared by reaction of a precursor thiol with dipyridyl disulfide) and either peptide thiol 28a or N-terminal cysteinyl peptide 28b are allowed to react at room temperature under an inert atmosphere in an appropriate solvent system buffered to pH 6.5-7.5 (Widdison, Wilhelm et al. 2006). Suitable solvents may include chloroform, THF, methanol, DMF, DMSO, tert-butanol, water or mixtures thereof.

Scheme 25

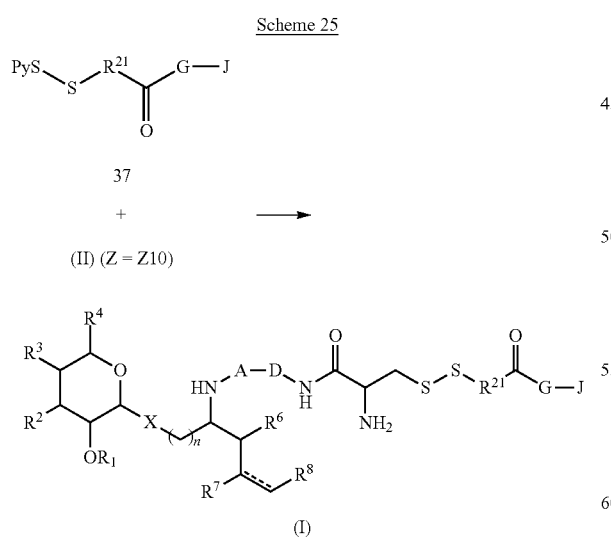

Z is Z10: The compound of formula (II) and disulfide-functionalized peptide 37, are reacted under the conditions described above.

General Method (15) for Coupling of Antigen to Compounds of Formula (II) by Diels-Alder Cycloaddition where Z is Z12

Scheme 26

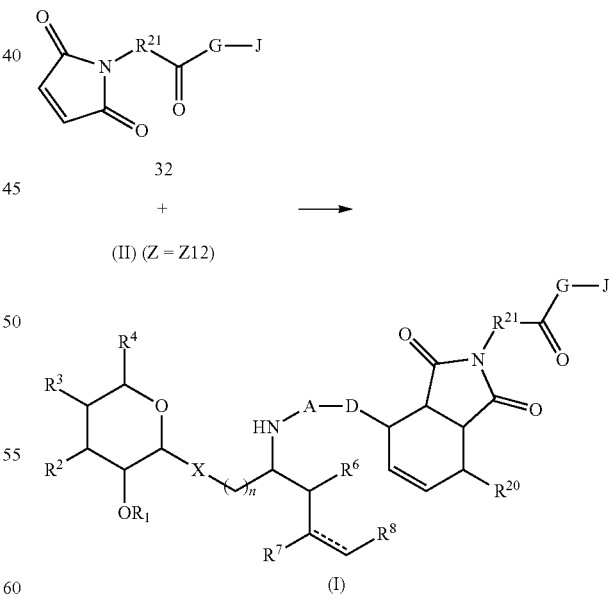

Z is Z12: The compound of formula (II), the diene moiety of which is either commercially available or obtained following literature methods (Hudlicky, Koszyk et al. 1980; Choi, Ha et al. 1989), and maleimido-functionalized peptide 32 are allowed to react in an appropriate solvent system (e.g., chloroform, THF, methanol, DMF, DMSO, tert-butanol, water or mixtures thereof) at pH≤6.5 (de Araujo, Palomo et al. 2006).

General Method (16) for Coupling of Antigen to Compounds of Formula (I) by Native Chemical Ligation where Z is Z13

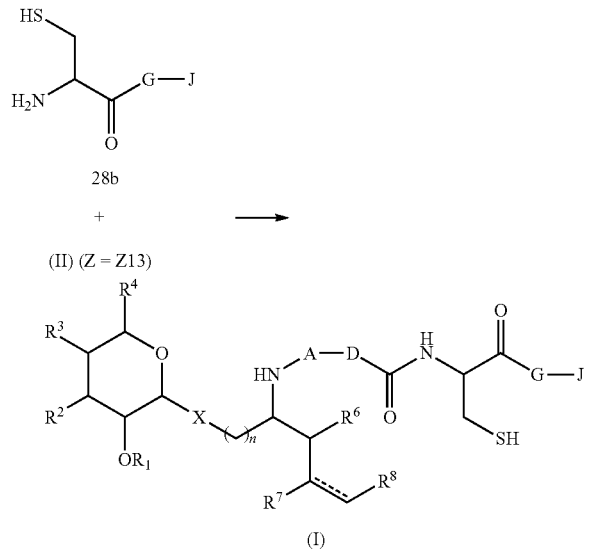

The compound of formula (II) and N-terminal cysteinyl peptide 28b are allowed to react in an appropriate solvent system (e.g., chloroform, THF, methanol, DMF, DMSO, tert-butanol, water or mixtures thereof) following literature protocols (Hackenberger and Schwarzer 2008).

General Method (17) for Coupling of Antigen to Compounds of Formula (II) by Staudinger Ligation where Z is Z14 or Z4

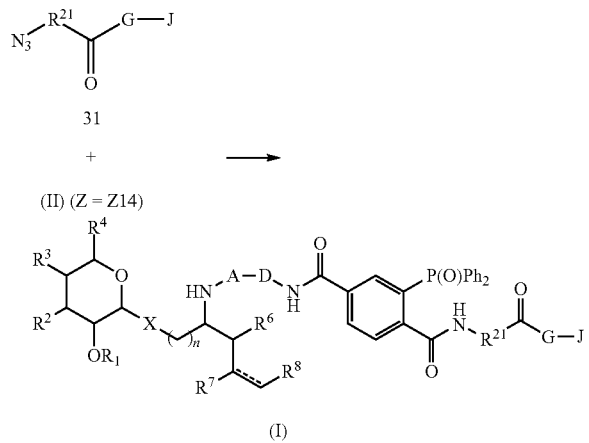

Z is Z14: The compound of formula (II) and azido peptide 31 are allowed to react in an appropriate solvent system (e.g., chloroform, THF, methanol, DMF, DMSO, tert-butanol, water or mixtures thereof) following literature protocols (Saxon and Bertozzi 2000).

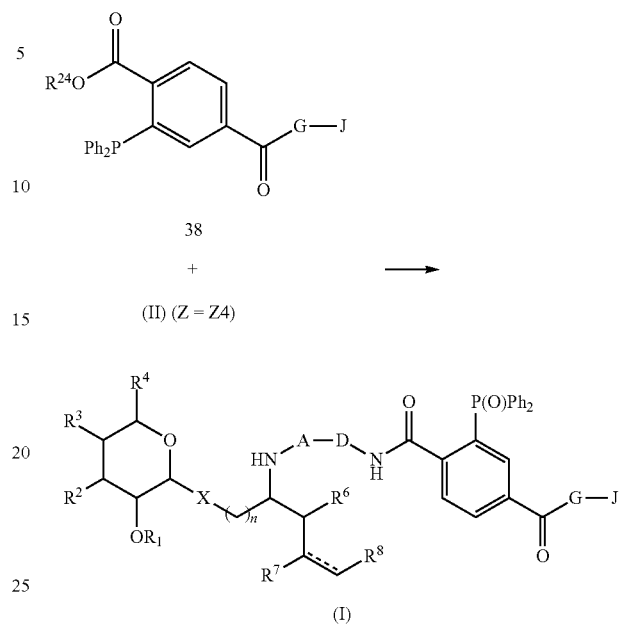

Z is Z4: The compound of formula (II) and peptide 38 (prepared following literature protocols) (Kiick, Saxon et al. 2002) are allowed to react as described above.

General Method (18) for Coupling of Antigen to Compounds of Formula (I) by Traceless Staudinger Ligation where Z is Z15 or Z4

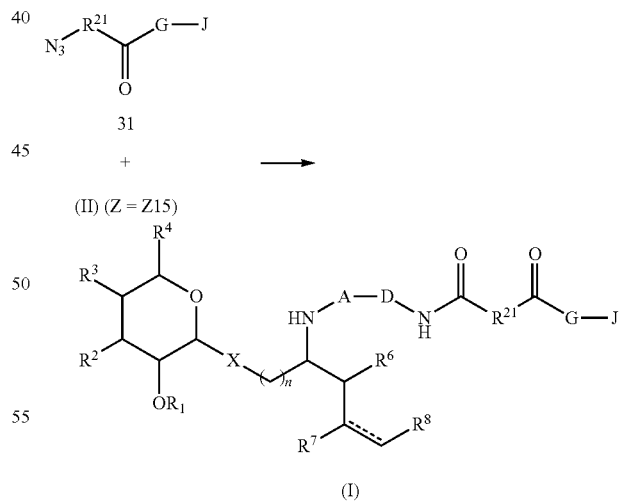

Z is Z15: The compound of formula (II), wherein the thioester group Z15 is prepared following literature procedures (Soellner, Tam et al. 2006), and azido peptide 31 are allowed to react in an appropriate solvent system (e.g. chloroform, THF, methanol, DMF, DMSO, tert-butanol, water or mixtures thereof) following literature protocols (Soellner, Tam et al. 2006; Tam, Soellner et al. 2007).

General Method (19) for Coupling of Antigen to Compounds of Formula (II) where Z is Z16 or Z17

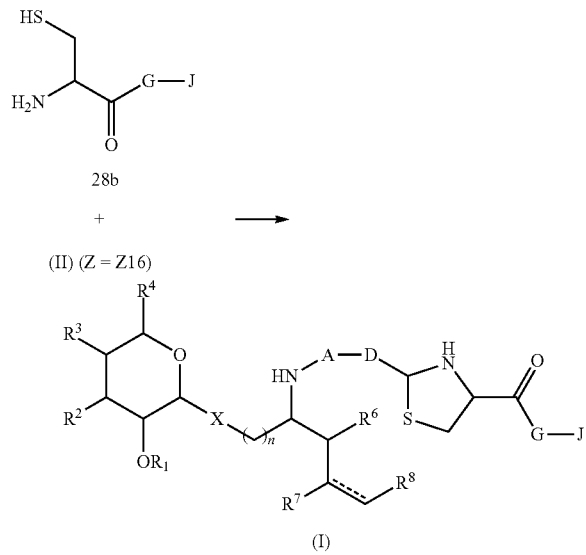

Scheme 31

Z is Z16: The compound of formula (II), wherein the aldehyde group Z16 is obtained from ozonolytic cleavage of a precursor alkene, or acidic deprotection of a precursor acetal, and N-terminal cysteinyl peptide 28b are allowed to react in an appropriate solvent system (e.g., chloroform, THF, methanol, DMF, DMSO, tert-butanol, water or mixtures thereof) at pH 5-7, following literature protocols (Liu and Tam 1994; Liu, Rao et al. 1996).

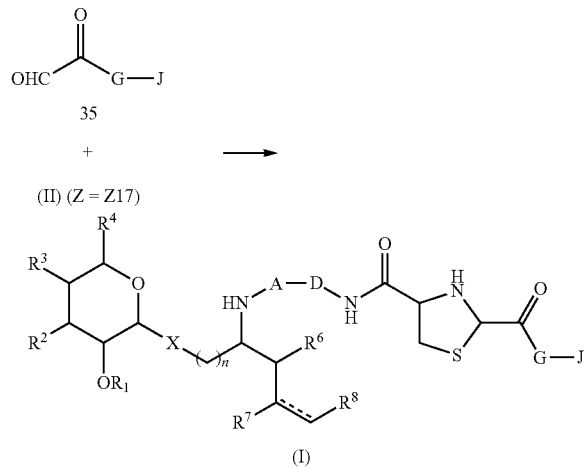

Scheme 32

Z is Z17: The compound of formula (II) and aldehyde-terminated peptide 35, are allowed to react as described above.

General Method (20) for the Synthesis of Peptidic Antigen G-J

Functionalised peptides are synthesised according to reported methods that utilize solid phase peptide synthesis (SPPS) (Amblard, Fehrentz et al. 2006). In particular, the Fmoc protection approach (Atherton, Fox et al. 1978; Fields and Noble 1990) on an appropriately functionalised resin (e.g. trityl chloride resin, 2-chlorotrityl chloride resin, Wang resin, Sasrin resin, HMPB resin) can be employed for the synthesis of functionalised peptides. Peptides with C-terminal amides are constructed on Rink amide, Pal, MBHA or Sieber resins. A brief description, using trityl chloride resin, follows:

Trityl chloride resin (1 g) is swollen in dry DCM for 30 mins. After this time Fmoc-AA-OH (1.131 g, 3.20 mmol) and DIPEA (0.669 ml, 3.84 mmol) are added with dry DCM under an argon atmosphere and the reaction stirred for 1 h. The resin is transferred to a sintered reaction vessel and washed with DCM. A solution containing HBTU (7.59 g) and 4.18 mL DIPEA (4.18 mL) in dry DMF (50 mL) is prepared and 8 mL of this solution is used for each coupling. The reaction sequence for coupling is as follows; swell resin in DCM for 30 mins, for each iteration (i), wash thoroughly with DMF (ii), deprotect with 20% piperidine in DMF for 5 mins (×2) (iii), wash with DMF (iv), swell with DCM (v), wash with DMF (vi), add amino acid and 8 mL of coupling solution and shake for 30 mins. Steps (i)-(vi) are repeated to end of peptide. Finally, while the peptide is still attached to the resin, an appropriately functionalised acid is coupled to the free N-terminus to give the fully protected, resin-bound, functionalized peptides 28-38.

Cleavage from the resin: the beads are treated with 95:2.5:2.5 TFA:TIS:water for 3 h, during this time the beads turn a bright red colour. After 3 h the beads are filtered and washed with TFA. The TFA is evaporated and the peptide precipitated and washed with ether to afford the crude peptide. The material is purified via reverse phase preparative HPLC, eluting with 10-50% acetonitrile water with 0.1% TFA. The material is characterised by LC-MS.

ABBREVIATIONS

Figure 1:
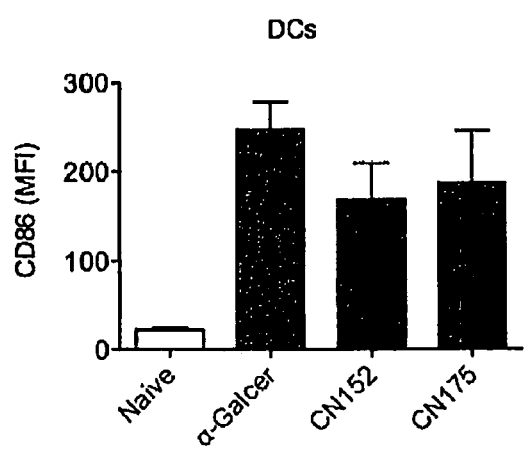
FIG. 1 shows CD86 expression on dendritic cells. The data show that injection of compounds of the invention induces activation of iNKT cells and subsequent maturation of dendritic cells, as indicated by up-regulation of expression of the activation marker CD86. Groups of C57BL/6 mice (n=3) are injected intravenously with 0.571 nmol of the indicated compounds and then the spleens removed 20 h later for the analysis of CD86 expression on CD11c$^+$ dendritic cells by antibody labelling and flow cytometry. Mean fluorescence index (MFI)±SEM are presented.
Figure 2:
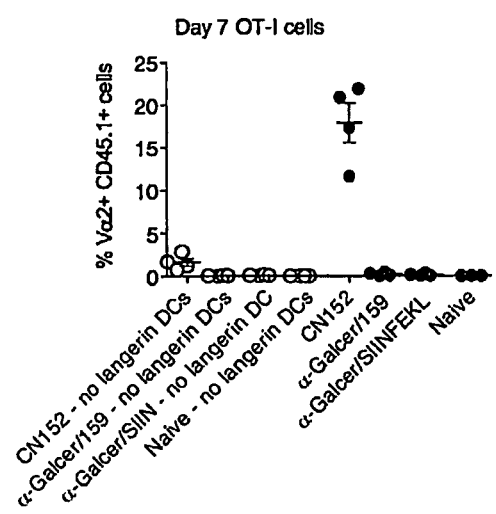
FIG. 2 shows enumeration of T cells with specificity for the peptide antigen SIINFEKL (SEQ ID NO:262) following intravenous administration of compounds of the invention as vaccines into mice. The compounds are injected to give the equivalent molar dose of SIINFEKL (SEQ ID NO:262) peptide in each case. To increase sensitivity of the assay, all mice are initially donated a cohort of 10,000 SIINFEKL (SEQ ID NO:262)-specific T cells from a transgenic mouse encoding a T cell receptor for this antigen (OT-1 mice) by intravenous injection of the cells one day before the vaccines are administered. To discriminate the donated T cells from those of the host, the donated cells exhibit congenic expression of the CD45.1 variant of the CD45 molecule. It is therefore possible to enumerate SIINFEKL (SEQ ID NO:262)-specific T cells in blood by flow cytometry using antibodies for CD45.1 together with antibodies for the transgenic T cell receptor (Vα2). Experiments are conducted in lang-EGFPDTR (enhanced green fluorescent protein/diphtheria toxin receptor) mice, which express the human diphtheria toxin receptor from the langerin promoter. This enables the selective depletion of langerin$^+$ CD8α$^+$ DCs by administration of diphtheria toxin in some animals before the compounds are administered (Farrand, Dickgreber, et al. 2009). Control animals are injected with the diluent phosphate-buffered saline (PBS). The data show that injection of the α-GalCer-SIINFEKL (SEQ ID NO:262) conjugate (CN152) induces a larger population of SIINFEKL (SEQ ID NO:262)-specific T cells than injection of the admixed components (α-GalCer/SIINFEKL SEQ ID) NO:262)), or admixed derivatives of these components (α-GalCer/CN159 or CN146/CN159), and that this response is dependent on langerin⁺ CD8α⁺ DCs. Each dot represents a different animal; mean per treatment group±SEM are presented.
Figure 3:
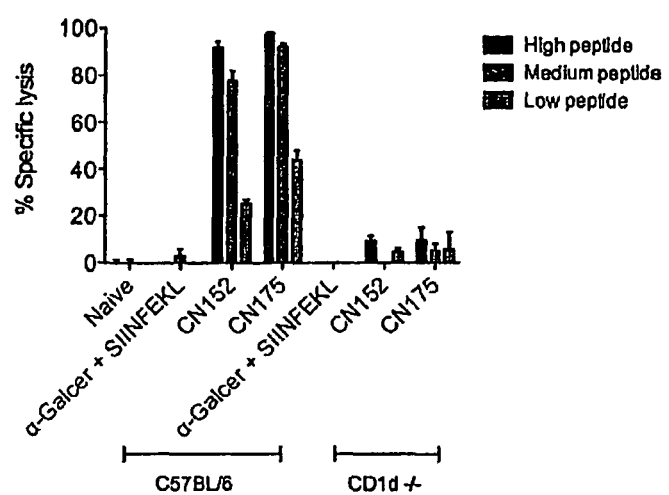
FIG. 3 shows the cytotoxic capacity of T cells with specificity for the peptide antigen SIINFEKL (SEQ ID NO:262) following intravenous administration of compounds of the invention as vaccines into wild type mice, or mice that are deficient in expression of CD1d. The compounds are injected to give the equivalent molar dose of SIINFEKL (SEQ ID NO:262) peptide, in each case of 0.571 nmol. Flow cytometry is used to assess the killing of target cells comprised of syngeneic splenocytes loaded ex vivo with 5 µM SIINFEKL (SEQ ID NO:262) injected intravenously 7 days after vaccination. To discriminate the targets from host tissue, the injected cells are labelled with the fluorescent dye carboxyfluorescein succinimidyl ester (CFSE). A cohort syngeneic splenocytes (without peptide) labelled with the fluorescent dye cell tracker orange are also injected to serve as controls. Killing is defined as the percentage of peptide-loaded targets killed relative to control cells. Each treatment group contained 5 animals. Control animals are injected with the diluent phosphate-buffered saline (PBS). The data show that injection of the conjugates (i.e. either CN152 or CN175) induces SIINFEKL (SEQ ID NO:262-specific T cells with greater cytotoxic capacity than injection of the admixed components (α-GalCer/SIINFEKL (SEQ ID NO:262)), and that this response is dependent on NKT cells, which are absent in CD1d-deficient animals. Mean percentage of killing per group±SEM are shown.
Figure 4:
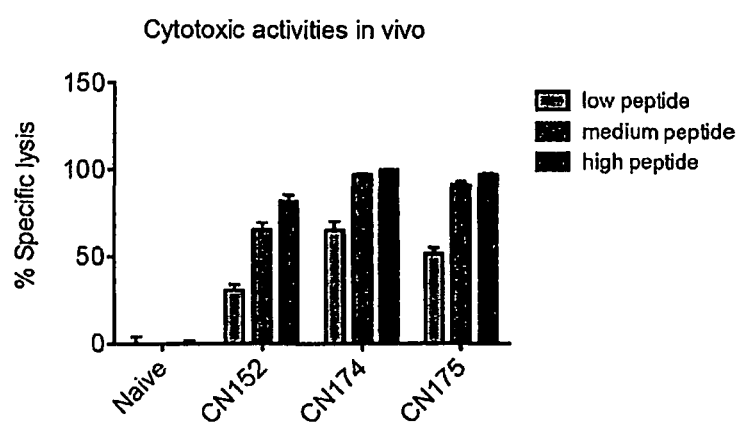
FIG. 4 shows the cytotoxic capacity of T cells with specificity for the peptide antigen SIINFEKL (SEQ ID NO: 262) following intravenous administration of compounds of the invention as vaccines into mice (n=5 per treatment group). Cytotoxic activity is assessed as in FIG. 3. Mean percentage of killing per group±SEM are shown.
Figure 5:
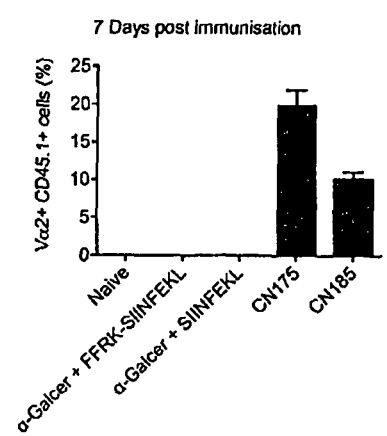
FIG. 5 shows enumeration of T cells with specificity for the peptide antigen SIINFEKL (SEQ ID NO:262) following intravenous administration of compounds of the invention, or peptide derivatives with α-Galcer, as vaccines into mice (n=5 per treatment group). Accumulation of antigen-specific T cells in the blood in response to vaccination is measured 7 days later, as described for FIG. 2.
Figure 6:
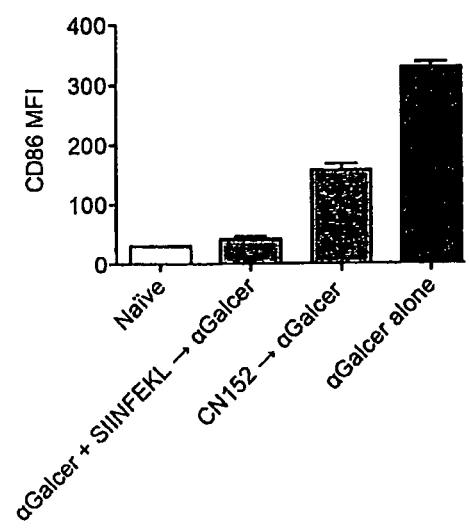
FIG. 6 shows the impact of prior vaccination with the compounds of the invention on responses to free α-GalCer two weeks later. Flow cytometry is used to assess CD86 upregulation on splenic dendritic cells after intravenous injection of 200 ng α-GalCer, which is used as a readout of NKT cell activity. Mean fluorescence index (MFI)±SEM are presented. In each case where the original vaccine contains free α-GalCer rather than the α-GalCer conjugate (CN152, which contains the peptide SIINFEKL (SEQ ID NO:262)), the NKT cells become exhausted and are not able to respond to a later dose of free α-GalCer, with CD86 levels staying similar to naïve control animals injected with phosphate-buffered saline (PBS). In contrast, when the conjugate CN152 is used to initially vaccinate animals, exhaustion is not complete, with some upregulation of CD86 is observed on dendritic cells upon subsequent exposure to free α-GalCer. Each dot represents a different animal; mean per treatment group (n=3)±SEM are presented. *p<0.001, p<0.01, * p<0.05.
Figure 7:
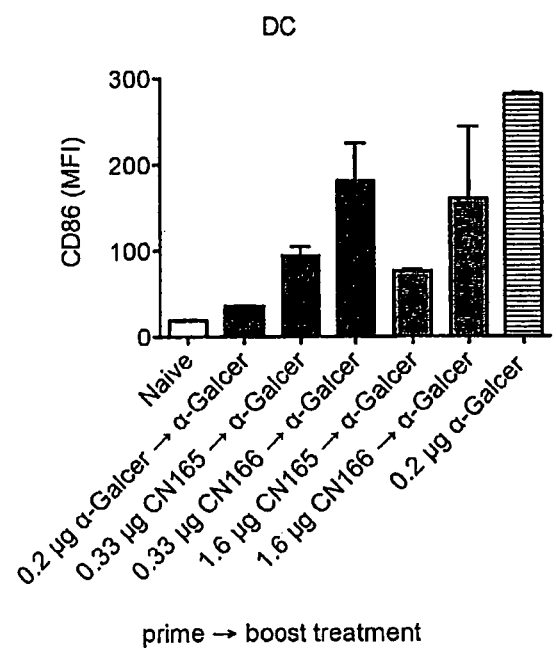
FIG. 7 shows the impact of administration of the indicated prodrug compounds of the invention (CN165 and CN166) on responses to free α-GalCer two weeks later, assessed as described for FIG. 6.
Figure 8:
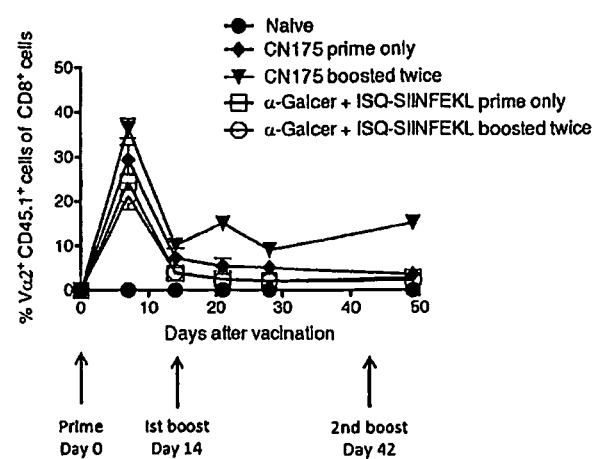
FIG. 8 shows enumeration of T cells with specificity for the peptide antigen SIINFEKL (SEQ ID NO: 262) following intravenous administration of CN175 (0.571 nmol), or peptide ISQ-SIINFEKL (0.571 nmol) with α-Galcer (0.571 nmol), as vaccines into mice, assessed at the indicated time times in blood as described for FIG. 2. The data show that priming (day 0) with the α-GalCer-SIINFEKL (SEQ ID NO: 262) conjugate CN175 or ISQ-SIINFEKL (SEQ ID NO: 141) with α-GalCer induces, in both cases, a significant population of SIINFEKL (SEQ ID NO:262)-specific T cells, day 7, as compared to the control group. In contrast, boosting with CN175 (day 14) and not with admixed ISQ-SIINFEKL (SEQ ID NO: 141)/α-GalCer induces a secondary T cell response at day 21. Similarly, a second boosting step at with CN175 (day 42) and not with admixed ISQ-SIINFEKL (SEQ ID NO: 141)/α-GalCer induces a further T cell response at day 49.
Figure 9:
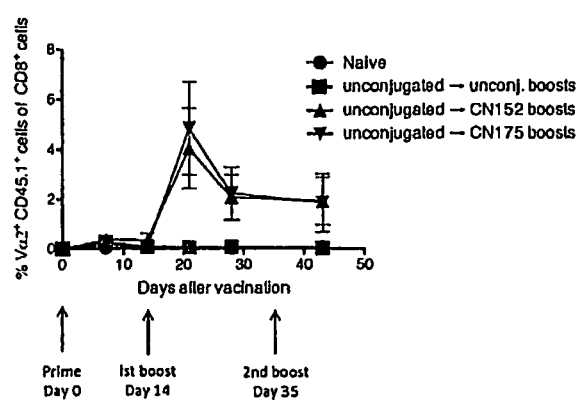
FIG. 9 shows enumeration of T cells with specificity for the peptide antigen SIINFEKL (SEQ ID NO: 262) following initial priming by intravenous administration of SIINFEKL (SEQ ID NO: 262) with α-Galcer ("unconjugated") followed by repeated boosting with the indicated compounds of the invention (CN175 or CN152), or with more unconjugated vaccine. The data show that boosting with SIINFEKL (SEQ ID NO: 262) and α-GalCer at either day 14 or 35 does not induce an easily measurable T cell response in the blood. In contrast, boosting with either CN152 or CN175 at day 14 or 35 induces measurable T cell responses at day 21 or 42.
Figure 10:
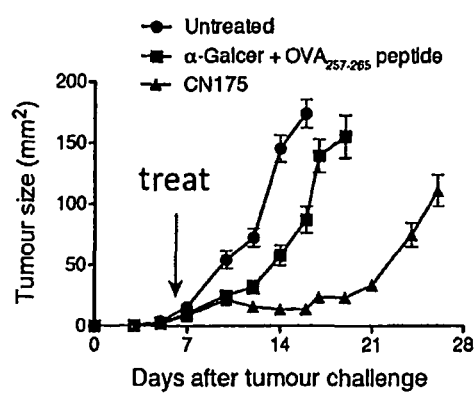
FIG. 10 shows the antitumour effect of vaccination with conjugate vaccine CN175 (0.571 nmol) compared to vaccination with SIINFEKL (SEQ ID NO: 262) peptide (0.571 nmol) and α-GalCer (0.571 nmol) together. Progression of subcutaneous B16.OVA tumours is monitored in animals treated five days after tumour challenge with intravenous CN175 or SIINFEK (SEQ ID NO: 262) L peptide and α-GalCer or with PBS. The mean tumour sizes per group (n=5)±SEM are shown. These data show that vaccination with CN175 results in superior anti-tumour activity as compared to the control or admixed groups.
Figure 11:
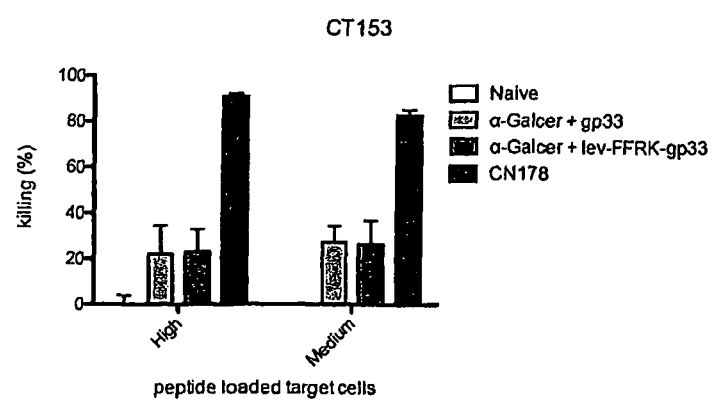
FIG. 11 shows the cytotoxic capacity of T cells with specificity for the peptide antigen gp33 (KAVYNFATM (SEQ ID NO: 129)) following intravenous administration of compounds of the invention (i.e. CN178, which contains gp33) or mixtures of the peptide antigen and α-GalCer as vaccines into mice. Flow cytometry is used to assess the killing of target cells comprised of syngeneic splenocytes loaded ex vivo with 5 µM KAVYNFATM (SEQ ID NO: 129) injected intravenously 7 days after vaccination. The data show that injection of the conjugate CN178 induces KAVYNFATM (SEQ ID NO: 129)-specific T cells with increased cytotoxic capacity as compared to the admixed groups.
Figure 12:
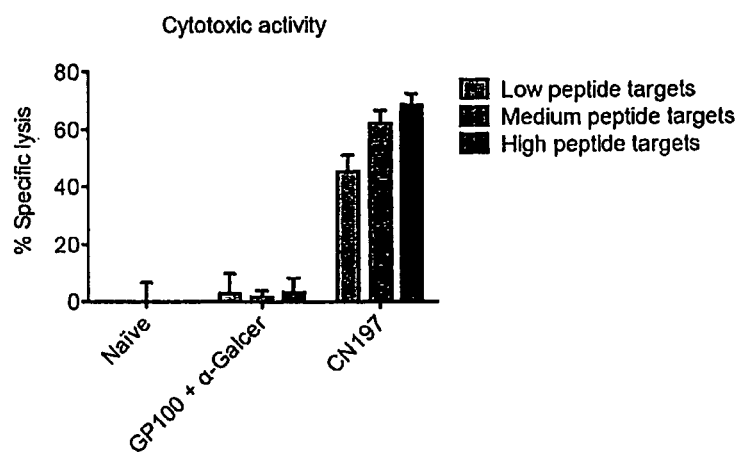
FIG. 12 shows the cytotoxic capacity of T cells with specificity for the peptide antigen PRNQDWLGV (amino acids 8-16 of SEQ ID NO: 413) from gp100 following intravenous administration of compounds of the invention (i.e. CN197) or mixtures of the peptide antigen and α-GalCer as vaccines into mice. All animals received a cohort of 10000 gp100-specific T cells before vaccination. Flow cytometry is used to assess the killing of target cells comprised of syngeneic splenocytes loaded ex vivo with 5 μM PRNQDDWLGV (amino acids 8-16 of SEQ ID NO: 413) injected intravenously 7 days after vaccination. The data show that injection of the conjugate CN197 induces PRNQDWLGV (amino acids 8-16 of SEQ ID NO: 413)-specific T cells with increased cytotoxic capacity as compared to the admixed groups.
Figure 13:
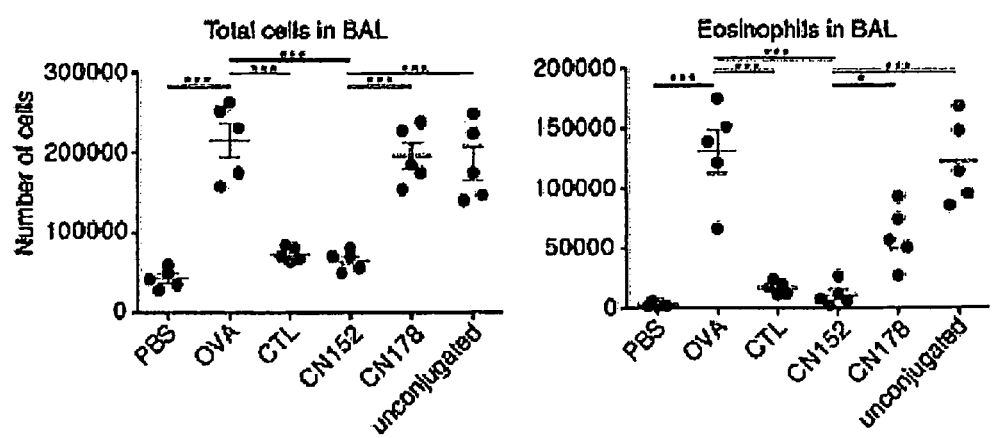
FIG. 13 shows allergen-specific prodrug vaccines reduce allergic airway inflammation in sensitized animals. Treatment with the compounds CN152 or CN178, admixed α-GalCer and OVA$_{257}$, or in vitro-activated allergen-specific CTL, is assessed in mice initially sensitized by i.p administration with OVA in alum on day 1 and 14, and then challenged with OVA by intranasal administration on day 24. Control animals receive intranasal PBS instead of challenge, and positive control groups receive challenge but no treatment ("OVA"). The prodrug vaccines and admixed α-GalCer and peptide are administered seven days before challenge (day 17), while the in vitro activated OVA$_{257}$-specific CTL are administered one day before challenge (day 23). The total numbers of cells in BAL fluid (left), and numbers of eosinophils (right), are evaluated three days after challenge by flow cytometry. The data show the antigen-specific vaccine CN152 and not CN178 or admixed vaccines reduces the total number of infiltration cells into the BAL. The data also show CN152 is superior to both CN178 and admixed groups in suppressing eosinophil infiltration.
Figure 14:
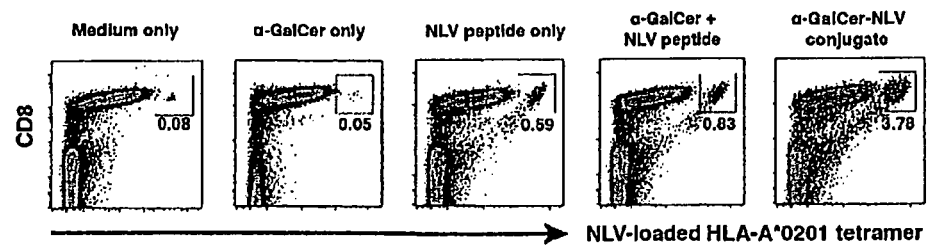
FIG. 14 shows analysis of NLVPMVATV (SEQ ID NO: 199)-specific T cell populations in human peripheral blood mononuclear cells after one week of culture with α-GalCer alone, NLVPMVATV (SEQ ID NO: 199) peptide alone, admixed peptide and α-GalCer, or conjugate compound CN188 ("α-GalCer-NLV-conjugate"). Assessment is by flow cytometry with fluorescent HLA-A2/NLVPMVATV (SEQ ID NO: 199) pentamers together with antibodies to CD8 and CD3. The percentage of peptide-specific CD8$^+$ T cells of all T cells (CD3$^+$ cells) is shown.

NMR Nuclear magnetic resonance spectrometry
HRMS High resolution mass spectrometry
ESI Electrospray ionisation
Cbz Benzyloxycarbonyl
RT Room temperature
THF Tetrahydrofuran
PBS Phosphate-buffered saline
HPLC High performance liquid chromatography
FCS Fetal calf serum
MS Mass spectrometry
LC-MS Liquid chromatography-mass spectrometry
TFA Trifluoroacetic acid
TLC Thin layer chromatography
DMF Dimethylformamide
DMSO Dimethylsulfoxide
DCM Dichloromethane
NMP N-methyl-2-pyrrolidone
DDQ 2,3-Dichloro-5,6-dicyano-1,4-benzoquinone
PMB p-Methoxybenzyl
DMAP 4-Dimethylaminopyridine
TMS Trimethylsilyl
DCC N,N'-dicyclohexylcarbodiimide
DIPEA N,N-diisopropylethylamine
TBDPS tert-Butyldiphenylsilyl
TBAF Tetra-n-butylammonium fluoride
THP Tetrahydropyranyl
EEDQ 2-Ethoxy-1-ethoxycarbonyl-1,2-dihydroquinoline
EDCI 1-Ethyl-3-(3-dimethylaminopropyl)carbodiimide
CAN Ceric ammonium nitrate
Tbeoc-Thz N-(2-(tert-Butyldisulfanyl)ethoxycarbonyl)-L-thiazolidine-4-carboxylic acid
HBTU 2-(1H-benzotriazol-1-yl)-1,1,3,3-tetramethyluronium hexaflurophosphate.
TCEP Tris(2-carboxyethyl)phosphine)
TBTA Tris(benzyltriazolylmethyl)amine
THPTA Tris(3-hydroxypropyltriazolylmethyl)amine
Bim(Py)$_2$ ((2-Benzimidazolyl)methyl)-bis-((2-pyridyl)methyl)amine
EDTA Ethylenediaminetetraacetic acid
IPA isopropyl alcohol

EXAMPLES

The examples described herein are for purposes of illustrating embodiments of the invention. Other embodiments, methods, and types of analyses are within the capabilities of persons of ordinary skill in the art and need not be described in detail herein. Other embodiments within the scope of the art are considered to be part of this invention. Anhydrous solvents are obtained commercially. Air sensitive reactions are carried out under Ar. Thin layer chromatography (TLC) is performed on aluminium sheets coated with 60 F$_{254}$ silica. Flash column chromatography is performed on Merck or SiliCycle silica gel (40-63 μm) or SiliCycle reversed phase (C18) silica gel (40-63 μm). NMR spectra are recorded on a Bruker 500 MHz spectrometer. $^1$H NMR spectra are referenced to tetramethylsilane at 0 ppm (internal standard) or to residual solvent peak (CHCl$_3$ 7.26 ppm, CHD$_2$OD 3.31 ppm, CHD$_2$S(O)CD$_3$ 2.50 ppm). $^{13}$C NMR spectra are referenced to tetramethylsilane at 0 ppm (internal standard) or to the deuterated solvent peak (CDCl$_3$ 77.0 ppm, CD$_3$OD 49.0 ppm, CD$_3$S(O)CD$_3$ 39.52 ppm). CDCl$_3$-CD$_3$OD solvent mixtures are always referenced to the methanol peak. High resolution electrospray ionization mass spectra are recorded on a Q-T of Premier mass spectrometer.

Example 1.1—Synthesis of (2S,3S,4R)-2-Amino-1-O-α-D-galactopyranosyl-4-O-hexacosanoyl octadecane-1,3,4-triol (CN089) via hydrogenolysis of compound 1

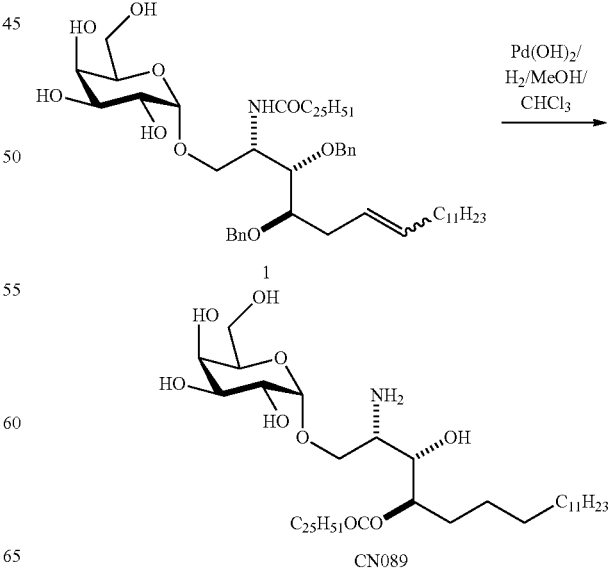

A mixture of compound 1 (324 mg, 0.303 mmol) and 20% Pd(OH)$_2$/C (300 mg) in 3:7 CHCl$_3$/MeOH (30 mL) is stirred under a hydrogen balloon at 35° C. for 21 h. The mixture is filtered through celite, washing with 3:1 CHCl$_3$/MeOH (2×100 mL), and the filtrate is concentrated. The crude residue is purified by silica gel chromatography (1:4 i-PrOH/CHCl$_3$ then 1:4 EtOH/CHCl$_3$) to afford the title compound CN089 (45 mg, 17%) as a white solid. $^1$H NMR (500 MHz, CDCl$_3$/CD$_3$OD 2:1) δ 0.87-0.90 (m, 6H), 1.22-1.36 (m, 68H), 1.54-1.67 (m, 3H), 1.79-1.84 (m, 1H), 2.35-2.38 (m, 2H), 3.27-3.30 (m, 1H), 3.51-3.55 (m, 1H), 3.70-3.72 (m, 1H), 3.75 (dd, J=3.3, 10.0 Hz, 1H), 3.79-3.81 (m, 2H), 3.83-3.86 (m, 2H), 3.97 (d, J=3.3 Hz, 1H), 4.11 (dd, J=2.9, 10.8 Hz, 1H), 4.87 (d, J=3.8 Hz, 1H), 4.92 (dt, J=2.8, 8.8 Hz, 1H); $^{13}$C NMR (126 MHz, CDCl$_3$/CD$_3$OD 2:1) δ 14.2, 23.0, 25.3, 25.4, 29.5, 29.65, 29.66, 29.68, 29.74, 29.9, 29.96, 29.99, 30.03, 31.5, 32.3, 34.8, 53.2, 62.2, 64.9, 69.3, 70.1, 70.3, 71.15, 71.18, 73.5, 99.9, 174.6; HRMS-ESI m/z calcd for C$_{50}$H$_{100}$NO$_9$ [M+H]$^+$ 858.7398. found 858.7396.

Example 1.2—Synthesis of (2S,3S,4R)-2-Amino-1-O-α-D-galactopyranosyl-4-O-hexacosanoyl octadecane-1,3,4-triol (CN089) Via Isomerization of α-GalCer

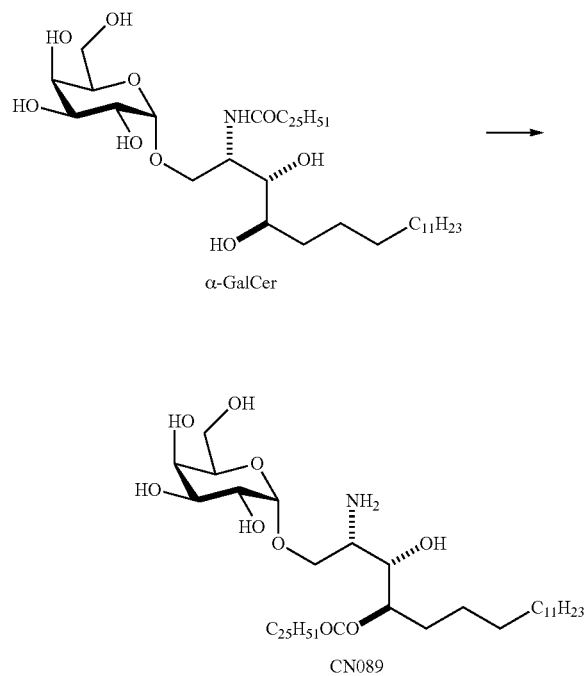

α-GalCer (195 mg, 0.227 mmol) is heated under Ar in 10:1:2 1,4-dioxane/water/1 M HCl (61 mL) at 85° C. for 35 min, then cooled to 5° C. The collected precipitate is purified on silica gel (MeOH/CH$_2$Cl$_2$=10:90 to 20:80) to afford the title compound CN089 as a white solid (121 mg, 62%).

Example 2—Synthesis of (2S,3S,4R)-1-O-α-D-Galactopyranosyl-4-hexacosanoyl-2-((4-oxopentanoyloxy)methoxycarbonylamino) octadecane-1,3,4-triol (CN146)

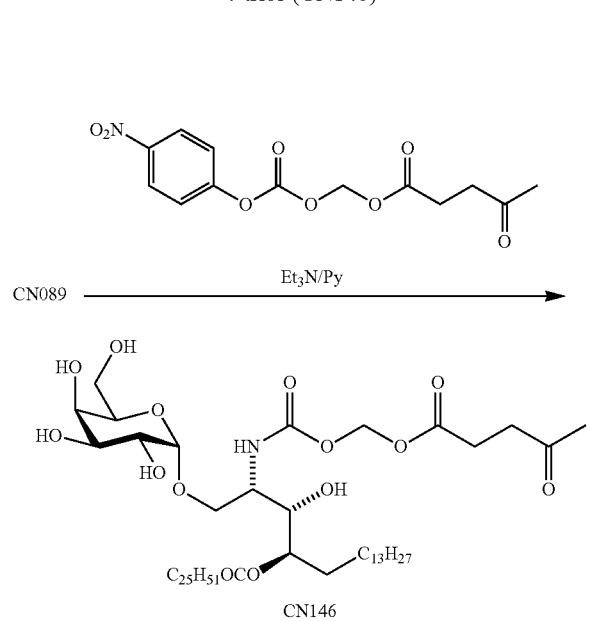

Example 2.1—(4-Nitrophenoxy)carbonyloxymethyl 4-oxopentanoate (41)

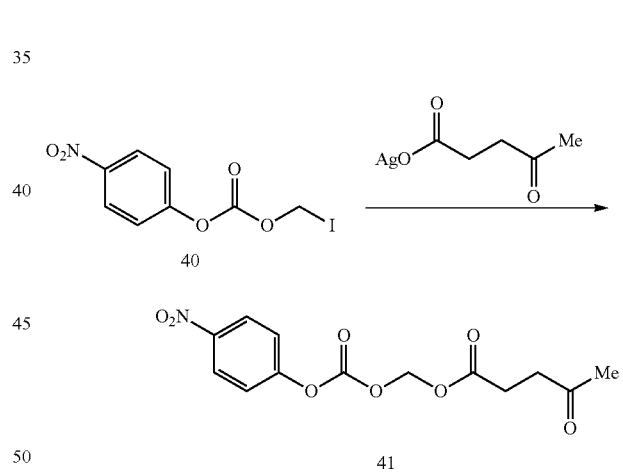

The silver salt of levulinic acid is prepared by adding a solution of AgNO$_3$ (700 mg, 4.1 mmol) in water (10 mL) to the sodium salt of levulinic acid (4.3 mmol in ~10 mL water, prepared by basification of levulinic acid with 1 M aq NaOH to pH 7-8). After 30 min, the resultant precipitate is isolated by filtration and washed with cold water followed by Et$_2$O. The product is dried under vacuum to afford the silver salt as a white solid (636 mg, 69%). A mixture of iodomethyl 4-nitrophenyl carbonate (40) (Gangwar, Pauletti et al. 1997) (105 mg, 0.325 mmol, dried by azeotropic distillation with toluene), 4 Å molecular sieves (~250 mg) and silver levulinate (89 mg, 0.40 mmol) in dry toluene (1.5 mL) is protected from light and stirred at 40° C. After 4 h, the mixture is diluted with Et$_2$O, filtered through celite, and concentrated under reduced pressure. The crude residue is purified by silica gel chromatography (30% to 40% EtOAc/petroleum ether) to afford the title compound (41) (85 mg, 84%) as a colourless oil. $^1$H NMR (500 MHz, CDCl$_3$) δ 2.20 (s, 3H), 2.67-2.70 (m, 2H), 2.80-2.83 (m, 2H), 5.88 (s, 2H), 7.38-7.48 (m, 2H), 8.24-8.34 (m, 2H); $^{13}$C NMR (126 MHz, CDCl$_3$) δ 27.7, 29.7, 37.6, 82.5, 121.8, 125.4, 145.7, 151.5, 155.1, 171.2, 206.0; HRMS (ESI): m/z calcd for C$_{13}$H$_{13}$NO$_8$Na [M+Na]$^+$ 334.0539. found 334.0544.

Example 2.2—(2S,3S,4R)-1-O-α-D-Galactopyranosyl-4-hexacosanoyl-2-((4-oxopentanoyloxy)methoxycarbonylamino) octadecane-1,3,4-triol (CN146)

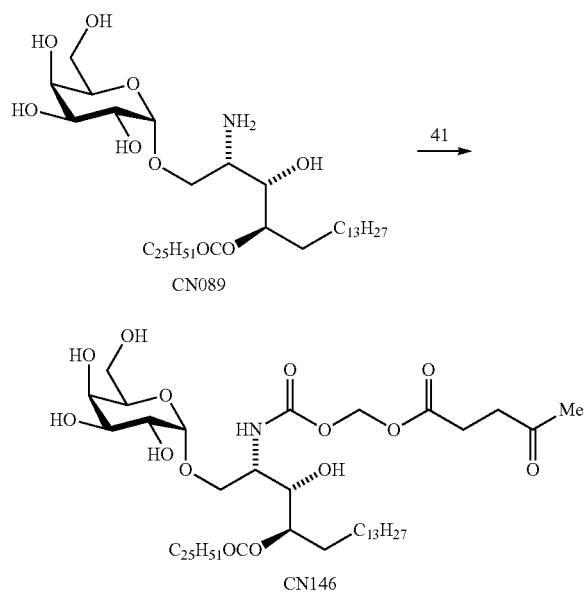

To a solution of amine CN089 (22 mg, 0.026 mmol) in d$_5$-pyridine (0.30 mL) is added a solution of (4-nitrophenoxy)carbonyloxymethyl 4-oxopentanoate (41) (8.0 mg, 0.026 mmol) in CDCl$_3$ (0.15 mL). The progress of the reaction is followed in an NMR tube. After 3 h at rt, NEt$_3$ (2.5 mg, 0.025 mmol) is added and the reaction is allowed to continue for a further 2.25 h, after which time >95% of the amine CN089 has been consumed. The volatiles are concentrated under reduced pressure and the crude residue is purified by silica gel chromatography (1.5:40:60 to 1.5:45:55 MeOH/dioxane/CHCl$_3$) to afford the title compound CN146 (14.1 mg, 53%) as a white solid. $^1$H NMR (500 MHz, 1:1 CDCl$_3$/CD$_3$OD) δ 0.88-0.90 (m, 6H), 1.24-1.34 (m, 68H), 1.60-1.72 (m, 4H), 2.21 (s, 3H), 2.31-2.42 (m, 2H), 2.62-2.64 (m, 2H), 2.80-2.83 (m, 2H), 3.71-3.83 (m, 8H), 3.88 (br d, J=10.1 Hz, 1H), 3.95 (br d, J=2.2 Hz, 1H), 4.86 (d, J=3.2 Hz, 1H) 4.94-4.98 (m, 1H), 5.68-5.76 (m, 2H); $^{13}$C NMR (126 MHz, 1:1 CDCl$_3$/CD$_3$OD) δ 14.3, 23.2, 25.6, 25.9, 28.3, 29.3, 29.7, 29.79, 28.84, 29.86, 29.92, 30.0, 30.1, 30.15, 30.18, 30.21, 32.43, 32.44, 35.1, 38.1, 53.0, 62.3, 68.1, 69.7, 70.4, 70.8, 71.4, 72.1, 75.2, 80.7, 100.5, 155.6, 172.7, 175.0, 208.5; HRMS (ESI): m/z calcd for C$_{57}$H$_{107}$NO$_{14}$Na [M+Na]$^+$ 1052.7589. found 1052.7578.

Example 3—Synthesis of (2S,3S,4R)-1-O-α-D-Galactopyranosyl-4-hexacosanoyl-2-(6-(azido)hexanoylmethoxycarbonylamino) octadecane-1,3,4-triol (CN215)

Example 3.1—(4-Nitrophenoxy)carbonyloxymethyl 6-azidohexanoate (50)

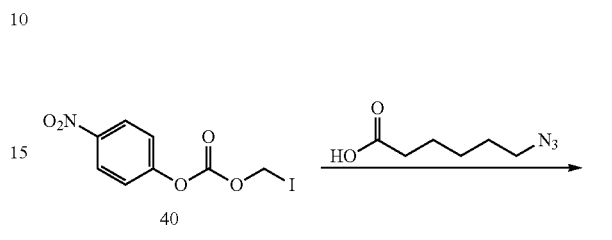

A mixture of iodomethyl 4-nitrophenyl carbonate (40) (Gangwar, Pauletti et al. 1997) (340 mg, 1.05 mmol), 6-azidohexanoic acid (210 mg, 1.34 mmol), silver oxide (100 mg, 0.43 mmol) and 4 Å molecular sieves (~500 mg) in dry acetonitrile (5 mL) is protected from light and stirred at rt. After 24 h, the mixture is filtered through celite, washed with EtOAc (20 mL) and concentrated under reduced pressure. The crude residue is purified by silica gel chromatography (EtOAc/toluene 0:10 to 1:4) to afford the title compound 50 as a colourless oil (150 mg, 40%). $^1$H NMR (500 MHz, CDCl$_3$) δ 1.42-1.48 (m, 2H), 1.60-1.66 (m, 2H), 1.68-1.74 (m, 2H), 2.45 (dd, J=7.4, 7.4 Hz, 2H), 3.28 (dd, 6.8, 6.8 Hz, 2H), 7.41 (dd, J=2.2, 9.2 Hz, 2H), 8.29 (dd, J=2.2, 9.2 Hz, 2H); $^{13}$C NMR (126 MHz, CDCl$_3$) δ 23.9, 26.0, 28.4, 33.5, 51.6, 82.5, 121.6, 125.3, 145.6, 151.4, 155.0, 171.6; HRMS-ESI: m/z calcd for C$_{14}$H$_{16}$N$_4$O$_7$Na [M+Na]$^+$ 375.0917. found 375.0917.

Example 3.2—(2S,3S,4R)-1-O-α-D-Galactopyranosyl-4-hexacosanoyl-2-(6-(azido)hexanoyloxymethoxycarbonylamino) octadecane-1,3,4-triol (CN215)

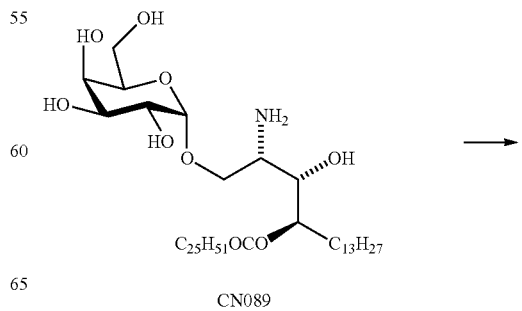

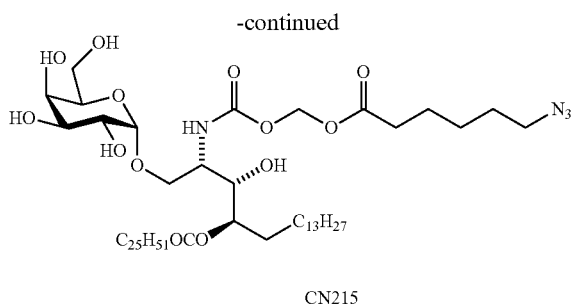

CN215

To a solution of amine CN089 (25 mg, 0.029 mmol) in pyridine (1 mL) is added a solution of (4-nitrophenoxy) carbonyloxymethyl 6-azidohexanoate (50) (20 mg, 0.056 mmol) in CH$_2$Cl$_2$ (0.15 mL) followed by Et$_3$N (1 mL). After 0.5 h at rt, the mixture is diluted with MeOH and concentrated under reduced pressure. The crude residue is purified by silica gel chromatography (MeOH/CHCl$_3$ 0:10 to 2:8) to afford the title compound CN215 as a white solid (21 mg, 67%). $^1$H NMR (500 MHz, 3:1 CDCl$_3$/CD$_3$OD) δ 0.87-0.90 (m, 6H), 1.23-1.35 (m, 68H), 1.40-1.46 (m, 2H), 1.60-1.71 (m, 8H), 2.33-2.37 (m, 2H), 2.40 (dd, J=7.5, 7.5 Hz, 2H), 3.29 (dd, J=6.7, 6.7 Hz, 2H), 3.72-3.80 (m, 8H), 3.87 (dd, J=2.3, 10.3 Hz, 1H), 3.96 (d, J=2.9 Hz, 1H), 4.86 (d, J=3.7 Hz, 1H), 4.91-4.94 (m, 1H), 5.73 (s, 2H), 6.78 (d, J=8.5 Hz, 1H); $^{13}$C NMR (126 MHz, 3:1 CDCl$_3$/CD$_3$OD) δ 13.6, 22.3, 23.7, 24.7, 25.0, 25.8, 28.2, 28.5, 28.9, 29.0, 29.1, 29.2, 29.3, 31.6, 33.4, 34.3, 50.9, 51.8, 61.5, 67.5, 68.7, 69.5, 70.0, 70.3, 71.3, 74.3, 79.8, 99.5, 154.5, 172.5, 174.2; HRMS-ESI: m/z calcd for C$_{58}$H$_{110}$N$_4$O$_{13}$Na [M+Na]$^+$ 1093.7967. found 1093.7972.

Example 4—Synthesis of (2S,3S,4R)-1-O-α-D-Galactopyranosyl-4-hexacosanoyl-2-(6-(maleimido)hexanoylmethoxycarbonylamino) octadecane-1,3,4-triol (CN157)

Example 4.1—(4-Nitrophenoxy)carbonyloxymethyl 6-maleimidohexanoate (51)

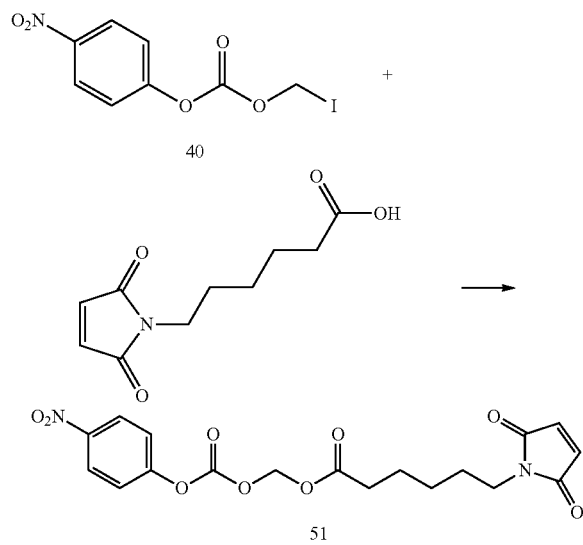

To a mixture of iodomethyl 4-nitrophenyl carbonate (40) (Gangwar, Pauletti et al. 1997) (70 mg, 0.22 mmol), 6-maleimidohexanoic acid (40 mg, 0.19 mmol) and 4 Å molecular sieves (~500 mg) in dry acetonitrile (5 mL) is added Ag$_2$O (25 mg, 0.11 mmol) and the reaction is stirred, protected from light. After 3 h, the mixture is diluted with EtOAc, filtered through celite, and concentrated under reduced pressure. The crude residue is purified by silica gel chromatography (EtOAc/petroleum ether=0:1 to 4:6) to afford the title compound 51 as a colourless oil (25 mg, 33%). $^1$H NMR (500 MHz, CDCl$_3$) δ 1.32-1.38 (m, 2H), 1.59-1.65 (m, 2H), 1.67-1.73 (m, 2H), 2.42 (dd, J=7.3, 7.3 Hz, 2H), 3.52 (dd, J=7.3, 7.3 Hz, 2H), 5.88 (s, 2H), 6.69 (s, 2H), 7.40-7.44 (m, 2H), 8.28-8.31 (m, 2H); $^{13}$C NMR (126 MHz, CDCl$_3$) δ 23.9, 26.0, 28.1, 29.7, 33.6, 37.5, 82.5, 121.7, 122.4, 125.4, 134.1, 145.7, 151.5, 155.1, 107.8, 171.7; HRMS (ESI) m/z calcd for C$_{18}$H$_{18}$N$_2$O$_9$Na [M+Na]$^+$: 429.0910. found 429.0905.

Example 4.2—(2S,3S,4R)-1-O-α-D-Galactopyranosyl-4-hexacosanoyl-2-(6-(maleimido)hexanoylmethoxycarbonylamino) octadecane-1,3,4-triol (CN157)

CN089 →

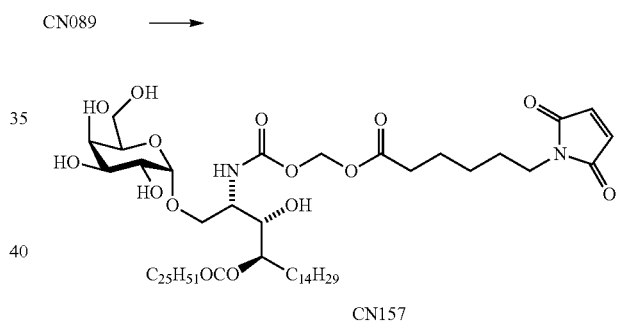

CN157

To a solution of amine CN089 (21 mg, 0.024 mmol) in dry pyridine (3 mL) is added a solution of (4-nitrophenoxy) carbonyloxymethyl 6-maleimidohexanoate (51) (8.0 mg, 0.026 mmol) in CH$_2$Cl$_2$ (3 mL) followed by Et$_3$N (2 mL). After 2 h the volatiles are concentrated under reduced pressure and the crude residue is purified by silica gel chromatography (MeOH/CHCl$_3$=0:1 to 2:8) to afford the title compound CN157 as a white solid (14 mg, 23%). $^1$H NMR (500 MHz, 3:1 CDCl$_3$/CD$_3$OD) δ 0.87-0.90 (m, 6H), 1.23-1.34 (m, 70H), 1.58-1.70 (m, 8H), 2.33-2.39 (m, 4H), 3.52 (dd, J=7.3, 7.3 Hz, 2H), 3.71-3.79 (m, 8H), 3.88 (dd, J=2.5, 10.3 Hz, 1H), 3.96 (d, J=3.0 Hz, 1H), 4.86 (d, J=3.6 Hz, 1H), 4.93 (m, 1H), 5.70-5.75 (m, 1H), 6.73 (s, 2H); $^{13}$C NMR (126 MHz, 3:1 CDCl$_3$/CD$_3$OD) δ 14.2, 22.9, 24.2, 25.3, 25.6, 26.3, 28.4, 29.1, 29.4, 29.6, 29.7, 29.9, 32.2, 33.9, 34.8, 37.8, 52.4, 62.1, 68.1, 69.3, 70.1, 70.5, 70.9, 72.0, 74.9, 80.4, 100.1, 134.4, 155.1, 171.4, 173.1, 174.8; HRMS (ESI) m/z calcd for C$_{62}$H$_{112}$N$_2$O$_{15}$Na [M+Na]$^+$: 1147.7960. found 1147.7960.

Example 5—Synthesis of (2S,3S,4R)-1-O-α-D-Galactopyranosyl-4-O-hexacosanoyl-2-(N-Cbz-Phe-Lys-4-aminobenzyloxycarbonylamino) octadecane-1,3,4-triol (CN166)

Example 5.1—N-Cbz-Phe-Lys(Alloc)OH (42)

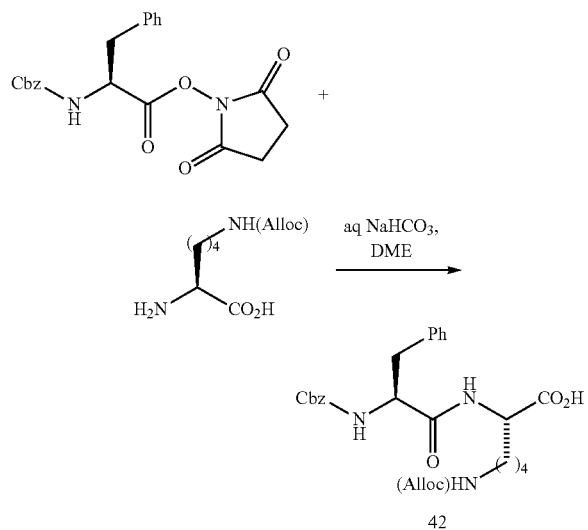

The title compound is synthesised in 59% yield, following the literature procedure (Dubowchik, Firestone et al. 2002). ¹H NMR (500 MHz, d6-DMSO) δ 1.26-1.45 (m, 4H), 1.57-1.65 (m, 1H), 1.69-1.77 (m, 1H), 2.73 (dd, J=11.1, 13.7 Hz, 1H), 2.92-3.04 (m, 3H), 4.16-4.20 (m, 1H), 4.28-4.33 (m, 1H), 4.44-4.49 (m, 2H), 4.94 (s, 2H), 5.15 (app dq, J=1.4, 10.4 Hz, 1H), 5.25 (app dq, J=1.7, 17.2 Hz, 1H), 5.85-5.93 (m, 1H), 7.13-7.34 (10H), 7.43 (d, J=8.9 Hz, 1H), 8.16-8.21 (m, 1H); ¹³C NMR (126 MHz, d6-DMSO) δ 22.6, 29.0, 30.8, 37.4, 39.8 (obscured by solvent), 52.0, 55.9, 64.1, 65.2, 116.8, 126.2, 127.4, 127.6, 128.0, 128.2, 129.2, 133.8, 137.0, 138.1, 155.8, 155.9, 171.6, 173.5; HRMS-ESI [M+Na]⁺ calcd for $C_{27}H_{33}N_3NaO_7$: 534.2216. Found 534.2209.

Example 5.2—N-Cbz-Phe-Lys(Alloc)-4-aminobenzyl alcohol (43)

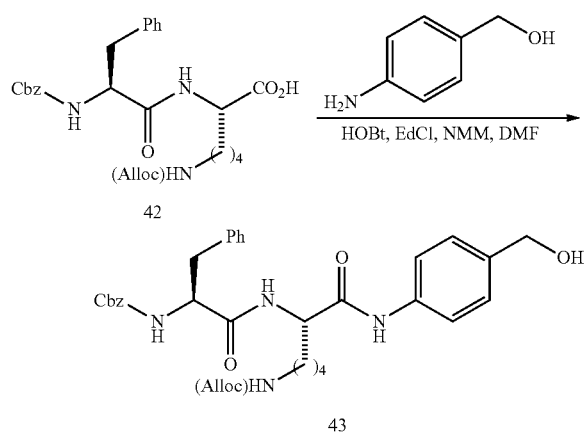

A mixture of dipeptide 42 (243 mg, 0.475 mmol), 1-hydroxybenzotriazole hydrate (74 mg, 0.54 mmol) and 4-aminobenzyl alcohol (118 mg, 0.958 mmol) is dissolved in THF (5 mL) under Ar and cooled in an ice bath. N-Methyl morpholine (54 μL, 0.49 mmol) is added, followed by EDCI (97 mg, 0.51 mmol) and the mixture is stirred on ice for 2 h, then at rt for 2 h. The mixture is acidified to pH ~3 with aq citric acid and extracted with EtOAc, and the extracts are dried (brine, MgSO₄) and concentrated under reduced pressure. The solid residue is triturated with diethyl ether, and subsequently purified twice by column chromatography on silica gel (first column: MeOH/CH₂C₂=2:98 to 7:93; second column EtOAc/petroleum ether=8:2 to 1:0) to afford the title compound 43 (70 mg, 24%) as a white solid. ¹H NMR (500 MHz, CDCl₃+3 drops CD₃OD) δ 1.28-1.36 (m, 2H), 1.47-1.53 (m, 2H), 1.61-1.70 (m, 1H), 1.82-1.89 (m, 1H), 2.96-3.00 (m, 1H), 3.08-3.13 (m, 3H), 4.41-4.45 (m, 2H), 4.50-4.54 (m, 2H), 4.62 (s, 2H), 5.03-5.10 (m, 2H), 5.17-5.19 (m, 1H), 5.25-5.29 (m, 1H), 5.84-5.92 (m, 1H), 7.13-7.19 (m, 5H), 7.27-7.35 (m, 7H), 7.51 (d, J=8.5 Hz, 2H); ¹³C NMR (126 MHz, CDCl₃+3 drops CD₃OD) δ 22.0, 28.8, 30.9, 37.9, 39.8, 53.2, 55.9, 64.1, 65.2, 66.8, 117.2, 119.9, 126.7, 127.3, 127.5, 127.6, 127.9, 128.2, 128.3, 128.8, 132.5, 135.7, 136.7, 136.9, 155.9, 156.5, 169.4, 171.5; HRMS-ESI [M+Na]⁺ calcd for $C_{34}H_{40}N_4NaO_7$: 639.2795. Found 639.2786.

Example 5.3—N-Cbz-Phe-Lys(Alloc)-4-aminobenzyl 4-nitrophenyl carbonate (44)

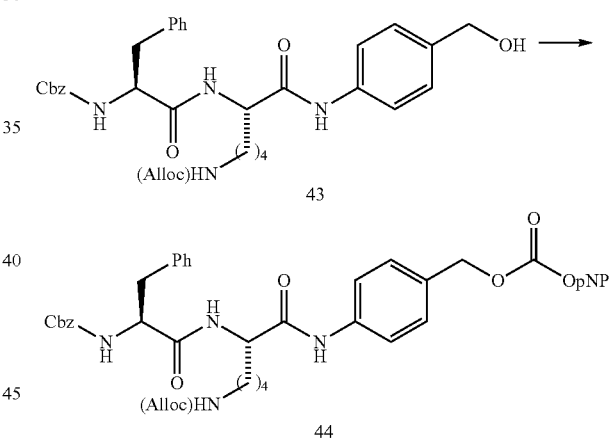

To an ice-cooled solution of alcohol 43 (70 mg, 0.11 mmol) in dry THF (5 mL) is added pyridine (46 μL, 0.57 mmol), followed by 4-nitrophenyl chloroformate (46 mg, 0.23 mmol) and the mixture is stirred at rt overnight. After diluting with EtOAc, the organic phase is washed with 10% aq citric acid and water, then dried (brine, MgSO₄) and concentrated under reduced pressure. The solid residue is triturated with toluene, and subsequently purified column chromatography on silica gel (MeOH/CH₂Cl₂=0:100 to 5:95) to afford the title compound 44 (63 mg, 71%) as a white solid. ¹H NMR (500 MHz, CDCl₃+3 drops CD₃OD) δ 1.27-1.37 (m, 2H), 1.48-1.54 (m, 2H), 1.61-1.70 (m, 1H), 1.83-1.91 (m, 1H), 2.98-3.03 (dd, J=7.2, 13.3 Hz, 1H), 3.09-3.16 (m, 3H), 4.41-4.46 (m, 2H), 4.50-4.57 (m, 2H), 5.07 (s, 2H), 5.18 (d, J=10.5 Hz, 1H), 5.25-5.29 (m, 3H), 5.84-5.92 (m, 1H), 7.13-7.19 (m, 5H), 7.27-7.42 (m, 9H), 7.61 (d, J=8.0 Hz, 2H), 8.27 (d, J=9.1 Hz, 2H); ¹³C NMR (126 MHz, CDCl₃+3 drops CD₃OD) δ 22.0, 28.8, 30.7, 37.8, 39.8, 53.2, 55.8, 65.2, 66.8, 70.3, 117.2, 119.8, 121.4, 124.9, 126.7, 127.6, 127.9, 128.2, 128.3, 128.8, 129.2, 129.6, 132.5, 135.6, 135.7, 138.3, 145.1, 152.1, 155.2, 155.9, 156.5, 169.5, 171.5; HRMS-ESI [M+Na]⁺ calcd for $C_{41}H_{43}N_5NaO_{11}$: 804.2857. Found 804.2852.

Example 5.4—(2S,3S,4R)-1-O-α-D-Galactopyranosyl-4-O-hexacosanoyl-2-[N-Cbz-Phe-Lys(ε-N-Alloc)-4-aminobenzyloxycarbonylamino] octadecane-1,3,4-triol (45)

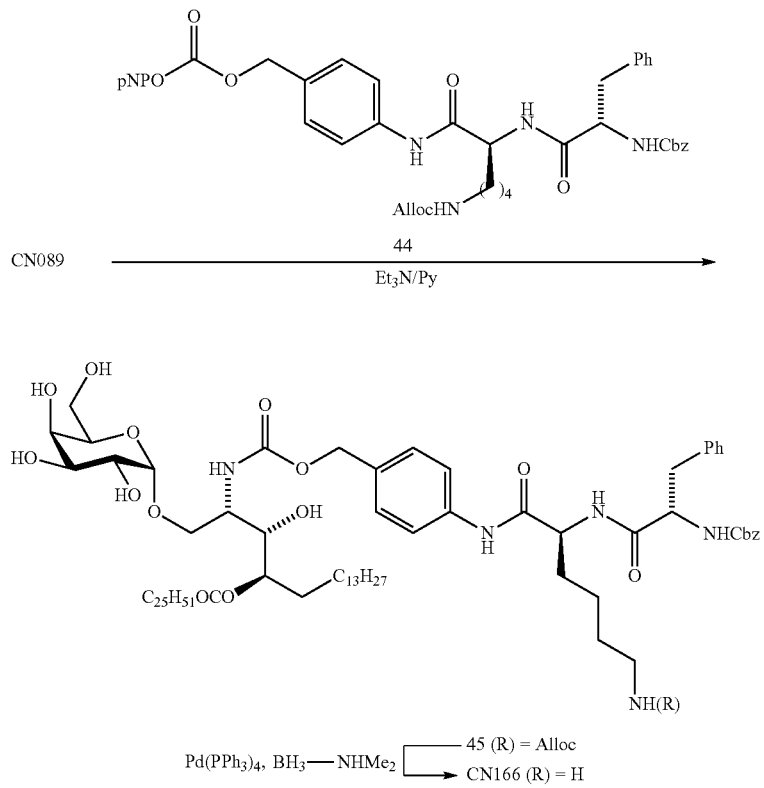

To a mixture of CN089 (18 mg, 0.021 mmol) in pyridine (0.25 mL) under Ar is added pNP-carbonate 44 (18 mg, 0.023 mmol) suspended in 17:1 CHCl₃-MeOH (0.53 mL), followed by Et₃N (4.5 μL, 0.032 mmol) and the mixture is stirred at rt. After 18 h, a further portion of Et₃N (6 μL, 0.043 mmol) is added. After a further 16 h, the volatiles are gently concentrated on a rotary evaporator and more pyridine (0.25 mL) is added, followed by Et₃N (4 μL, 0.029 mmol). After 24 h, the excess carbonate reagent is quenched with Et₂NH (10 μL, 10 min) and the mixture is concentrated to dryness. The crude residue is purified by column chromatography on silica gel (MeOH/CHCl₃=0:1 to 1:9) to afford the title compound 45 (16.4 mg, 52%) as a white solid. ¹H NMR (500 MHz, 1:1 CDCl₃/CD₃OD) δ 0.87-0.90 (m, 6H), 1.15-1.42 (m, 70H), 1.48-1.55 (m, 2H), 1.60-1.74 (m, 5H), 1.84-1.91 (m, 1H), 2.31-2.41 (m, 2H), 2.94 (dd, J=8.4, 13.7 Hz, 1H), 3.10-3.16 (m, 3H), 3.68-3.81 (m, 8H), 3.86 (dd, J=2.2, 10.4 Hz, 1H), 3.89 (d, J=2.8 Hz, 1H), 4.42-4.46 (m, 2H), 4.50-4.51 (m, 2H), 4.85 (d, J=3.7 Hz, 1H), 4.96-5.00 (m, 1H), 5.03-5.10 (m, 4H), 5.15-5.18 (m, 1H), 5.25-5.29 (m, 1H), 5.85-5.92 (m, 1H), 7.14-7.23 (m, 5H), 7.27-7.35 (m, 7H), 7.56 (d, J=8.1 Hz, 2H); ¹³C NMR (126 MHz, 1:1 CDCl₃/CD₃OD) δ 14.30, 14.32, 23.2, 25.6, 25.9, 29.2, 29.7, 29.88, 29.91, 29.93, 30.08, 30.13, 30.19, 30.22, 30.3, 32.2, 32.46, 32.48, 35.1, 38.6, 40.9, 52.9, 54.4, 57.1, 62.4, 65.9, 67.0, 67.4, 68.5, 69.7, 70.4, 70.9, 71.4, 72.3, 75.3, 100.6, 117.6, 120.8, 120.9, 127.4, 128.3, 128.6, 128.98, 129.02, 129.2, 129.3, 129.8, 133.3, 133.6, 137.0, 137.1, 138.4, 157.4, 158.0, 171.1, 173.0, 175.1; HRMS-ESI [M+Na]⁺ calcd for $C_{85}H_{137}N_5NaO_{17}$: 1522.9907. Found 1522.9888.

Example 5.5—(2S,3S,4R)-1-O-α-D-Galactopyranosyl-4-O-hexacosanoyl-2-(N-Cbz-Phe-Lys-4-aminobenzyloxycarbonylamino) octadecane-1,3,4-triol (CN166)

To a mixture of compound 45 (16 mg, 0.011 mmol) and borane-dimethylamine complex (3.4 mg, 0.058 mmol) dissolved in freshly degassed 14:1 CH₂Cl₂-MeOH (0.16 mL), is added a catalytic amount of Pd(PPh₃)₄ (approx 0.5 mg, 0.4 μmol) and the mixture is stirred at rt under Ar. After 80 min, the rxn mixture is filtered through a short plug of silica (0.15 g), washing with 50% to 75% MeOH/CH₂Cl₂ (12 mL of each). The washings are concentrated and purified by column chromatography on C18 silica gel (MeOH+0.5% TFA) to afford the TFA salt of the title compound CN166 (15.4 mg, 94%) as a colourless glass. ¹H NMR (500 MHz, 1:1 CDCl₃/CD₃OD) δ 0.87-0.90 (m, 6H), 1.15-1.51 (m, 70H), 1.60-1.75 (m, 7H), 1.87-1.94 (m, 1H), 2.31-2.41 (m, 2H), 2.86-2.90 (br m, 2H), 2.95 (dd, J=8.4, 13.8 Hz, 1H), 3.13 (dd, J=6.1, 13.8 Hz, 1H), 3.67-3.80 (m, 8H), 3.85-3.87 (m, 2H), 4.38-4.41 (m, 1H), 4.46-4.49 (m, 1H), 4.85 (d, J=3.6 Hz, 1H), 4.97-5.13 (m, 5H), 7.12-7.16 (m, 1H), 7.19-7.20 (m, 4H), 7.28-7.36 (m, 7H), 7.56 (d, J=8.0 Hz, 2H); ¹³C NMR (126 MHz, 1:1 CDCl₃/CD₃OD) δ 14.31, 14.33, 22.9, 23.23, 23.24, 25.7, 26.0, 27.4, 29.3, 29.8, 29.9, 30.0, 30.1, 30.18, 30.24, 30.26, 30.28, 30.31, 31.9, 32.52, 32.54, 35.2, 38.5, 40.0, 53.1, 54.2, 57.3, 62.4, 67.0, 67.4, 68.6, 69.7, 70.5, 70.9, 71.4, 72.4, 75.4, 100.8, 120.9, 127.5, 128.2, 128.7, 129.05, 129.10, 129.2, 129.8, 133.6, 137.0, 137.1, 138.4, 157.5, 157.6, 171.0, 173.3, 175.2; HRMS-ESI [M+Na]$^+$ calcd for $C_{81}H_{133}N_5NaO_{15}$: 1438.9696. Found 1438.9686.

Example 6—Synthesis of (2S,3S,4R)-1-O-α-D-Galactopyranosyl-4-O-hexacosanoyl-2-(N-Cbz-Val-Cit-4-aminobenzyloxycarbonylamino) octadecane-1,3,4-triol (CN165)

Example 6.1—N-Cbz-Val-Cit-4-aminobenzyl alcohol (47)

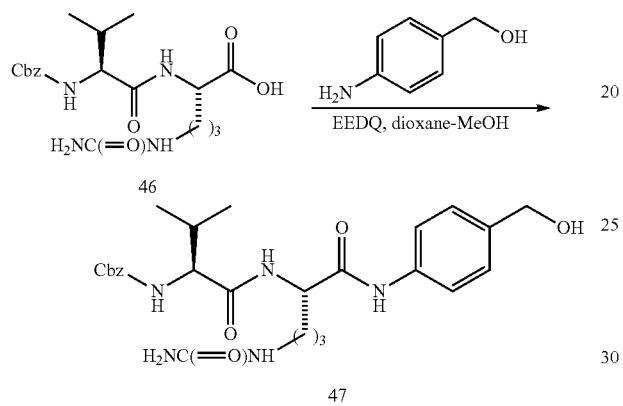

A mixture of acid 46 (Dubowchik, Firestone et al. 2002) (200 mg, 0.49 mmol) and 4-aminobenzyl alcohol (64 mg, 0.52 mmol) is stirred under Ar at 20° C. in 1:1 MeOH/1,4-dioxane (6 mL) until the starting materials are nearly dissolved (1 h). EEDQ (242 mg, 0.98 mmol) is added and stirring is continued at 20° C. for 3.5 d. The solvents are removed under reduced pressure and the solid residue is triturated with EtOAc, and subsequently purified by column chromatography on silica gel (MeOH/CH$_2$Cl$_2$=5:95 to 15:85) to afford the title compound 47 (106 mg, 42%) as a white solid. $^1$H NMR (500 MHz, CD$_3$OD) δ 0.95 (d J=6.8 Hz, 3H), 0.97 (d J=6.8 Hz, 3H), 1.52-1.63 (m, 2H), 1.71-1.78 (m, 1H), 1.87-1.94 (m, 1H), 2.03-2.11 (m, 1H), 3.07-3.12, (m, 1H), 3.15-3.21, (m, 1H), 3.98 (d, J=6.8 Hz, 1H), 4.50-4.52 (m, 1H), 4.55 (s, 2H), 5.10 (s, 2H), 7.26-7.36 (m, 7H), 7.54 (d, J=8.0 Hz, 2H); $^{13}$C NMR (126 MHz, CD$_3$OD) δ 18.6, 19.7, 27.8, 30.5, 31.9, 40.3, 55.0, 62.3, 64.8, 67.8, 121.3, 128.6, 128.8, 129.0, 129.5, 138.2, 138.6, 138.8, 158.8, 162.3, 172.2, 174.4; HRMS-ESI [M+Na]$^+$ calcd for $C_{26}H_{35}N_5NaO_6$: 536.2485. Found 536.2495.

Example 6.2—N-Cbz-Val-Cit-4-aminobenzyl 4-nitrophenyl carbonate (48)

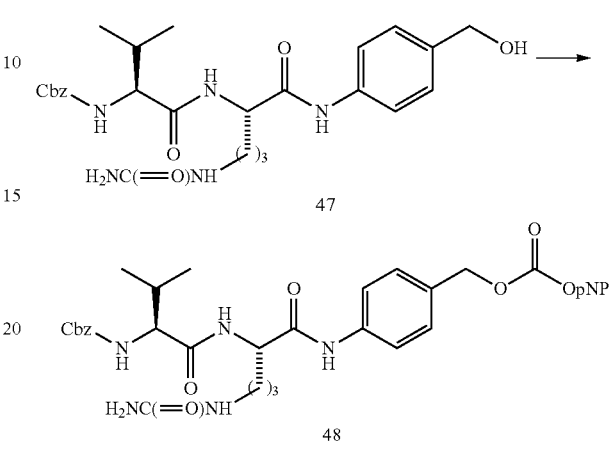

To a solution of alcohol 47 (30 mg, 0.058 mmol) and bis(4-nitrophenyl) carbonate (23 mg, 0.076 mmol) in anhydrous DMF (0.5 mL) under Ar is added pyridine (0.10 mL), followed by i-Pr$_2$NEt (10.5 μL, 0.060 mmol) and the reaction is stirred at rt. After 16 h, the mixture is concentrated under reduced pressure and the crude residue is purified by column chromatography on silica gel (MeOH/CH$_2$Cl$_2$=0:1 to 1:9), to afford the title compound 48 (30 mg, 76%) as a white solid. $^1$H NMR (500 MHz, 5:1 CDCl$_3$/CD$_3$OD) δ 0.94 (d J=6.8 Hz, 3H), 0.98 (d J=6.8 Hz, 3H), 1.51-1.57 (m, 2H), 1.67-1.74 (m, 1H), 1.88-1.95 (m, 1H), 2.05-2.13 (m, 1H), 3.09-3.14, (m, 1H), 3.20-3.26, (m, 1H), 4.01 (d, J=6.4 Hz, 1H), 4.56 (dd, J=4.9, 9.0 Hz, 1H), 5.08-5.14 (m, 2H), 5.26 (s, 2H), 7.29-7.41 (m, 9H), 7.64 (d, J=8.0 Hz, 2H), 8.26-8.29 (m, 2H); $^{13}$C NMR (126 MHz, 5:1 CDCl$_3$/CD$_3$OD) δ 17.8, 19.2, 26.3, 29.3, 31.0, 39.1, 53.3, 60.8, 67.2, 70.8, 120.2, 121.9, 125.4, 127.9, 128.3, 128.6, 129.7, 130.1, 136.3, 138.8, 145.5, 152.6, 155.7, 157.1, 160.5, 170.6, 172.6; HRMS-ESI [M+Na]$^+$ calcd for $C_{33}H_{38}N_6NaO_{10}$: 701.2536. Found 701.2540.

Example 6.3—(2S,3S,4R)-1-O-α-D-Galactopyranosyl-4-O-hexacosanoyl-2-(N-Cbz-Val-Cit-4-aminobenzyloxycarbonylamino) octadecane-1,3,4-triol (CN165)

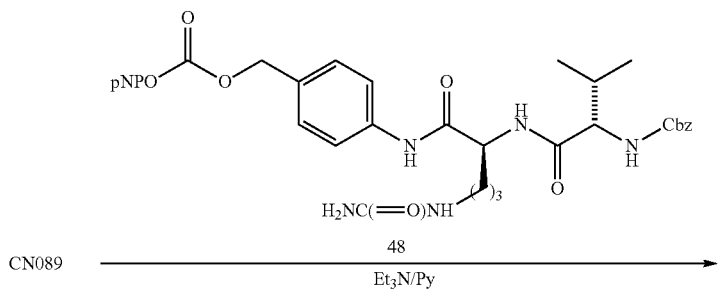

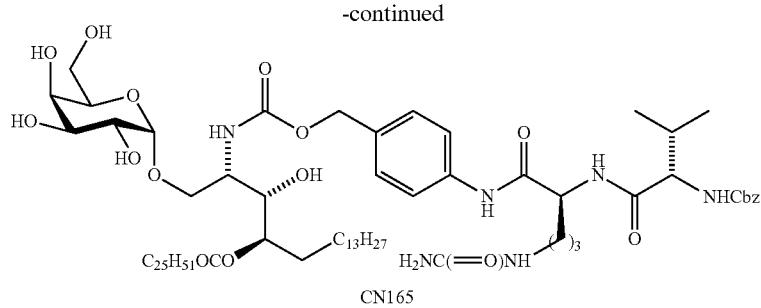

CN165

To a mixture of CN089 (17 mg, 0.020 mmol) in pyridine (0.25 mL) under Ar is added pNP-carbonate 48 (15 mg, 0.022 mmol) dissolved in pyridine (0.25 mL), followed by Et$_3$N (4.5 μL, 0.032 mmol) and the mixture is stirred at rt. After 18 h, a further portion of Et$_3$N (3 μL, 0.022 mmol) is added and the reaction is stirred for a further 4 h before quenching excess carbonate reagent with Et$_2$NH (10 μL, 10 min). The mixture is concentrated to dryness and the crude residue is purified by column chromatography on silica gel (MeOH/CHCl$_3$=5:95 to 15:85), followed by column chromatography on C18 silica gel (MeOH), and finally by preparative HPLC (Phenomenex Luna C18(2), 5 μm, 30×250 mm, 35° C., 50 mL/min; Mobile phase A=80:20:0.05 MeOH/water/TFA; Mobile phase B=100:0.05 MeOH/TFA; 0-10 min: 0-100% B; 10-34 min: 100% B; 34-35 min: 100-0% B; 35-37 min: 100% A) to afford the title compound CN165 (21 mg, 76%) as a white solid. $^1$H NMR (500 MHz, 2:1 CDCl$_3$/CD$_3$OD) δ 0.87-0.90 (m, 6H), 0.94 (d J=6.7 Hz, 3H), 0.98 (d J=6.5 Hz, 3H), 1.20-1.40 (m, 68H), 1.50-1.76 (m, 7H), 1.87-1.96 (m, 1H), 2.05-2.13 (m, 1H), 2.29-2.41 (m, 2H), 3.07-3.15 (m, 1H), 3.18-3.26 (m, 1H), 3.63-3.81 (m, 8H), 3.83-3.90 (m, 2H), 4.01 (d, J=6.4 Hz, 1H), 4.52-4.57 (m, 1H), 4.80-4.86 (m, 1H), 4.91-5.00 (m, 2H), 5.04-5.16 (m, 3H), 7.27-7.37 (m, 7H), 7.57 (d, J=8.0 Hz, 2H); $^{13}$C NMR (126 MHz, 2:1 CDCl$_3$/CD3OD) δ 14.2, 18.1, 19.4, 23.0, 25.4, 25.6, 26.7, 29.2, 29.5, 29.65, 29.67, 29.7, 29.86, 29.88, 29.92, 29.95, 29.98, 30.02, 31.2, 32.2, 34.9, 39.3, 52.5, 53.7, 61.1, 62.3, 66.7, 67.4, 68.4, 69.3, 70.3, 70.6, 70.8, 72.3, 75.0, 100.3, 120.5, 128.2, 128.5, 128.8, 129.0, 133.0, 136.6, 138.1, 157.0, 157.6, 161.3, 171.0, 173.1, 174.9; HRMS-ESI [M+Na]$^+$ calcd for C$_{77}$H$_{132}$N$_6$NaO$_{16}$: 1419.9598. Found 1419.9584.

Example 7—Synthesis of (2S,3S,4R)-1-O-α-D-Galactopyranosyl-4-O-hexacosanoyl-2-(N-(6-azidohexanoyl)-Val-Cit-4-aminobenzyloxycarbonylamino) octadecane-1,3,4-triol (CN172)

Example 7.1—N-(6-Azidohexanoyl)-Val-Cit-4-aminobenzyl alcohol (53)

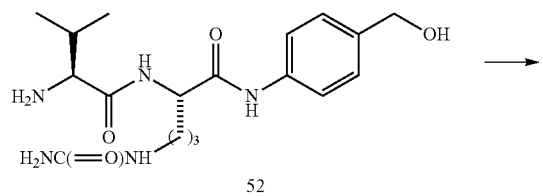

52

→

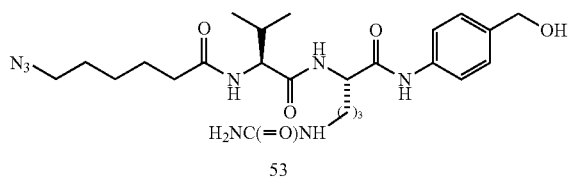

53

To a stirred solution of 6-azidohexanoic acid (85.0 mg, 0.541 mmol) in anhydrous CH$_2$Cl$_2$ (3.3 mL) at 0° C. is added by Et$_3$N (80 μL, 0.57 mmol), followed by isobutyl chloroformate (68 μL, 0.52 mmol). After 30 min, the solution is transferred by cannula to a separate flask containing amine 52 (Dubowchik, Firestone et al. 2002) (166 mg, 0.438 mmol) dissolved in 3:1 CH$_2$Cl$_2$-MeOH (4 mL) at 0° C. The original flask is rinsed with CH$_2$Cl$_2$ (2×0.5 mL), which is transferred to the second flask. After 5 min, the reaction mixture is warmed to rt and stirred for 2.5 h. After concentration of the solvents under reduced pressure, the resulting solid is triturated successively with toluene, diethyl ether, acetone and MeCN, and purified by column chromatography on silica gel (MeOH/CHC$_3$=10:90 to 14:86) to afford the title compound 53 as a white solid (160 mg, 71%). $^1$H NMR (500 MHz, 2:1 CDCl$_3$/CD$_3$OD) δ 0.95-97 (m, 6H), 1.39-1.45 (m, 2H), 1.53-1.77 (m, 7H), 1.88-1.95 (m, 1H), 2.04-2.11 (m, 1H), 2.29 (t, J=7.5 Hz, 2H), 3.09-3.15, (m, 1H), 3.20-3.26 (1H), 3.28 (t, J=6.9 Hz, 2H), 4.19, (d, J=7.3 Hz, 1H), 4.54 (dd, J=5.0, 8.8 Hz, 1H), 4.59 (s, 2H), 7.31 (d, J=8.5 Hz, 2H), 7.54 (d, J=8.5 Hz, 2H); $^{13}$C NMR (126 MHz, 2:1 CDCl$_3$/CD$_3$OD) δ 18.4, 19.4, 25.6, 26.6, 28.9, 29.6, 31.0, 36.2, 39.4, 51.6, 53.6, 59.4, 64.3, 120.5, 127.9, 137.4, 137.7, 161.0, 170.9, 172.8, 174.9; HRMS-ESI [M+Na]$^+$ calcd for C$_{24}$H$_{38}$N$_8$NaO$_5$: 541.2863. found 541.2860.

Example 7.2—N-(6-Azidohexanoyl)-Val-Cit-4-aminobenzyl 4-nitrophenyl carbonate (54)

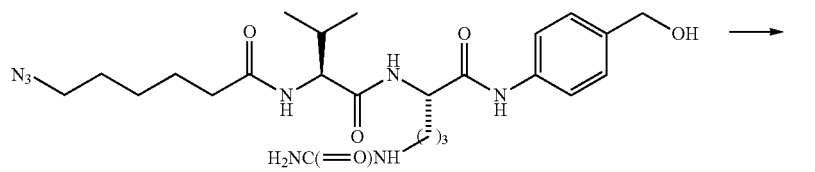

53

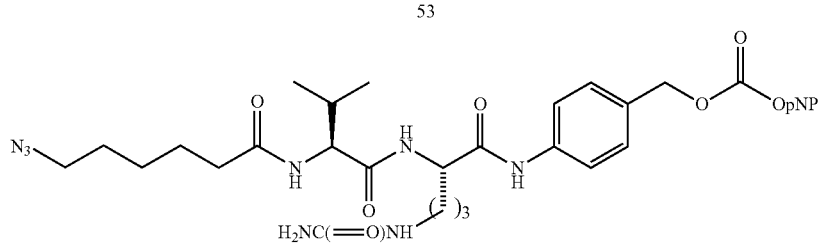

54

To a mixture of alcohol 53 (158 mg, 0.305 mmol) in anhydrous DMF (2.5 mL) is added N,N-diisopropylethylamine (66 µL, 0.38 mmol) followed by bis(4-nitrophenyl) carbonate (116 mg, 0.381 mmol) and the reaction is stirred under Ar at rt for 41 h. After concentrating the mixture under high vacuum, the crude product is purified by column chromatography on silica gel (MeOH/CH$_2$Cl$_2$=6:94 to 11:89) to afford the title compound 54 as an off-white solid (206 mg, 99%). $^1$H NMR (500 MHz, d6-DMSO) δ 0.84 (d, J=6.8 Hz, 3H), 0.87 (d, J=6.7 Hz, 3H), 1.27-1.33 (m, 2H), 1.34-1.64 (m, 7H), 1.68-1.75 (m, 1H), 1.95-2.02 (m, 1H), 2.13-2.24 (m, 2H), 2.92-2.98 (m, 1H), 3.00-3.06, (m, 1H), 4.18-4.21 (m, 1H), 4.38-4.42 (m, 1H), 5.24 (s, 2H), 5.39 (s, 2H), 5.96 (t, J=5.7 Hz, 1H), 7.41 (d, J=8.4 Hz, 2H), 7.55-7.58 (m, 2H), 7.65 (d, J=8.4 Hz, 2H), 7.81 (d, J=8.6 Hz, 1H), 8.06 (d, J=7.5 Hz, 1H), 8.29-8.33 (m, 2H), 10.03 (s, 1H); $^{13}$C NMR (126 MHz, d6-DMSO) δ 18.2, 19.2, 24.8, 25.7, 26.8, 27.9, 29.2, 30.3, 34.9, 38.5, 50.5, 53.1, 57.6, 70.2, 119.0, 122.5, 125.3, 129.3, 129.4, 139.3, 145.1, 151.9, 155.3, 158.8, 170.7, 171.3, 172.3; HRMS-ESI [M+Na]; calcd for C$_{31}$H$_{41}$N$_9$NaO$_9$: 706.2925. found 706.2913.

Example 7.3—(2S,3S,4R)-1-O-α-D-Galactopyranosyl-4-O-hexacosanoyl-2-(N-(6-azidohexanoyl)-Val-Cit-4-aminobenzyloxycarbonylamino) octadecane-1,3,4-triol (CN172)

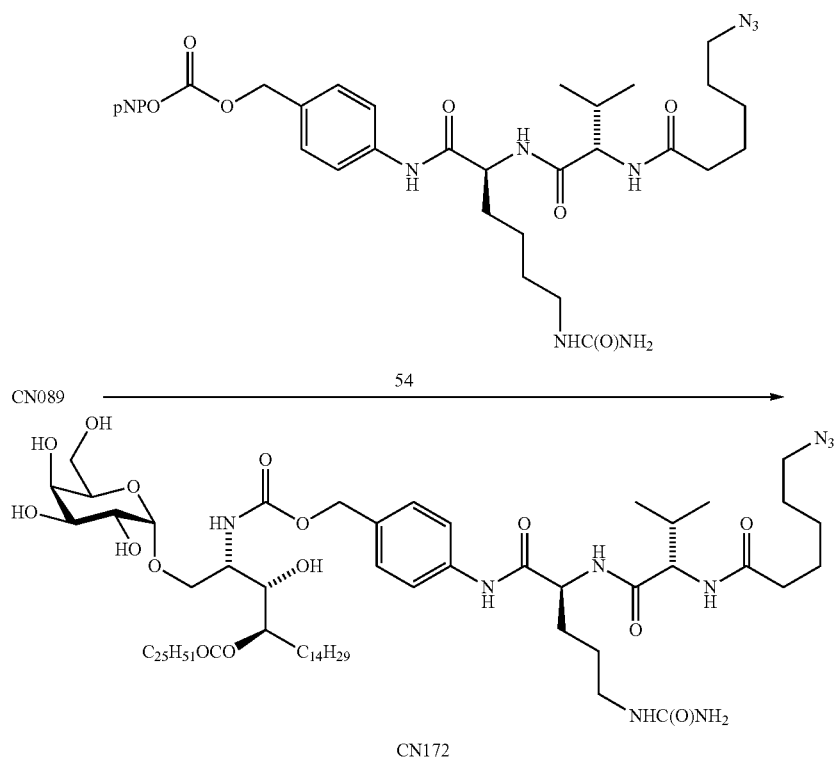

To a mixture of CN089 (61 mg, 0.071 mmol) and pNP-carbonate 54 (54 mg, 0.079 mmol) in anhydrous pyridine (1.0 mL) under Ar is added Et$_3$N (20 µL, 0.14 mmol) and the mixture is stirred at rt. After 26 h, the mixture is concentrated to dryness under high vacuum, and the crude residue is purified by column chromatography on silica gel (MeOH/CH$_2$Cl$_2$=5:95 to 20:80), followed by column chromatography on C18 silica gel (MeOH/CH$_2$Cl$_2$=100:0 to 90:10), to afford the title compound CN172 as a white solid (57 mg, 57%). $^1$H NMR (500 MHz, 2:1 CDCl$_3$/CD$_3$OD) δ 0.87-0.90 (m, 6H), 0.95-0.98 (m, 6H), 1.24-1.37 (m, 68H), 1.39-1.45 (m, 2H), 1.53-1.77 (m, 11H), 1.87-1.94 (m, 1H), 2.04-2.11 (m, 1H), 2.27-2.32 (m, 2H), 2.33-2.40 (m, 2H), 3.09-3.14 (m, 1H), 3.21-3.26 (m, 1H), 3.28 (t, J=6.8 Hz, 2H), 3.66-3.80 (m, 8H), 3.85-3.87 (m, 2H), 4.18 (d, J=7.3 Hz, 1H), 4.53 (dd, J=5.1, 8.6 Hz, 1H), 4.85 (d, J=3.7 Hz, 1H), 4.93-4.99 (m, 2H), 5.10-5.18 (m, 1H), 7.32 (d, J=8.3 Hz, 2H), 7.57 (d, J=8.3 Hz, 2H); $^{13}$C NMR (126 MHz, 2:1 CDCl$_3$/CD$_3$OD) δ 14.2, 18.5, 19.4, 23.0, 25.4, 25.6, 25.7, 26.7, 28.9, 29.2, 29.6, 29.69, 29.72, 29.8, 29.90, 29.92, 29.96, 30.02, 30.06, 31.0, 32.3, 35.0, 36.2, 39.4, 51.6, 52.6, 53.7, 59.4, 62.3, 66.8, 68.4, 69.4, 70.2, 70.7, 71.0, 72.3, 75.1, 100.4, 120.5, 129.1, 133.0, 138.3, 157.1, 161.1, 171.0, 172.9, 175.0; HRMS-ESI [M+Na]$^+$ calcd for C$_{75}$H$_{135}$N$_9$NaO$_{15}$: 1424.9941. found 1424.9940.

Example 8—Synthesis of (2S,3S,4R)-1-O-α-D-Galactopyranosyl-4-O-hexacosanoyl-2-(N-(5-hexenoyl)-Val-Cit-4-aminobenzyloxycarbonylamino) octadecane-1,3,4-triol (CN173)

Example 8.1—N-(5-Hexenoyl)-Val-Cit-4-aminobenzyl alcohol (55)

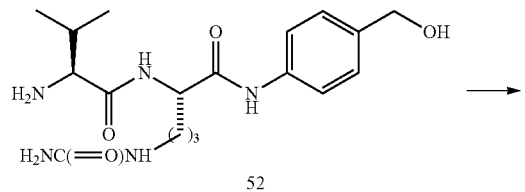

52

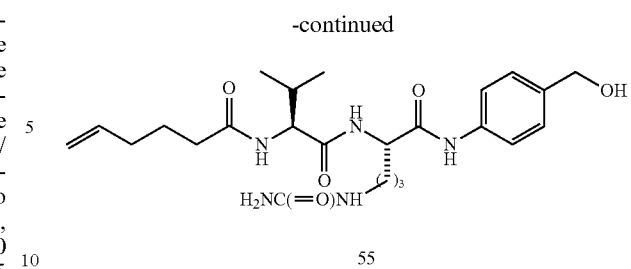

55

To a stirred solution of 5-hexenoic acid (39 mg, 0.34 mmol) in anhydrous CH$_2$Cl$_2$ (2 mL) at 0° C. is added by Et$_3$N (50 µL, 0.36 mmol), followed by isobutyl chloroformate (43 µL, 0.33 mmol). The solution is warmed to rt and stirred for 45 min, before transferring by cannula to a separate flask containing amine 52 (Dubowchik, Firestone et al. 2002) (100 mg, 0.264 mmol) in 5:1 CH$_2$Cl$_2$-MeOH (2.4 mL) at 0° C. The original flask is rinsed with CH$_2$Cl$_2$ (0.5 mL), which is transferred to the second flask. After 10 min, the reaction mixture is warmed to rt and MeOH (1 mL) is added to aid stirring of the heterogeneous mixture. After 85 min at rt, the reaction is quenched with Et$_2$NH (25 µL) and the solvents are concentrated under reduced pressure. The resulting solid is triturated successively with diethyl ether and CH$_2$Cl$_2$ to afford the title compound 55 as an off-white solid (114 mg, 91%). $^1$H NMR (500 MHz, d6-DMSO) δ 0.84 (d, J=6.7 Hz, 3H), 0.86 (d, J=6.7 Hz, 3H), 1.32-1.48 (m, 2H), 1.53-1.64 (m, 3H), 1.67-1.74 (m, 1H), 1.95-2.02 (m, 3H), 2.13-2.24 (m, 2H), 2.91-2.97 (m, 1H), 2.99-3.05, (m, 1H), 4.19 (dd, J=6.9, 8.5 Hz, 1H), 4.36-4.41 (m, 1H), 4.42 (d, J=5.7 Hz, 2H), 4.93-4.96 (m, 1H), 4.98-5.02 (m, 1H), 5.07 (t, J=5.7 Hz, 1H), 5.38 (s, 2H), 5.74-5.84 (m, 1H), 5.97 (t, J=5.6 Hz, 1H), 7.23 (d, J=8.4 Hz, 2H), 7.54 (d, J=8.4 Hz, 2H), 7.81 (d, J=8.5 Hz, 1H), 8.03 (d, J=7.6 Hz, 1H), 9.88 (s, 1H); $^{13}$C NMR (126 MHz, d6-DMSO) δ 18.2, 19.2, 24.6, 26.7, 29.3, 30.3, 32.7, 34.6, 38.6, 53.0, 57.7, 62.6, 115.0, 118.9, 126.9, 137.4, 137.5, 138.3, 158.8, 170.3, 171.2, 172.3; HRMS-ESI [M+Na]$^+$ calcd for C$_{24}$H$_{37}$N$_5$NaO$_5$: 498.2692. found 498.2699.

Example 8.2—N-(5-Hexenoyl)-Val-Cit-4-aminobenzyl 4-nitrophenyl carbonate (56)

55

56

To a solution of alcohol 55 (110 mg, 0.231 mmol) in anhydrous DMF (2.0 mL) is added bis(4-nitrophenyl) carbonate (95 mg, 0.31 mmol) followed by N,N-diisopropylethylamine (48 μL, 0.28 mmol) and the reaction is stirred under Ar at rt for 7 h. The product is precipitated by the addition of diethyl ether and filtered, washing with diethyl ether and CH$_2$Cl$_2$. The crude product is purified by column chromatography on silica gel (MeOH/CH$_2$Cl$_2$=2:98 to 6:94) to afford the title compound 56 as a white solid (80 mg, 54%). $^1$H NMR (500 MHz, d6-DMSO) δ 0.84 (d, J=6.8 Hz, 3H), 0.87 (d, J=6.7 Hz, 3H), 1.33-1.49 (m, 2H), 1.55-1.64 (m, 3H), 1.68-1.75 (m, 1H), 1.95-2.02 (m, 3H), 2.13-2.24 (m, 2H), 2.91-2.98 (m, 1H), 3.00-3.06, (m, 1H), 4.19 (dd, J=6.8, 8.6 Hz, 1H), 4.37-4.41 (m, 1H), 4.93-4.96 (m, 1H), 4.98-5.02 (m, 1H), 5.24 (s, 2H), 5.39 (s, 2H), 5.75-5.84 (m, 1H), 5.97 (t, J=5.6 Hz, 1H), 7.41 (d, J=8.5 Hz, 2H), 7.55-7.58 (m, 2H), 7.65 (d, J=8.5 Hz, 2H), 7.81 (d, J=8.6 Hz, 1H), 8.07 (d, J=7.5 Hz, 1H), 8.29-8.32 (m, 2H), 10.04 (s, 1H); $^{13}$C NMR (126 MHz, d6-DMSO) δ 18.2, 19.2, 24.6, 26.8, 29.2, 30.3, 32.7, 34.6, 38.5, 53.1, 57.7, 70.2, 114.9, 119.0, 122.6, 125.4, 129.3, 129.4, 138.3, 139.3, 145.2, 151.9, 155.3, 158.9, 170.7, 171.3, 172.3; HRMS-ESI [M+Na]$^+$ calcd for C$_{31}$H$_{40}$N$_6$NaO$_9$: 663.2754. found 663.2764.

Example 8.3—(2S,3S,4R)-1-O-α-D-Galactopyranosyl-4-O-hexacosanoyl-2-(N-(5-hexenoyl)-Val-Cit-4-aminobenzyloxycarbonylamino) octadecane-1,3,4-triol (CN173)

To a solution of CN089 (17 mg, 0.020 mmol) in anhydrous pyridine (0.3 mL) is added pNP-carbonate 56 (16 mg, 0.025 mmol), Et$_3$N (9 μL, 0.065 mmol) and MeOH (0.1 mL), and the mixture is stirred at rt. After 22 h, further Et$_3$N (5 μL, 0.036 mmol) is added and stirring is continued for a further 19 h. The reaction is quenched with Et$_2$NH (15 μL) and the mixture is concentrated to dryness under high vacuum. Purification by column chromatography on silica gel (MeOH/CH$_2$Cl$_2$=10:90 to 14:86), followed by trituration of the product with water, affords the title compound CN173 as a white solid (14.8 mg, 55%). $^1$H NMR (500 MHz, 2:1 CDCl$_3$/CD$_3$OD) δ 0.87-0.90 (m, 6H), 0.95-0.97 (m, 6H), 1.22-1.39 (m, 68H), 1.52-1.76 (m, 9H), 1.87-1.95 (m, 1H), 2.03-2.12 (m, 3H), 2.27-2.30 (m, 2H), 2.33-2.38 (m, 2H), 3.08-3.13 (m, 1H), 3.21-3.26 (m, 1H), 3.66-3.80 (m, 8H), 3.85-3.87 (m, 2H), 4.19 (d, J=7.3 Hz, 1H), 4.54 (dd, J=5.0, 8.7 Hz, 1H), 4.85 (d, J=3.7 Hz, 1H), 4.93-5.05 (m, 4H), 5.10-5.19 (m, 1H), 5.75-5.83 (m, 1H), 7.32 (d, J=8.1 Hz, 2H), 7.56 (d, J=8.1 Hz, 2H); $^{13}$C NMR (126 MHz, 2:1 CDCl$_3$/CD$_3$OD) δ 14.2, 18.5, 19.4, 23.0, 25.2, 25.4, 25.7, 26.6, 29.2, 29.5, 29.66, 29.69, 29.8, 29.87, 29.89, 29.93, 29.96, 29.99, 30.04, 31.0, 32.3, 33.5, 34.9, 35.7, 39.3, 52.6, 53.7, 59.4, 62.3, 66.8, 68.4, 69.4, 70.2, 70.6, 70.9, 72.3, 75.0, 100.4, 115.5, 120.4, 129.1, 132.9, 138.1, 138.2, 157.0, 161.1, 171.0, 172.8, 174.9, 175.0; HRMS-ESI [M+Na]$^+$ calcd for C$_{75}$H$_{134}$N$_6$NaO$_{15}$: 1381.9829. found 1381.9825.

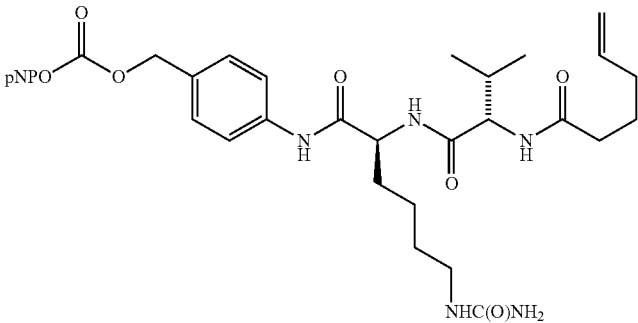

CN089 →56→

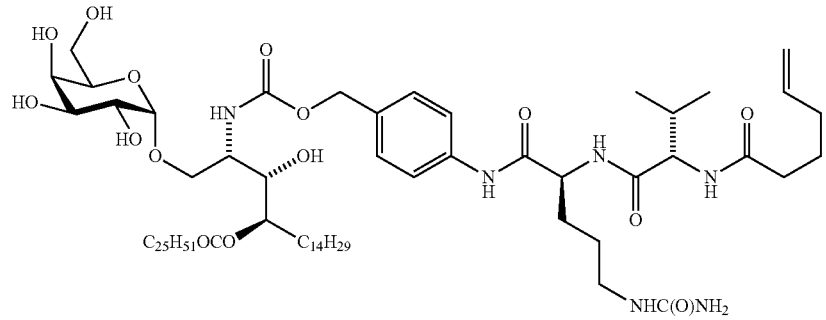

CN173

Example 9—Synthesis of (2S,3S,4R)-1-O-α-D-Galactopyranosyl-4-O-hexacosanoyl-2-(N-levulinoyl-Val-Cit-4-aminobenzyloxycarbonylamino) octadecane-1,3,4-triol (CN171)

Example 9.1—N-Levulinoyl-Val-Cit-4-aminobenzyl alcohol (57)

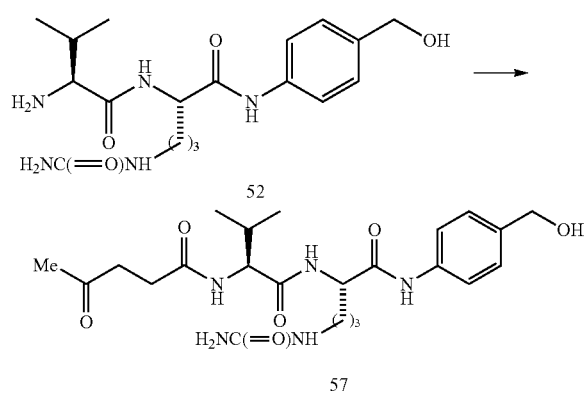

To a stirred solution of levulinic acid (40 mg, 0.34 mmol) in anhydrous $CH_2Cl_2$ (2.0 mL) at 0° C. is added $Et_3N$ (50 μL, 0.36 mmol), followed by isobutyl chloroformate (43 μL, 0.33 mmol). The solution is warmed to rt and stirred for 45 min, before transferring by cannula to a separate flask containing amine 52 (Dubowchik, Firestone et al. 2002) (100 mg, 0.264 mmol) in 5:1 $CH_2Cl_2$-MeOH (2.4 mL) at 0° C. The original flask is rinsed with $CH_2Cl_2$ (0.5 mL), which is transferred to the second flask. After 5 min, the reaction mixture is warmed to rt and MeOH (1 mL) is added to aid stirring of the heterogeneous mixture. After 85 min at rt, the reaction is quenched with $Et_2NH$ (25 μL) and the solvents are concentrated under reduced pressure. The resulting solid is triturated successively with diethyl ether and $CH_2Cl_2$, and purified by column chromatography on silica gel (MeOH/$CH_2Cl_2$=10:90 to 18:82) to afford the title compound 57 as a white solid (94 mg, 75%). $^1H$ NMR (500 MHz, d6-DMSO) δ 0.84 (d, J=6.8 Hz, 3H), 0.86 (d, J=6.8 Hz, 3H), 1.32-1.48 (m, 2H), 1.56-1.63 (m, 1H), 1.68-1.75 (m, 1H), 1.94-2.03 (m, 1H), 2.07 (s, 3H), 2.35-2.46 (m, 2H), 2.59-2.70 (m, 2H), 2.91-2.98 (m, 1H), 2.99-3.05, (m, 1H), 4.16 (dd, J=6.6, 8.4 Hz, 1H), 4.35-4.39 (m, 1H), 4.43 (d, J=5.7 Hz, 2H), 5.07 (t, J=5.7 Hz, 1H), 5.38 (s, 2H), 5.95 (t, J=5.7 Hz, 1H), 7.23 (d, J=8.4 Hz, 2H), 7.54 (d, J=8.4 Hz, 2H), 7.88 (d, J=8.4 Hz, 1H), 7.98 (d, J=7.7 Hz, 1H), 9.79 (s, 1H); $^{13}C$ NMR (126 MHz, d6-DMSO) δ 18.1, 19.2, 26.8, 29.0, 29.3, 29.6, 30.3, 38.1, 38.6 53.1, 57.8, 62.6, 118.8, 126.9, 137.4, 137.5, 158.8, 170.3, 171.1, 171.7, 207.5; HRMS-ESI [M+Na]$^+$ calcd for $C_{23}H_{35}N_5NaO_6$: 500.2485. found 500.2485.

Example 9.2—N-Levulinoyl-Val-Cit-4-aminobenzyl 4-nitrophenyl carbonate (58)

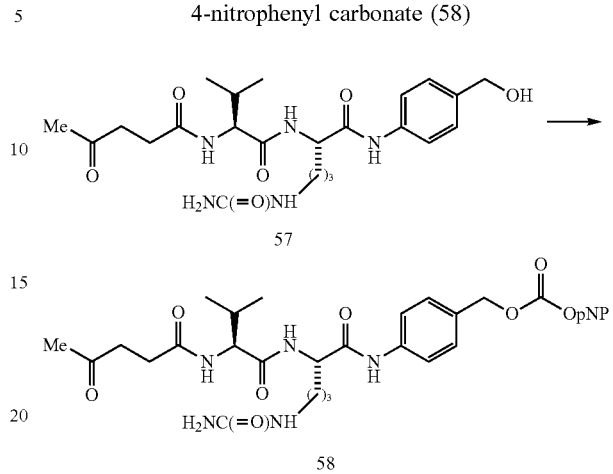

To a solution of alcohol 57(89 mg, 0.19 mmol) in anhydrous DMF (1.7 mL) is added bis(4-nitrophenyl) carbonate (67 mg, 0.22 mmol) followed by N,N-diisopropylethylamine (39 μL, 0.22 mmol) and the reaction is stirred under Ar at rt for 7 h. The product is precipitated by the addition of diethyl ether and filtered, washing with diethyl ether and $CH_2Cl_2$. The crude product is purified by column chromatography on silica gel (MeOH/$CH_2Cl_2$=4:96 to 8:92) to afford the title compound 58 as a white solid (70 mg, 58%). $^1H$ NMR (500 MHz, 2:3 $CDCl_3/CD_3OD$) δ 1.00-1.03 (m, 6H), 1.53-1.69 (m, 2H), 1.78-1.86 (m, 1H), 1.98-2.05 (m, 1H), 2.08 (s, 3H), 2.15-2.23 (m, 1H), 2.44-2.50 (m, 1H), 2.61 (ddd, J=5.1, 8.7, 15.6 Hz, 1H), 2.76-2.82 (m, 1H), 2.88 (ddd, J=5.4, 8.7, 18.6 Hz, 1H), 3.13-3.23 (m, 1H), 4.16 (d, J=6.1 Hz, 1H), 4.52 (dd, J=4.7, 9.7 Hz, 1H), 5.27 (s, 2H), 7.40-7.44 (m, 4H), 7.69 (d, J=8.6 Hz, 2H), 8.21-8.31 (m, 2H); $^{13}C$ NMR (126 MHz, 2:3 $CDCl_3/CD_3OD$) δ 18.3, 19.5, 27.3, 29.6, 29.76, 29.83, 30.7, 39.0, 39.9, 54.4, 60.6, 71.3, 120.9, 122.7, 125.9, 130.1, 131.1, 139.6, 146.3, 153.4, 156.5, 161.5, 171.7, 173.3, 175.2, 210.3; HRMS-ESI [M+Na]$^+$ calcd for $C_{30}H_{38}N_6NaO_{10}$: 665.2547. found 665.2553.

Example 9.3—(2S,3S,4R)-1-O-α-D-Galactopyranosyl-4-O-hexacosanoyl-2-(N-levulinoyl-Val-Cit-4-aminobenzyloxycarbonylamino) octadecane-1,3,4-triol (CN171)

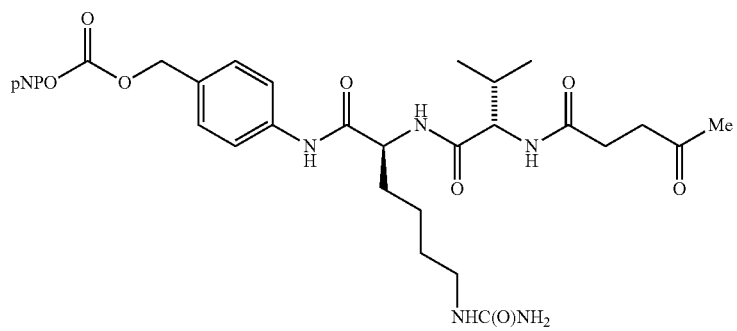

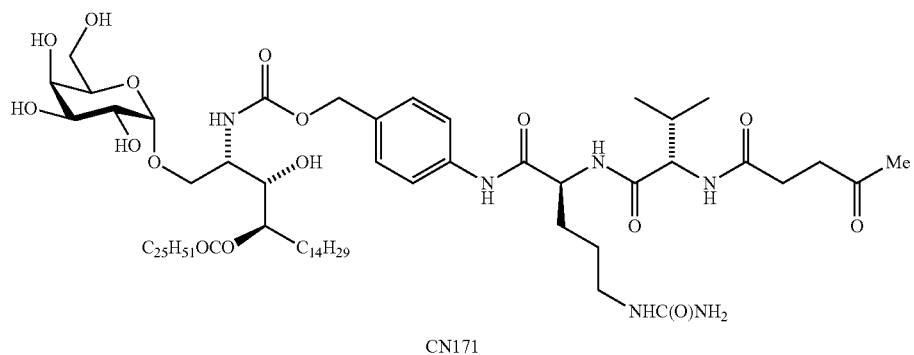

CN171

To a mixture of CN089 (16 mg, 0.019 mmol) and pNP-carbonate 58 (14 mg, 0.022 mmol) in 10:3.5:1 pyridine/MeOH/CHC$_3$ (0.58 mL) is added Et$_3$N (5 μL, 0.036 mmol) and the mixture is stirred at rt. After 6 h, further Et$_3$N (5 μL, 0.036 mmol) is added and stirring is continued for a further 15 h. The reaction is quenched with Et$_2$NH (5 μL) and the mixture is concentrated to dryness under high vacuum. Purification by column chromatography on silica gel (MeOH/CH$_2$Cl$_2$=10:90 to 20:80), followed by preparative HPLC (Phenomenex Luna C18(2), 5 μm, 30×250 mm, 40° C., 50 mL/min; Mobile phase A=80:20:0.05 MeOH/water/TFA; Mobile phase B=100:0.05 MeOH/TFA; 0-10 min: 0-100% B; 10-29 min: 100% B; 29-30 min: 100-0% B; 30-31 min: 100% A) affords the 3-O-acyl regioisomer CN217 (3.2 mg, 13%) followed by the title compound CN171. A final trituration with water gives the product as a white solid (6.4 mg, 25%). $^1$H NMR (500 MHz, 2:1 CDCl$_3$/CD$_3$OD) δ 0.87-0.90 (m, 6H), 0.99-1.01 (m, 6H), 1.22-1.40 (m, 68H), 1.52-1.73 (m, 6H), 1.76-1.84 (m, 1H), 1.95-2.03 (m, 1H), 2.08 (s, 3H), 2.15-2.24 (m, 1H), 2.31-2.41 (m, 2H), 2.43-2.48 (m, 1H), 2.57-2.62 (m, 1H), 2.74-2.80 (m, 1H), 2.89 (ddd, J=5.3, 8.8, 18.7 Hz, 1H), 3.12-3.24 (m, 2H), 3.66-3.81 (m, 8H), 3.85-3.88 (m, 2H), 4.16 (d, J=6.1 Hz, 1H), 4.51 (dd, J=4.6, 9.4 Hz, 1H), 4.85 (d, J=3.6 Hz, 1H), 4.93-5.00 (m, 2H), 5.09-5.16 (m, 1H), 7.32 (d, J=8.3 Hz, 2H), 7.61 (d, J=8.3 Hz, 2H); $^{13}$C NMR (126 MHz, 2:1 CDCl$_3$/CD$_3$OD) δ 14.2, 18.1, 19.4, 23.0, 25.4, 25.7, 26.8, 29.2, 29.56, 29.60, 29.69, 29.71, 29.74, 29.8, 29.90, 29.92, 29.95, 29.98, 30.01, 30.1, 30.4, 32.27, 32.29, 35.0, 38.8, 39.5, 52.6, 53.9, 60.1, 62.3, 66.8, 68.4, 69.4, 70.2, 70.7, 71.0, 72.3, 75.1, 100.4, 120.5, 129.0, 133.0, 138.3, 157.1, 161.0, 171.1, 172.9, 174.7, 175.0, 210.0; HRMS-ESI [M+Na]$^+$ calcd for C$_{74}$H$_{132}$N$_6$NaO$_{16}$: 1383.9598. found 1383.9594.

Data for CN217: $^1$H NMR (500 MHz, 2:1 CDCl$_3$/CD$_3$OD) δ 0.87-0.90 (m, 6H), 0.99-1.01 (m, 6H), 1.23-1.42 (m, 68H), 1.48-1.71 (m, 6H), 1.77-1.85 (m, 1H), 1.96-2.03 (m, 1H), 2.08 (s, 3H), 2.16-2.23 (m, 1H), 2.30-2.38 (m, 2H), 2.42-2.47 (m, 1H), 2.57-2.63 (m, 1H), 2.74-2.80 (m, 1H), 2.87-2.93 (m, 1H), 3.13-3.25 (m, 2H), 3.53-3.57 (m, 1H), 3.62-3.79 (m, 6H), 3.84 (d, J=2.7 Hz, 1H), 3.88 (dd, J=4.8, 10.8 Hz, 1H), 4.14-4.17 (m, 1H), 4.18-4.21 (m, 1H), 4.49-4.53 (m, 1H), 4.84-4.87 (m, 1H), 4.91-4.97 (m, 2H), 5.12-5.17 (m, 1H), 7.31 (d, J=8.3 Hz, 2H), 7.60 (d, J=8.3 Hz, 2H); $^{13}$C NMR (126 MHz, 2:1 CDCl$_3$/CD$_3$OD) δ selected peaks: 14.2, 18.1, 19.4, 23.0, 25.3, 25.8, 26.8, 29.6, 29.7, 30.0, 30.3, 32.3, 33.5, 34.7, 38.8, 39.4, 52.1, 54.0, 60.2, 62.3, 66.8, 69.3, 70.3, 70.6, 71.1, 76.6, 100.2, 120.5, 129.0; HRMS-ESI [M+Na]$^+$ calcd for C$_{74}$H$_{132}$N$_6$NaO$_{18}$: 1383.9598. found 1383.9586.

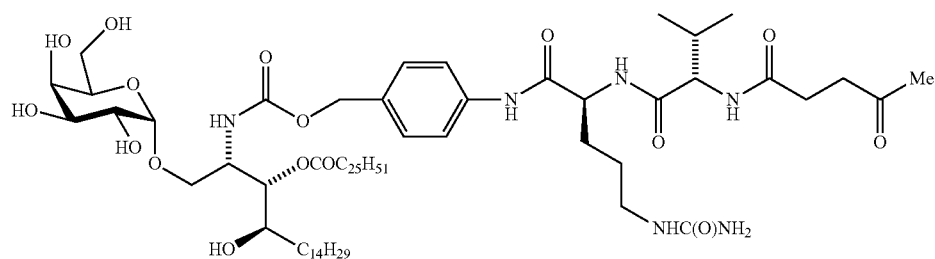

CN217

Example 10—Synthesis of (2S,3S,4R)-1-O-α-D-Galactopyranosyl-4-O-hexacosanoyl-2-(N-maleimidohexanoyl-Val-Cit-4-aminobenzyloxycarbonylamino) octadecane-1,3,4-triol (CN211)

Example 10.1—N-Fluorenylmethoxycarbonyl-Val-Cit-4-aminobenzyl 4-nitrophenyl carbonate (BJC209)

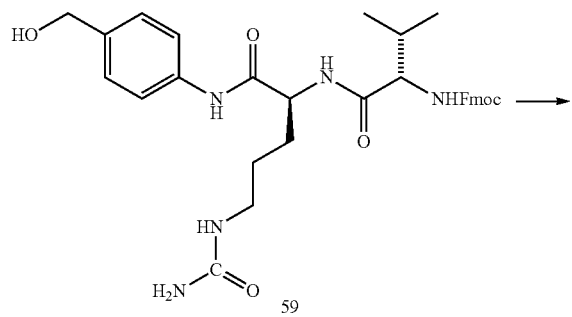

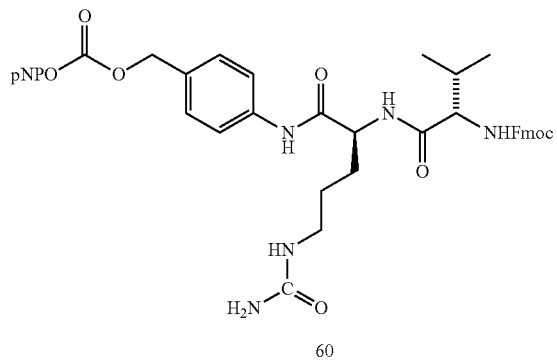

To a solution of alcohol 59 (Dubowchik, Firestone et al. 2002) (270 mg, 0.45 mmol) in DMF (4 mL) under Ar is added bis(4-nitrophenyl) carbonate (220 mg, 0.72 mmol), followed by i-Pr$_2$NEt (90 μL, 0.51 mmol) and the reaction is stirred at rt. After 18 h, the mixture is diluted with MeOH (10 mL) then concentrated under reduced pressure and the residue is azeotroped with toluene (4×10 mL). The crude product is purified by column chromatography on silica gel (MeOH/CHCl$_3$=0:1 to 1:4), to afford the title compound 60 as a yellow solid (219 mg, 64%). $^1$H NMR (500 MHz, 3:1 CDCl$_3$/CD$_3$OD) δ 0.95 (d, J=6.8 Hz, 3H), 0.97 (d, J=6.8 Hz, 3H), 1.50-1.60 (m, 2H), 1.68-1.75 (m, 1H), 1.89-1.96 (m, 1H), 2.06-2.13 (m, 1H), 3.08-3.13, (m, 1H), 3.21-3.26, (m, 1H), 4.00 (d, J=6.5 Hz, 1H), 4.22 (dd, J=6.5, 6.5 Hz, 1H), 4.35-4.38 (m, 1H), 4.45-4.49 (m, 1H), 4.56-4.58 (m, 1H), 5.25 (s, 2H), 7.31 (dd, J=7.5, 7.5 Hz, 2H), 7.38-7.41 (m, 6H), 7.61-7.64 (m, 4H), 7.77 (d, J=7.7 Hz, 2H); $^{13}$C NMR (126 MHz, 3:1 CDCl$_3$/CD$_3$OD) δ 18.1, 19.3, 26.6, 29.5, 31.2, 39.2, 53.5, 61.0, 67.3, 70.9, 120.2, 120.4, 122.1, 125.2, 125.3, 125.5, 127.3, 128.0, 129.8, 139.0, 141.6, 144.0, 144.1, 145.7, 152.8, 155.9, 157.4, 160.8, 170.9, 172.9; HRMS-ESI: m/z calcd for C$_{40}$H$_{42}$N$_6$O$_{10}$Na [M+Na]$^+$ 789.2860. found 789.2853.

Example 10.2—(2S,3S,4R)-1-O-α-D-Galactopyranosyl-4-O-hexacosanoyl-2-(N-fluorenylmethoxycarbonyl-Val-Cit-4-aminobenzyloxycarbonylamino) octadecane-1,3,4-triol (61)

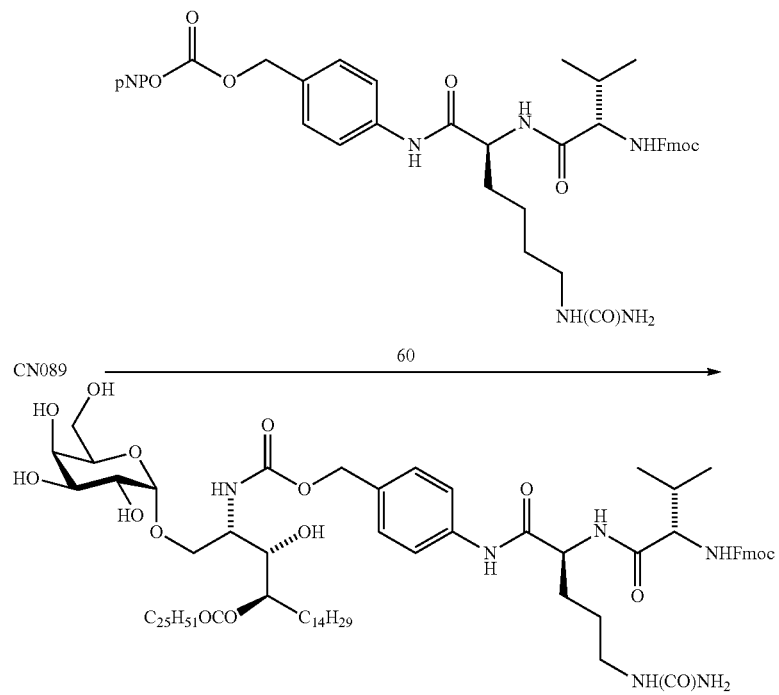

To a mixture of CN089 (112 mg, 0.131 mmol) and pNP-carbonate 60 (138 mg, 0.180 mmol) in anhydrous pyridine (1.8 mL) under Ar is added Et$_3$N (24 μL, 0.17 mmol) and the mixture is stirred at rt. After 23 h, the mixture is concentrated to dryness under high vacuum, and the crude residue is purified by column chromatography on silica gel (MeOH/CH$_2$Cl$_2$=5:95 to 13:87) to afford the title compound 61 as a white solid (122 mg, 63%). $^1$H NMR (500 MHz, 2:3 CDCl$_3$/CD$_3$OD) δ 0.87-0.90 (m, 6H), 0.95-0.98 (m, 6H), 1.24-1.37 (m, 68H), 1.51-1.78 (m, 7H), 1.89-1.96 (m, 1H), 2.07-2.13 (m, 1H), 2.32-2.42 (m, 2H), 3.07-3.13 (m, 1H), 3.20-3.25 (m, 1H), 3.66-3.81 (m, 8H), 3.84-3.87 (m, 2H), 3.99 (d, J=6.7 Hz, 1H), 4.24 (t, J=6.9 Hz, 1H), 4.37 (dd, J=6.9, 10.5 Hz, 1H), 4.45 (dd, J=6.9, 10.5 Hz, 1H), 4.54 (dd, J=5.2, 8.6 Hz, 1H), 4.84 (d, J=3.7 Hz, 1H), 4.97-5.03 (m, 2H), 5.06-5.10 (m, 1H), 7.30-7.33 (m, 4H), 7.38-7.41 (m, 2H), 7.58 (d, J=8.1 Hz, 2H), 7.63-7.65 (m, 2H), 7.78 (d, J=7.6 Hz, 2H); $^{13}$C NMR (126 MHz, 2:1 CDCl$_3$/CD$_3$OD) δ 14.3, 18.2, 19.4, 23.0, 25.5, 25.7, 26.7, 29.2, 29.6, 29.27, 29.74, 29.8, 29.93, 29.95, 29.98, 30.02, 30.05, 30.08, 30.10, 31.4, 32.3, 35.0, 39.4, 47.6, 52.7, 53.8, 61.2, 62.3, 66.8, 67.4, 68.4, 69.4, 70.2, 70.7, 71.0, 72.3, 75.1, 100.4, 120.3, 120.5, 125.40, 125.44, 127.5, 128.2, 129.1, 133.0, 138.2, 141.7, 144.2, 144.3, 157.1, 157.6, 161.1, 171.1, 173.2, 175.0; HRMS-ESI m/z calcd for C$_{84}$H$_{137}$N$_6$O$_{16}$ [M+H]$^+$: 1486.0091. found 1486.0099.

Example 10.3—(2S,3S,4R)-1-O-α-D-Galactopyranosyl-4-O-hexacosanoyl-2-(Val-Cit-4-aminobenzyloxycarbonylamino) octadecane-1,3,4-triol (62)

To a mixture of compound 61 (125 mg, 0.0841 mmol) in DMF (2 mL) is added piperidine (0.2 mL) at 0° C. The mixture is stirred at 0° C. for 5 min, then at rt for 40 min. The solvents are concentrated to dryness under high vacuum, and the crude residue is purified by column chromatography on silica gel (MeOH/CH$_2$Cl$_2$=15:85 to 35:65) to afford the title compound 62 as a white solid (95 mg, 89%). $^1$H NMR (500 MHz, 2:1 CDCl$_3$/CD$_3$OD) δ 0.87-0.91 (m, 9H), 1.00 (d, J=6.9 Hz, 3H), 1.23-1.35 (m, 68H), 1.49-1.77 (m, 7H), 1.87-1.94 (m, 1H), 2.07-2.13 (m, 1H), 2.32-2.39 (m, 2H), 3.10-3.16 (m, 1H), 3.21 (d, J=4.9 Hz, 1H), 3.24-3.29 (m, 1H), 3.65-3.80 (m, 8H), 3.85-3.87 (m, 2H), 4.57 (dd, J=5.3, 8.5 Hz, 1H), 4.85 (d, J=3.7 Hz, 1H), 4.92-4.99 (m, 2H), 5.10-5.15 (m, 1H), 7.33 (d, J=8.3 Hz, 2H), 7.56 (d, J=8.3 Hz, 2H); $^{13}$C NMR (75 MHz, 3:1 CDCl$_3$/CD$_3$OD) δ 14.1, 16.8, 19.5, 22.8, 25.2, 25.5, 26.4, 29.0, 29.4, 29.5, 29.6, 29.7, 29.8, 29.9, 30.0, 31.9, 32.1, 34.8, 39.2, 52.3, 53.1, 60.4, 62.1, 66.6, 68.2, 69.2, 70.0, 70.5, 70.6, 72.2, 74.9, 100.1, 120.3, 128.9, 132.9, 138.0, 156.8, 160.8, 171.1, 174.8, 175.7; HRMS-ESI m/z calcd for C$_{69}$H$_{127}$N$_6$O$_{14}$ [M+H]$^+$: 1263.9410. found 1263.9419.

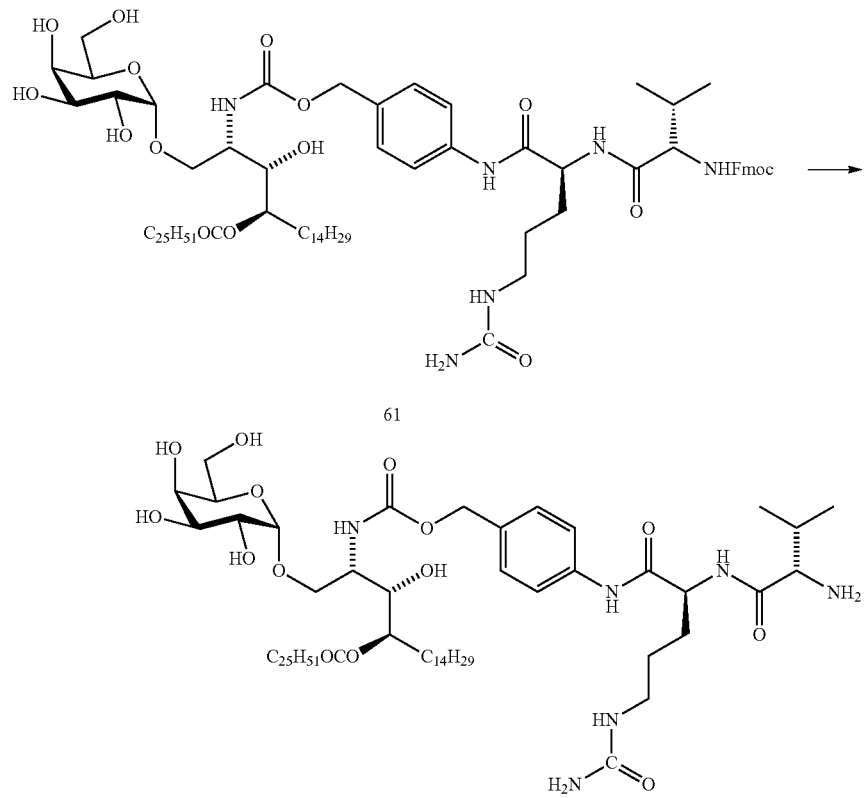

Example 10.4—(2S,3S,4R)-1-O-α-D-Galactopyranosyl-4-O-hexacosanoyl-2-(N-maleimidohexanoyl-Val-Cit-4-aminobenzyloxycarbonylamino) octadecane-1,3,4-triol (CN211)

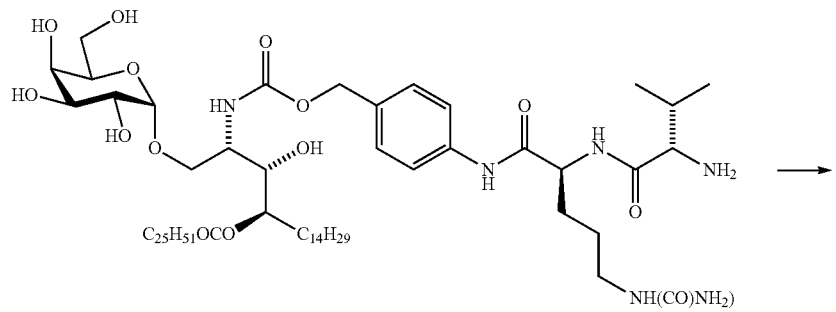

62

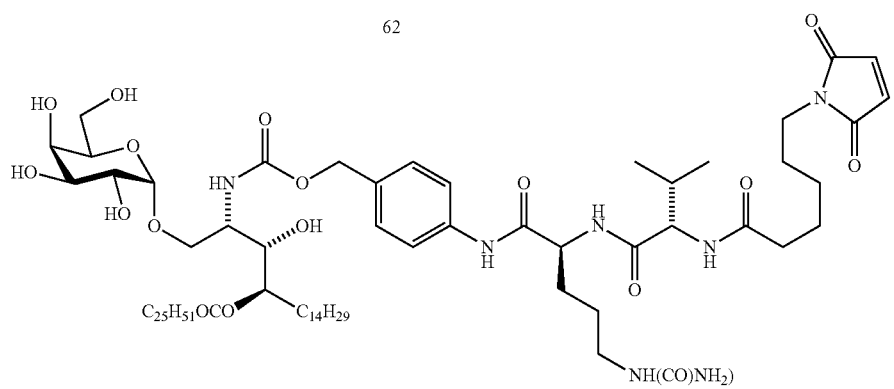

CN211

To a solution of amine 62 (10.4 mg, 0.00823 mmol) and 6-maleimidohexanoic acid NHS ester (Leonard and Brunckova 2010) (3.3 mg, 0.011 mmol) in DMF (80 uL) is added Et$_3$N (0.9 mg, 0.009 mmol) and the mixture is stirred at rt. After 4 h, the mixture is concentrated under high vacuum, and the crude residue is purified by column chromatography on silica gel (MeOH/CH$_2$Cl$_2$=8:92 to 14:86) to afford the title compound CN211 as a white solid (11.2 mg, 93%). $^1$H NMR (500 MHz, 2:1 CDCl$_3$/CD$_3$OD) δ 0.87-0.90 (m, 6H), 0.94-0.97 (m, 6H), 1.23-1.36 (m, 70H), 1.49-1.77 (m, 11H), 1.87-1.94 (m, 1H), 2.03-2.10 (m, 1H), 2.24-2.30 (m, 2H), 2.31-2.41 (m, 2H), 3.09-3.14 (m, 1H), 3.20-3.26 (m, 1H), 3.51 (t, J=7.2 Hz, 2H), 3.66-3.81 (m, 8H), 3.85-3.87 (m, 2H), 4.17 (d, J=7.4 Hz, 1H), 4.53 (dd, J=5.1, 8.6 Hz, 1H), 4.85 (d, J=3.8 Hz, 1H), 4.92-4.98 (m, 2H), 5.10-5.15 (m, 1H), 6.74 (s, 2H), 7.31 (d, J=8.1 Hz, 2H), 7.56 (d, J=8.1 Hz, 2H); $^{13}$C NMR (126 MHz, 2:1 CDCl$_3$/CD$_3$OD) δ 14.2, 18.5, 19.4, 23.0, 25.4, 25.5, 25.6, 26.6, 28.5, 29.2, 29.5, 29.58, 29.63, 29.65, 29.73, 29.84, 29.86, 29.90, 29.93, 29.97, 30.01, 31.0, 32.2, 34.9, 36.2, 37.9, 39.3, 52.5, 53.7, 59.4, 62.3, 66.7, 68.4, 69.4, 70.2, 70.6, 70.8, 72.3, 75.0, 100.3, 120.4, 129.0, 132.9, 134.5, 138.2, 157.0, 161.0, 171.0, 171.5, 172.8, 174.9; HRMS-ESI m/z calcd for C$_{79}$H$_{137}$N$_7$NaO$_{17}$ [M+Na]$^+$: 1478.9969. found 1478.9971.

Example 11—Synthesis of (2S,3S,4R)-1-O-α-D-Galactopyranosyl-4-O-hexacosanoyl-2-(N-(bicyclo[6.1.0]non-4-yn-9-ylmethoxycarbonyl)-Val-Cit-4-aminobenzyloxycarbonylamino) octadecane-1,3,4-triol (CN209)

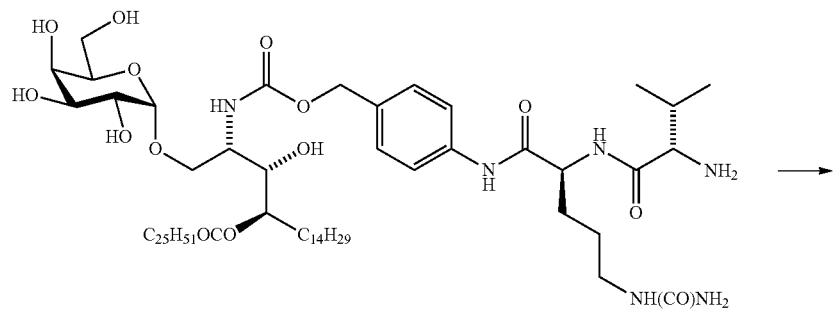

62

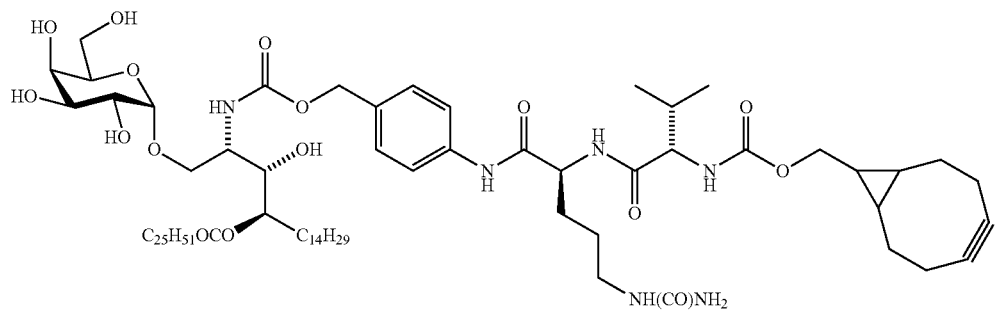

CN209

To a solution of amine 62 (6.5 mg, 0.0051 mmol) in DMF (50 μL) is added bicyclo[6.1.0]non-4-yn-9-ylmethyl 4-nitrophenyl carbonate (Dommerholt, Schmidt et al. 2010) (2.0 mg, 0.0063 mmol) followed by Et$_3$N (1.5 μL, 0.011 mmol) and the mixture is stirred at rt. After 20 h, the mixture is concentrated under high vacuum, and the crude residue is purified by column chromatography on silica gel (MeOH/CH$_2$Cl$_2$=5:95 to 15:85) to afford the title compound CN209 as a white solid (6.4 mg, 86%). $^1$H NMR (500 MHz, 2:3 CDCl$_3$/CD$_3$OD) δ 0.68-0.78 (m, 3H), 0.88-0.90 (m, 6H), 0.95 (d, J=6.8 Hz, 3H), 0.99 (d, J=6.8 Hz, 3H), 1.23-1.41 (m, 70H), 1.50-1.78 (m, 7H), 1.89-1.96 (m, 1H), 2.08-2.14 (m, 3H), 2.22-2.30 (m, 2H), 2.32-2.42 (m, 4H), 3.09-3.14 (m, 1H), 3.20-3.26 (m, 1H), 3.66-3.81 (m, 8H), 3.84-3.87 (m, 2H), 3.95-4.03 (m, 3H), 4.55 (dd, J=5.3, 8.3 Hz, 1H), 4.84 (d, J=3.7 Hz, 1H), 4.97-5.03 (m, 2H), 5.06-5.11 (m, 1H), 7.30-7.33 (m, 2H), 7.58 (d, J=8.2 Hz, 2H); $^{13}$C NMR (126 MHz, 2:3 CDCl$_3$/CD$_3$OD) δ 14.34, 14.36, 18.3, 19.6, 21.7, 23.29, 23.31, 23.7, 23.8, 24.4, 25.8, 26.0, 27.2, 29.3, 29.9, 30.00, 30.03, 30.2, 30.25, 30.31, 30.34, 30.4, 31.6, 32.59, 32.62, 33.9, 35.2, 39.8, 53.2, 54.2, 61.5, 62.5, 67.0, 68.6, 69.8, 70.2, 70.6, 71.0, 71.6, 72.4, 75.4, 99.3, 100.8, 120.8, 129.3, 133.4, 138.7, 157.6, 158.5, 161.6, 171.5, 173.7, 175.2; HRMS-ESI m/z calcd for C$_{80}$H$_{138}$N$_6$NaO$_{16}$ [M+Na]$^+$: 1462.0067. found 1462.0061.

Example 12—Synthesis of (2S,3S,4R)-1-O-α-D-Galactopyranosyl-4-O-hexacosanoyl-2-(N-(biotinoyl)-Val-Cit-4-aminobenzyloxycarbonylamino) octadecane-1,3,4-triol (CN201)

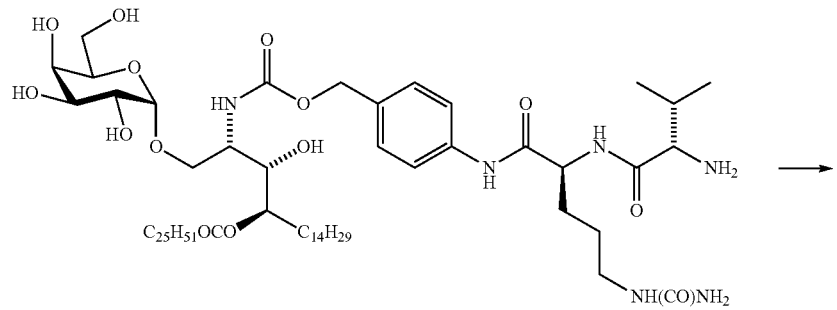

62

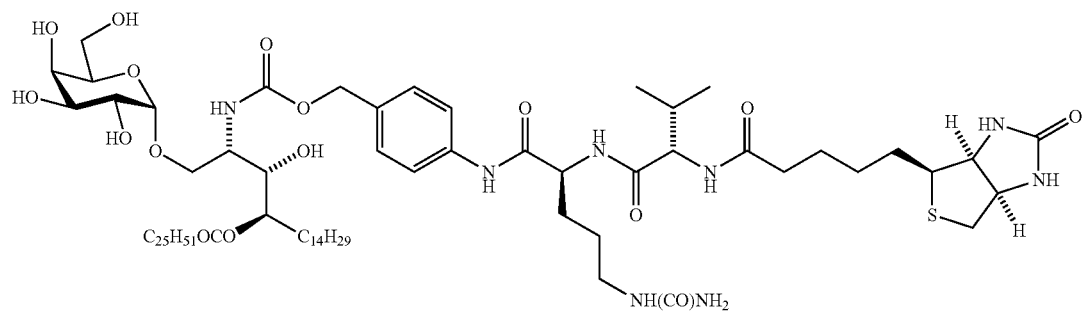

CN201

To a solution of amine 62 (10.9 mg, 0.00862 mmol) in DMF (0.10 mL) is added D-(+)-biotin NHS ester (5.4 mg, 0.016 mmol) followed by Et$_3$N (3.2 mg, 0.032 mmol) and the mixture is stirred at rt for 2 days. The heterogeneous mixture is diluted with MeOH (1 mL) and water (0.2 mL), and filtered, washing with MeOH. The collected precipitate is purified by column chromatography on silica gel (MeOH/CHCl$_3$=10:90 to 30:70) to afford the title compound CN201 as a white solid (8.3 mg, 64%). $^1$H NMR (500 MHz, 2:1 CDCl$_3$/CD$_3$OD) δ 0.87-0.90 (m, 6H), 0.95-0.98 (m, 6H), 1.23-1.35 (m, 68H), 1.41-1.47 (m, 2H), 1.50-1.79 (m, 11H), 1.87-1.94 (m, 1H), 2.06-2.13 (m, 1H), 2.24-2.41 (m, 4H), 2.74 (d, J=12.8 Hz, 1H), 2.93 (dd, J=5.0, 12.8 Hz, 1H), 3.10-3.22 (m, 3H), 3.66-3.80 (m, 8H), 3.84-3.87 (m, 2H), 4.18 (d, J=6.8 Hz, 1H), ~4.30 (m, 1H), 4.48-4.53 (m, 2H), 4.85 (d, J=3.7 Hz, 1H), 4.93-4.98 (m, 2H), 5.12-5.16 (m, 1H), 7.32 (d, J=8.3 Hz, 2H), 7.58 (d, J=8.3 Hz, 2H); $^{13}$C NMR (126 MHz, 2:1 CDCl$_3$/CD$_3$OD) δ 14.2, 18.4, 19.5, 23.0, 25.4, 25.7, 26.0, 26.7, 28.34, 28.37, 29.2, 29.5, 29.6, 29.70, 29.72, 29.79, 29.91, 29.93, 29.96, 30.02, 30.8, 32.3, 35.0, 35.8, 39.5, 40.6, 52.6, 54.0, 55.8, 59.5, 60.6, 62.2, 62.3, 66.8, 68.4, 69.4, 70.3, 70.7, 70.9, 72.3, 75.1, 100.4, 120.5, 129.1, 133.0, 138.3, 157.1, 161.1, 164.9, 171.1, 173.0, 175.0, 175.3; HRMS-ESI m/z calcd for C$_{79}$H$_{140}$N$_8$NaO$_{16}$S [M+Na]$^+$: 1512.0006. found 1512.0006.

Example 13—Synthesis of (2S,3S,4R)-1-O-α-D-Galactopyranosyl-4-O-hexacosanoyl-2-(N-(ω-mercapto(poly(ethyleneoxy))acetyl)-Val-Cit-4-aminobenzyloxycarbonylamino) octadecane-1,3,4-triol (CN200)

Example 13.1—(2S,3S,4R)-1-O-α-D-Galactopyranosyl-4-O-hexacosanoyl-2-(N-(ω-(isobutoxycarbonylthio)(poly(ethyleneoxy))acetyl)-Val-Cit-4-aminobenzyloxycarbonylamino) octadecane-1,3,4-triol (63)

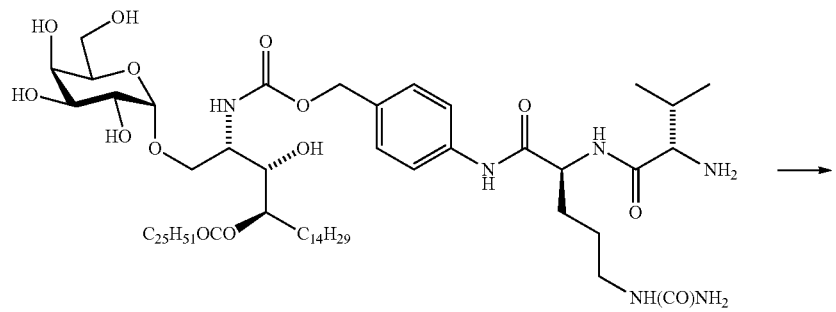

62

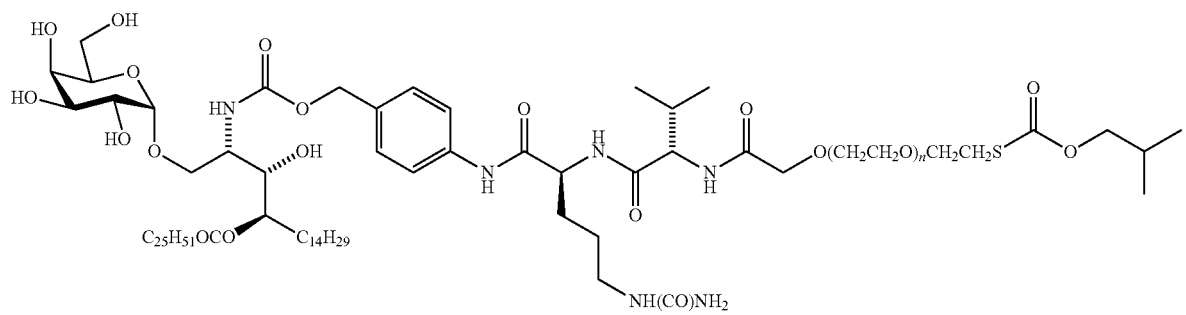

63
n~19-32

To a solution of ω-mercaptopoly(ethyleneoxy)acetic acid (average Mw 1,000) (5.9 mg, 0.0053 mmol) in anhydrous CH$_2$Cl$_2$ (0.2 mL) at 0° C. is added i-Pr$_2$NEt (7.4 mg, 0.057 mmol), followed by isobutyl chloroformate (6.2 μL, 0.048 mmol). The solution is stirred at 0° C. for 45 min, then at rt for 15 min, before concentrating to dryness. The residue is co-evaporated twice with toluene to drive off excess isobutyl chloroformate reagent. The mixed anhydride intermediate is dissolved in 18:1 chloroform/MeOH (0.95 mL), and stirred with i-Pr$_2$NEt (2.0 μL, 0.012 mmol) and amine 62 (3.1 mg, 0.0025 mmol) at rt for 2 days. After concentration of the solvents under reduced pressure, the residue is loaded (as a 1:1 MeOH/water solution) onto a cartridge containing 200 mg of end-capped cyclohexyl-bonded silica gel (Isolute CH(EC)). After removing more polar components, the product is eluted with MeOH/water (9:1 to 1:0). Further purification by preparative HPLC (Phenomenex Luna C18(1), 5 μm, 250×10 mm; 40° C.; 2.8 mL/min; mobile phase=80:20 IPA/MeOH) gives the title compound 63 as a colourless glass (3.2 mg, 53%). $^1$H NMR (500 MHz, 2:1 CDCl$_3$/CD$_3$OD) δ 0.87-0.90 (m, 6H), 0.95 (d, J=6.7 Hz, 6H), 0.97 (d, J=6.8 Hz, 3H), 0.99 (d, J=6.8 Hz, 3H), 1.23-1.35 (m, 68H), 1.49-1.77 (m, 7H), 1.88-2.02 (m, 2H), 2.11-2.18 (m, 1H), 2.31-2.40 (m, 2H), 3.07 (t, J=6.5 Hz, 2H), 3.10-3.15 (m, 1H), 3.21-3.26 (m, 1H), 3.61-3.81 (m, ~110H), 3.85-3.88 (m, 2H), 4.01 (d, J=6.6 Hz, 1H), 4.07 (s, 2H), 4.25 (d, J=7.0 Hz, 1H), 4.55 (dd, J=5.1, 8.8 Hz, 1H), 4.85 (d, J=3.7 Hz, 1H), 4.93-4.99 (m, 2H), 5.10-5.15 (m, 1H), 7.32 (d, J=8.4 Hz, 2H), 7.57 (d, J=8.4 Hz, 2H); 13C NMR (126 MHz, 2:1 CDCl3/CD3OD) δ 14.2, 18.4, 19.1, 19.5, 23.0, 25.4, 25.7, 26.7, 28.3, 29.2, 29.6, 29.7, 29.8, 29.9, 30.0, 30.8, 31.3, 32.3, 35.0, 39.3, 52.6, 53.7, 58.9, 62.3, 66.8, 68.4, 69.4, 70.2, 70.3, 70.5, 70.6, 70.7, 70.8, 70.9, 71.3, 72.3, 74.0, 75.0, 100.4, 120.5, 129.1, 133.0, 138.3, 157.1, 161.1, 171.1, 171.4, 171.6, 172.1, 174.9; HRMS-ESI m/z calcd for C$_{126}$H$_{236}$N$_6$Na$_2$O$_{42}$S [M(n=24)+2Na]$^{2+}$: 1291.8016. found 1291.7981.

Example 13.2—(2S,3S,4R)-1-O-α-D-Galactopyranosyl-4-O-hexacosanoyl-2-(N-(ω-mercapto(poly (ethyleneoxy))acetyl)-Val-Cit-4-aminobenzyloxycarbonylamino) octadecane-1,3,4-triol (CN200)

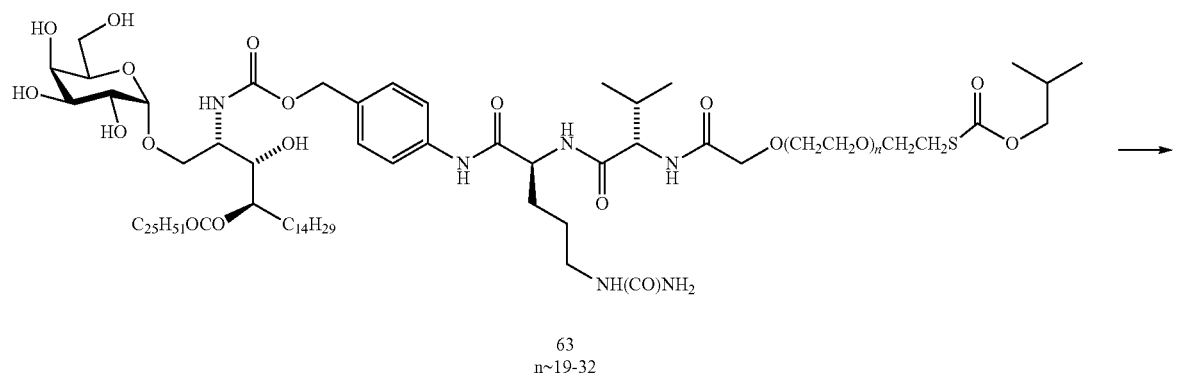

63
n~19-32

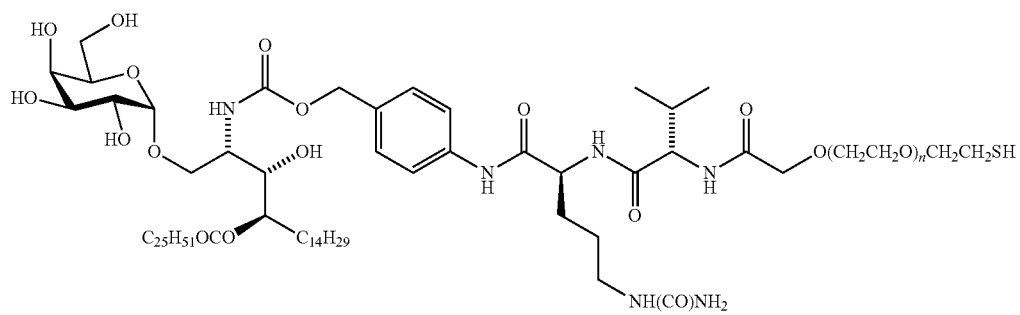

CN201
n~19-32

To a solution of thiocarbonate 63 (3 mg, 1.2 umol) in MeOH (0.5 mL) is added buffered hydroxylamine (0.5 mL, 0.5 M NH2OH.HCl, 25 mM EDTA dissolved in PBS and adjusted to pH 7.4 with 3.0 M NaOH). The reaction vial is incubated under Ar at 40° C. for 42 h. The mixture is purified by passage through a cartridge containing 1 g of endcapped C18 silica, (MeOH/IPA=1:0 to 1:1) to give the a mixture of the title compound CN200 and unreacted starting material. HRMS-ESI m/z calcd for C$_{121}$H$_{228}$N$_8$Na$_2$O$_{40}$S [M(n=24)+2Na]$^{2+}$: 1241.7754. found 1241.7739.

Example 14—Synthesis of (2S,3S,4R)-1-O-α-D-Galactopyranosyl-4-O-(4-fluorophenylundecanoyl)-2-(N-(6-azidohexanoyl)Val-Cit-4-aminobenzyloxycarbonylamino) octadecane-1,3,4-triol (CN213)

Example 14.1—(2S,3S,4R)-2-Amino-1-O-α-D-galactopyranosyl-4-O-(4-fluorophenylundecanoyl) octadecane-1,3,4-triol (65)

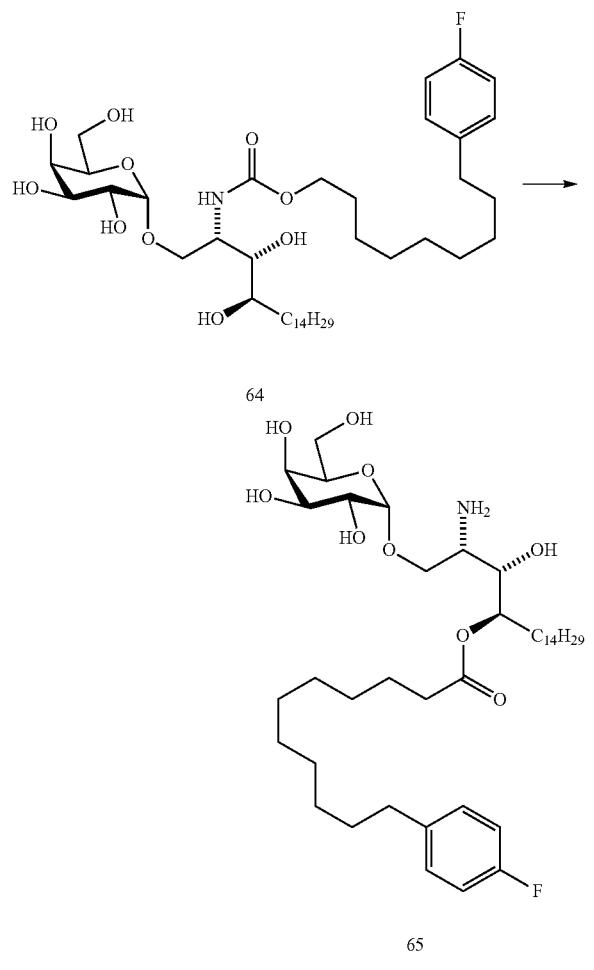

A solution of compound 64 (20 mg, 0.027 mmol) (Li, X., Fujio, M. et al. 2010) in 1,4-dioxane (3 mL) and 1 M HCl (0.6 mL) is heated at 80° C. for 1 h. The mixture is diluted with CHCl$_3$/MeOH (1:1, 30 mL) and concentrated under reduced pressure. The crude residue is purified by column chromatography on silica gel (MeOH/CHCl$_3$=0:10 to 3:7) to afford the title compound 65 as a white solid (14 mg, 70%). $^1$H NMR (500 MHz, CDCl$_3$/CD$_3$OD 5:1) δ 0.88 (t, J=6.9, 6.9 Hz, 3H), 1.24-1.32 (m, 38H), 1.54-1.64 (m, 5H), 1.76-1.83 (m, 1H), 2.34 (dd, J=7.5, 7.5 Hz, 2H), 2.57 (dd, J=7.7, 7.7 Hz, 2H), 3.24-3.27 (m, 1H), 3.54 (dd, J=9.7, 9.7 Hz, 2H), 3.76-3.87 (m, 6H), 3.97 (br d, J=2.8 Hz), 4.09 (dd, J=2.8, 10.6 Hz), 4.88 (d, J=3.7 Hz), 6.92-6.96 (m, 2H), 7.10-7.14 (m, 2H); $^{13}$C NMR (126 MHz, CDCl$_3$/CD$_3$OD 5:1) δ 13.0, 21.9, 24.2, 24.4, 28.4, 28.58, 28.63, 28.67, 28.73, 28.77, 28.82, 29.0, 30.4, 30.9, 31.2, 33.7, 34.3, 52.2, 61.0, 64.1, 68.3, 68.6, 69.1, 69.3, 70.2, 70.4, 72.5, 99.0, 113.9, 114.1, 128.9, 129.0, 137.8, 159.6, 161.5, 173.4; $^{19}$F NMR (470 MHz CDCl$_3$/CD$_3$OD 5:1) δ −118.68; HRMS-ESI m/z calcd for C$_{41}$H$_{73}$NO$_9$F [M+H]$^+$ 742.5266. found 742.5269.

Example 14.2—(2S,3S,4R)-1-O-α-D-Galactopyranosyl-4-O-(4-fluorophenyl undecanoyl)-2-(N-(6-azidohexanoyl)-Val-Cit-4-aminobenzyloxycarbonylamino) octadecane-1,3,4-triol (CN213)

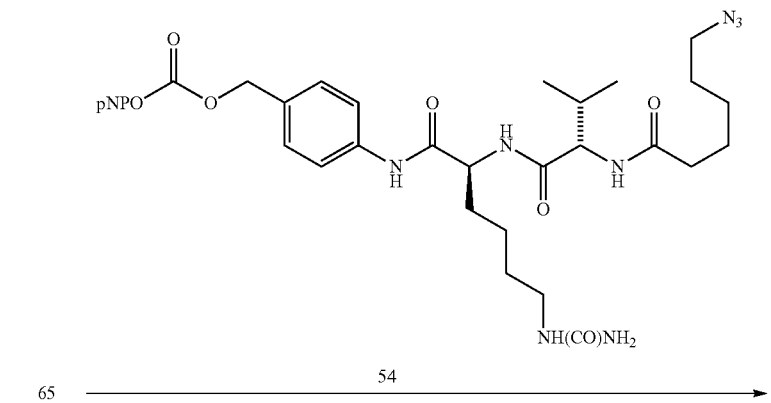

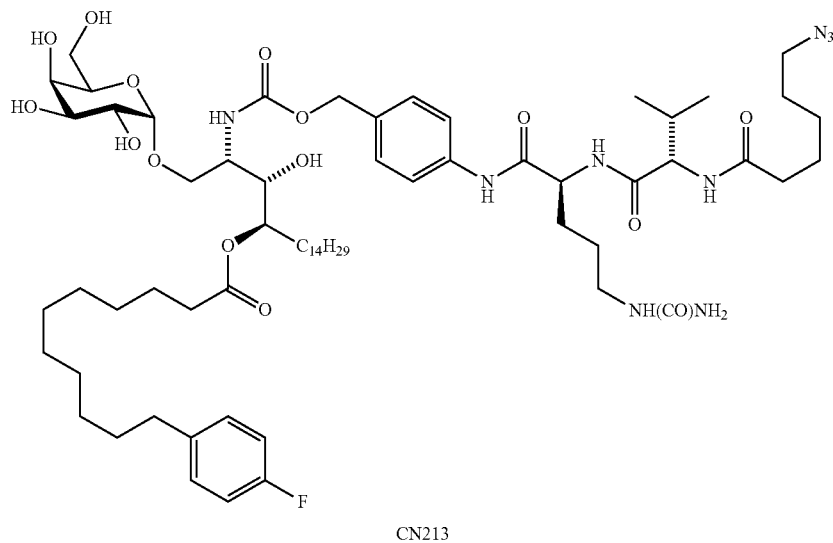

CN213

To a mixture of amine 65 (14 mg, 0.018 mmol) and pNP-carbonate 54 (20 mg, 0.029 mmol) in anhydrous pyridine (0.26 mL) under Ar is added Et$_3$N (3.6 µL, 0.026 mmol) and the mixture is stirred at rt. After 24 h, a further portion of Et$_3$N (1.6 µL, 0.012 mmol) is added. After a further 8 h, the volatiles are removed under reduced pressure. The crude residue is purified by column chromatography on silica gel (MeOH/CHCl$_3$=0:1 to 3:7) to afford the title compound CN213 as a white solid (17 mg, 71%). $^1$H NMR (500 MHz, 5:1 CDCl$_3$/CD$_3$OD) δ 0.88 (t, J=6.9, 6.9 Hz, 3H), 0.94-0.97 (m, 6H), 1.25-1.35 (m, 38H), 1.39-1.45 (m, 2H), 1.52-1.76 (m, 12H), 1.86-1.93 (m, 1H), 2.03-2.10 (m, 1H), 2.29 (ddd, J=1.3, 7.5. 7.5 Hz, 2H), 2.33-2.37 (m, 2H), 2.57 (dd, J=7.6, 7.6 Hz, 2H), 3.08-3.13 (m, 1H), 3.20-3.24 (m, 1H), 3.28 (dd, J=7.0, 7.0 Hz, 2H), 3.65-3.77 (m, 8H), 3.84-3.87 (m, 2H), 4.52-4.55 (m, 1H), 4.84 (d, 3.8 Hz, 1H), 4.94-4.97 (m, 2H), 5.13-5.15 (m, 1H), 6.93-6.97 (m, 2H), 7.10-7.14 (m, 2H), 7.32 (d, J=8.4 Hz, 2H), 7.56 (d, J=8.4 Hz, 2H); $^{13}$C NMR (126 MHz, CDCl$_3$/CD$_3$OD 5:1) δ 13.6, 17.8, 18.8, 22.3, 24.7, 24.9, 25.0, 26.0, 28.2, 28.6, 28.8, 28.9, 29.0, 29.1, 29.17, 29.23, 29.3, 30.4, 31.3, 31.6, 34.2, 34.7, 35.5, 38.6, 50.9, 51.8, 53.0, 58.7, 61.6, 66.1, 67.7, 68.7, 69.5, 69.9, 70.2, 71.7, 74.3, 99.7, 114.4, 114.5, 119.8, 128.4, 129.27, 129.33, 132.3, 137.5, 138.2, 156.3, 159.9, 160.3, 161.8, 170.3, 172.1, 174.1, 174.2; $^{19}$F NMR (470 MHz CDCl$_3$/CD$_3$OD 5:1) δ -118.86; HRMS-ESI m/z calcd for C$_{66}$H$_{109}$N$_9$O$_{15}$F [M+H]$^+$ 1286.8022. found 1286.8027.

Example 15—Synthesis of (2S,3S,4R)-2-Amino-1-O-α-D-galactopyranosyl-4-O-hexacosanoyl nonane-1,3,4-triol (CN214)

Example 15.1—(2S,3S,4R)-2-Amino-1-O-α-D-galactopyranosyl-4-O-hexacosanoyl nonane-1,3,4-triol (67)

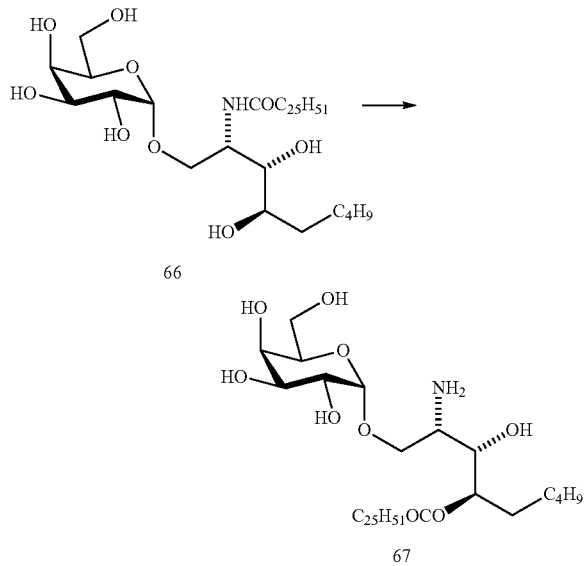

Compound 66 (Enzo Life Sciences, 10.2 mg, 0.014 mmol) is heated under Ar in 10:1:1.3 1,4-dioxane/water/1 M HCl (3.57 mL) at 83° C. for 30 min, then cooled to rt. After lyophilisation, the resulting solid is purified on silica gel (MeOH/CHCl$_3$=15:85 to 25:75) to afford the title compound 67 as a white solid (6.1 mg, 60%). $^1$H NMR (500 MHz, CDCl$_3$/CD$_3$OD 2:1) δ 0.87-0.91 (m, 6H), 1.22-1.40 (m, 50H), 1.54-1.67 (m, 3H), 1.78-1.84 (m, 1H), 2.35-2.38 (m, 2H), 3.26-3.29 (m, 1H), 3.51-3.55 (m, 1H), 3.71-3.73 (m, 1H), 3.76 (dd, J=3.3, 10.0 Hz, 1H), 3.79-3.81 (m, 2H), 3.83-3.86 (m, 2H), 3.97 (d, J=3.3 Hz, 1H), 4.11 (dd, J=3.0, 10.7 Hz, 1H), 4.88 (d, J=3.8 Hz, 1H), 4.93 (dt, J=3.0, 8.7 Hz, 1H); $^{13}$C NMR (126 MHz, CDCl$_3$/CD$_3$OD 2:1) δ 14.1, 14.2, 22.8, 23.0, 25.0, 25.4, 29.5, 29.68, 29.71, 29.9, 30.00, 30.03, 30.05, 31.4, 31.9, 32.3, 34.8, 53.1, 62.2, 65.4, 69.4, 70.2, 70.4, 71.2, 71.6, 73.7, 100.0, 174.6; HRMS-ESI [M+H]$^+$ calcd for C$_{41}$H$_{82}$NO$_9$: 732.5990. found 732.5984.

Example 15.2—(2S,3S,4R)-1-O-α-D-Galactopyranosyl-4-O-hexacosanoyl-2-(N-(6-azidohexanoyl)-Val-Cit-4-aminobenzyloxycarbonylamino) nonane-1,3,4-triol (CN214)

to afford the title compound CN214 as a white solid (7.0 mg, 66%). $^1$H NMR (500 MHz, 2:1 CDCl$_3$/CD$_3$OD) δ 0.87-0.90 (m, 6H), 0.95-0.97 (m, 6H), 1.23-1.35 (m, 50H), 1.39-1.46 (m, 2H), 1.52-1.77 (m, 11H), 1.87-1.94 (m, 1H), 2.04-2.11 (m, 1H), 2.27-2.32 (m, 2H), 2.33-2.40 (m, 2H), 3.09-3.14 (m, 1H), 3.21-3.26 (m, 1H), 3.28 (t, J=6.9 Hz, 2H), 3.66-3.80 (m, 8H), 3.84-3.87 (m, 2H), 4.19 (d, J=7.3 Hz, 1H), 4.54 (dd, J=5.1, 8.7 Hz, 1H), 4.85 (d, J=3.8 Hz, 1H), 4.94-5.01 (m, 2H), 5.10-5.18 (m, 1H), 7.32 (d, J=8.5 Hz, 2H), 7.57 (d, J=8.5 Hz, 2H); $^{13}$C NMR (126 MHz, 2:1 CDCl$_3$/CD$_3$OD) δ 14.1, 14.2, 18.5, 19.4, 22.8, 23.0, 25.3, 25.4, 25.6, 26.6, 28.9, 29.0, 29.5, 29.59, 29.63, 29.65, 29.8, 29.95, 29.98, 31.00, 31.9, 32.2, 34.9, 36.2, 39.3, 51.5, 52.5, 53.7, 59.4, 62.3, 66.7, 68.4, 69.4, 70.2, 70.6, 70.9, 72.2, 75.0, 100.3, 120.4, 129.0, 132.9, 138.2, 157.0, 161.0, 171.0,

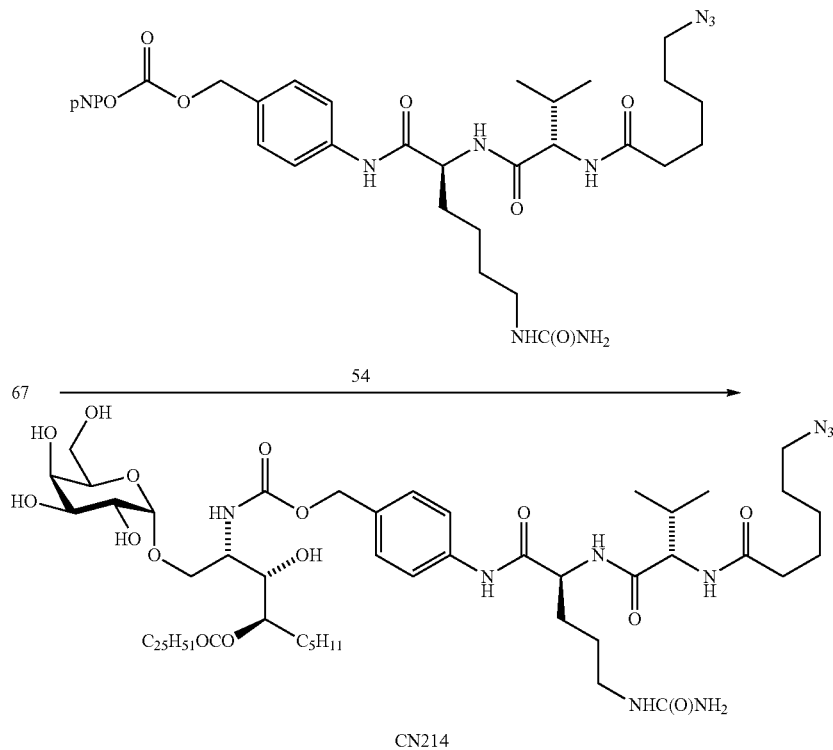

CN214

To a mixture of amine 67 (6.1 mg, 0.0083 mmol) and pNP-carbonate 54 (10 mg, 0.015 mmol) in anhydrous pyridine (0.12 mL) under Ar is added Et$_3$N (0.7 μL, 0.012 mmol) and the mixture is stirred at rt. After 24 h, further Et$_3$N (0.7 μL, 0.005 mmol) is added and stirring is continued for a further 8 h. The mixture is concentrated to dryness under high vacuum, and the crude residue is purified by column chromatography on silica gel (MeOH/CHCl$_3$=2:98 to 20:80)

172.8, 174.91, 174.95; HRMS-ESI [M+Na]$^+$ calcd for C$_{66}$H$_{117}$N$_9$NaO$_{15}$: 1298.8567 found 1298.8553.

Example 16—(2S,3S,4R)-1-O-α-D-Galactopyranosyl-4-hexacosanoyl-2-((4-(2-(FFRKSIINFEKL)-2-oxoethoxy)imino)pentanoyloxy)methoxycarbonylamino) octadecane-1,3,4-triol (CN152)

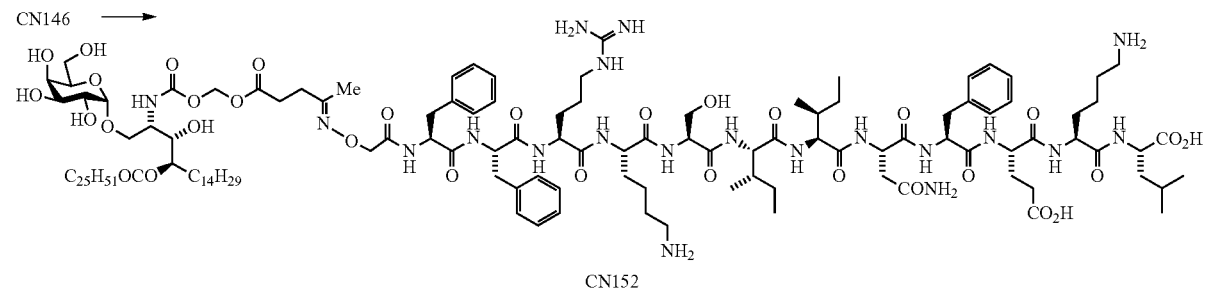

CN152

To a stirred suspension of peptide 2-(aminooxy)acetyl-FFRKSIINFEKL (in which residues 5-12 comprise SEQ ID NO: 262) (5.1 mg, 3.16 mmol) in THF/MeOH (2:1, 600 µL) is added an aqueous mixture of water/aniline/TFA (200:6:4, 300 µL). Once dissolved, a solution of ketone CN146 (2.5 mg, 2.4 mmol), dissolved in THF/MeOH (1:1, 600 µL) is added and the reaction mixture is stirred at 25° C. for 48 h. The solvent is removed and the crude product purified by preparative HPLC (Phenomenex Luna C18(2), 5 µm, 250×30 mm, 30° C., 40 mL/min; Mobile phase A=100:0.1 water/TFA; Mobile phase B=100:0.1 MeOH/TFA; 0-15 min: 50-100% B; 15-23 min: 100% B; 23-25 min: 100-50% B; 25-26 min: 50% B) to give the title compound CN152 (2.1 mg, 33%). $^1$H NMR (500 MHz, d6-DMSO) δ 0.68-0.95 (m, 24H), 1.02-1.45 (m, 74H), 1.70-1.50 (m, 27H), 1.80 (s, 3H), 2.5-2.3 (m, 6H), 2.90-2.71 (m, 8H), 3.21-2.92 (m, 6H), 3.69-3.42 (m, 12H), 4.60-4.08 (m, 18H), 4.63 (s, 1H), 4.76 (brs, 1H), 5.02 (brs, 1H), 5.06 (brs, 1H), 5.68-5.61 (m, 2H), 8.39-7.32 (m, 22H), 7.42 (m, 15H), 6.92 (s, 1H); $^{13}$C NMR (126 MHz, d6-DMSO) δ 73.1 (C-5'), 79.8 (C-2"), 99.5 (H-1); HRMS (ESI): m/z calcd for $C_{134}H_{226}N_{20}O_{32}$ [M+2H]$^{2+}$ 1313.8336. found 1313.8358.

min: 100% B; 23-25 min: 100-50% B; 25-26 min: 50% B) to give the title compound CN178 (2.0 mg, 0.74 µmol, 76%, 94.0% pure by HPLC). $^1$H NMR (500 MHz, d6-DMSO) δ 0.66-0.78 (m, 6H), 0.78-0.95 (m, 9H), 0.95-1.42 (m, 79H), 1.42-1.73 (m, 17H), 1.73-1.82 (m, 3H), 1.82-1.93 (m, 2H), 1.93-2.06 (m, 5H), 2.23-2.33 (m, 2H), 2.33-2.39 (m, 1H), 2.70-2.89 (m, 6H), 3.08-3.15 (m, 2H), 3.40-3.73 (m, 14H), 3.75-3.82 (m, 1H), 3.88 (t, J=8.1 Hz, 1H), 3.97-4.16 (m, 3H), 4.17-4.40 (m, 9H), 4.40-4.55 (m, 5H), 4.55-4.63 (m, 1H), 4.65 (d, J=3.1 Hz, 1H), 4.70-4.74 (m, 2H), 4.77 (t, J=6.4 Hz, 1H), 4.83-4.89 (m, 1H), 5.01 (d, J=6.2 Hz, 1H), 5.04-5.09 (m, 1H), 5.15 (d, J=5.6 Hz, 1H), 5.18 (d, J=3.6 Hz, 1H), 5.60-5.69 (m, 2H), 6.60 (d, J=8.3 Hz, 2H), 6.91-6.95 (m, 1H), 6.98 (d, J=8.3 Hz, 2H), 7.05-7.32 (m, 15H), 7.31-8.27 (m, 23H), 9.12 (br, s, 1H); HRMS-ESI m/z calcd for $C_{137}H_{225}N_{21}O_{32}S$ [M+2H]$^{2+}$ 1354.3173. found 1354.3180.

Example 17—CN178

Example 18—CN185

CN146 →

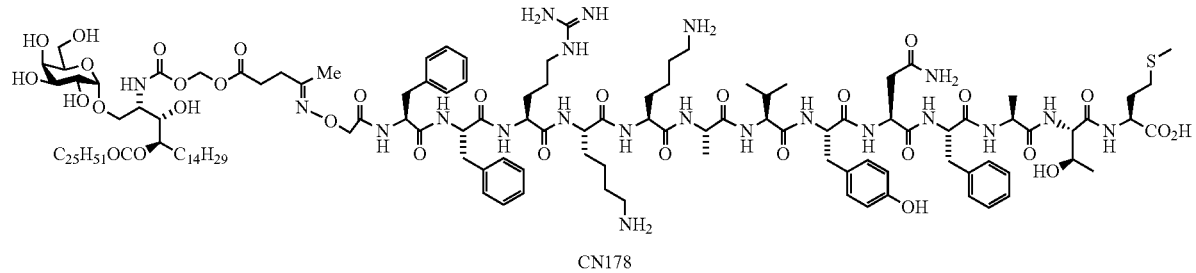

CN178

To a stirred suspension of peptide 2-(aminooxy)acetyl-FFRKKAVYNFATM (in which residues 5-13 comprise SEQ ID NO: 129) (2 mg, 1.17 µmol) in THF/MeOH (2:1, 600 µL) is added an aqueous mixture of water/aniline/TFA (200:6:4, 300 µL). Once dissolved, a solution of ketone CN146 (1 mg, 0.97 µmol) in THF/MeOH (1:1, 600 µL) is added and the reaction mixture stirred at 25° C. for 48 h. The solvent is

CN215 →

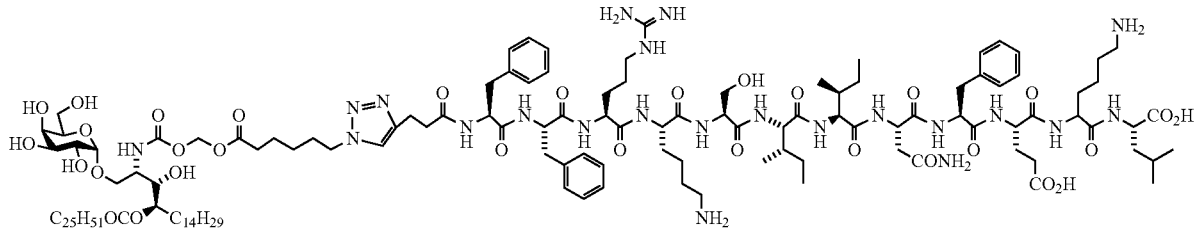

CN185 removed and the crude product purified by preparative HPLC (Phenomenex Luna C18(2), 5 µm, 250×30 mm, 30° C., 40 ml/min; Mobile phase A=100:0.1 water/TFA; Mobile phase B=100:0.1 MeOH/TFA; 0-15 min: 50-100% B; 15-23

To a stirred solution of peptide 4-pentynoyl-FFRKSIIN-FEKL (in which residues 5-12 comprise SEQ ID NO: 262) (4.5 mg, 2.80 µmol) and CN215 (3.03 mg, 2.16 µmol) in DMSO (600 µL) and MeOH (280 µL) is added TBTA (0.33 mg, 0.6 µmol) in CHCl₃ (280 µL) followed by an aqueous solution of 0.25 mM CuSO₄ (100 µL). A small amount of copper foil (5 mm×2 mm) is added and the reaction mixture is stirred at rt for 18 h. The reaction mixture is concentrated by passing an Ar stream over the reaction mixture and the residue is centrifuged with an aqueous solution of 0.05 M EDTA (pH 7.7) (2×10 mL), water (2×10 mL) and the remaining pellet is lyophilized from water (3 mL). The crude product is purified by preparative HPLC (Phenomenex Luna C18(1), 5 µm, 250×10 mm, 40° C., 2.1 mL/min; Mobile phase A=100:0.05 water/TFA; Mobile phase B=100:0.0.05 MeOH/TFA; 0-7 min: 80-100% B; 7-14 min: 100% B; 14-15 min: 100-80% B; 15-20 min: 80% B) to give the title compound CN185 (2.55 mg, 44%, 97.8% pure by HPLC); HRMS-ESI m/z calcd for $C_{138}H_{232}N_{22}O_{31}$ $[M+2H]^{2+}$ 1347.3548. found 1347.3610.

aniline/TFA (200:6:4, 100 µL), and the mixture is stirred at 25° C. for 48 h. The solvent is removed and the crude product is purified by preparative HPLC (Phenomenex Luna C18(1), 5 µm, 250×10 mm, 40° C., 1.8 mL/min; Mobile phase A=100:0.05 water/TFA; Mobile phase B=100:0.0.05 MeOH/TFA; 0-5 min: 80-100% B; 5-15 min: 100% B; 15-16 min: 100-80% B; 16-20 min: 80% B) to give the title compound CN174 (0.3 mg, 2.5%, 95.1% pure by HPLC); HRMS-ESI m/z calcd for $C_{151}H_{251}N_{25}O_{34}$ $[M+2H]^{2+}$ 1479.9262. found 1479.9421.

Example 19—CN174

Example 20—CN175

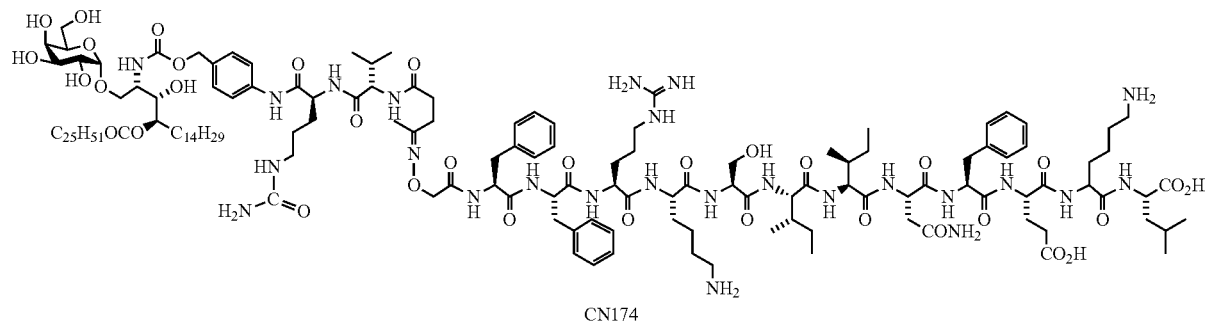

To a stirred suspension of peptide 2-(aminooxy)acetyl-FFRKSIINFEKL (in which residues 5-12 comprise SEQ ID NO: 262) (9 mg, 5.57 µmol) in THF/MeOH (2:1, 600 µL) is added an aqueous mixture of water/aniline/TFA (200:6:4, 300 µL). Once dissolved, a solution of ketone CN171 (5.7

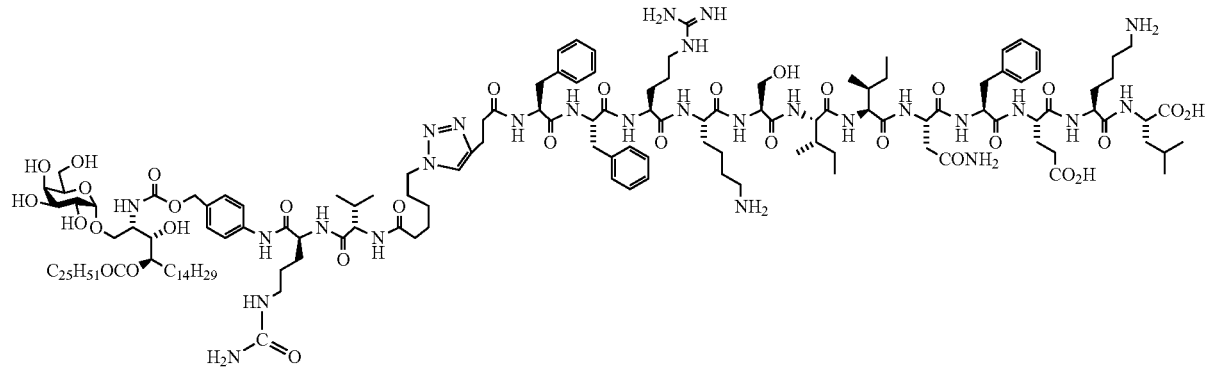

mg, 4.2 µmol) in THF/MeOH (1:1, 600 µL) is added to the reaction mixture, followed by a further portion of water/

To a stirred solution of peptide 4-pentynoyl-FFRKSIIN-FEKL (in which residues 5-12 comprise SEQ ID NO: 262)

(5.03 mg, 3.10 μmol), CN172 (3.03 mg, 2.16 μmol) and TBTA (0.80 mg, 1.5 mol) in DMSO (280 μL) is added CHCl$_3$ (280 μL) and MeOH (280 μL) followed by an aqueous solution of 0.25 mM CuSO$_4$ (107 μL). A small amount of copper foil (5 mm×2 mm) is added and the reaction mixture is stirred at 20° C. for 48 h. The volatiles are removed under reduced pressure to give a residue which is centrifuged with an aqueous solution of 0.1 M EDTA (pH 7.7) (2×10 mL), water (2×10 mL) and the remaining pellet is dried under high vacuum. The crude product is purified by preparative HPLC (Phenomenex Luna C18(1), 5 μm, 250× 10 mm, 40° C., 1.8 mL/min; Mobile phase A=100:0.05 water/TFA; Mobile phase B=100:0.0.05 MeOH/TFA; 0-5 min: 80-100% B; 5-15 min: 100% B; 15-16 min: 100-80% B; 16-20 min: 80% B) to give the title compound CN175 (1.6 mg, 25%, 97.9% pure by HPLC); HRMS-ESI m/z calcd for C$_{155}$H$_{257}$N$_{27}$O$_{33}$ [M+2H]$^{2+}$ 1512.9553. found 1512.9609.

Example 21—CN194

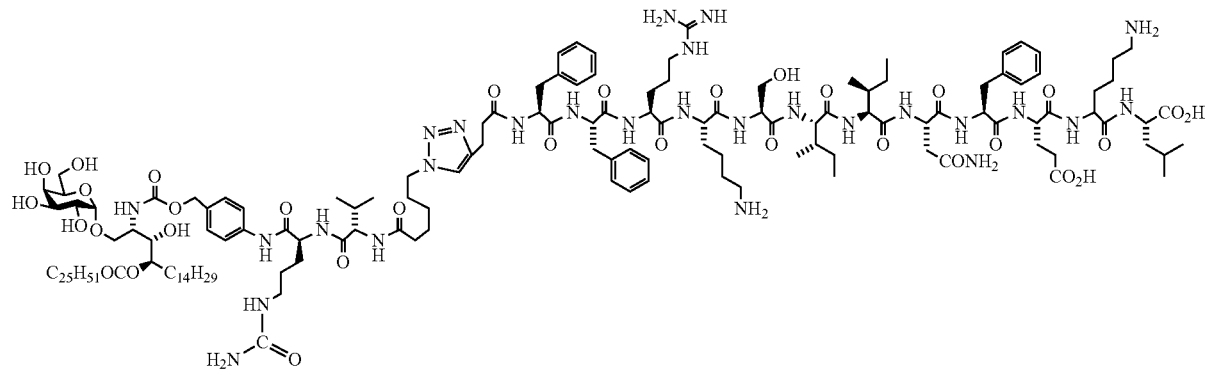

CN194

To a stirred solution of peptide 4-pentynoyl-FFRKNLVP-MVATV (in which residues 5-13 comprise SEQ ID NO: 199) (2.0 mg, 1.25 μmol), CN172 (1.0 mg, 0.71 μmol) and TBTA (0.29 mg, 0.55 μmol) in DMSO (93 μL) is added CHCl$_3$ (93 μL) and MeOH (93 μL) followed by an aqueous solution of 0.25 mM CuSO$_4$ (31 μL). A small amount of copper foil (5 mm×2 mm) is added and the reaction mixture is stirred at 20° C. for 15 h. The volatiles are removed under reduced pressure to give a residue which is centrifuged with an aqueous solution of 0.025 M EDTA (pH 7.7) (2×10 mL), water (2×10 mL) and the remaining pellet is dried under high vacuum. The crude product is purified by preparative HPLC (Phenomenex Luna C18(2), 5 μm, 250×30 mm, 30° C., 40 ml/min; Mobile phase A=100:0.1 water/TFA; Mobile phase B=100:0.1 MeOH/TFA; 0-15 min: 50-100% B; 15-23 min: 100% B; 23-25 min: 100-50% B; 25-26 min: 50% B) to give the title compound CN194 (1.65 mg, 77%, 94.2% pure by HPLC); HRMS-ESI m/z calcd for C$_{152}$H$_{256}$N$_{27}$O$_{32}$SNa [M+H+Na]$^{2+}$ 1513.9439. found 1513.9397.

Example 22—CN188

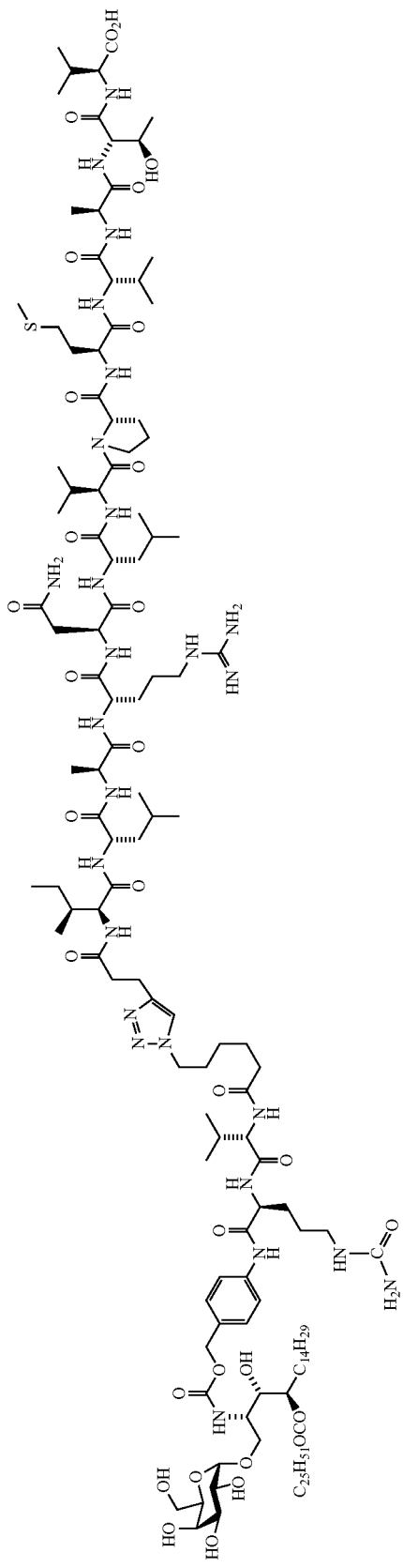

To a stirred solution of peptide 4-pentynoyl-ILARNLVP-MVATV (in which residues 5-13 comprise SEQ ID NO: 199) (2.12 mg, 1.44 µmol), CN172 (0.99 mg, 0.71 µmol) and TBTA (0.22 mg, 0.41 µmol) in DMSO (93 µL) is added CHCl$_3$ (93 µL) and MeOH (93 µL) followed by an aqueous solution of 0.25 mM CuSO$_4$ (31 µL). A small amount of copper foil (5 mm×2 mm) is added and the reaction mixture is stirred at 20° C. for 15 h. The volatiles are removed under reduced pressure to give a residue which is centrifuged with an aqueous solution of 0.025 M EDTA (pH 7.7) (2×10 mL), water (2×10 mL) and the remaining pellet is dried under high vacuum. The crude product is purified by preparative HPLC (Phenomenex Luna C18(2), 5 µm, 250×30 mm, 30° C., 40 ml/min; Mobile phase A=100:0.1 water/TFA; Mobile phase B=100:0.1 MeOH/TFA; 0-15 min: 50-100% B; 15-23 min: 100% B; 23-25 min: 100-50% B; 25-26 min: 50% B) to give the title compound CN194 (1.00 mg, 50%, 94.8% pure by HPLC); HRMS-ESI m/z calcd for C$_{143}$H$_{253}$N$_{26}$O$_{32}$SNa [M+H+Na]$^{2+}$ 1451.4306. found 1451.4269.

Example 23—CN197

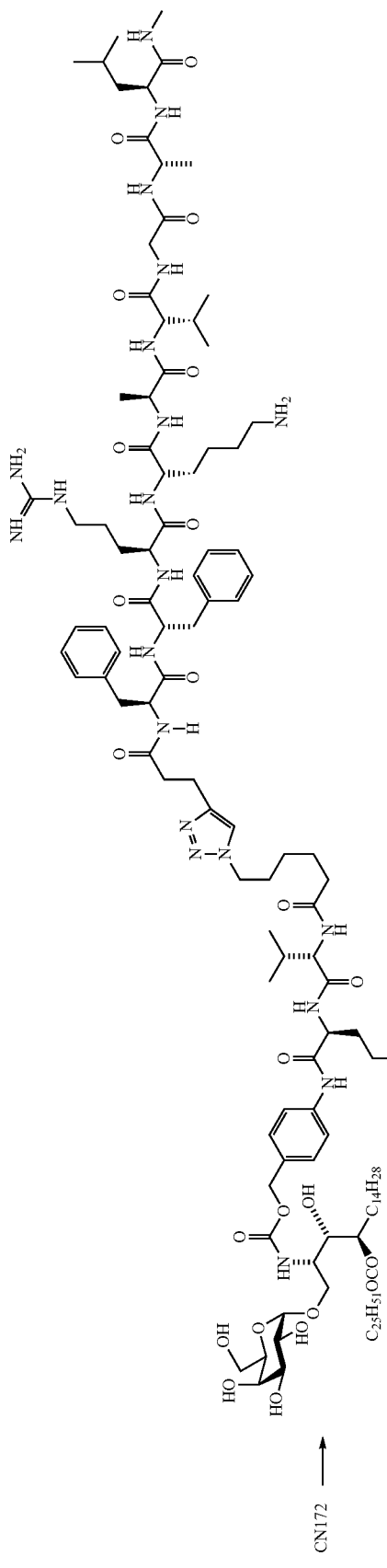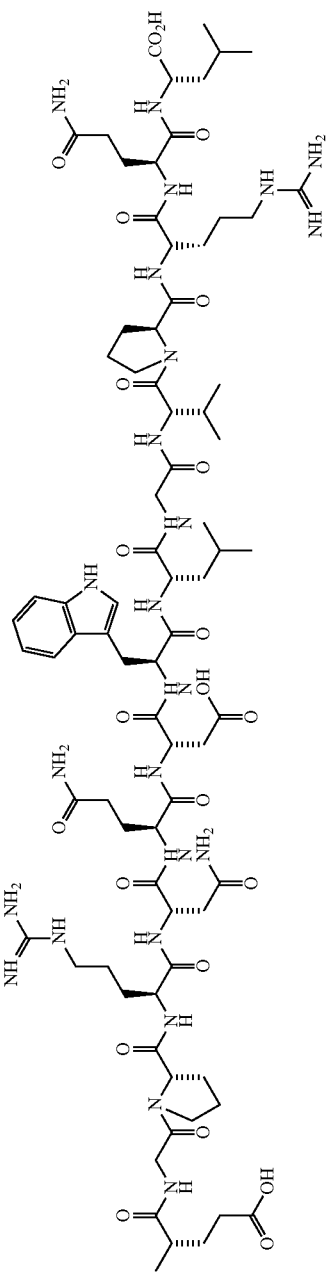

To a stirred solution of peptide 4-pentynoyl-FFRKAV-GALEGPRNQDWLGVPRQL (in which residues 5-24 comprise SEQ ID NO: 413) (7.72 mg, 2.73 μmol), CN172 (2.02 mg, 1.44 μmol) and TBTA (0.42 mg, 0.79 μmol) in DMSO (186 μL) is added CHCl$_3$ (186 μL) and MeOH (186 μL) followed by an aqueous solution of 0.25 mM CuSO$_4$ (62 μL). A small amount of copper foil (5 mm×2 mm) is added and the reaction mixture is stirred at 20° C. for 13 h. The volatiles are removed under reduced pressure to give a residue which is centrifuged with an aqueous solution of 0.05 M EDTA (pH 7.7) (2×10 mL), water (3×10 mL) and the remaining pellet is dried under high vacuum. The crude product is purified by preparative HPLC (Phenomenex Luna C18(1), 5 μm, 250×10 mm, 40° C., 2.0 mL/min; Mobile phase A=100:0.05 water/TFA; Mobile phase B=100:0.0.05 MeOH/TFA; 0-8 min: 80-100% B; 8-15 min: 100% B; 15-16 min: 100-80% B; 16-20 min: 80% B) to give the title compound CN197 (4.90 mg, 80%, 95.1% pure by HPLC); HRMS-ESI m/z calcd for C$_{206}$H$_{338}$N$_{47}$O$_{48}$ [M+3H]$^{3+}$ 1413.5073. found 1413.4989.

Example 24—CN196

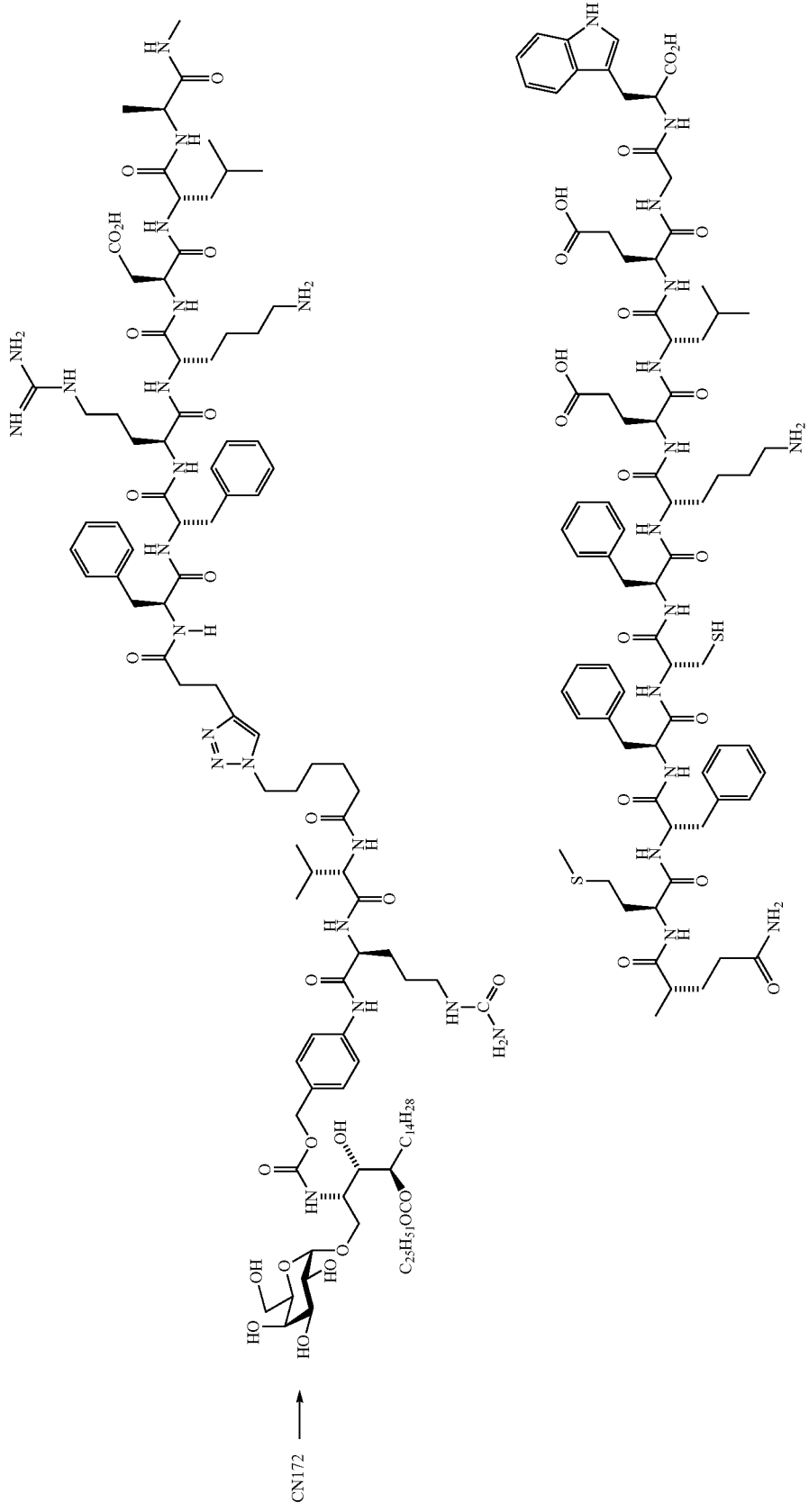

To a stirred solution of peptide 4-pentynoyl-FFRKD-LAQMFFCFKELEGW (in which residues 5-19 comprise SEQ ID NO: 412) (7.07 mg, 2.80 µmol), CN172 (2.02 mg, 1.44 µmol) and TBTA (0.40 mg, 0.75 µmol) in DMSO (186 µL) is added $CHCl_3$ (186 µL) and MeOH (186 µL) followed by an aqueous solution of 0.25 mM $CuSO_4$ (62 µL). A small amount of copper foil (5 mm×2 mm) is added and the reaction mixture is stirred at 20° C. for 48 h. The volatiles are removed under reduced pressure to give a residue which is centrifuged with an aqueous solution of 0.05 M EDTA (pH 7.7) (2×10 mL), water (2×10 mL) and the remaining pellet is dried under high vacuum. The crude product is dissolved in DMSO (500 µL) and treated with TCEP-HCl (6 mg, 0.021 mmol) for 18 h then purified by preparative HPLC (Phenomenex Luna C18(1), 5 µm, 250×10 mm, 40° C., 2.0 mL/min; Mobile phase A=100:0.05 water/TFA; Mobile phase B=100:0.0.05 MeOH/TFA; 0-8 min: 80-100% B; 8-15 min: 100% B; 15-16 min: 100-80% B; 16-20 min: 80% B) to give the title compound CN197 (2.03 mg, 36%, 96.2% pure by HPLC); HRMS-ESI m/z calcd for $C_{198}H_{306}N_{35}O_{43}S_2[M+3H]^{3+}$ 1309.0680. found 1309.0685.

Example 25—CN203

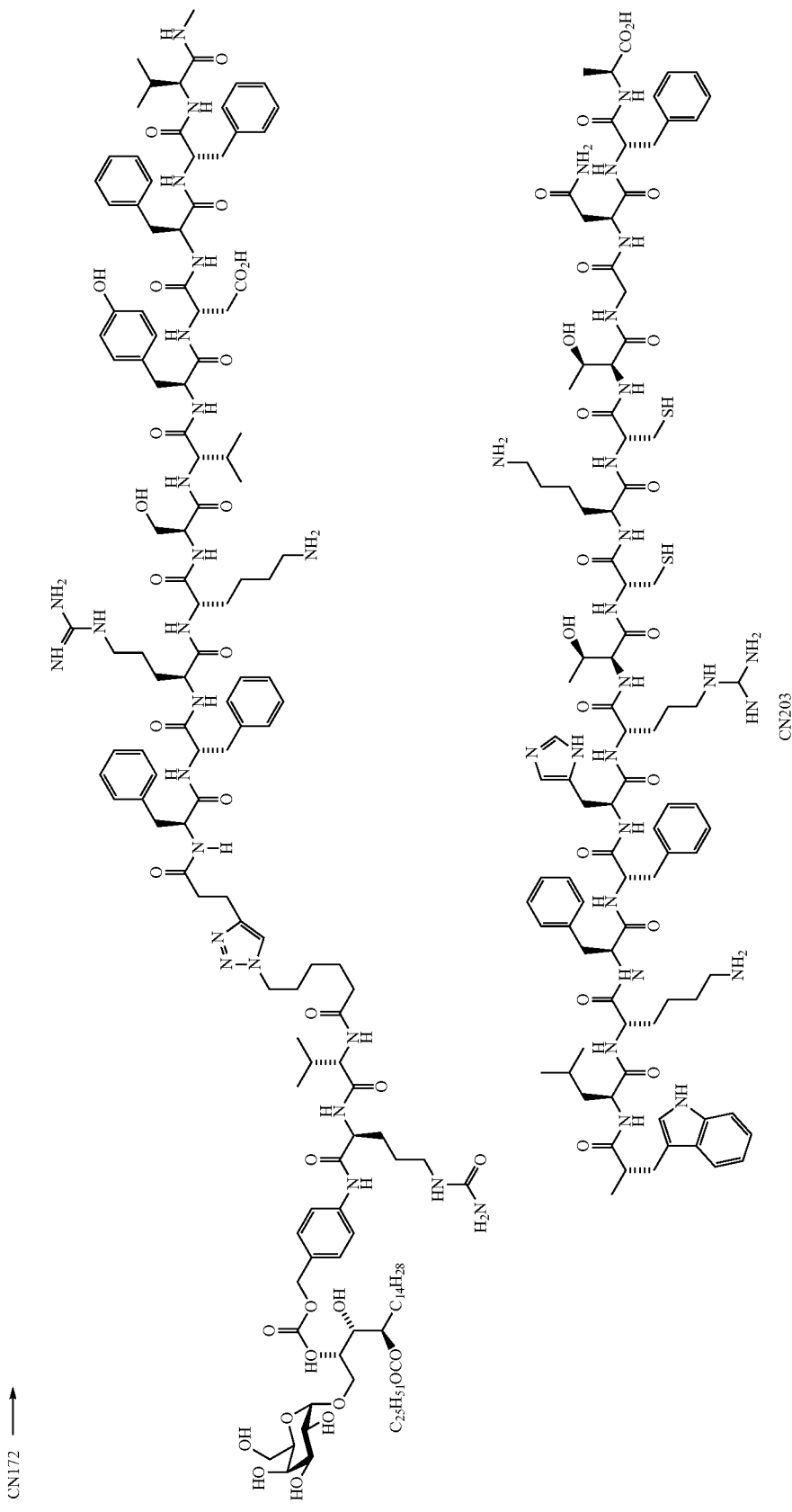

To a stirred solution of peptide 4-pentynoyl-FFRKSVYD-FFVWLKFFHRTCKCTGNFA (in which residues 5-27 comprise SEQ ID NO:411) (5.1 mg, 1.5 μmol), CN172 (1.02 mg, 0.73 μmol) and TBTA (0.21 mg, 0.40 μmol) in DMSO (90 μL) is added CHCl$_3$ (90 μL) and MeOH (90 μL) followed by an aqueous solution of 0.25 mM CuSO$_4$ (30 μL). A small amount of copper foil (5 mm×2 mm) is added and the reaction mixture is stirred at 20° C. for 20 h. The volatiles are removed under reduced pressure to give a residue which is centrifuged with an aqueous solution of 0.05 M EDTA (pH 7.7) (2×10 mL), water (10 mL) and the remaining pellet is dried under high vacuum. An aqueous solution of TCEP-HCl (4.5 mg, 0.016 mmol) in water (90 μL) neutralized with K$_2$CO$_3$ (5 mg) is added to a solution of the crude product in HFIP (1.2 mL) and Et$_3$N (60 μL). After 11 h the reduced product is purified by preparative HPLC (Phenomenex Luna C18(1), 5 μm, 250×10 mm, 40° C., 2.0 mL/min; Mobile phase A=100:0.05 water/TFA; Mobile phase B=100:0.0.05 MeOH/TFA; 0-10 min: 80-100% B; 10-13 min: 100% B; 13-13.5 min: 100-80% B; 13.5-17.5 min: 80% B) to give the title compound CN203 (1.1 mg, 31%, 94.8% pure by HPLC); HRMS-ESI m/z calcd for C$_{245}$H$_{370}$N$_{49}$O$_{51}$S$_2$ [M+3H]$^{3+}$ 1626.9024. found 1626.9104.

Example 26—CN189

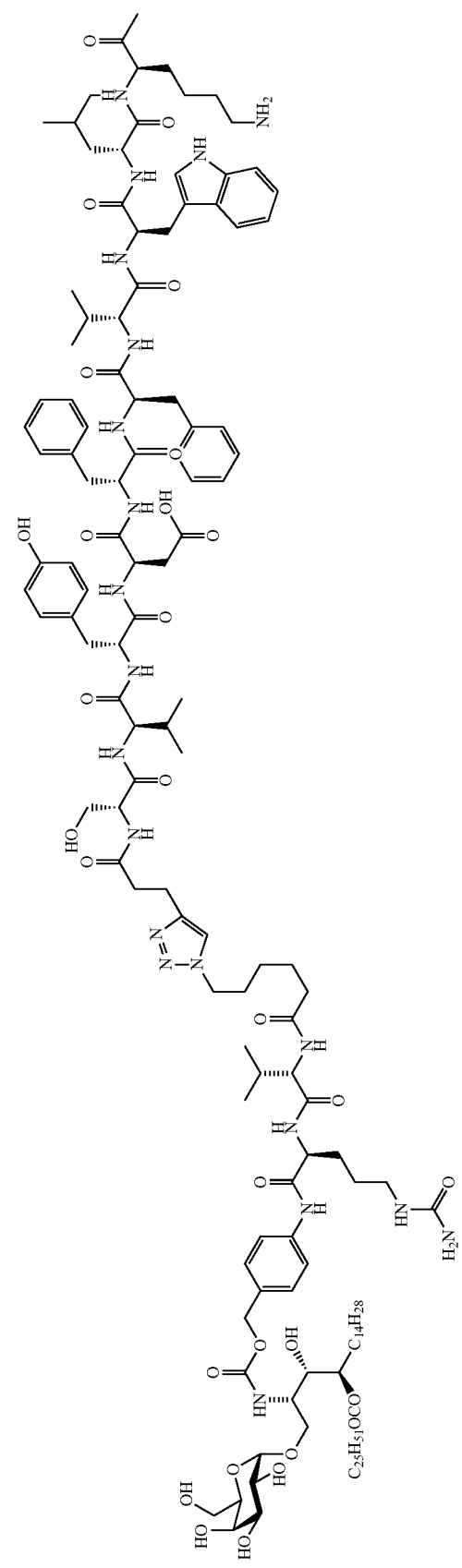
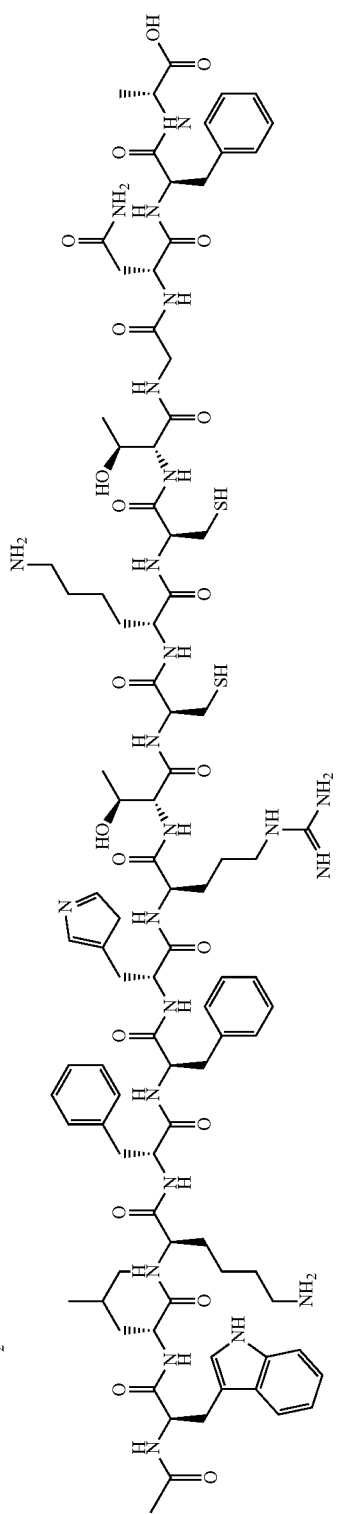

To a stirred solution of peptide 4-pentynoyl-SVYD-FFVWLKFFHRTCKCTGNFA (SEQ ID NO:411) (1.8 mg, 0.62 µmol), CN172 (0.51 mg, 0.36 µmol) and TBTA (0.38 mg, 0.72 µmol) in DMSO (30 µL) is added MeOH (60 µL) and CHCl$_3$ (45 µL) followed by an aqueous solution of 0.25 mM CuSO$_4$ (15 µL). A small amount of copper foil (5 mm×2 mm) is added and the reaction mixture is stirred at 20° C. for 48 h. The volatiles are removed under reduced pressure to give a residue which is centrifuged with an aqueous solution of 0.05 M EDTA (pH 7.7) (2×10 mL), water (10 mL) and the remaining pellet is dried under high vacuum. The crude product is dissolved in DMSO (900 µL) and treated with TCEP-HCl (10 mg, 0.034 mmol) for 18 h then purified by preparative HPLC (Phenomenex Luna C18(1), 5 µm, 250× 10 mm, 40° C., 2.0 mL/min; Mobile phase A=100:0.05 water/TFA; Mobile phase B=100:0.0.05 MeOH/TFA; 0-8 min: 80-100% B; 8-15 min: 100% B; 15-16 min: 100-80% B; 16-20 min: 80% B) to give the title compound CN189 (0.5 mg, 33%, 82% pure by HPLC); HRMS-ESI m/z calcd for C$_{215}$H$_{328}$N$_{41}$O$_{47}$S$_2$ [M+3H]$^{3+}$ 1434.1248. found 1434.1223.

Example 27—CN191

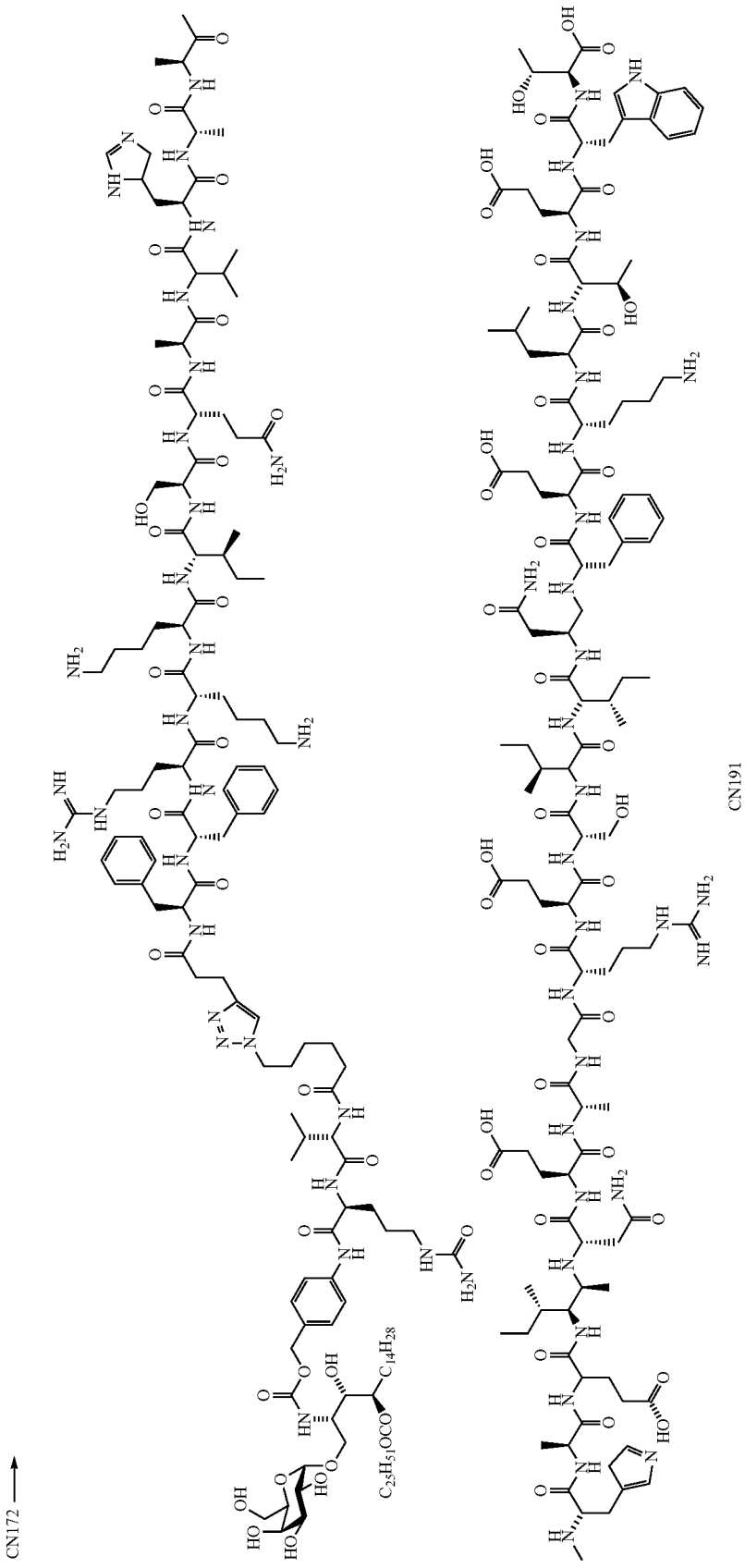

To a stirred solution of peptide 4-pentynoyl-FFRK-KISQAVHAAHAEINEAGRESIINFEKL-TEWT (in which residues 5-35 comprise SEQ ID NO: 141) (5.3 mg, 1.3 µmol), and CN172 (1 mg, 0.71 µmol) in DMSO (140 µL) and MeOH (140 µL) is added TBTA (0.26 mg, 0.49 µmol) in $CHCl_3$ (140 µL) followed by an aqueous solution of 0.25 mM $CuSO_4$ (50 µL). A small amount of copper foil (5 mm×2 mm) is added and the reaction mixture is stirred at rt for 18 h. The reaction mixture is concentrated by passing an Ar stream over the reaction mixture and the residue is centrifuged with an aqueous solution of 0.05 M EDTA (pH 7.7) (2×10 mL), water (10 mL) and the remaining pellet is lyophilized from water (3 mL). The crude product is purified by preparative HPLC (Phenomenex Luna C18(2), 5 µm, 250×30 mm, 30° C., 40 ml/min; Mobile phase A=100:0.1 water/TFA; Mobile phase B=100:0.1 MeOH/TFA; 0-15 min: 50-100% B; 15-23 min: 100% B; 23-25 min: 100-50% B; 25-26 min: 50% B) to give the title compound CN191 (2.7 mg, 69%, 97.6% pure by HPLC); HRMS-ESI m/z calcd for $C_{264}H_{426}N_{61}O_{69}$ $[M+3H]^{3+}$ 1852.3822. found 1852.3904.

Example 28—CN206

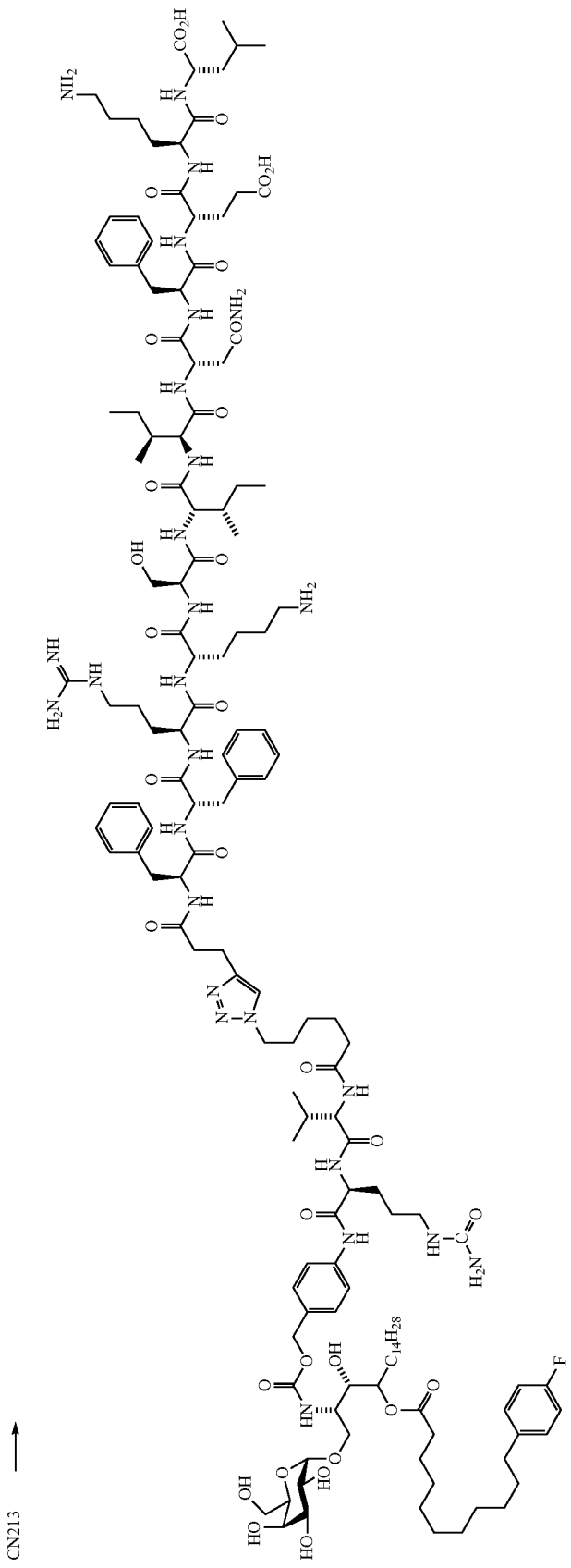

To a stirred solution of peptide 4-pentynoyl-FFRKSIIN-FEKL (in which residues 5-12 comprise SEQ ID NO: 262) (6.2 mg, 3.8 µmol), and CN213 (2.5 mg, 1.9 µmol) in DMSO (200 µL) and MeOH (200 µL) is added TBTA (0.74 mg, 1.4 µmol) in CHCl$_3$ (200 µL) followed by an aqueous solution of 0.25 mM CuSO$_4$ (50 µL). A small amount of copper foil (5 mm×2 mm) is added and the reaction mixture is stirred at rt for 18 h. The reaction mixture is concentrated by passing an Ar stream over the reaction mixture and the residue is centrifuged with an aqueous solution of 0.05 M EDTA (pH 7.7) (2×10 mL), water (10 mL) and the remaining pellet is lyophilized from water (3 mL). The crude product is purified by preparative HPLC (Phenomenex Luna C18(2), 5 µm, 250×30 mm, 30° C., 40 ml/min; Mobile phase A=40:60:0.05 water/MeOH/TFA; Mobile phase B=100:0.05 MeOH/TFA; 0-14 min: 0-100% B; 14-16 min: 100% B; 16-16.5 min: 100-0% B; 16.5-18 min: 0% B) to give the title compound CN206 (1.24 mg, 22%, 95.8% pure by HPLC); HRMS-ESI m/z calcd for $C_{146}H_{230}FN_{27}O_{33}$ $[M+2H]^{2+}$ 1454.8488. found 1454.8557.

Example 29—CN207

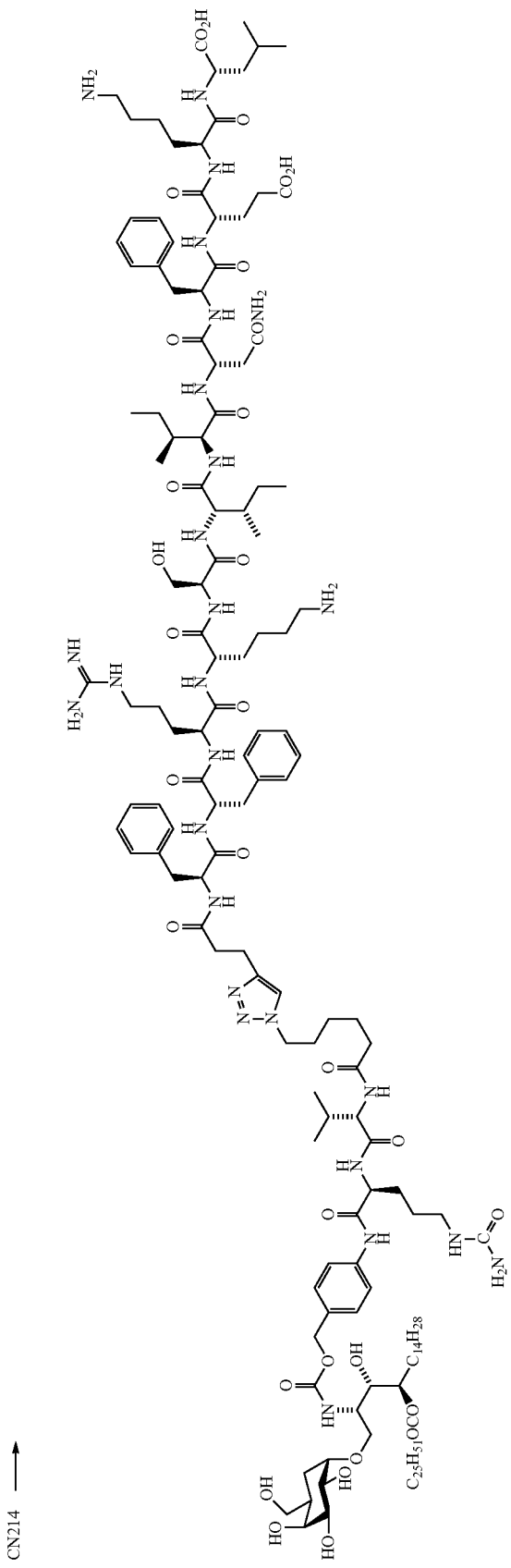

To a stirred solution of peptide 4-pentynoyl-FFRKSIIN-FEKL (in which residues 5-12 comprise SEQ ID NO: 262) (4.8 mg, 3.0 µmol), and CN214 (2.0 mg, 1.6 µmol) in DMSO (200 µL) and MeOH (200 µL) is added TBTA (0.59 mg, 1.1 µmol) in CHCl$_3$ (200 µL) followed by an aqueous solution of 0.25 mM CuSO$_4$ (50 µL). A small amount of copper foil (5 mm×2 mm) is added and the reaction mixture is stirred at rt for 18 h. The reaction mixture is concentrated by passing an Ar stream over the reaction mixture and the residue is centrifuged with an aqueous solution of 0.05 M EDTA (pH 7.7) (2×10 mL), water (10 mL) and the remaining pellet is lyophilized from water (3 mL). The crude product is purified by preparative HPLC (Phenomenex Luna C18(2), 5 µm, 250×30 mm, 30° C., 40 ml/min; Mobile phase A=40:60:0.05 water/MeOH/TFA; Mobile phase B=100:0.05 MeOH/TFA; 0-14 min: 0-100% B; 14-17 min: 100% B; 17-17.5 min: 100-0% B; 17.5-19 min: 0% B) to give the title compound CN207 (2.22 mg, 49%, 94.9% pure by HPLC); HRMS-ESI m/z calcd for C$_{146}$H$_{239}$N$_{27}$O$_{33}$ [M+2H]$^{2+}$ 1449.8849. found 1449.8951.

Example 30—CN212

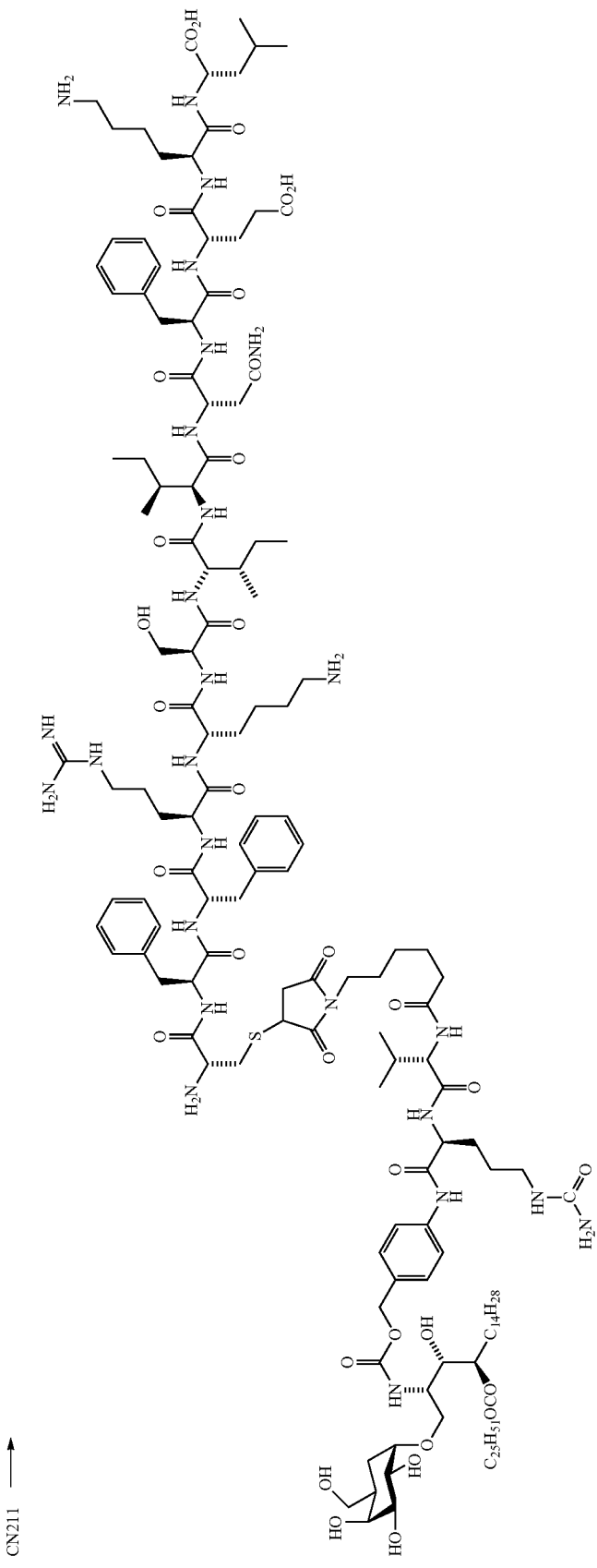

Peptide CFFRKSIINFEKL (in which residues 6-13 comprise SEQ ID NO: 262) (1.4 mg, 0.85 mol) and CN211 (0.85 mg, 0.58 μmol) are dissolved in deoxygenated DMF (75 μL) under Ar and stirred at rt for 4 h. After concentration of the solvent, the crude product is purified by preparative HPLC (Phenomenex Luna C18(1), 5 μm, 250×10 mm, 40° C., 1.8 mL/min; Mobile phase A=100:0.05 water/TFA; Mobile phase B=100:0.0.05 MeOH/TFA; 0-5 min: 80-100% B; 5-15 min: 100% B; 15-16 min: 100-80% B; 16-20 min: 80% B) to give the title compound CN212. HRMS-ESI m/z calcd for $C_{157}H_{260}N_{26}O_{35}S$ $[M+2H]^{2+}$: 1550.9542. found 1550.9521.

Example 31—CN210

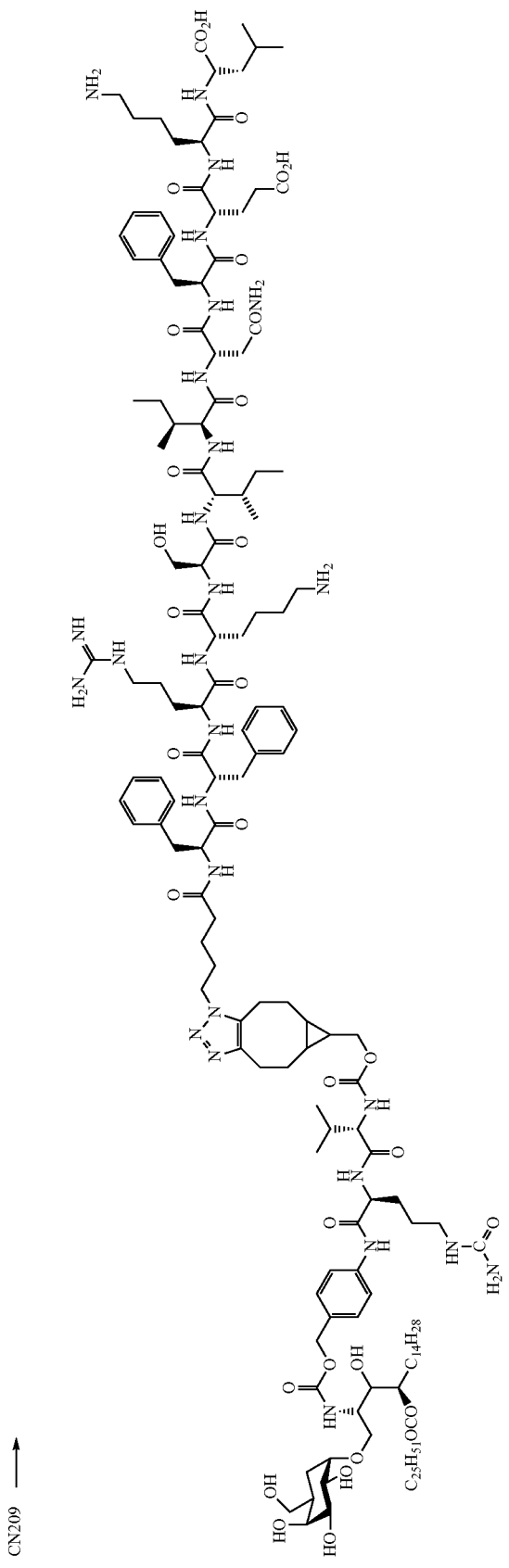

To a stirred solution of peptide 5-azidopentanoyl-FFRK-SIINFEKL (in which residues 5-12 comprise SEQ ID NO: 262) (0.43 mg, 0.26 μmol) in DMSO (22 μL) is added a solution of CN209 (0.25 mg, 0.17 μmol) in CHCl$_3$/MeOH (1:1, 45 μL), followed by water (8.6 μL), and the reaction mixture is stirred at rt for 24 h. After concentration of the solvent, the crude product is purified by preparative HPLC (Phenomenex Luna C18(1), 5 μm, 250×10 mm, 40° C., 1.8 mL/min; Mobile phase A=100:0.05 water/TFA; Mobile phase B=100:0.0.05 MeOH/TFA; 0-5 min: 80-100% B; 5-15 min: 100% B; 15-16 min: 100-80% B; 16-20 min: 80% B) to give the title compound CN210. HRMS-ESI m/z calcd for C$_{160}$H$_{263}$N$_{27}$O$_{34}$ [M+2H]$^{2+}$: 1553.4840. found 1553.4850.

Example 32—CN205

199
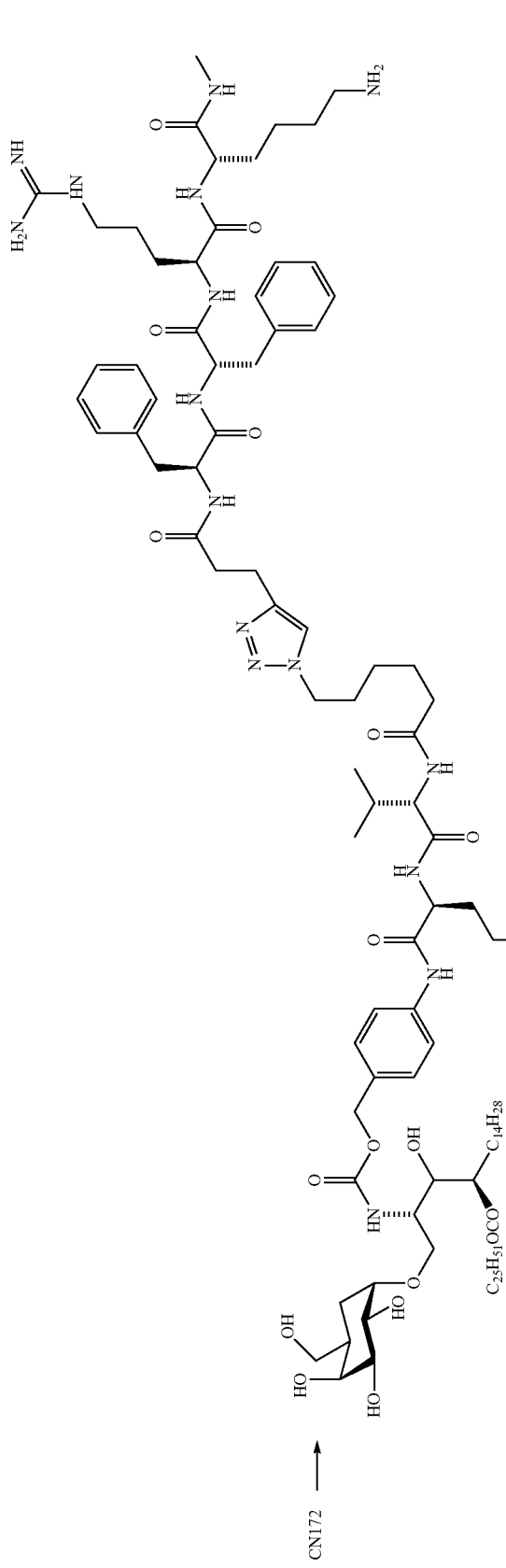
200
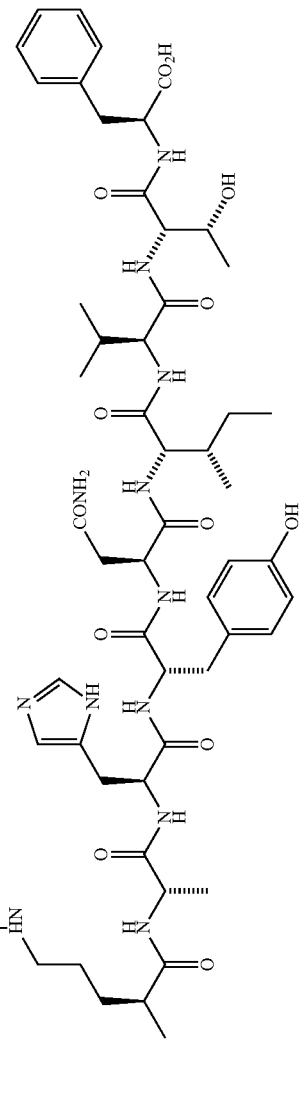

To a stirred solution of peptide 4-pentynoyl-FFRKRAHYNIVTF (in which residues 5-13 comprise SEQ ID NO: 414) (4.6 mg, 2.6 µmol), CN172 (2 mg, 1.4 µmol) in DMSO (140 µL) and MeOH (140 µL) is added a solution of TBTA (0.54 mg, 0.99 µmol) in CHCl$_3$ (140 µL) followed by an aqueous solution of 0.25 mM CuSO$_4$ (50 µL). A small amount of copper foil (5 mm×2 mm) is added and the reaction mixture is stirred at rt for 18 h. The volatiles are removed under reduced pressure to give a residue which is centrifuged with an aqueous solution of 0.05 M EDTA (pH 7.7) (2×10 mL), water (10 mL) and the remaining pellet is dried under high vacuum. The crude product is purified by preparative HPLC (Phenomenex Luna C18(2), 5 µm, 250× 30 mm, 30° C., 40 ml/min; Mobile phase A=40:60:0.05 water/MeOH/TFA; Mobile phase B=100:0.05 MeOH/TFA; 0-10 min: 0-100% B; 10-16 min: 100% B; 16-16.5 min: 100-0% B; 16.5-18 min: 0% B) to give the title compound CN205 (2.5 mg, 56%, 96.7% pure by HPLC). HRMS-ESI m/z calcd for $C_{162}H_{258}N_{32}O_{33}$ [M+2H]$^{2+}$ 1591.4747. found 1591.4823.

Example 33—Formulating Compounds of the Invention for Intravenous Injection

Compounds of the invention are formulated analogously to reported methods for α-GalCer. Briefly, solubilisation of α-GalCer is based on excipient proportions described by Giaccone et al. (Giaccone, Punt et al. 2002). Thus, 100 µL of a 10 mg/mL solution of α-GalCer or a compound of the invention in 9:1 THF/MeOH is added to 1.78 mL of an aqueous solution of Tween 20 (15.9 mg), sucrose (177 mg) and L-histidine (23.8 mg). This homogeneous mixture is freeze dried and the resulting foam is stored under Ar at −18° C. This material is reconstituted with 1.0 mL of PBS or water prior to serial dilutions in PBS to achieve final injectable solutions of α-GalCer or compounds of the invention.

Example 34—HPLC-ESI-MSMS Quantification of α-GalCer

Quantification of the amount of α-GalCer in various test samples of compounds of the invention is made by HPLC-ESI-MSMS analysis using a Waters 2795 HPLC and a Waters Q-TOF Premier™ Tandem Mass Spectrometer. The chromatography used a Phenomenex Kinetex C18 2.6 mm 3.0×50 mm column eluting with isocratic methanol containing 10 mM ammonium formate+0.5% formic acid at a flow rate of 0.2 mL/min. α-GalCer is monitored by selective reactant monitoring of 898.7 to 696.7 Da. The estimate of amount of α-GalCer is made by comparison of ion count integrals to a standard curve run on the same day or by comparison to test samples spiked with a known amount of α-GalCer. The level of α-GalCer is determined on freshly reconstituted formulated samples unless otherwise stated

| Compound | α-GalCer/injection |
|---|---|
| CN152 | 0.05 ng |
| CN165 | 0.028 ng |
| CN166 | 0.136 ng |

Example 35—Biological Studies

Mice. Breeding pairs of the inbred strains C57BL/6 (CD45.2$^+$) and B6.SJL-Ptprc$^a$ Pepc$^b$/BoyJ (CD45.1$^+$) are obtained from Jackson Laboratories, Bar Harbor, Me., and from the Animal Resource Centre, Canning Vale, Western Australia. Also used are lang-DTREGFP and lang-EGFP knock in mice, which express the human diphtheria toxin (DT) receptor and/or enhanced green fluorescent protein (EGFP) under the control of the langerin promoter, CD1d$^{-/-}$ mice, which are devoid of Vα14 iNKT cells, TLR2$^{-/-}$ mice (17), OT-I mice, which are transgenic for a TCR recognizing an H-2K$^b$-restricted epitope from chicken OVA (OVA$_{257-264}$) and OT-Ill mice, with a TCR recognizing the I-A$^b$-restricted epitope OVA$_{323-339}$. For adoptive transfer experiments OT-I animals are crossed with B6.SJL-Ptprc$^a$ Pepc$^b$/BoyJ animals, so that the congenic marker CD45.1 could be used to discriminate the transferred cells. All mice are maintained in the Biomedical Research Unit of the Malaghan Institute of Medical Research. Experiments are approved by a national Animal Ethics Committee and performed according to established national guidelines.

Administration of Compounds of the Invention.

Each compound of the invention is supplied as formulated product (see example 33), and diluted in phosphate-buffered saline (PBS) for injection (0-2.0 nmol/mouse) by intravenous injection into the lateral tail vein. In humans the expected therapeutic dose lies in the 50-4800 (µg/m$^2$) range (Giaccone, Punt et al. 2002). Note, 0.23 nmol in a mouse is a human equivalent dose of 30 µg/m$^2$ for α-GalCer. Higher doses are likely for other administration routes.

All antibody labeling is performed on ice in FACS buffer (PBS supplemented with 1% FCS, 0.05% sodium azide, and 2 mM EDTA). Non-specific FcR-mediated antibody staining is blocked by incubation for 10 min with anti-CD16/32 Ab (24G2, prepared in-house from hybridoma supernatant). Flow cytometry is performed on a BD Biosciences FACSCalibur or BD LSRII SORP flow cytometer with data analysis using FlowJo software (Tree Star, Inc., OR, USA).

Phenotyping DC from Spleen.

Antibody staining and flow cytometry is used to examine the expression of maturation markers on dendritic cells in the spleen following injection of compounds of the invention. Splenocyte preparations are prepared by gentle teasing of splenic tissue through gauze in Iscove's Modified Dulbecco's Medium with 2 mM glutamine, 1% penicillin-streptomycin, 5×10-5 M 2-mercapto-ethanol and 5% fetal bovine serum (all Invitrogen, Auckland, New Zealand), followed by lysis of red blood cells with RBC lysis buffer (Puregene, Gentra Systems, Minneapolis, Minn., USA). Antibody staining is performed in PBS 2% fetal bovine serum and 0.01% sodium azide. The anti-FcgRII monoclonal antibody 2.4G2 is used at 10 mg/ml to inhibit non-specific staining. Monoclonal antibodies (all BD Biosciences Pharmingen, San Jose, Calif., USA) are used to examine expression of the maturation markers CD40, CD80 and CD86 on CD11c+ dendritic cells.

Analysis of Peptide-Specific T Cell Proliferation In Vivo

Pooled lymph node cell suspensions are prepared from animals of a cross between OT-I mice, which express a transgenic T cell receptor (TCR) specific for the ovalbumin epitope SIINFEKL in the context of H-2K$^b$ molecules, and B6.SJL-Ptprc$^a$ Pepc$^b$/BoyJ mice, which are congenic with C57BL/6 mice for the CD45.1$^+$ marker. The samples are enriched for CD8$^+$ cells using antibody coated magnetic beads (Miltenyi), and then transferred into recipient mice (1×10$^4$ per mouse). Groups of recipient animals (n=5) are immunized with compounds of the invention one day later. Doses are chosen to provide equivalent molar values of SIINFEKL peptide. Control animals receive phosphate-buffered saline. After seven days, blood samples are collected from the lateral tail vein and stained directly ex vivo with antibodies for TCR Vα2, CD45.1 and CD8 to detect the SIINFEKL-specific CD8+ T cells by flow cytometry.

Analysis of Peptide-Specific T Cell-Mediated Cytotoxicity In Vivo

The cytotoxic capacity of induced CD8+ T cell responses is measured by VITAL assay (Hermans, Silk et al. 2004). Mice are immunized with the compounds of the invention, or PBS, and then injected intravenously seven days later with two populations of syngeneic splenocytes; those loaded with 500 nM, SIINFEKL-peptide and labelled with 1.65 nM carboxyfluorescein succinimidyl ester (CFSE), or those loaded with peptide and labelled with 10 µM cell tracker orange (CTO). Specific lysis of the peptide-loaded targets is monitored by flow cytometry of blood or spleen samples 24 h later. Mean percent survival of peptide-pulsed (CFSE+) targets is calculated relative to that of the control population (CTO+), and cytotoxic activity is expressed as percent specific lysis (100−mean percent survival of peptide-pulsed targets).

Analysis of Anti-Tumour Activity.

Groups of C57BL/6 mice (n=5) receive a subcutaneous injection into the flank of $1\times10^5$ B16.OVA melanoma cells, which express a cDNA encoding the chicken ovalbumin (OVA) sequence. The different groups are treated 7 days later, when tumours are fully engrafted, by intravenous injection of one of the following; 200 µg OVA protein together with 200 ng α-GalCer, 200 µg OVA protein together with 200 ng of a compound of the invention, or PBS. Mice are monitored for tumour growth every 3-4 days, and tumour size for each group calculated as the mean of the products of bisecting diameters (±SEM). Measurements are terminated for each group when the first animal develops a tumour exceeding 200 mm$^2$.

Assessment of Human T Cells.

Peripheral blood mononuclear cells from CMV seropositive donors are cultured for 8 d in the presence of α-GalCer, NLVPMVATV peptide, admixed a-GalCer and peptide or the conjugate CN188 in complete medium (IMDM supplemented with 5% Human AB serum). α-GalCer 500 ng/ml (=582.5 nM), CN188 and NLVPMVATV used molar equivalent of 582.5 nM.

Flow cytometry with fluorescent HLA-A2/NLVPMVATV tetramer (PE-conjugated, Immudex) and antibodies for CD3 (Alexa Fluor 700 CD3, Biolegend) and CD8 (APC-H7 CD8, BD) are used to detect peptide-specific T cells. Proportions of NLVPMVATV-specific CD8+ T cells are determined by gating out doublets and dead cells (with DAPI), by gating on lymphocyte population by forward and side scatter, and then by selecting for CD3 positive and CD19 (FITC CD19, BD) negative cells. A separate staining panel with PE-conjugated loaded CD1d tetramer is used to detect iNKT cells.

Where the foregoing description reference has been made to integers having known equivalents thereof, those equivalents are herein incorporated as if individually set forth.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

INDUSTRIAL APPLICABILITY

The invention relates to sphingoglycolipid analogues and peptide derivatives thereof, which are useful in treating or preventing diseases or such as those relating to infection, atopic disorders, autoimmune diseases or cancer.

REFERENCES

Alexander, J., R. Cargill, et al. (1988). "(Acyloxy)alkyl carbamates as novel bioreversible prodrugs for amines: increased permeation through biological membranes." *J Med Chem* 31(2): 318-322.

Alexander, J., J Sidney, et al. (1994) "Development of high potency universal DR-restricted helper epitopes by modification of high affinity DR-blocking peptides." *Immunity* 1 (9), 751-61.

Amblard, M., J. A. Fehrentz, et al. (2006). "Methods and protocols of modern solid phase Peptide synthesis." *Mol Biotechnol* 33(3): 239-254.

Amsberry, K. L. and R. T. Borchardt (1991). "Amine prodrugs which utilize hydroxy amide lactonization. I. A potential redox-sensitive amide prodrug." *Pharm Res* 8(3): 323-330.

Amsberry, K. L., A. E. Gerstenberger, et al. (1991). "Amine prodrugs which utilize hydroxy amide lactonization. II. A potential esterase-sensitive amide prodrug." *Pharm Res* 8(4): 455-461.

Atherton, E., H. Fox, et al. (1978). "A mild procedure for solid phase peptide synthesis: use of fluorenylmethoxycarbonylamino-acids." *Journal of the Chemical Society, Chemical Communications* (13): 537-539.

Atwell, G. J., B. M. Sykes, et al. (1994). "Relationships between structure and kinetics of cyclization of 2-aminoaryl amides: potential prodrugs of cyclization-activated aromatic mustards." *J Med Chem* 37(3): 371-380.

Baadsgaard, H. and W. D. Treadwell (1955). "Zur Kenntnis der komplexen Wolframcyanide K4[W(CN)8], 2H2O und K3[W(CN)8], H2O." *Helvetica Chimica Acta* 38(7): 1669-1679.

Baek, D. J., J.-H. Seo, et al. (2011). "The 3-Deoxy Analogue of α-GalCer: Disclosing the Role of the 4-Hydroxyl Group for CD1d-Mediated NKT Cell Activation." *ACS Medicinal Chemistry Letters* 2(7): 544-548.

Banchet-Cadeddu, A., E. Henon, et al. (2011). "The stimulating adventure of KRN 7000." *Org Biomol Chem* 9(9): 3080-3104.

Bendelac, A., P. B. Savage, et al. (2007). "The biology of NKT cells." *Annu Rev Immunol* 25: 297-336.

Berinstein, N. L., M. Karkada, et al. (2012). "First-in-man application of a novel therapeutic cancer vaccine formulation with the capacity to induce multi-functional T cell responses in ovarian, breast and prostate cancer patients." *Journal of translational medicine* 10, 156.

Bettinotti, M. P., C. J. Kim, et al. (1998). "Stringent allele/epitope requirements for MART-1/Melan A immunodominance: implications for peptide-based immunotherapy." *J Immunol* 161(2): 877-889.

Borg, N. A., K. S. Wun, et al. (2007). "CD1d-lipid-antigen recognition by the semi-invariant NKT T-cell receptor." *Nature* 448(7149): 44-49.

Brossart, P., K. S. Heinrich, et al. (1999). "Identification of HLA-A2-restricted T-cell epitopes derived from the MUC1 tumor antigen for broadly applicable vaccine therapies." *Blood* 93(12): 4309-4317.

Butler, R. N., C. B. O'Regan, et al. (1978). "Reactions of fatty acids with amines. Part 2. Sequential thermal reactions of stearic (octadecanoic) acid with some 1,2- and 1,3-aminoalcohols and bis-amines." *Journal of the Chemical Society, Perkin Transactions* 1(4): 373-377.

Cai, H., Z. H. Huang, et al. (2011). "Towards a fully synthetic MUC1-based anticancer vaccine: efficient conjugation of glycopeptides with mono-, di-, and tetravalent lipopeptides using click chemistry." *Chemistry* 17(23): 6396-6406.

Campos, L. M., K. L. Killops, et al. (2008). "Development of Thermal and Photochemical Strategies for Thiol-Ene Click Polymer Functionalization." *Macromolecules* 41(19): 7063-7070.

Carpino, L. A., S. A. Triolo, et al. (1989). "Reductive lactonization of strategically methylated quinone propionic acid esters and amides." *The Journal of Organic Chemistry* 54(14): 3303-3310.

Chang, J. (2006). "Efficient amplification of melanoma-specific CD8+ T cells using artificial antigen presenting complex." *Exp Mol Med* 38(6): 591-598.

Chaudhary, A., M. Girgis, et al. (2003). "Using mixed anhydrides from amino acids and isobutyl chloroformate in N-acylations: a case study on the elucidation of mechanism of urethane formation and starting amino acid liberation using carbon dioxide as the probe." *Tetrahedron Lett* 44(29): 5543-5546.

Chen, G., J. Schmieg, et al. (2004). "Efficient synthesis of alpha-C-galactosyl ceramide immunostimulants: use of ethylene-promoted olefin cross-metathesis." *Org Lett* 6(22): 4077-4080.

Choi, J. K., D. C. Ha, et al. (1989). ".alpha.-acylamino radical cyclizations: application to the synthesis of a tetracyclic substructure of gelsemine." *The Journal of Organic Chemistry* 54(2): 279-290.

Ciesielski, M. J., D. Kozbor, et al. (2008). "Therapeutic effect of a T helper cell supported CTL response induced by a survivin peptide vaccine against murine cerebral glioma." *Cancer Immunol Immunother* 57(12): 1827-1835.

Davidson, E. J., R. L. Faulkner, et al. (2004). "Effect of TA-CIN (HPV 16 L2E6E7) booster immunisation in vulval intraepithelial neoplasia patients previously vaccinated with TA-HPV (vaccinia virus encoding HPV 16/18 E6E7)." *Vaccine* 22(21-22): 2722-2729.

de Araujo, A. D., J. M. Palomo, et al. (2006). "Diels-Alder ligation of peptides and proteins." *Chemistry* 12(23): 6095-6109.

Deng, S., J. Mattner, et al. (2011). "Impact of sugar stereochemistry on natural killer T cell stimulation by bacterial glycolipids." *Org Biomol Chem* 9(22): 7659-7662.

Dere, R. T. and X. Zhu (2008). "The first synthesis of a thioglycoside analogue of the immunostimulant KRN7000." *Org Lett* 10(20): 4641-4644.

Dirksen, A., T. M. Hackeng, et al. (2006). "Nucleophilic catalysis of oxime ligation." *Angew Chem Int Ed Enal* 45(45): 7581-7584.

Dommerholt, J.; Schmidt, S. et al. (2010). "Readily accessible bicyclononynes for bioorthogonal labeling and three-dimensional imaging of living cells." *Angew Chem Int Ed* 49: 9422-9425.

Dondoni, A. (2008). "The emergence of thiol-ene coupling as a click process for materials and bioorganic chemistry." *Angew Chem Int Ed* 47: 8995-8997

Drefahl, G. and H.-H. Hörhold (1961). "Aminoalkohole, XV. Stereoselektive Darstellung und konfigurative Zuordnung der diastereomeren DL-3-Amino-1.2-diphenyl-propanole-(1) (zum Mechanismus der Ringschlußreaktion von Aminoalkoholen mit Benzimidsäureester)." *Chemische Berichte* 94(6): 1641-1656.

Du, W., S. S. Kulkarni, et al. (2007). "Efficient, one-pot syntheses of biologically active alpha-linked glycolipids." *Chem Commun (Camb)* (23): 2336-2338.

Dubowchik, G. M., R. A. Firestone, et al. (2002). "Cathepsin B-labile dipeptide linkers for lysosomal release of doxorubicin from internalizing immunoconjugates: model studies of enzymatic drug release and antigen-specific in vitro anticancer activity." *Bioconjug Chem* 13(4): 855-869.

Ebensen, T., C. Link, et al. (2007). "A pegylated derivative of alpha-galactosylceramide exhibits improved biological properties." *J Immunol* 179(4): 2065-2073.

Enomoto, N., E. Hyde, el al. (2012). "Allergen-specific CTL require perforin expression to suppress allergic airway inflammation." *J Immunol* 188 (4), 1734-41.

Fang, G. M., J. X. Wang, et al. (2012). "Convergent chemical synthesis of proteins by ligation of Peptide hydrazides." *Angew Chem Int Ed Engl* 51(41): 10347-10350.

Farrand, K. J., N. Dickgreber, et al. (2009). "Langerin+ CD8alpha+dendritic cells are critical for cross-priming and IL-12 production in response to systemic antigens." *J Immunol* 183 (12), 7732-42.

Fields, G. B. and R. L. Noble (1990). "Solid phase peptide synthesis utilizing 9-fluorenylmethoxycarbonyl amino acids." *Int J Pept Protein Res* 35(3): 161-214.

Friedrichs, B., S. Siegel, et al. (2006). "Survivin-derived peptide epitopes and their role for induction of antitumor immunity in hematological malignancies." *Leuk Lymphoma* 47(6): 978-985.

Fujii, S., K. Shimizu, et al. (2003). "Activation of natural killer T cells by alpha-galactosylceramide rapidly induces the full maturation of dendritic cells in vivo and thereby acts as an adjuvant for combined CD4 and CD8 T cell immunity to a coadministered protein." *J Exp Med* 198 (2): 267-279.

Gangwar, S., G. M. Pauletti, et al. (1997). "Synthesis of a Novel Esterase-Sensitive Cyclic Prodrug of a Hexapeptide Using an (Acyloxy)alkoxy Promoiety." *The Journal of Organic Chemistry* 62(5): 1356-1362.

Geoghegan, K. F. and J. G. Stroh (1992). "Site-directed conjugation of nonpeptide groups to peptides and proteins via periodate oxidation of a 2-amino alcohol. Application to modification at N-terminal serine." *Bioconjug Chem* 3(2): 138-146.

Giaccone, G., C. J. Punt, et al. (2002). "A phase I study of the natural killer T-cell ligand alpha-galactosylceramide (KRN7000) in patients with solid tumors." *Clin Cancer Res* 8(12): 3702-3709.

Greenwald, R. B., Y. H. Choe, et al. (2000). "Drug delivery systems based on trimethyl lock lactonization: poly(ethylene glycol) prodrugs of amino-containing compounds." *J Med Chem* 43(3): 475-487.

Greenwald, R. B., A. Pendri, et al. (1999). "Drug delivery systems employing 1,4- or 1,6-elimination: poly(ethylene glycol) prodrugs of amine-containing compounds." *J Med Chem* 42(18): 3657-3667.

Hackenberger, C. P. and D. Schwarzer (2008). "Chemoselective ligation and modification strategies for peptides and proteins." *Angew Chem Int Ed Engl* 47(52): 10030-10074.

Hatakeyama, T., N. Nakagawa, et al. (2009). "Iron-Catalyzed Negishi Coupling Toward an Effective Olefin Synthesis." *Organic letters* 11(20): 4496-4499.

Hermans, I. F., J. D. Silk, et al. (2003). "NKT cells enhance CD4+ and CD8+ T cell responses to soluble antigen in vivo through direct interaction with dendritic cells." *J Immunol* 171(10): 5140-5147.

Hermans, I. F., J. D. Silk, et al. (2004). "The VITAL assay: a versatile fluorometric technique for assessing CTL- and NKT-mediated cytotoxicity against multiple targets in vitro and in vivo." *J Immunol Methods* 285(1): 25-40.

Hong, S., M. T. Wilson, et al. (2001). "The natural killer T-cell ligand alpha-galactosylceramide prevents autoimmune diabetes in non-obese diabetic mice." *Nat Med* 7(9): 1052-1056.

Howell, A. R., R. C. So, et al. (2004). "Approaches to the preparation of sphinganines." *Tetrahedron* 60(50): 11327-11347.

Huarte, E., P. Sarobe, et al. (2002). "Enhancing immunogenicity of a CTL epitope from carcinoembryonic antigen by selective amino acid replacements." *Clin Cancer Res* 8(7): 2336-2344.

Hudlicky, T., F. F. Koszyk, et al. (1980). "Cyclopentene annulation via intramolecular addition of diazoketones to 1,3-dienes. Applications to the synthesis of cyclopentanoid terpenes." *The Journal of Organic Chemistry* 45(25): 5020-5027.

Iha, R. K., B. A. van Horn, et al. (2010). "Complex, degradable polyester materials via ketoxime ether-based functionalization: Amphiphilic, multifunctional graft copolymers and their resulting solution-state aggregates." *Journal of Polymer Science Part A: Polymer Chemistry* 48(16): 3553-3563.

Isidro-Llobet, A., M. Alvarez, et al. (2009). "Amino acid-protecting groups." *Chem Rev* 109(6): 2455-2504.

Jager, E., H. Hohn, et al. (2002). "Peptide-specific CD8+ T-cell evolution in vivo: response to peptide vaccination with Melan-A/MART-1." *Int J Cancer* 98(3): 376-388.

Johansen, S. K., H. T. Kornø, et al. (1999). "Synthesis of Carbasugars from Aldonolactones: Ritter-Type Epoxide Opening in the Synthesis of Polyhydroxylated Aminocyclopentanes." *Synthesis* 1999(01): 171,177.

Karbach, J., S. Gnjatic, et al. (2010). "Tumor-reactive CD8+ T-cell responses after vaccination with NY-ESO-1 peptide, CpG 7909 and Montanide ISA-51: association with survival." *Int J Cancer* 126(4): 909-918.

Kawano, T., J. Cui, et al. (1997). "CD1d-restricted and TCR-mediated activation of valpha14 NKT cells by glycosylceramides." *Science* 278(5343): 1626-1629.

Kiick, K. L., E. Saxon, et al. (2002). "Incorporation of azides into recombinant proteins for chemoselective modification by the Staudinger ligation." *Proc Natl Acad Sci USA* 99(1): 19-24.

Kinjo, Y., P. Illarionov, et al. (2011). "Invariant natural killer T cells recognize glycolipids from pathogenic Gram-positive bacteria." *Nature Immunology*: 1-10.

Lee, A., K. J. Farrand, et al. (2006). "Novel synthesis of alpha-galactosyl-ceramides and confirmation of their powerful NKT cell agonist activity." *Carbohydr Res* 341(17): 2785-2798.

Leonard, N. M.; Brunckova, J. (2010). "In situ formation of N-trifluoroacetoxy succinimide (TFA-NHS): one-pot formation of succinimidyl esters, N-trifluoroacetyl amino acid succinimidyl esters, and N-maleoyl amino acid succinimidyl esters." *J Org Chem* 76: 9169-9174.

Levy, A., J. Pitcovski, et al. (2007). "A melanoma multi-epitope polypeptide induces specific CD8+ T-cell response." *Cell Immunol* 250(1-2): 24-30.

Li, Y., E. Girardi, et al. (2010). "The Vα14 invariant natural killer T cell TCR forces microbial glycolipids and CD1d into a conserved binding mode." *Journal of Experimental Medicine* 207(11): 2383-2393.

Li, X., Fujio, M. et al. (2010). "Design of a potent CD1d-binding NKT cell ligand as a vaccine adjuvant." *PNAS* 107(29): 13010-13015.

Li, Z., Y. Oka, et al. (2008). "Identification of a VT1 protein-derived peptide, WT1, as a HLA-A 0206-restricted, WT1-specific CTL epitope." *Microbiol Immunol* 52(11): 551-558.

Liu, C.-F., C. Rao, et al. (1996). "Orthogonal Ligation of Unprotected Peptide Segments through Pseudoproline Formation for the Synthesis of HIV-1 Protease Analogs." *Journal of the American Chemical Society* 118(2): 307-312.

Liu, C.-F. and J. P. Tam (1994). "Chemical Ligation Approach To Form a Peptide Bond between Unprotected Peptide Segments. Concept and Model Study." *Journal of the American Chemical Society* 116(10): 4149-4153.

Lu, X.-L., Z.-H. Liang, et al. (2006). "Induction of the Epstein-Barr Virus Latent Membrane Protein 2 Antigen-specific Cytotoxic T Lymphocytes Using Human Leukocyte Antigen Tetramer-based Artificial Antigen-presenting Cells." *Acta Biochimica et Biophysica Sinica* 38(3): 157-163.

Lu, X., L. Song, et al. (2006). "Synthesis and evaluation of an alpha-C-galactosylceramide analogue that induces Th1-biased responses in human natural killer T cells." *Chembiochem* 7(11): 1750-1756.

Majireck, M. M. and S. M. Weinreb (2006). "A study of the scope and regioselectivity of the ruthenium-catalyzed [3+2]-cycloaddition of azides with internal alkynes." *J Org Chem* 71(22): 8680-8683.

Morita, M., K. Motoki, et al. (1995). "Structure-activity relationship of alpha-galactosylceramides against B16-bearing mice." *J Med Chem* 38(12): 2176-2187.

Motoki, K., M. Morita, et al. (1995). "Immunostimulatory and antitumor activities of monoglycosylceramides having various sugar moieties." *Biol Pharm Bull* 18(11): 1487-1491.

Nicolaou, M. G., C.-S. Yuan, et al. (1996). "Phosphate Prodrugs for Amines Utilizing a Fast Intramolecular Hydroxy Amide Lactonization." *The Journal of Organic Chemistry* 61(24): 8636-8641.

Noppen, C., F. Levy, et al. (2000). "Naturally processed and concealed HLA-A2.1-restricted epitopes from tumor-associated antigen tyrosinase-related protein-2." *Int J Cancer* 87(2): 241-246.

O'Reilly, C. and P. V. Murphy (2011). "Synthesis of alpha-S-glycosphingolipids based on uronic acids." *Org Lett* 13(19): 5168-5171.

Parekh, V. V., M. T. Wilson, et al. (2005). "Glycolipid antigen induces long-term natural killer T cell anergy in mice." *J Clin Invest* 115(9): 2572-2583.

Park, J. J., J. H. Lee, et al. (2008). "Synthesis of all stereoisomers of KRN7000, the CD1d-binding NKT cell ligand." *Bioorg Med Chem Lett* 18(14): 3906-3909.

Petersen, T. R., D. Sika-Paotonu, et al. (2010). "Potent anti-tumor responses to immunization with dendritic cells loaded with tumor tissue and an NKT cell ligand." *Immunol Cell Biol* 88(5): 596-604.

Plettenburg, O., V. Bodmer-Narkevitch, et al. (2002). "Synthesis of alpha-galactosyl ceramide, a potent immunostimulatory agent." *J Org Chem* 67(13): 4559-4564.

Presolski, S. I.; Hong, V. et al. (2010). "Tailored ligand acceleration of the Cu-catalyzed azide-alkyne cycloaddition reaction: practical and mechanistic implications." *J Am Chem Soc* 132: 14570-14576.

Pu, J. and R. W. Franck (2008). "C-Galactosylceramide Diastereomers via Sharpless Asymmetric Epoxidation Chemistry." *Tetrahedron* 64(37): 8618-8629.

Raju, R., B. F. Castillo, et al. (2009). "Synthesis and evaluation of 3"- and 4"-deoxy and -fluoro analogs of the immunostimulatory glycolipid, KRN7000." *Bioorg Med Chem Lett* 19(15): 4122-4125.

Rostovtsev, V. V., L. G. Green, et al. (2002). "A stepwise huisgen cycloaddition process: copper(I)-catalyzed regioselective "ligation" of azides and terminal alkynes." *Angew Chem Int Ed Enal* 41(14): 2596-2599.

Sakurai, K. and D. Kahne (2010). "Design and Synthesis of Functionalized Trisaccharides as p53-Peptide Mimics." *Tetrahedron Lett* 51(29): 3724-3727.

Saxon, E. and C. R. Bertozzi (2000). "Cell surface engineering by a modified Staudinger reaction." *Science* 287 (5460): 2007-2010.

Schmitz, M., P. Diestelkoetter, et al. (2000). "Generation of survivin-specific CD8+ T effector cells by dendritic cells pulsed with protein or selected peptides." *Cancer Res* 60(17): 4845-4849.

Schneider, G., L. Hackler, et al. (1985). "Ritter-reaction on steroids: Ring expansion of steroid oxethans into dihydrooxazines." *Tetrahedron* 41(16): 3377-3386.

Semmling, V., V. Lukacs-Kornek, et al. (2010). "Alternative cross-priming through CCL17-CCR4-mediated attraction of CTLs toward NKT cell-licensed DCs." *Nat Immunol* 11(4): 313-320.

Silk, J. D., I. F. Hermans, et al. (2004). "Utilizing the adjuvant properties of CD1d-dependent NK T cells in T cell-mediated immunotherapy." *J Clin Invest* 114(12): 1800-1811.

Soellner, M. B., A. Tam, et al. (2006). "Staudinger ligation of peptides at non-glycyl residues." *J Org Chem* 71(26): 9824-9830.

Speiser, D. E. and P. Romero (2010). "Molecularly defined vaccines for cancer immunotherapy, and protective T cell immunity." *Semin Immunol* 22(3): 144-154.

Tam, A., M. B. Soellner, et al. (2007). "Water-soluble phosphinothiols for traceless staudinger ligation and integration with expressed protein ligation." *J Am Chem Soc* 129(37): 11421-11430.

Tashiro, T., R. Nakagawa, et al. (2008). "RCAI-61, the 6'-O-methylated analog of KRN7000: its synthesis and potent bioactivity for mouse lymphocytes to produce interferon-y in vivo." *Tetrahedron Lett* 49(48): 6827-6830.

Trappeniers, M., S. Goormans, et al. (2008). "Synthesis and in vitro evaluation of alpha-GalCer epimers." *Chem Med Chem* 3(7): 1061-1070.

Tupin, E., A. Nicoletti, et al. (2004). "CD1d-dependent activation of NKT cells aggravates atherosclerosis." *J Exp Med* 199(3): 417-422.

Uchimura, A., T. Shimizu, et al. (1997). "Immunostimulatory activities of monoglycosylated α-d-pyranosylceramides." *Bioorganic & Medicinal Chemistry* 5(12): 2245-2249.

Veerapen, N., M. Brigl, et al. (2009). "Synthesis and biological activity of alpha-galactosyl ceramide KRN7000 and galactosyl (alpha1-->2) galactosyl ceramide." *Bioorg Med Chem Lett* 19(15): 4288-4291.

Widdison, W. C., S. D. Wilhelm, et al. (2006). "Semisynthetic maytansine analogues for the targeted treatment of cancer." *J Med Chem* 49(14): 4392-4408.

Wills-Karp, M., (1999). "Immunologic basis of antigen-induced airway hyperresponsiveness." *Annual review of immunology* 17, 255-81.

Wingender, G., P. Rogers, et al. (2011). "Invariant NKT cells are required for airway inflammation induced by environmental antigens." *J Exp Med* 208(6): 1151-1162.

Wipf, P. and J. G. Pierce (2006). "Expedient synthesis of the alpha-C-glycoside analogue of the immunostimulant galactosylceramide (KRN7000)." *Org Lett* 8(15): 3375-3378.

Wu, T.-N., K.-H. Lin, et al. (2011). "Avidity of CD1d-ligand-receptor ternary complex contributes to T-helper 1 (Th1) polarization and anticancer efficacy." *Proc Natl Acad Sci USA* 108(42): 17275-17280.

Zeng, D., Y. Liu, et al. (2003). "Activation of natural killer T cells in NZB/W mice induces Th1-type immune responses exacerbating lupus." *J Clin Invest* 112(8): 1211-1222.

Zhang, L., X. Chen, et al. (2005). "Ruthenium-catalyzed cycloaddition of alkynes and organic azides." *J Am Chem Soc* 127(46): 15998-15999.

---

The invention claimed is:

1. A compound of formula (I):

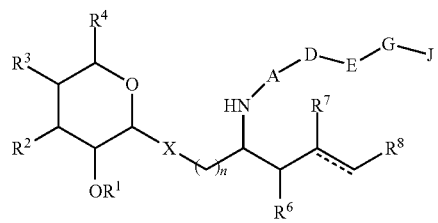

wherein:

A is a self-immolative linker group;

D is selected from the group consisting of:

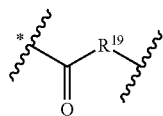

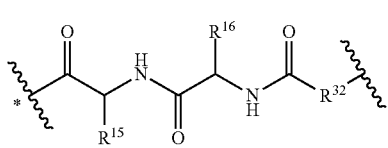

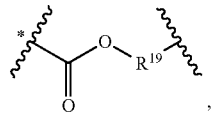

-continued

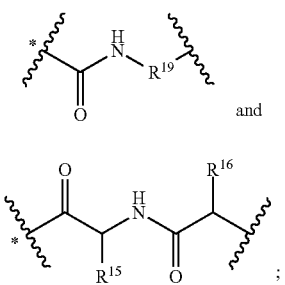
D4

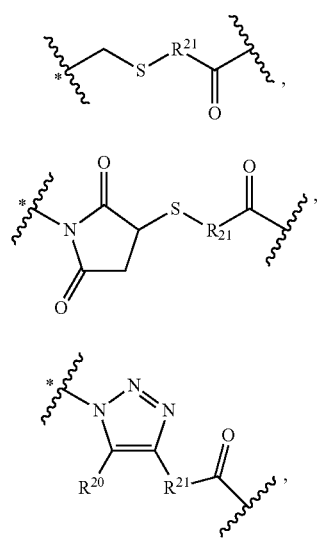
D5 wherein * denotes a point of attachment of group D to group A;

$R^{15}$ is a side chain of one of the following amino acids: L-lysine, L-citrulline, L-arginine, L-glutamine or L-threonine;

$R^{16}$ is a side chain of a hydrophobic amino acid;

$R^{19}$ is an alkylene group;

$R^{32}$ is an alkylene group or an O-alkylene group wherein the O is attached to the carbonyl group of D2;

E is selected from the group consisting of:

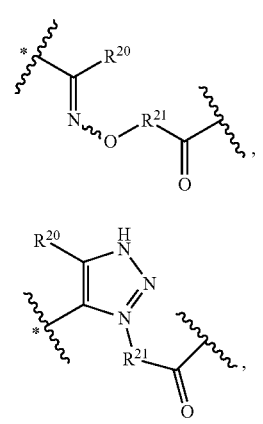

E1, E2, E3, E4, E5, E6, E7, E8, E9, E10, E11, E12, E13, E14, E15

-continued

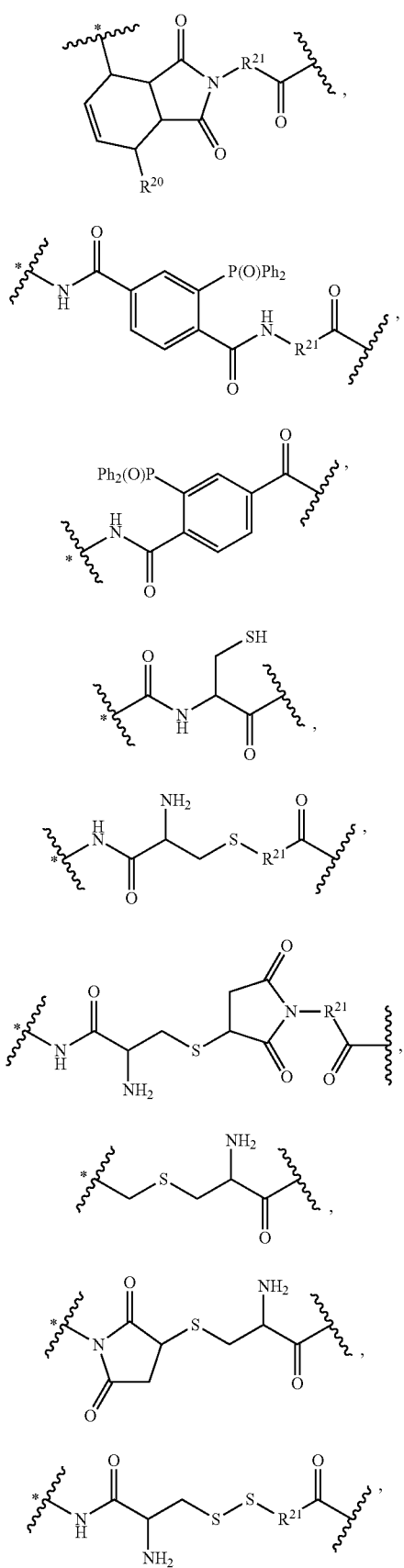

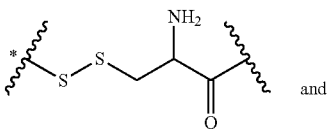

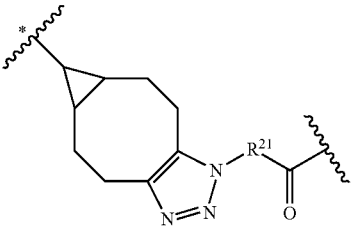

wherein * denotes a point of attachment of group E to group D;
R²⁰ is H or lower alkyl;
R²¹ is an alkylene group;
g is 0 when R²⁰ is H or g is 1 when R²⁰ is lower alkyl;
provided that E is E18 only when D is D1, D2 or D3 and provided that E is E1, E2, E3, E4, E5, E6, E7, E8, E9, E10, E11, E12, E13, E15, E20, E21, E93, E94 or E96 only when D is D1, D2, D3 or D4; and provided that E is E91, E92 or E95 only when D is D5 and provided that E is E97 only when D is D2;
G is absent or G is an amino acid sequence of up to 6 amino acids, attached through its N-terminus to group E and through its C-terminus to group J;
J is a peptidic antigen, optionally substituted at its N and/or C-termini with up to 6 amino acids selected from the group of natural flanking residues for the antigen, and optionally terminated with NH₂ at the C-terminus so as to provide a C-terminal amide, and attached to group G through its N-terminus or, wherein G is absent, attached to group E through its N-terminus;
$R^1$ is H or glycosyl, provided that if $R^1$ is glycosyl then $R^2$ and $R^3$ are both OH and $R^4$ is $CH_2OH$;
$R^2$ is selected from the group consisting of H, OH, F and $OR^{10}$; provided that if $R^2$ is H, F or $OR^{10}$, then $R^1$ is H, $R^3$ is OH and $R^4$ is $CH_2OH$;
$R^3$ is selected from the group consisting of H, OH, F and $OR^{10}$; provided that if $R^3$ is H, F or $OR^{10}$, then $R^1$ is H, $R^2$ is OH and $R^4$ is $CH_2OH$;
$R^4$ is $CH_3$, $CH_2OH$, $CH_2OCOR^{11}$, $CH_2OR^{10}$, $CH_2OR^{11}$, $CH_2OSO_3H$, $CH_2SH$, $CH_2SR^{11}$, $CH_2SOR^{11}$, $CH_2SO_2R^{11}$, $CH_2PO_3H2$, $CH_2OP(O)(OH)_2$, $CH_2OP(O)(OH)(OR^{11})$, $CH_2OP(O)(OR^{11})_2$, $CO_2H$, $CH_2NHCOR^{11}$, $CH_2NHCO_2R^{11}$, $CH_2NHCONH_2$, $CH_2NHCONHR^{11}$, $CH_2NHCON(R^{11})_2$, $CH_2N(R^{11})_2$, $CH_2NHSO_2R^{11}$; provided that if $R^4$ is other than $CH_2OH$, then $R^1$ is H and $R^2$ and $R^3$ are OH;
$R^6$ is $OR^{12}$, OH or H;
$R^7$ is $OR^{12}$, OH or H; provided that at least one of $R^6$ and $R^7$ is $OR^{12}$; wherein when $R^6$ is $OR^{12}$, $R^7$ is H, $R^8$ is $C_1$-$C_{15}$ alkyl and X is O, ---------- denotes an optional double bond linking the carbon adjacent to $R^7$ with the carbon adjacent to $R^8$;
$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{11}$ is lower alkyl, lower alkenyl or aralkyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

X is O, $CH_2$ or S;

n is 1 when X is O or S; or n is 0 or 1 when X is $CH_2$;

wherein where X is $CH_2$ then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$ or $CH_2OR^{11}$; and:

either $R^6$ is OH and $R^7$ is $OR^{12}$ and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is $OR^{12}$ and $R^7$ is H, and $R^8$ is $C_{13}H_{27}$ and the stereochemistry at carbon atoms 2 and 3 is (2S, 3S);

wherein where X is S then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$, $CH_2OR^{11}$ or $CO_2H$; and:

either $R^6$ is OH and $R^7$ is $OR^{12}$ and the stereochemistry at carbon atoms 2, 3 and 4 is (2S, 3S, 4R); or $R^6$ is $OR^{12}$ and $R^7$ is H and the stereochemistry at the carbon atoms 2 and 3 is (2S, 3S);

or a pharmaceutically acceptable salt thereof.

2. A compound of formula (II):

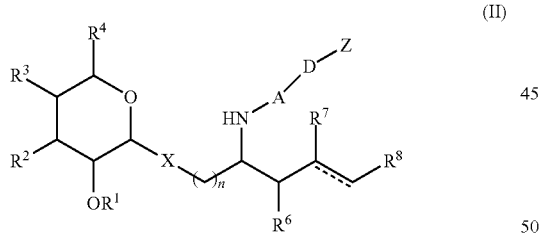

(II)

wherein A, D, X, $R^1$, $R^2$, $R^3$, $R^4$, $R^6$, $R^7$, $R^8$, $R^{10}$, $R^{11}$, $R^{12}$, $R^{15}$, $R^{16}$, $R^{32}$, and n are all as defined in claim 1;

Z is selected from the group consisting of:

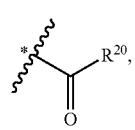
Z1

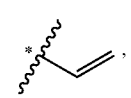
Z2

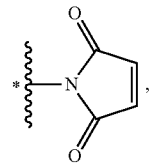
Z3

Z4

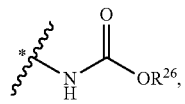
Z5

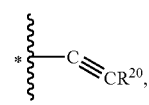
Z7

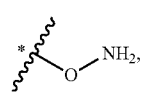
Z8

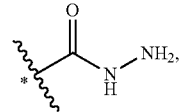
Z9

Z10

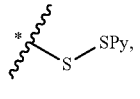
Z11

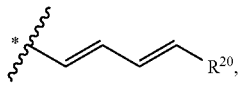
Z12

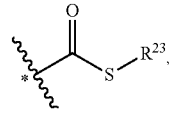
Z13

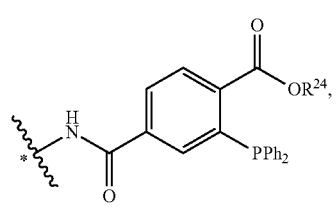
Z14

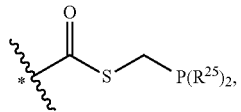
Z15

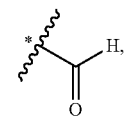
Z16

-continued

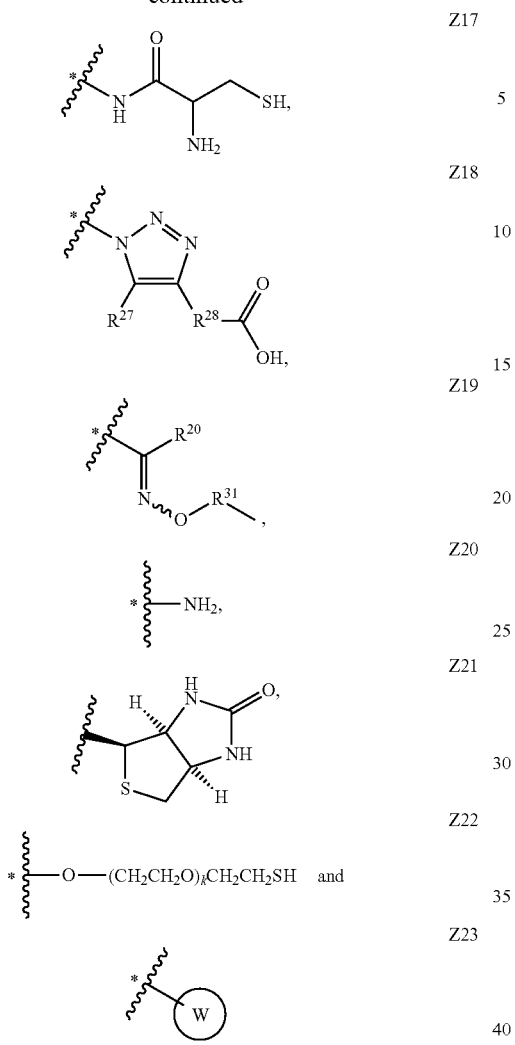

wherein * denotes a point of attachment of group Z to group D, except as defined for Z23;
$R^{20}$ is as defined above for formula (I);
$R^{23}$ is aryl, aralkyl or optionally substituted alkyl;
$R^{24}$ is lower alkyl;
$R^{25}$ is p-$C_6H_4L$ wherein L is H, methoxy, COOH, C(O)NHCH$_2$COOH or CH$_2$CH$_2$NMe$_2$;
$R^{26}$ is aralkyl;
$R^{27}$ is H or lower alkyl;
$R^{28}$ is alkylene;
$R^{31}$ is (CH$_2$CH$_2$O)$_k$
k is an integer from 2 to 100;
W is an optionally substituted cyclooctynyl ring; or W is a fused bicyclic or tricyclic ring system comprising an optionally substituted cyclooctynyl ring fused to one or more aryl groups or one or more cycloalkyl groups; wherein the cyclooctynyl ring optionally contains a N atom within the ring, which N atom is optionally substituted with an acyl group; and wherein the cyclooctynyl ring is optionally substituted with one or more substituents selected from the group consisting of halogen, hydroxyl, alkoxy and aralkyl wherein the aryl part of this group is optionally substituted with a carboxylic acid; and wherein * or one of the optional substituents comprises a point of attachment of Z23 to group D;

provided that Z is Z1, Z2, Z3, Z4, Z7, Z8, Z9, Z10, Z11, Z13, Z15, Z16, Z17 or Z18 only when D is D1, D2, D3 or D4 and provided that Z is Z12 only when D is D1, D2 or D3 and provided that Z is Z5 or Z20 only when D is D5, and provided that Z is Z21, Z22 or Z23 only when D is D2;

or a pharmaceutically acceptable salt thereof wherein the compound is not (2S, 3S, 4R)-1-O-α-D-Galactopyranosyl-4-hexacosanoyl-2-((4-oxopentanoyloxy)methoxycarbonylamino) octadecane-1,3, 4-triol.

3. The compound of claim 1, wherein A is selected from the group consisting of:

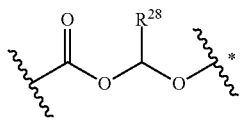

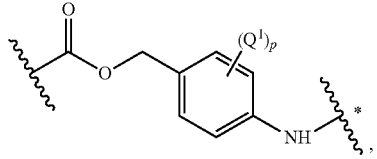

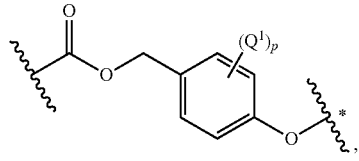

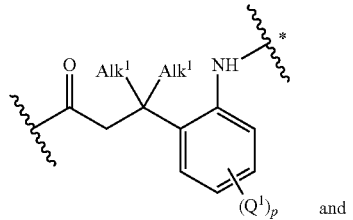

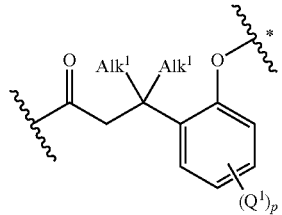

wherein * denotes a point of attachment of group A to group D;
each $Q^1$, the same or different, is independently selected from the group consisting of H, alkyl, alkoxy, halogen, nitro, aryl; or, together with the ring to which it is attached, forms a fused bicyclic aryl group;
p is an integer from 1 to 4;
Alk$^1$ is $C_1$-$C_4$ straight chain alkyl; and
$R^{28}$ is H or lower alkyl;
provided that A is A1 only when D is D1 and provided that A is A2 only when D is D2, D3 or D5 and provided that A is A3 only when D is D1, D3 or D4 and provided that A is A4 only when D is D2, D3 or D5 and provided that A is A5 only when D is D1, D3 or D4.

4. The compound of claim 3, wherein A is A1 or A2.
5. The compound of claim 1, wherein D is D1, D2 or D5.
6. The compound of claim 1, wherein E is E3, E4 or E97.
7. The compound of claim 1, wherein E is any one of E1 to E8, E93 or E94.
8. The compound of claim 1, wherein G is

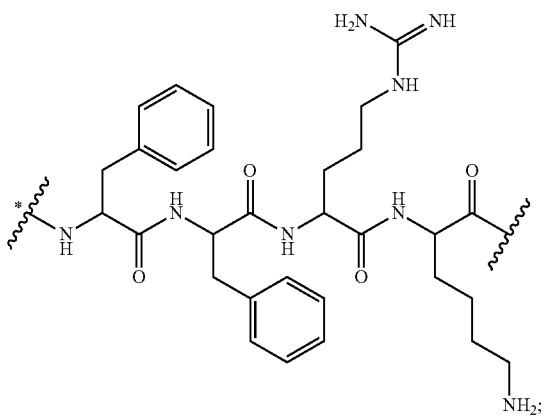 [SMILES: *NC(Cc1ccccc1)C(=O)NC(Cc1ccccc1)C(=O)NC(CCCNC(=N)N)C(=O)NC(CCCCN)C(*)=O]

wherein * denotes a point of attachment of group G to group E.

9. The compound of claim 1, wherein J is selected from the group consisting of:

AMLGTHTMEV (SEQ ID NO: 1), MLGTHTMEV (SEQ ID NO:2), EAAGIGILTV (SEQ ID NO:3), AAGIGILTV (SEQ ID NO:4), AADHRQLQLSISSCLQQL (SEQ ID NO:5), AAGIGILTVILGVL (SEQ ID NO:6), AARAVFLAL (SEQ ID NO:7), ACDPHSGHFV (SEQ ID NO:8), ACYEFLWGPRALVETS (SEQ ID NO:9), ADHRQLQLSISSCLQQL (SEQ ID NO: 10), AEEAAGIGILT (SEQ ID NO: 11), AEEAAGIGIL (SEQ ID NO:12), AELVHFLLL (SEQ ID NO:13), AELVHFLLLKYRAR (SEQ ID NO:14), AEPINIQTW (SEQ ID NO:15), AFLPWHRLF (SEQ ID NO:16), AGATGGRGPRGAGA (SEQ ID NO:17), ALCRWGLLL (SEQ ID NO:18), ALDVYNGLL (SEQ ID NO:19), ALFDIESKV (SEQ ID NO:20), ALGGHPLLGV (SEQ ID NO:21), ALIHHNTHL (SEQ ID NO:22), ALKDVEERV (SEQ ID NO:23), ALLAVGATK (SEQ ID NO:24), ALLEIASCL (SEQ ID NO:25), ALNFPGSQK (SEQ ID NO:26), ALPYWNFATG (SEQ ID NO:27), ALSVMGVYV (SEQ ID NO:28), ALWPWLLMAT (SEQ ID NO:29), ALWPWLLMA (SEQ ID NO:30), ALYVDSLFFL (SEQ ID NO:31), ANDPIFVVL (SEQ ID NO:32), APPAYEKLSAEQ (SEQ ID NO:33), APRGPHGGAASGL (SEQ ID NO:34), APRGVRMAV (SEQ ID NO:35), ARGPESRLL (SEQ ID NO:36), ASGPGGGAPR (SEQ ID NO:37), ATGFKQSSKALQRPVAS (SEQ ID NO:38), AVCPWTWLR (SEQ ID NO:39), AWISKPPGV (SEQ ID NO:40), AYVCGIQNSVSANRS (SEQ ID NO:41), CATWKVICKSCISQTPG (SEQ ID NO:42), CEFHACWPAFTVLGE (SEQ ID NO:43), CLSRRPWKRSWSAGSCPGMPHL (SEQ ID NO:44), CMTWNQMNL (SEQ ID NO:45), CQWGRLWQL (SEQ ID NO:46), CTACRWKKACQR (SEQ ID NO:47), DPARYEFLW (SEQ ID NO:48), DTGFYTLHVIKSDLVNEEATGQFRV (SEQ ID NO:49), DVTFNIICKKCG (SEQ ID NO:50), EAAGIGILTV (SEQ ID NO:51), EADPTGHSY (SEQ ID NO:52), EAFIQPITR (SEQ ID NO:53), EDLTVKIGDFGLATEKSRWSGSHQFEQLS (SEQ ID NO:54), EEAAGIGILTVI (SEQ ID NO:55), EEKLIVVLF (SEQ ID NO:56), EFYLAMPFATPM (SEQ ID NO:57), EGDCAPEEK (SEQ ID NO:58), EIIYPNASLLIQN (SEQ ID NO:59), EKIQKAFDDIAKYFSK (SEQ ID NO:60), ELTLGEFLKL (SEQ ID NO:61), ELVRRILSR (SEQ ID NO:62), ESRLLEFYLAMPF (SEQ ID NO:63), ETVSEQSNV (SEQ ID NO:64), EVDPASNTY (SEQ ID NO:65), EVDPIGHLY (SEQ ID NO:66), EVDPIGHVY (SEQ ID NO:67), EVISCKLIKR (SEQ ID NO:68), EVYDGREHSA (SEQ ID NO:69), EYLQLVFGI (SEQ ID NO:70), EYLSLSDKI (SEQ ID NO:71), EYSKECLKEF (SEQ ID NO:72), EYVIKVSARVRF (SEQ ID NO:73), FIASNGVKLV (SEQ ID NO:74), FINDEIFVEL (SEQ ID NO:75), FLDEFMEGV (SEQ ID NO:76), FLEGNEVGKTY (SEQ ID NO:77), FLFLLFFWL (SEQ ID NO:78), FLIIWQNTM (SEQ ID NO:79), FLLHHAFVDSIFEQWLQRHRP (SEQ ID NO:80), FLLLKYRAREPVTKAE (SEQ ID NO:81), FLTPKKLQCV (SEQ ID NO:82), FLWGPRALV (SEQ ID NO:83), FMNKFIYEI (SEQ ID NO:84), FMVEDETVL (SEQ ID NO:85), FPSDSWCYF (SEQ ID NO:86), FRSGLDSYV (SEQ ID NO:87), FSWAMDLDPKGA (SEQ ID NO:88), GARGPESRLLEFYLAMPFATPMEAELARRSLAQDAPPL (SEQ ID NO:89), GDNQIMPKAGLLIIV (SEQ ID NO:90), GELIGILNAAKVPAD (SEQ ID NO:91), GFKQSSKAL (SEQ ID NO:92), GLASFKSFLK (SEQ ID NO:93), GLCTLVAML (SEQ ID NO:94), GLPPDVQRV (SEQ ID NO:95), GLYDGMEHL1 (SEQ ID NO:96), GRAMLGTHTMEVTVY (SEQ ID NO:97), GVALQTMKQ (SEQ ID NO:98), GVGSPYVSRLLGICL (SEQ ID NO:99), AKFVAAWTLKAAA (SEQ ID NO: 100), GVLLKEFTVSGNILTIRLT (SEQ ID NO: 101), GVLVGVALI (SEQ ID NO: 102), GVYDGREHTV (SEQ ID NO:103), HLFGYSWYK (SEQ ID NO:104), HLIRVEGNLRVE (SEQ ID NO:105), HLSTAFARV (SEQ ID NO: 106), HLYQGCQVV (SEQ ID NO: 107), HQQYFYKIPILVINK (SEQ ID NO: 108), HTMEVTVYHR (SEQ ID NO: 109), IALNFPGSQK (SEQ ID NO: 110), IGRIAECILGMNPSR (SEQ ID NO: 111), IISAVVGIL (SEQ ID NO: 112), ILAKFLHWL (SEQ ID NO: 113), ILDSSEEDK (SEQ ID NO: 114), ILDTAGREEY (SEQ ID NO: 115), ILHNGAYSL (SEQ ID NO: 116), ILSRDAAPLPRPG (SEQ ID NO: 117), ILTVILGVL (SEQ ID NO: 118), IMDQVPFFS (SEQ ID NO: 119), IMDQVPFSV (SEQ ID NO: 120), IMIGVLVGV (SEQ ID NO: 121), INKTSGPKRGKHAWTHRLRE (SEQ ID NO: 122), ISGGPRISY (SEQ ID NO: 123), ISPNSVFSQWRVVCDSLEDYD (SEQ ID NO: 124), ISQAVHAAHAEINEAGR (SEQ ID NO: 125), ITDQVPFSV (SEQ ID NO: 126), ITKKVADLVGF (SEQ ID NO: 127), KASEKIFYV (SEQ ID NO: 128), KAVYNFATM (SEQ ID NO: 129), KCDICTDEY (SEQ ID NO:130), KEFTVSGNILT (SEQ ID NO:131), KEFTVSGNILTI (SEQ ID NO: 132), KELEGILLL (SEQ ID NO: 133), KHAWTHRLRERKQLVVYEEI (SEQ ID NO:134), KIFGSLAFL (SEQ ID NO:135), KIFSEVTLK (SEQ ID NO:136), KIFYVYMKRKYEAM (SEQ ID NO: 137), KIFYVYMKRKYEAMT (SEQ ID NO: 138), KILDAVVAQK (SEQ ID NO:139), KINKNPKYK (SEQ ID NO:140), KISQAVHAAHAEINEAGRESIINFEKLTEWT (SEQ ID NO:141), KKLLTQHFVQENYLEY (SEQ ID NO: 142), KMDAEHPEL (SEQ ID NO:

143), KNCEPVVPNAPPAYEKLSAE (SEQ ID NO: 144), KRYFKLSHLQMHSRKH (SEQ ID NO: 145), KSSEKIVYVYMKLNYEVMTK (SEQ ID NO: 146), KTWGQYWQV (SEQ ID NO: 147), KVAELVHFL (SEQ ID NO: 148), KVHPVIWSL (SEQ ID NO: 149), KVLEYVIKV (SEQ ID NO:150), KYDCFLHPF (SEQ ID NO:151), KYVGIEREM (SEQ ID NO:152), LAALPHSCL (SEQ ID NO:153), LAAQERRVPR (SEQ ID NO:154), LAGIGILTV (SEQ ID NO:155), LAMPFATPM (SEQ ID NO:156), LGFKVTLPPFMRSKRAADFH (SEQ ID NO:157), LGPGRPYR (SEQ ID NO:158), LHHAFVDSIF (SEQ ID NO:159), LIYRRRLMK (SEQ ID NO:160), LKEFTVSGNILTIRL (SEQ ID NO: 161), LKLSGVVRL (SEQ ID NO: 162), LLANGRMPTVLQCVN (SEQ ID NO: 163), LLDGTATLRL (SEQ ID NO: 164), LLEFYLAMPFATPM (SEQ ID NO:165), LLEFYLAMPFATPMEAELARRSLAQ (SEQ ID NO: 166), LLFGLALIEV (SEQ ID NO: 167), LLGATCMFV (SEQ ID NO: 168), LLGPGRPYR (SEQ ID NO:169), LLGRNSFEV (SEQ ID NO:170), LLKYRAREPVTKAE (SEQ ID NO:171), LLLDDLLVSI (SEQ ID NO: 172), LLLLTVLTV (SEQ ID NO:173), LLWSFQTSA (SEQ ID NO:174), LLYKLADLI (SEQ ID NO:175), LMLQNALTTM (SEQ ID NO:176), LPAVVGLSPGEQEY (SEQ ID NO:177), LPHSSSHWL (SEQ ID NO:178), LPRWPPPQL (SEQ ID NO:179), LPSSADVEF (SEQ ID NO:180), LSHLQMHSRKH (SEQ ID NO:181), LSRLSNRLL (SEQ ID NO:182), LTDLQPYMRQFVAHL (SEQ ID NO:183), LWWVNNQSLPVSP (SEQ ID NO:184), LYATVIHDI (SEQ ID NO:185), LYSACFWWL (SEQ ID NO:186), LYVDSLFFL (SEQ ID NO:187), MEVDPIGHLY (SEQ ID NO:188), MIAVFLPIV (SEQ ID NO:189), MIFEKHGFRRTTPP (SEQ ID NO:190), MKLNYEVMTKLGFKVTLPPF (SEQ ID NO: 191), MLAVISCAV (SEQ ID NO: 192), MLLAVLYCL (SEQ ID NO: 193), MLMAQEALAFL (SEQ ID NO: 194), MPFATPMEA (SEQ ID NO:195), MPREDAHFIYGYPKKGHGHS (SEQ ID NO:196), MSLQRQFLR (SEQ ID NO: 197), MVKISGGPR (SEQ ID NO: 198), NLVPMVATV (SEQ ID NO:199), NPPSMVAAGSVVAAV (SEQ ID NO:200), NSIVKSITVSASG (SEQ ID NO:201), NSNHVASGAGEAAIETQSSSSEEIV (SEQ ID NO:202), NSQPVWLCL (SEQ ID NO:203), NTYASPRFK (SEQ ID NO:204), NYARTEDFF (SEQ ID NO:205), NYKRCFPVI (SEQ ID NO:206), NYNNFYRFL (SEQ ID NO:207), PDTRPAPGSTAPPAHGVTSA (SEQ ID NO:208), PFATPMEAELARR (SEQ ID NO:209), PGSTAPPAHGVT (SEQ ID NO:210), PGTRVRAMAIYKQ (SEQ ID NO:211), PGVLLKEFTVSGNILTIRLTAADHR (SEQ ID NO:212), PLLENVISK (SEQ ID NO:213), PLPPARNGGL (SEQ ID NO:214), PLQPEQLQV (SEQ ID NO:215), PLTSIISAV (SEQ ID NO:216), PRALAETSYVKVLEY (SEQ ID NO:217), PVTWRRAPA (SEQ ID NO:218), PYYFAAELPPRNLPEP (SEQ ID NO:219), QCSGNFMGF (SEQ ID NO:220), QCTEVRADTRPWSGP (SEQ ID NO:221), QGAMLAAQERRVPRAAEVPR (SEQ ID NO:222), QGQHFLQKV (SEQ ID NO:223), QLAVSVILRV (SEQ ID NO:224), QNILLSNAPLGPQFP (SEQ ID NO:225), QQITKTEV (SEQ ID NO:226), QRPYGYDQIM (SEQ ID NO:227), QYSWFVNGTF (SEQ ID NO:228), RAGLQVRKNK (SEQ ID NO:229), REPFTKAEMLGSVIR (SEQ ID NO:230), REPVTKAEML (SEQ ID NO:231), RIAECILGM (SEQ ID NO:232), RKVAELVHFLLLKYR (SEQ ID NO:233), RKVAELVHFLLLKYRA (SEQ ID NO:234), RLLEFYLAMPFA (SEQ ID NO:235), RLLQETELV (SEQ ID NO:236), RLMKQDFSV (SEQ ID NO:237), RLPRIFCSC (SEQ ID NO:238), RLSSCVPVA (SEQ ID NO:239), RLVDDFLLV (SEQ ID NO:240), RMPEAAPPV (SEQ ID NO:241), RMPTVLQCVNVSVVS (SEQ ID NO:242), RNGYRALMDKS (SEQ ID NO:243), RNGYRALMDKSLHVGTQCALTRR (SEQ ID NO:244), RPGLLGASVLGLDDI (SEQ ID NO:245), RPHVPESAF (SEQ ID NO:246), RQKRILVNL (SEQ ID NO:247), RSDSGQQARY (SEQ ID NO:248), RTKQLYPEW (SEQ ID NO:249), RVIKNSIRLTL (SEQ ID NO:250), RVRFFFPSL (SEQ ID NO:251), RYQLDPKFI (SEQ ID NO:252), SAFPTTINF (SEQ ID NO:253), SAWISKPPGV (SEQ ID NO:254), SAYGEPRKL (SEQ ID NO:255), SEIWRDIDF (SEQ ID NO:256), SELFRSGLDSY (SEQ ID NO:257), SESIKKKVL (SEQ ID NO:258), SESLKMIF (SEQ ID NO:259), SFSYTLLSL (SEQ ID NO:260), SHETVIIEL (SEQ ID NO:261), SIINFEKL (SEQ ID NO:262), SLADTNSLAV (SEQ ID NO:263), SLFEGIDIYT (SEQ ID NO:264), SLFPNSPKWTSK (SEQ ID NO:265), SLFRAVITK (SEQ ID NO:266), SLGWLFLLL (SEQ ID NO:267), SLLMWITQC (SEQ ID NO:268), SLLMWITQCFLPVF (SEQ ID NO:269), SLLQHLIGL (SEQ ID NO:270), SLPYWNFATG (SEQ ID NO:271), SLSKILDTV (SEQ ID NO:272), SLYKFSPFPL (SEQ ID NO:273), SLYSFPEPEA (SEQ ID NO:274), SNDGPTLI (SEQ ID NO:275), SPRWWPTCL (SEQ ID NO:276), SPSSNRIRNT (SEQ ID NO:277), SQKTYQGSY (SEQ ID NO:278), SRFGGAVVR (SEQ ID NO:279), SSALLSIFQSSPE (SEQ ID NO:280), SSDYVIPIGTY (SEQ ID NO:281), SSKALQRPV (SEQ ID NO:282), SSPGCQPPA (SEQ ID NO:283), STAPPVHNV (SEQ ID NO:284), SVASTITGV (SEQ ID NO:285), SVDYFFVWL (SEQ ID NO:286), SVSESDTIRSISIAS (SEQ ID NO:287), SVYDFFVWL (SEQ ID NO:288), SYLDSGIHF (SEQ ID NO:289), SYLQDSDPDSFQD (SEQ ID NO:290), TFPDLESEF (SEQ ID NO:291), TGRAMLGTHTMEVTVYH (SEQ ID NO:292), TLDSQVMSL (SEQ ID NO:293), TLDWLLQTPK (SEQ ID NO:294), TLEEITGYL (SEQ ID NO:295), TLMSAMTNL (SEQ ID NO:296), TLNDECWPA (SEQ ID NO:297), TLPGYPPHV (SEQ ID NO:298), TLYQDDTLTLQAAG (SEQ ID NO:299), TMKQICKKEIRRLHQY (SEQ ID NO:300), TMNGSKSPV (SEQ ID NO:301), TPRLPSSADVEF (SEQ ID NO:302), TSCILESLFRAVITK (SEQ ID NO:303), TSEKRPFMCAY (SEQ ID NO:304), TSYVKVLHHMVKISG (SEQ ID NO:305), TTEWVETTARELPIPEPE (SEQ ID NO:306), TVSGNILTIR (SEQ ID NO:307), TYACFVSNL (SEQ ID NO:308), TYLPTNASL (SEQ ID NO:309), TYYRPGVNLSLSC (SEQ ID NO:310), VAELVHFLL (SEQ ID NO:311), VFGIELMEVDPIGHL (SEQ ID NO:312), VGQDVSVLFRVTGALQ (SEQ ID NO:313), VIFSKASSSLQL (SEQ ID NO:314), VISNDVCAQV (SEQ ID NO:315), VLDGLDVLL (SEQ ID NO:316), VLFYLGQY (SEQ ID NO:317), VLHWDPETV (SEQ ID NO:318), VLLKEFTVSG (SEQ ID NO:319), VLLQAGSLHA (SEQ ID NO:320), VLPDVFIRCV (SEQ ID NO:321), VLPDVFIRC (SEQ ID NO:322), VLRENTSPK (SEQ ID NO:323), VLYRYGSFSV (SEQ ID NO:324), VPGVLLKEFTVSGNILTIRLTAADHR (SEQ ID NO:325), VPLDCVLYRY (SEQ ID NO:326), VRIGH-

LYIL (SEQ ID NO:327), VSSFFSYTL (SEQ ID NO:328), VVLGVVFGI (SEQ ID NO:329), VVPCEPPEV (SEQ ID NO:330), VVVGAVGVG (SEQ ID NO:331), VYFFLPDHL (SEQ ID NO:332), WEKMKASEKIFYVYMKRK (SEQ ID NO:333), WLPFGFILI (SEQ ID NO:334), WNRQLYPEWTEAQRLD (SEQ ID NO:335), WQYFFPVIF (SEQ ID NO:336), WRRAPAPGA (SEQ ID NO:337), YACFVSNLATGRNNS (SEQ ID NO:338), YFSKKEWEKMKSSEKIVYVY (SEQ ID NO:339), YLEPGPVTA (SEQ ID NO:340), YLEPGPVTV (SEQ ID NO:341), YLNDHLEPWI (SEQ ID NO:342), YLQLVFGIEV (SEQ ID NO:343), YLSGANLNL (SEQ ID NO:344), YLVPQQGFFC (SEQ ID NO:345), YMDGTMSQV (SEQ ID NO:346), YMIMVKCWMI (SEQ ID NO:347), YRPRPRRY (SEQ ID NO:348), YSVYFNLPADTIYTN (SEQ ID NO:349), YSWRINGIPQQHTQV (SEQ ID NO:350), YVDFREYEYY (SEQ ID NO:351), YYWPRPRRY (SEQ ID NO:352), IMDQVPFFS (SEQ ID NO:353), SVDYFFVWL (SEQ ID NO:354), ALFDIESKV (SEQ ID NO:355), NLVPMVATV (SEQ ID NO:356) and GLCTLVAML (SEQ ID NO:357), SVASTITGV (SEQ ID NO:358), VMAGDIYSV (SEQ ID NO:359), ALADGVQKV (SEQ ID NO:360), LLGATCMFV (SEQ ID NO:361), SVFAGVVGV (SEQ ID NO:362), ALFDGDPHL (SEQ ID NO:363), YVDPVITSI (SEQ ID NO:364), STAPPVHNV (SEQ ID NO:365), LAALPHSCL (SEQ ID NO:366), SQDDIKGIQKLYGKRS (SEQ ID NO:367), FLPSDFFPSV (SEQ ID NO:368), FLPSDFFPSV (SEQ ID NO:369), TLGEFLKLDRERAKN (SEQ ID NO:370), TFSYVDPVITSISPKYGMET (SEQ ID NO:371), AMTQLLAGV (SEQ ID NO:372), KVFAGIPTV (SEQ ID NO:373), AIIDGVESV (SEQ ID NO:374), GLWHHQTEV (SEQ ID NO:375), NLDTLMTYV (SEQ ID NO:376), KIQEILTQV (SEQ ID NO:377), LTFGDVVAV (SEQ ID NO:378), TMLARLASA (SEQ ID NO:379), IMDQVPFSV (SEQ ID NO:380), MHQKRTAMFQDPQERPRKLPQLCTELQTTIHD (SEQ ID NO:381), LPQLCTELQTTI (SEQ ID NO:382), HDIILECVYCKQQLLRREVY (SEQ ID NO:383), KQQLLRREVYDFAFRDLCIVYRDGN (SEQ ID NO:384), RDLCIVYRDGNPYAVCDKCLKFYSKI (SEQ ID NO:385), DKCLKFYSKISEYRHYCYSLYGTTL (SEQ ID NO:386), HYCYSLYGTTLEQQYNKPLCDLLIR (SEQ ID NO:387), YGTTLEQQYNKPLCDLLIRCINCQKPLCPEEK (SEQ ID NO:388), RCINCQKPLCPEEKQRHLDKKQRFHNIRGRWT (SEQ ID NO:389), DKKQRFHNIRGRTGRCMSCCRSSRTRRETQL (SEQ ID NO:390), MHGDTPTLHEYMLDLQPETTDLYCYEQLNDSSEEE (SEQ ID NO:391), LYCYEQLNDSSEEEDEIDGPAGQAEPDRAHYNIVT (SEQ ID NO:392), GQAEPDRAHYNIVTFCCKCDSTLRLCVQSTHVDIR (SEQ ID NO:393), TLRLCVQSTHVDIRTLEDLLMGTLGIVCPICSQKP (SEQ ID NO:394), ALPFGFILV (SEQ ID NO:395), TLADFDPRV (SEQ ID NO:396), IMDQVPFSV (SEQ ID NO:397), SIMTYDFHGA (SEQ ID NO:398), AQYIKANSKFIGITEL (SEQ ID NO:399), FLYDDNQRV (SEQ ID NO:400), YLIELIDRV (SEQ ID NO:401), NLMEQPIKV (SEQ ID NO:402), FLAEDALNTV (SEQ ID NO:403), ALMEQQHYV (SEQ ID NO:404), ILDDIGHGV (SEQ ID NO:405), KLDVGNAEV (SEQ ID NO:406), TFEFTSFFY (SEQ ID NO:407), SWPDGAELPF (SEQ ID NO:408), GILGFVFTL (SEQ ID NO:409), ILRGSVAHK (SEQ ID NO:410) SVYDFFVWLKFFHRTCKCTGNFA (SEQ ID NO:411), DLAQMFFCFKELEGW (SEQ ID NO:412), AVGALEGPRNQDWLGVPRQL (SEQ ID NO:413) and RAHYNIVTF (SEQ ID NO:414).

10. The compound of claim 1, wherein n is 1, the stereochemistry of the 6-membered sugar ring of formula (I) is α-D-galacto, $R^6$ is OH and $R^7$ is $OR^{12}$.

11. The compound of claim 1, wherein n is 0, X is $CH_2$, the stereochemistry of the 6-membered sugar ring is α-D-galacto, $R^6$ is OH and $R^7$ is $OR^{12}$.

12. The compound of claim 1, wherein X is O, $R^6$ is $OR^{12}$, $R^7$ is H, $R^8$ is $C_1$-$C_{15}$ alkyl and ---------- is a double bond linking the carbon adjacent to $R^7$ with the carbon adjacent to $R^8$, and the stereochemistry at carbon atoms 2, 3 is (2S, 3S).

13. The compound of claim 1, wherein $R^8$ is $C_1$-$C_{15}$ alkyl.

14. The compound of claim 1, wherein $R^{11}$ is alkyl.

15. The compound of claim 1, wherein $R^{12}$ is acyl having a straight carbon chain from 6 to 30 carbon atoms long.

16. The compound of claim 1, selected from the group consisting of:

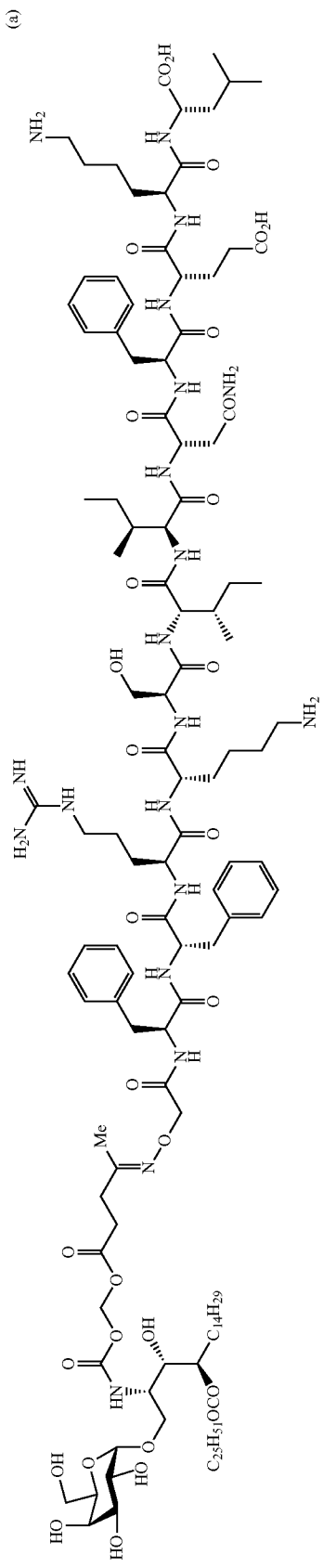
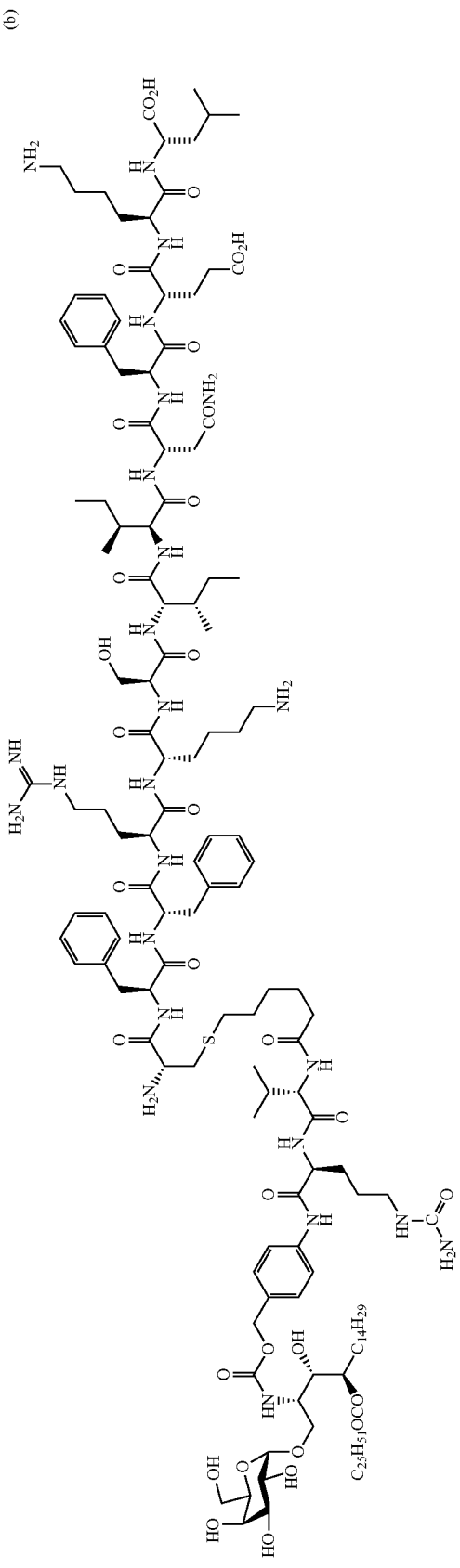

-continued
(c) 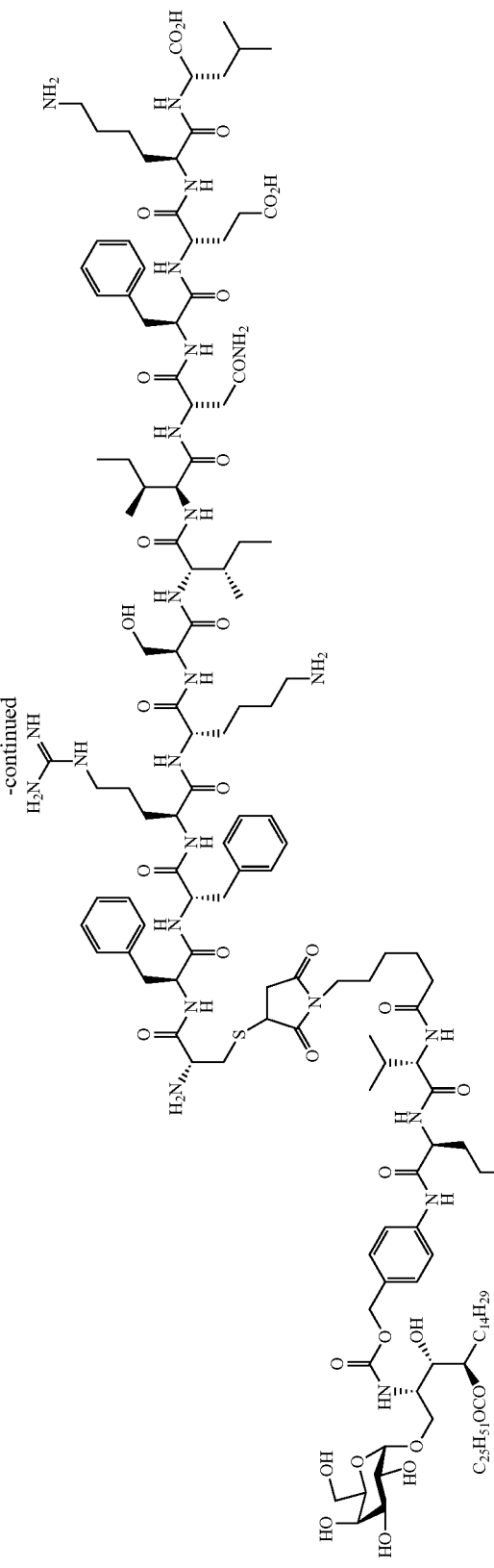
(d) 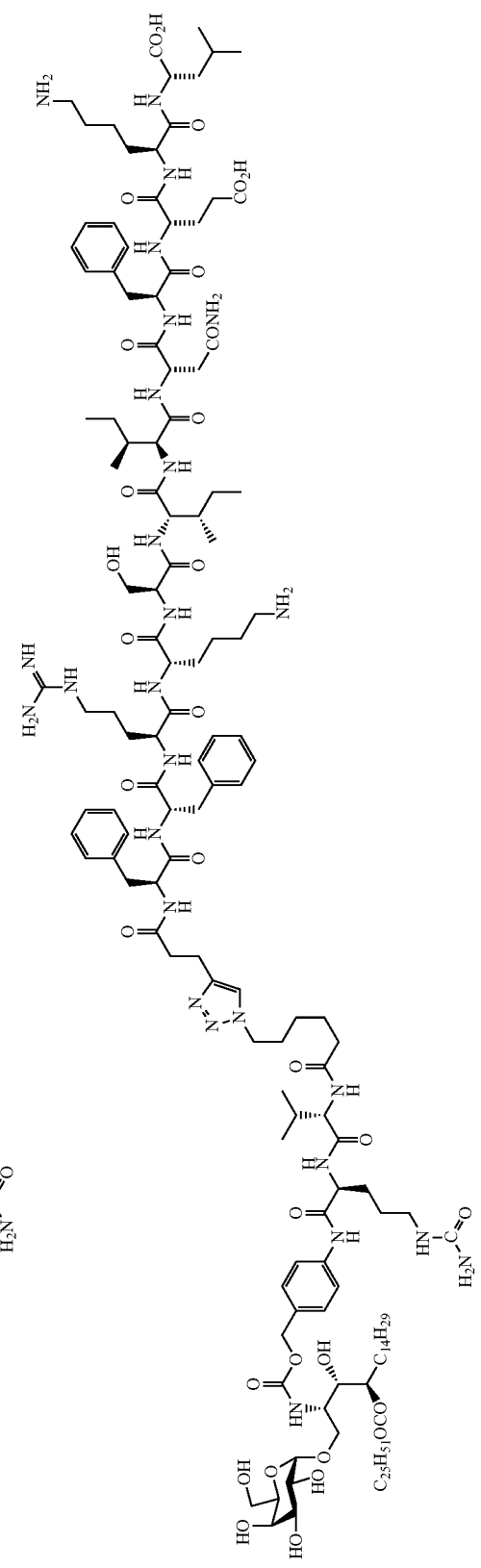

(e)
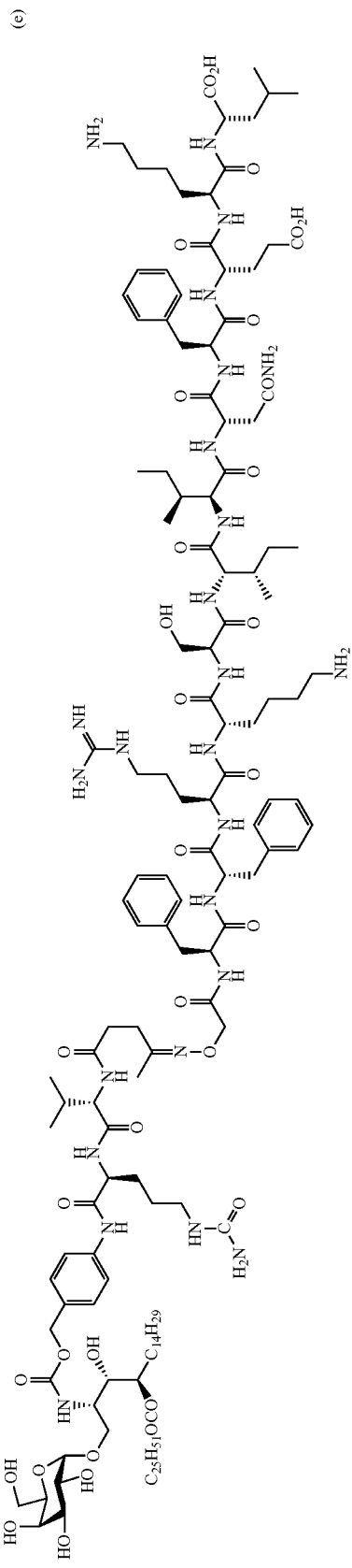
(f)
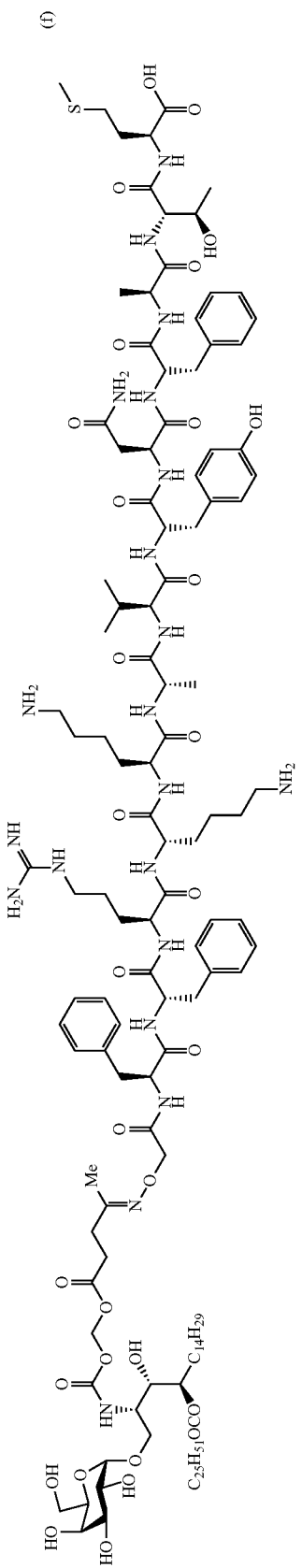

-continued
(g)
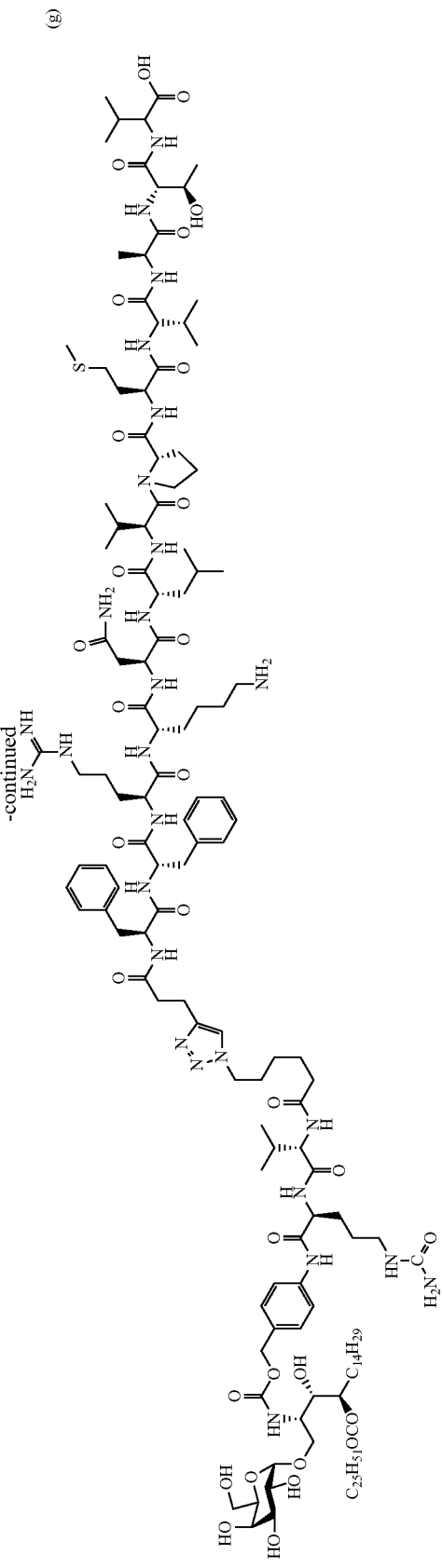
(h)
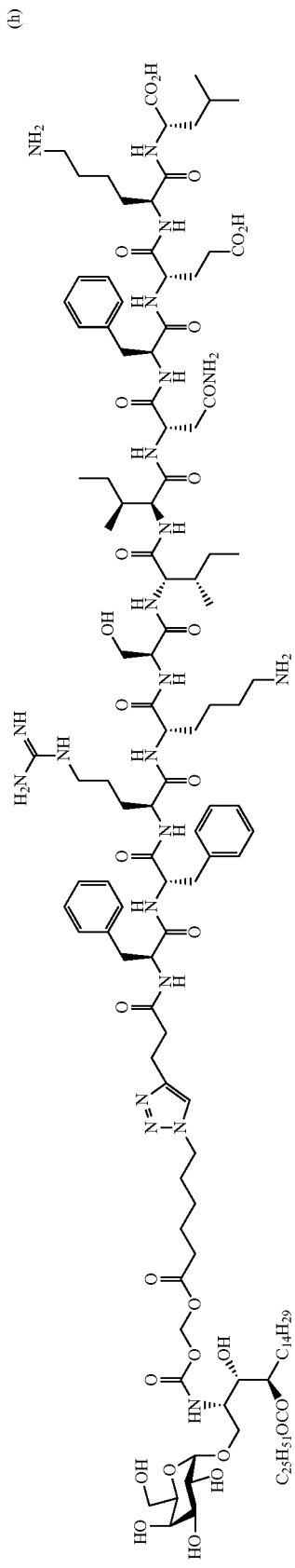

(i)
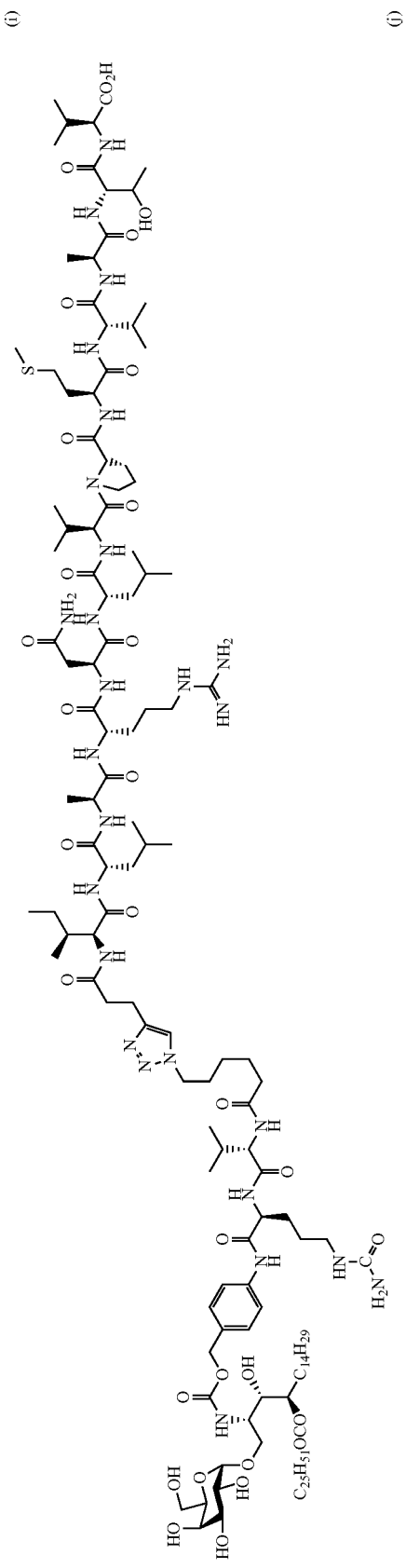
(j)
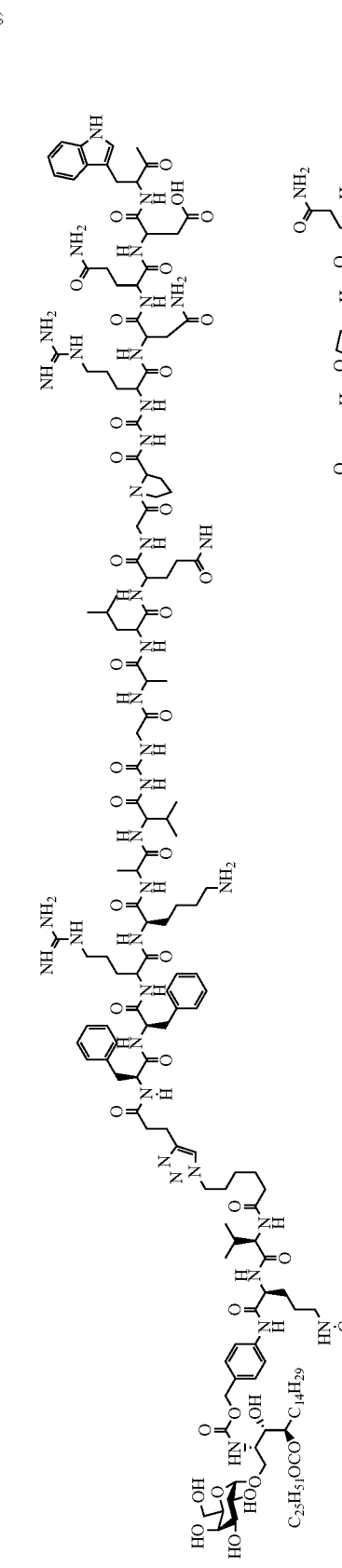

(k)
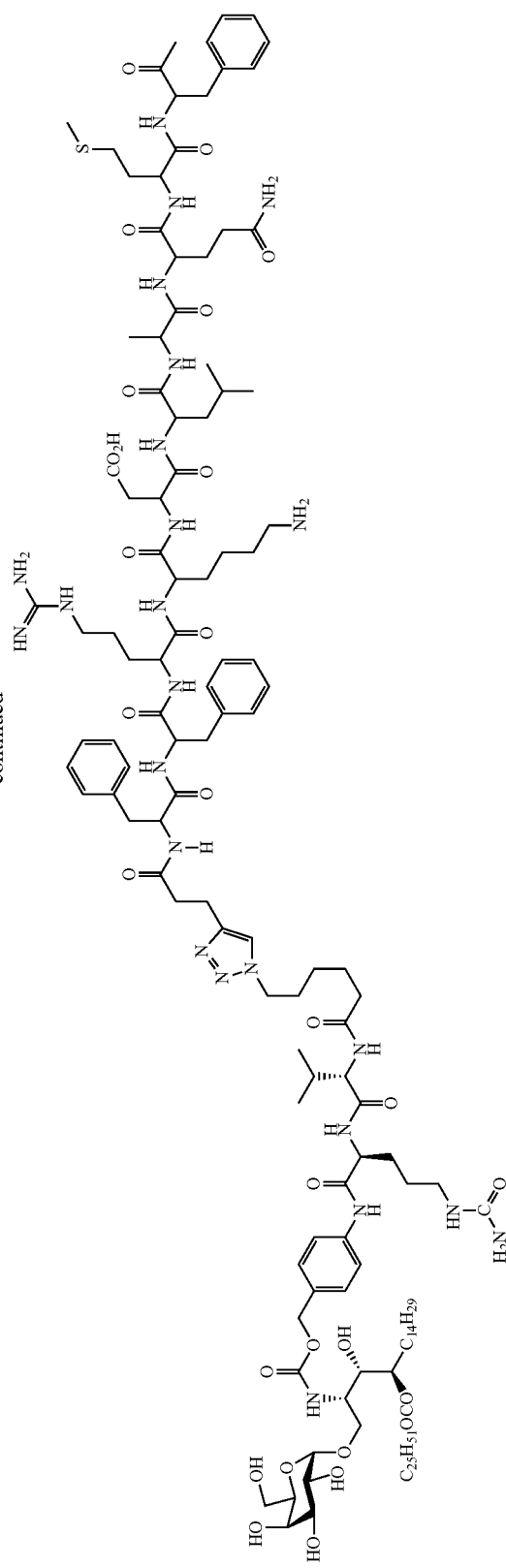
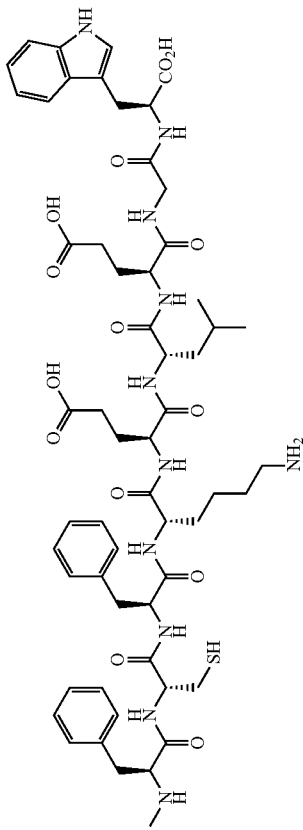

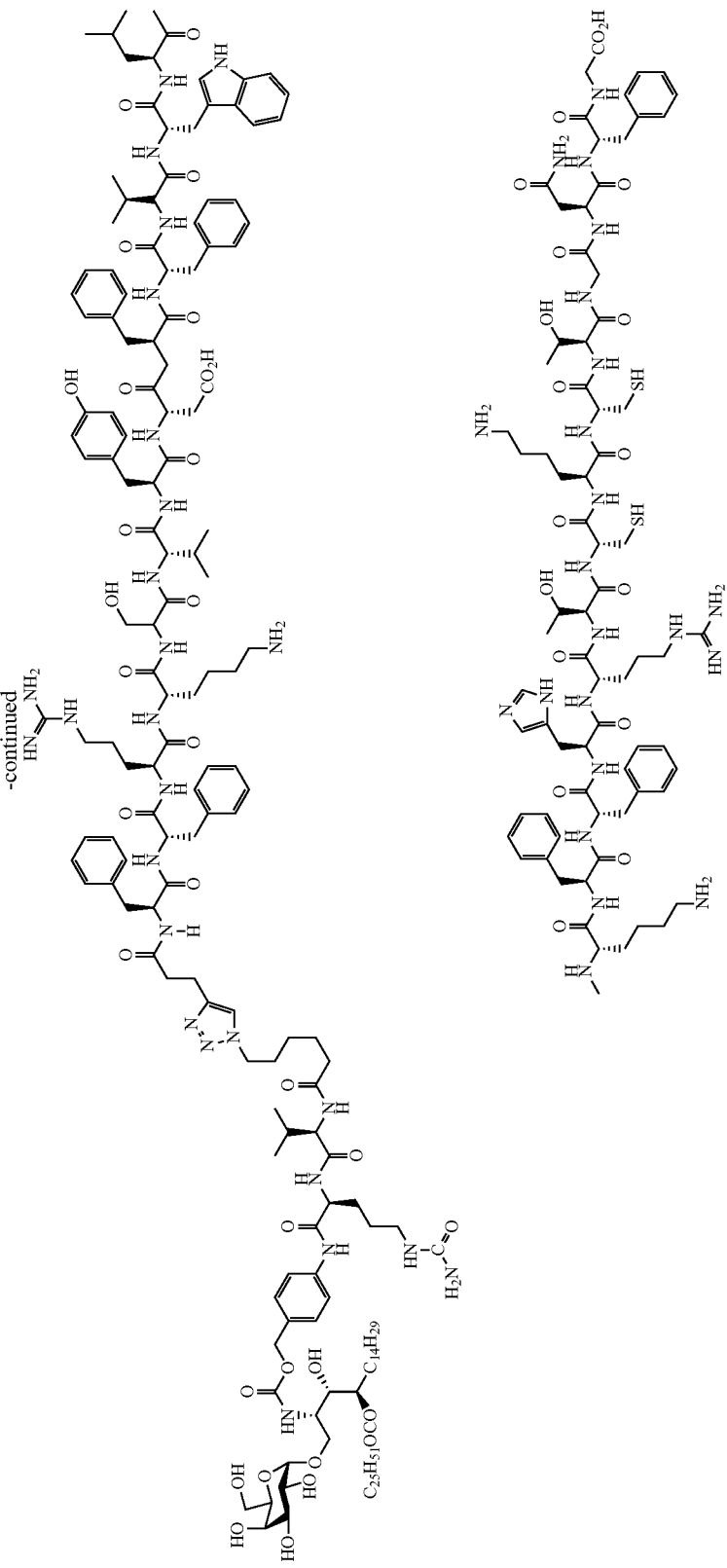

(m)
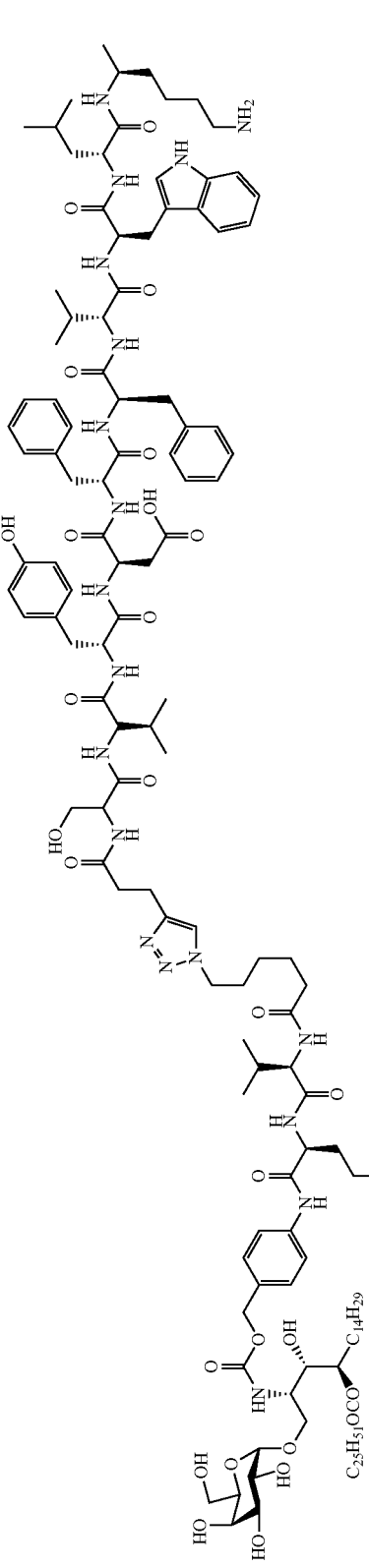
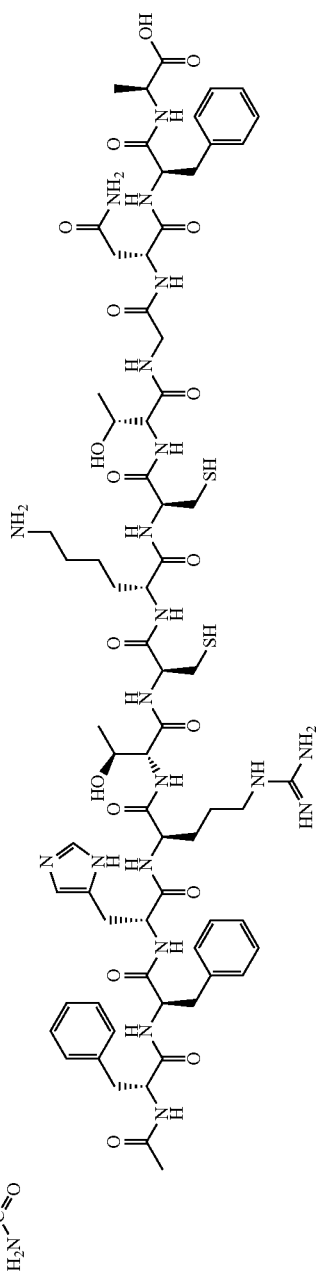

(n)
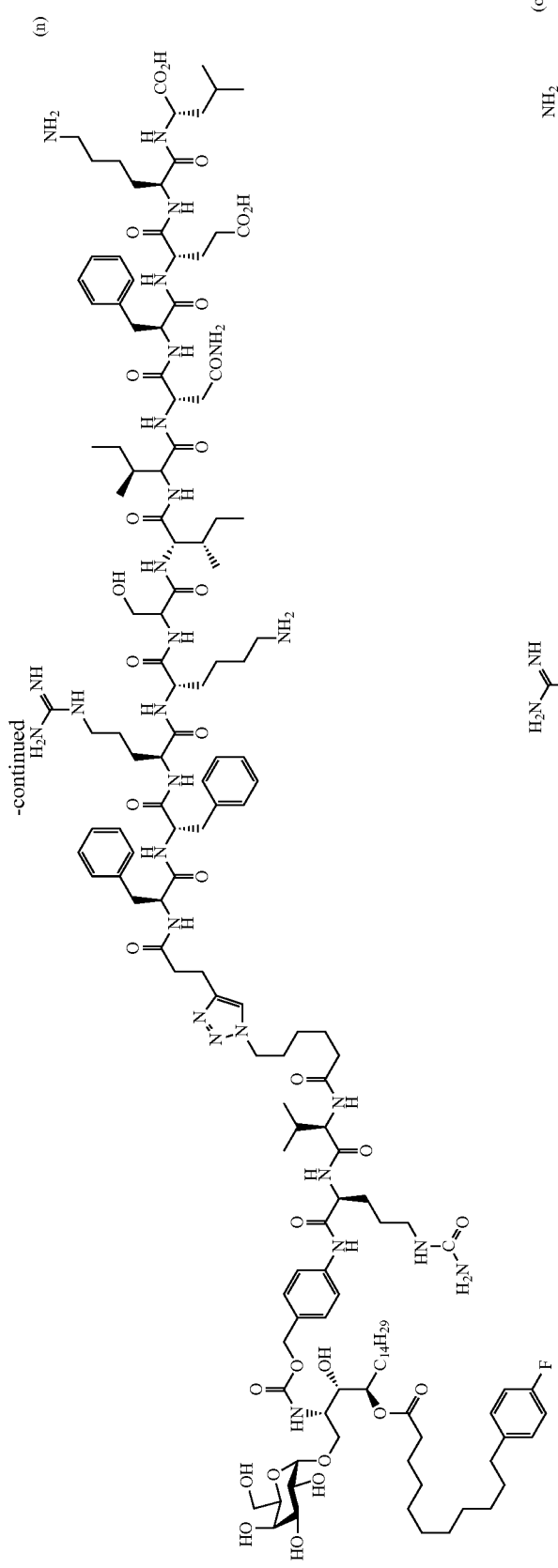
(o)
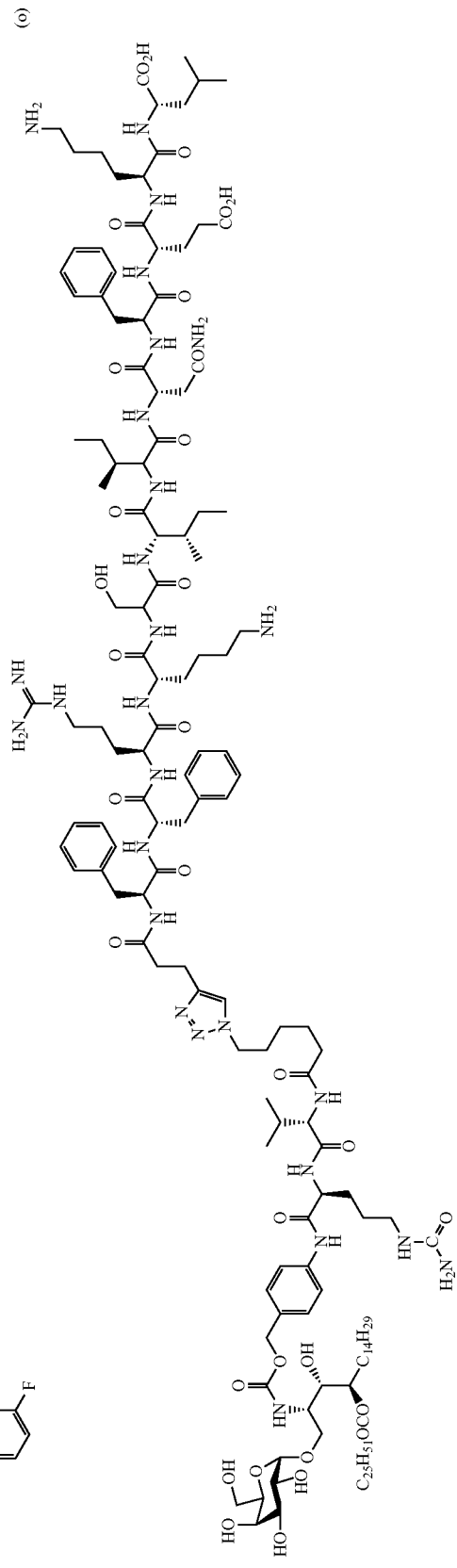

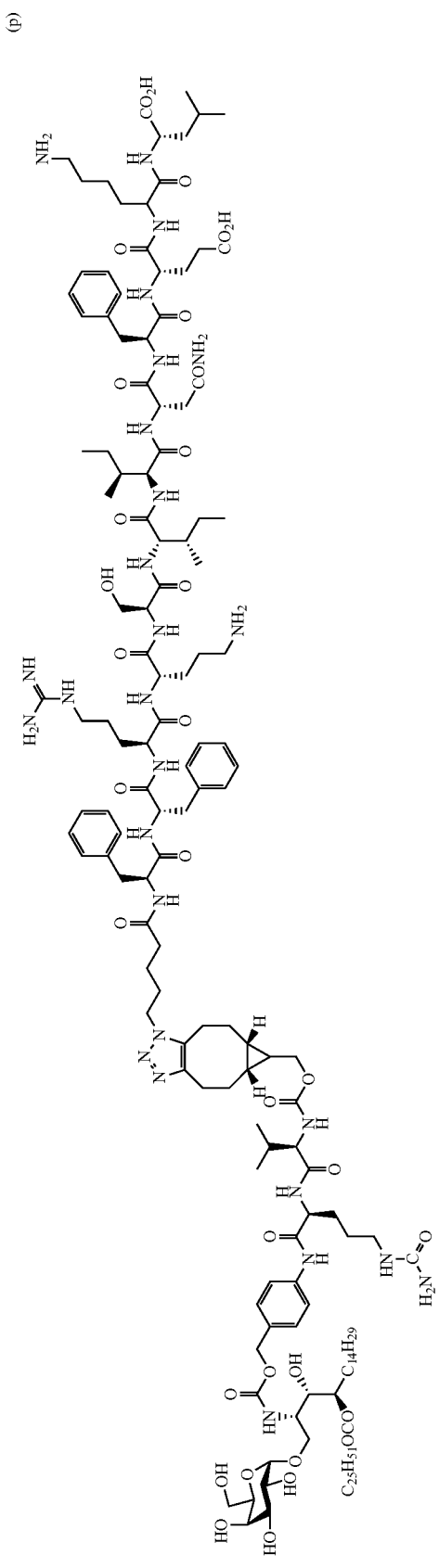
(p)
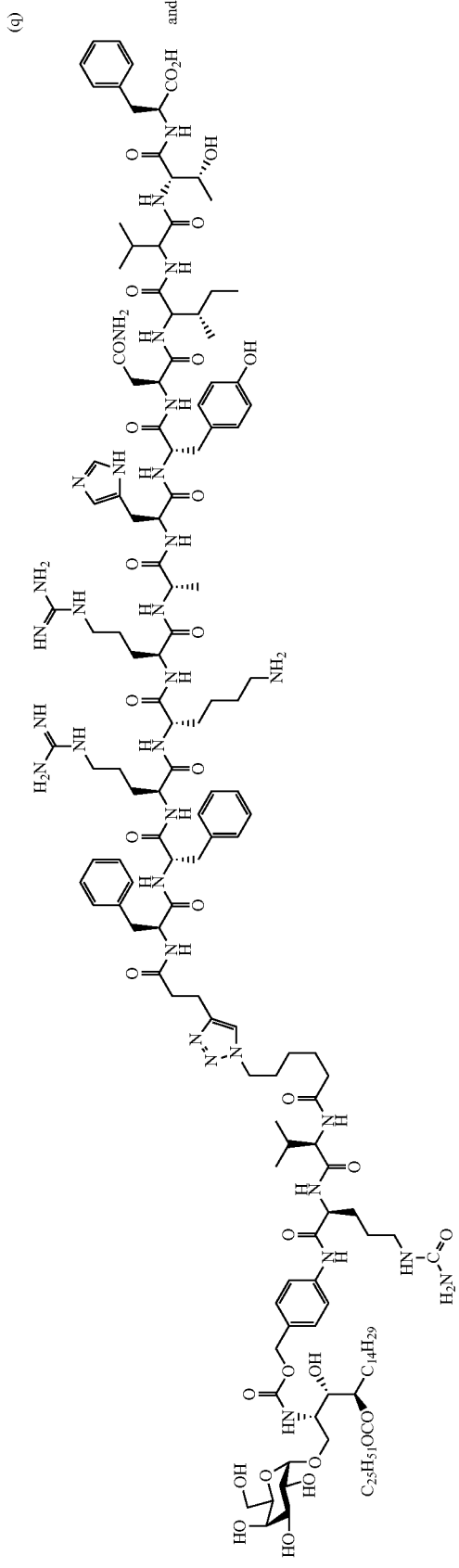
(q) and

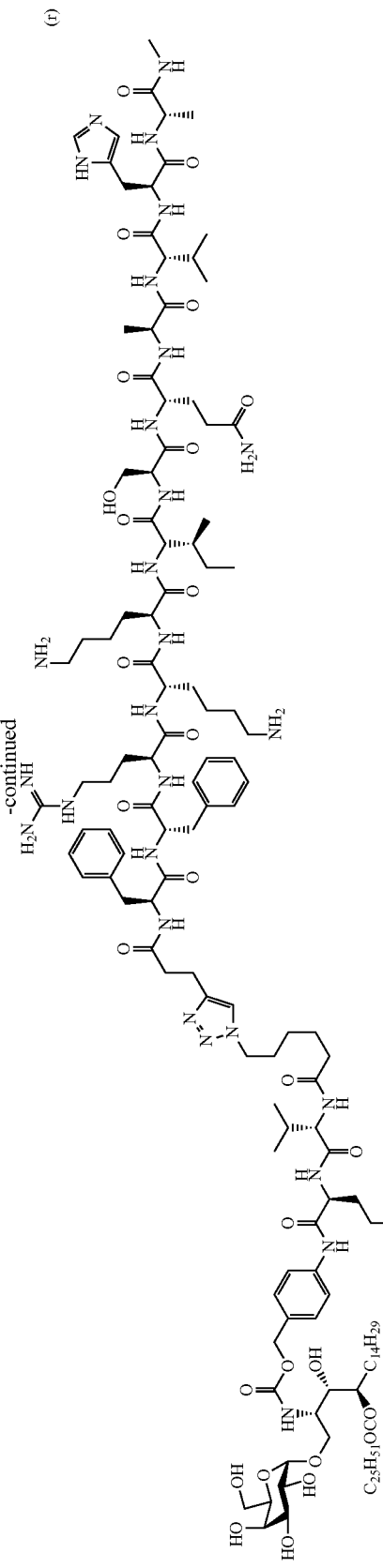
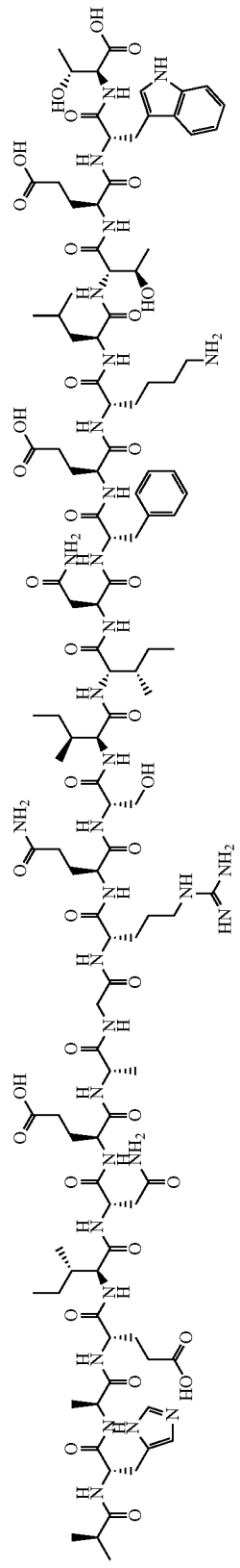

or a pharmaceutically acceptable salt thereof.
17. The compound of claim 2, selected from the group consisting of:
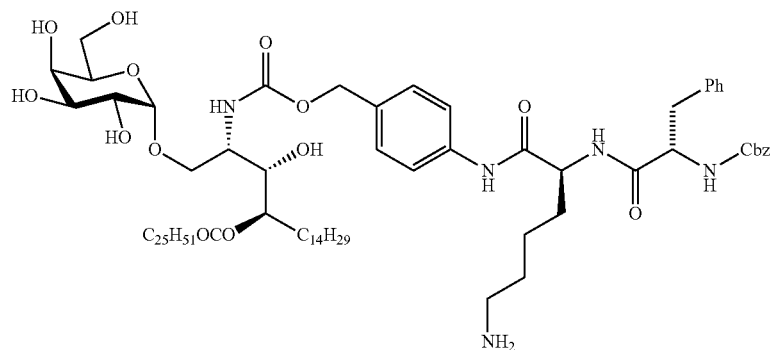
(aa)
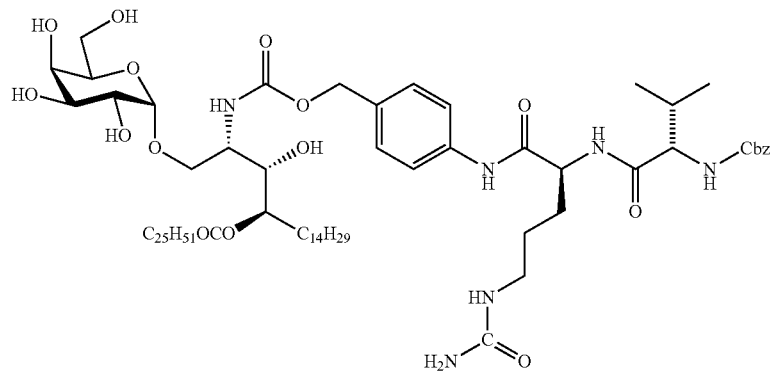
(bb)
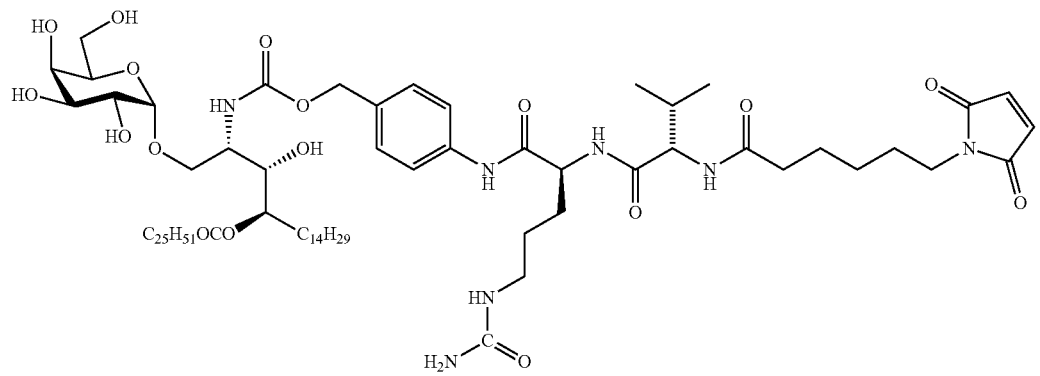
(cc)
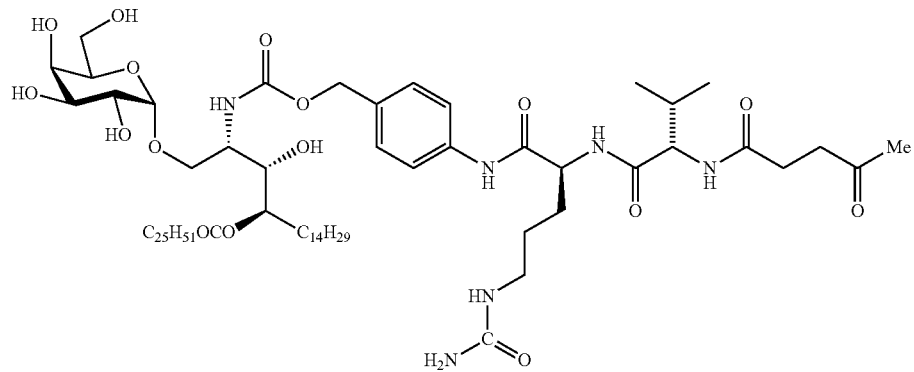
(dd)

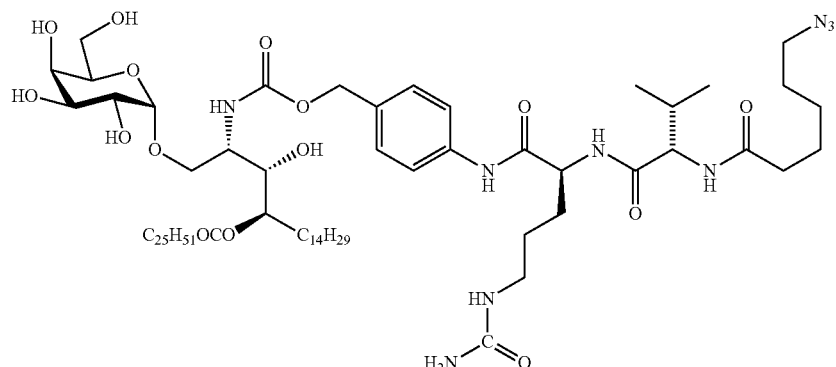
(ee)
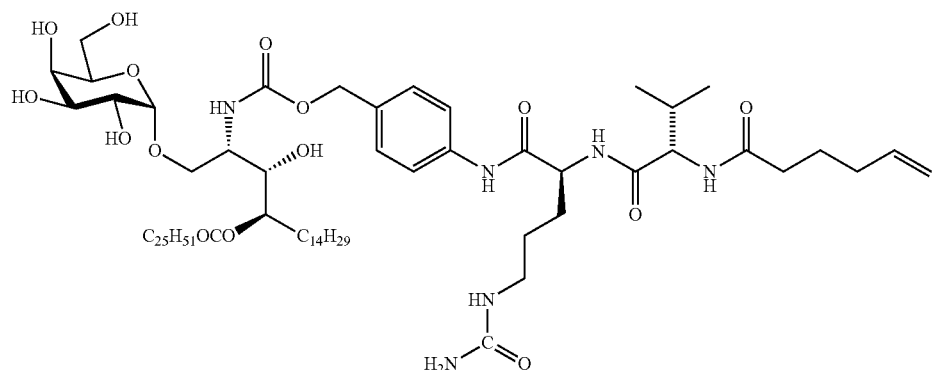
(ff)
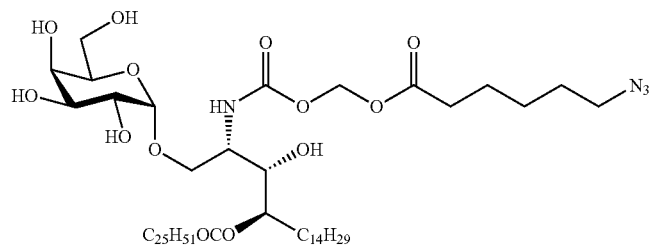
(gg)
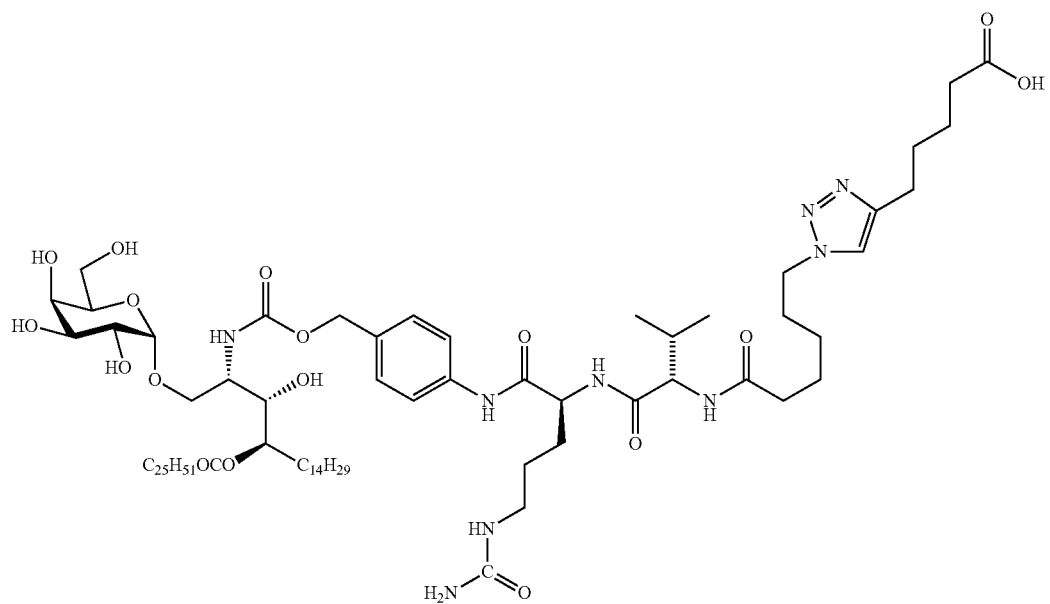
(hh)

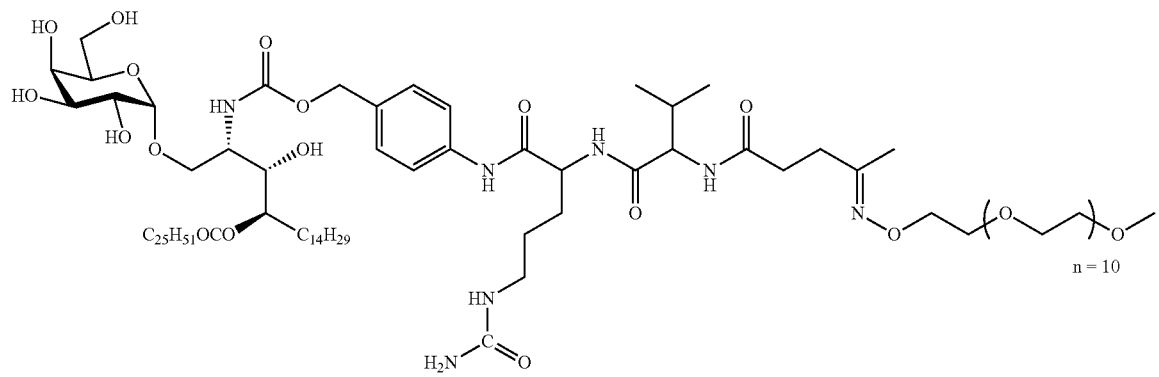
(ii)
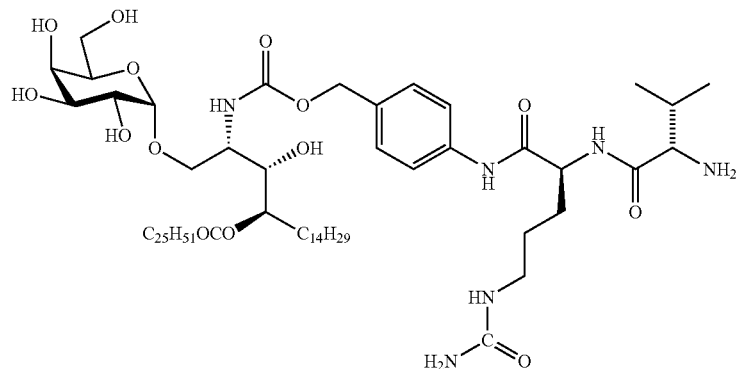
(jj)
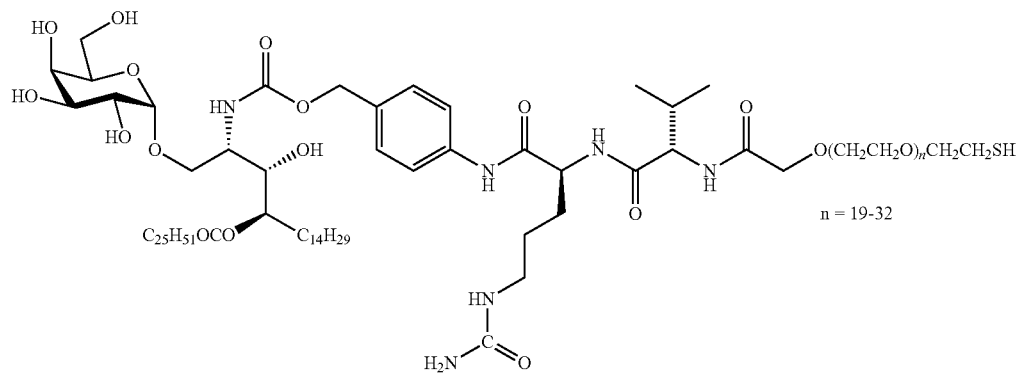
(kk)
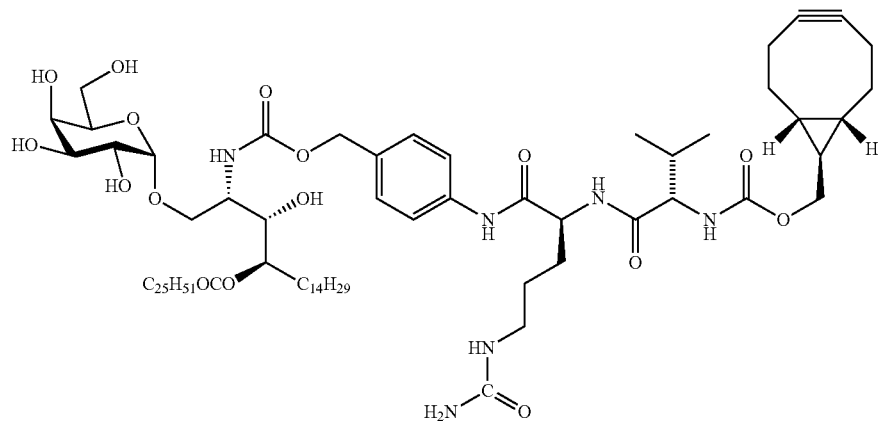
(ll)

(mm)
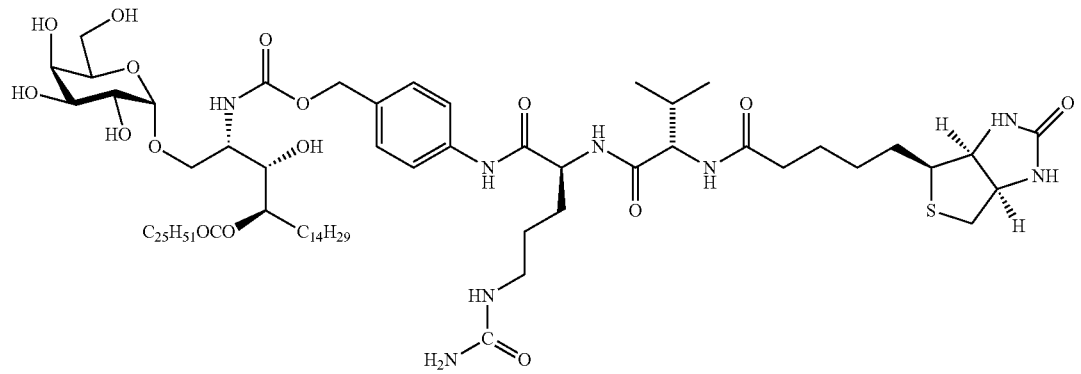
(nn)
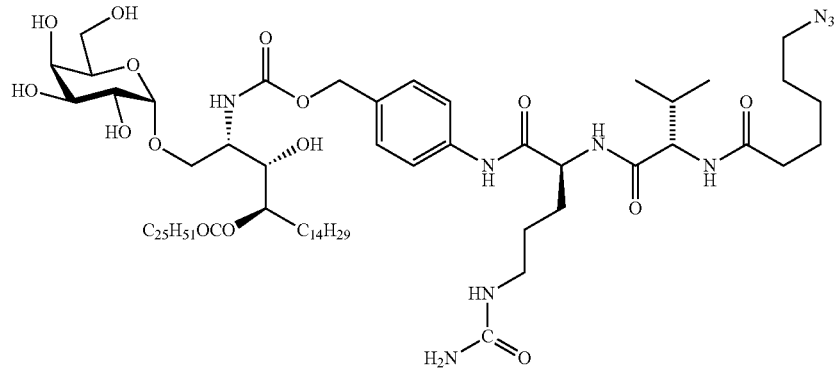
(oo)
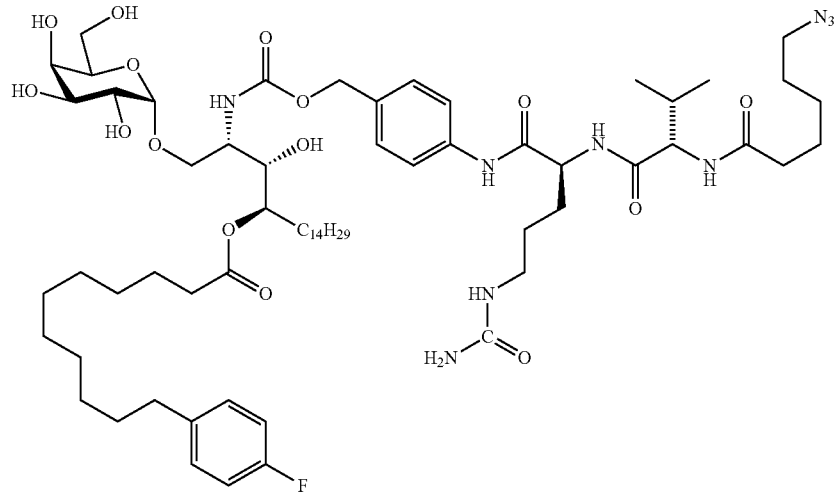
(pp)
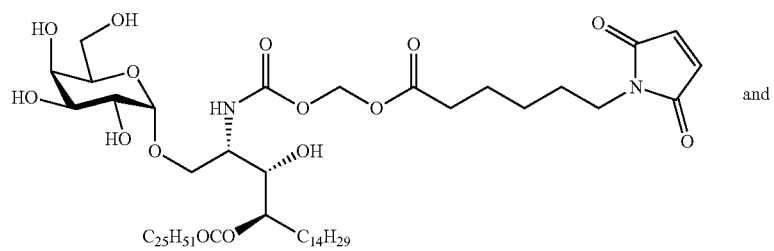
and

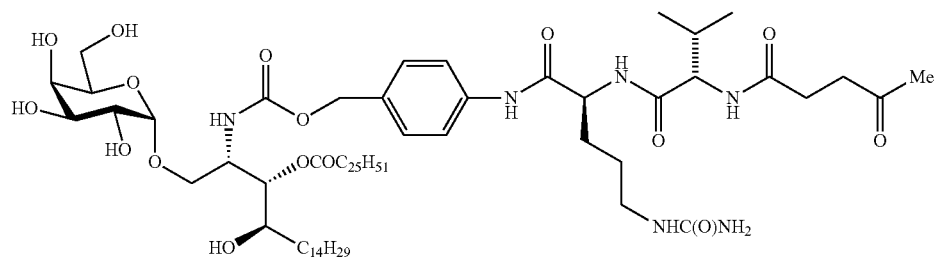

(qq)

or a pharmaceutically acceptable salt thereof.

18. A pharmaceutical composition comprising a pharmaceutically effective amount of the compound of claim 1 and optionally a pharmaceutically acceptable carrier.

19. The pharmaceutical composition of claim 18, wherein the pharmaceutical composition is a vaccine optionally comprising an antigen.

20. A method of treating or reducing a likelihood of occurrence of an infectious disease, an atopic disorder, an autoimmune disease, diabetes or cancer, comprising administering a pharmaceutically effective amount of the compound of claim 1 to a patient requiring treatment.

21. A compound selected from the group consisting of:

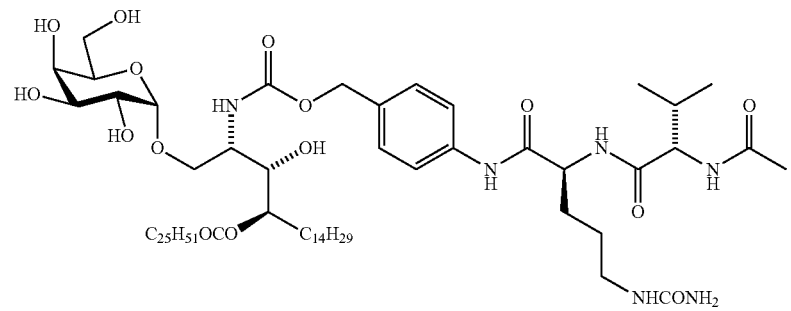

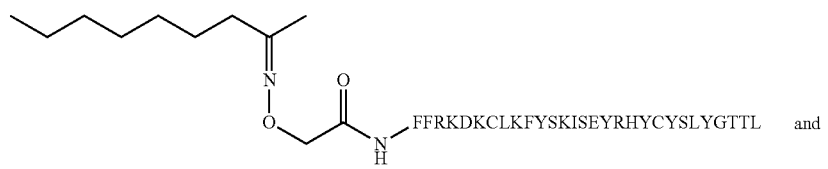

FFRKDKCLKFYSKISEYRHYCYSLYGTTL and

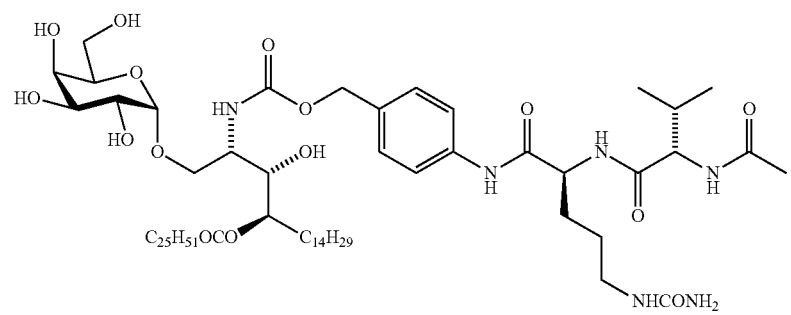

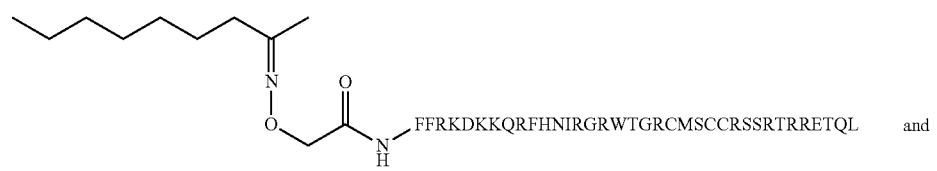

FFRKDKKQRFHNIRGRWTGRCMSCCRSSRTRRETQL and

-continued
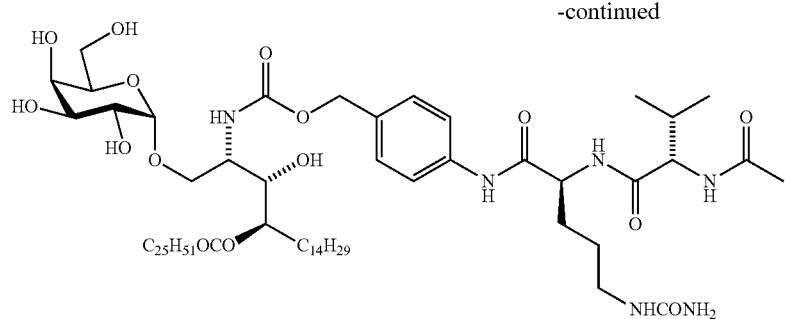
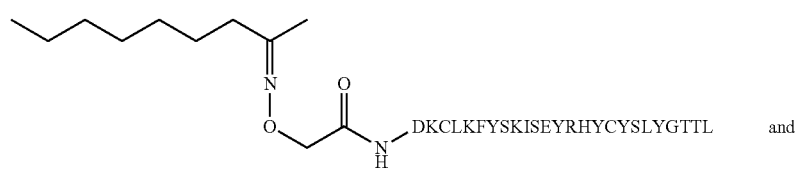
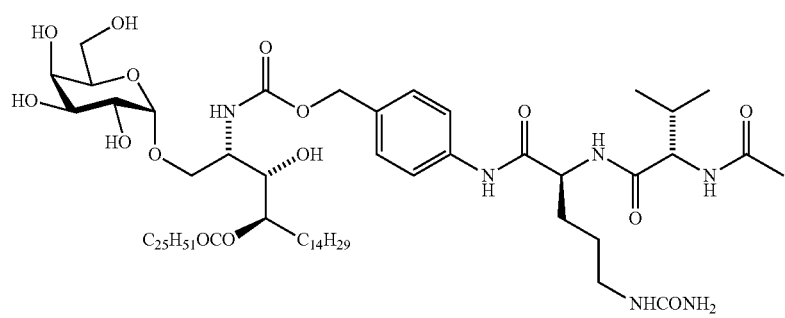
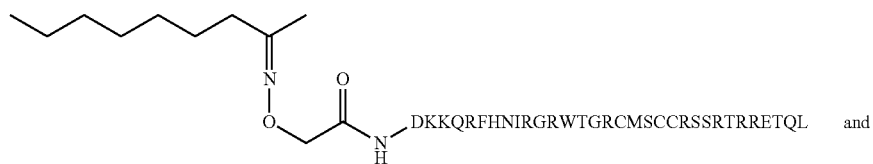
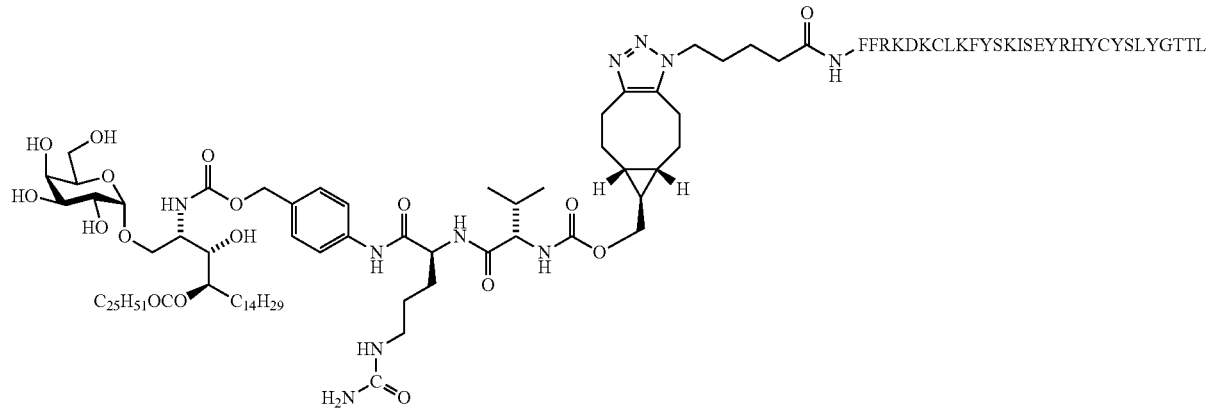
and

-continued
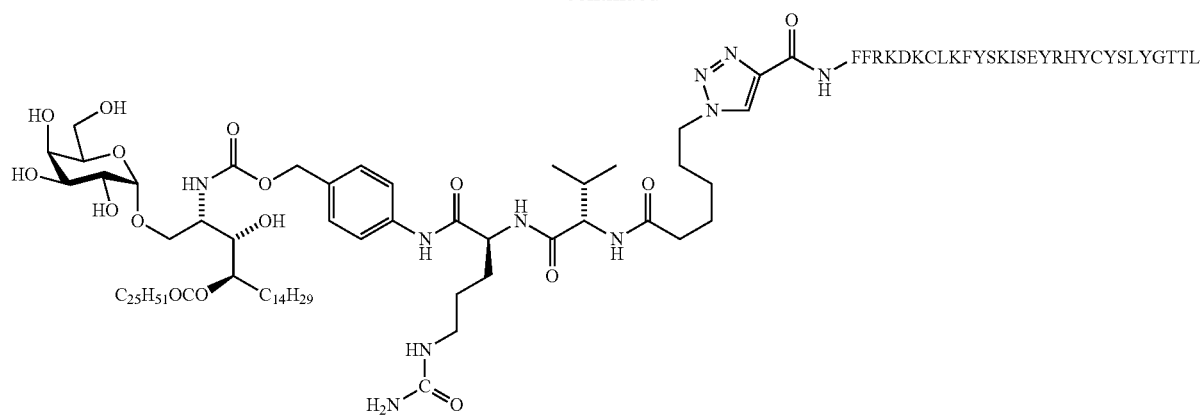
and
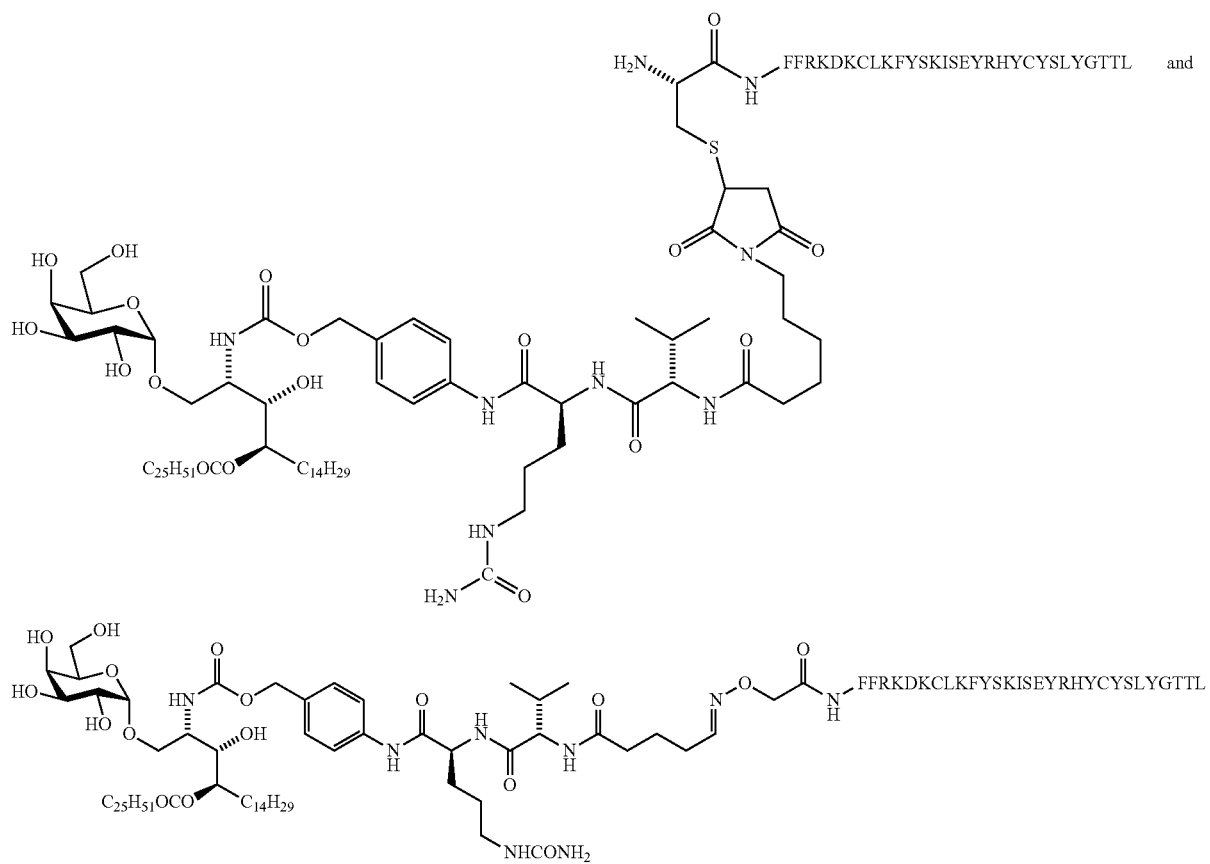
and
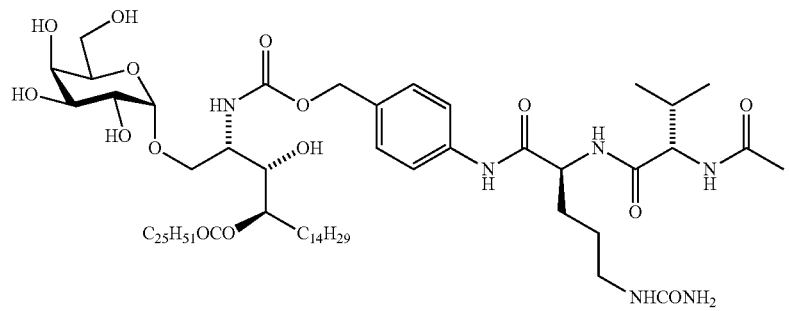

-continued
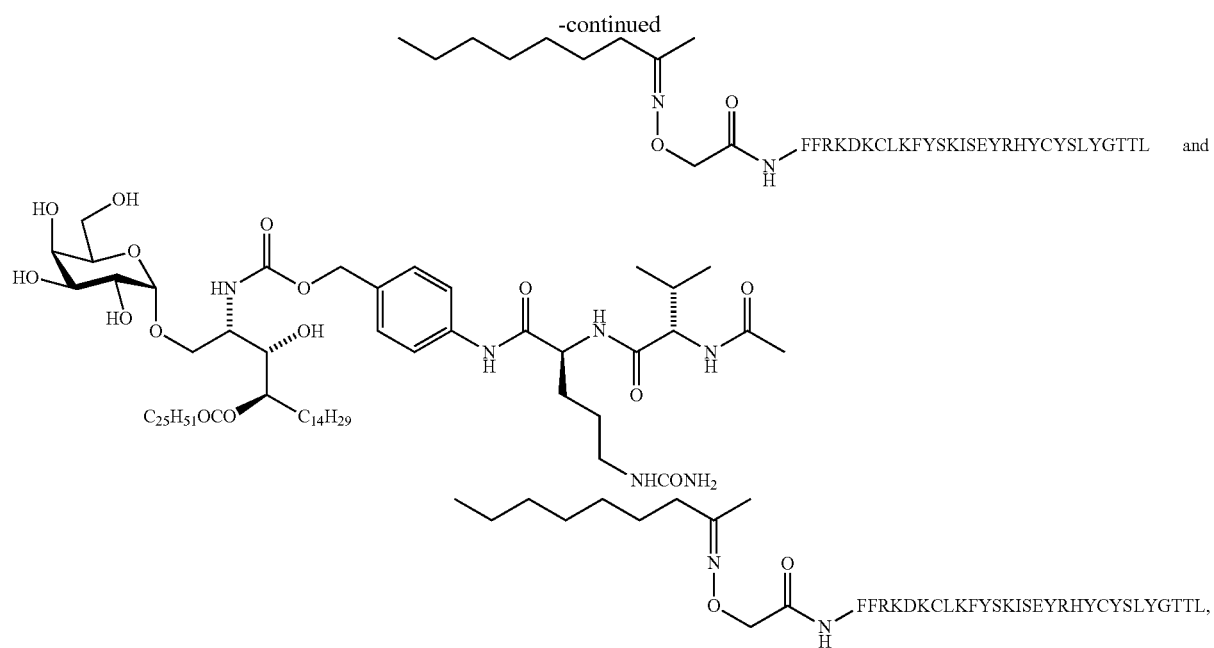
or a pharmaceutically acceptable salt thereof.
* * * * *

UNITED STATES PATENT AND TRADEMARK OFFICE
CERTIFICATE OF CORRECTION

PATENT NO.         : 9,764,037 B2                          Page 1 of 18
APPLICATION NO.    : 14/649902
DATED              : September 19, 2017
INVENTOR(S)        : Regan James Anderson et al.

It is certified that error appears in the above-identified patent and that said Letters Patent is hereby corrected as shown below:

In the Claims

Column 352, Lines 55-60 Claim 1:

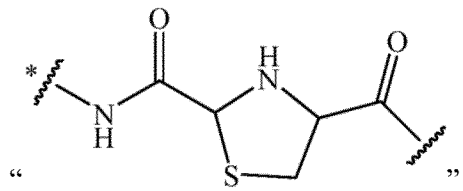

"                                                        "

Should read:

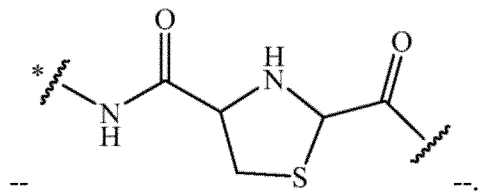

--                                                      --.

Column 354, Line 50 Claim 1:
"$CH_2SO_2R^{11}$, $CH_2PO_3H2$, $CH_2OP(O)(OH)_2$,"
Should read:
--$CH_2SO_2R^{11}$, $CH_2PO_3H_2$, $CH_2OP(O)(OH)_2$,--.

Signed and Sealed this
Thirtieth Day of June, 2020

Andrei Iancu
*Director of the United States Patent and Trademark Office*

CERTIFICATE OF CORRECTION (continued)
U.S. Pat. No. 9,764,037 B2

Column 374, compound (j) Claim 16:

"
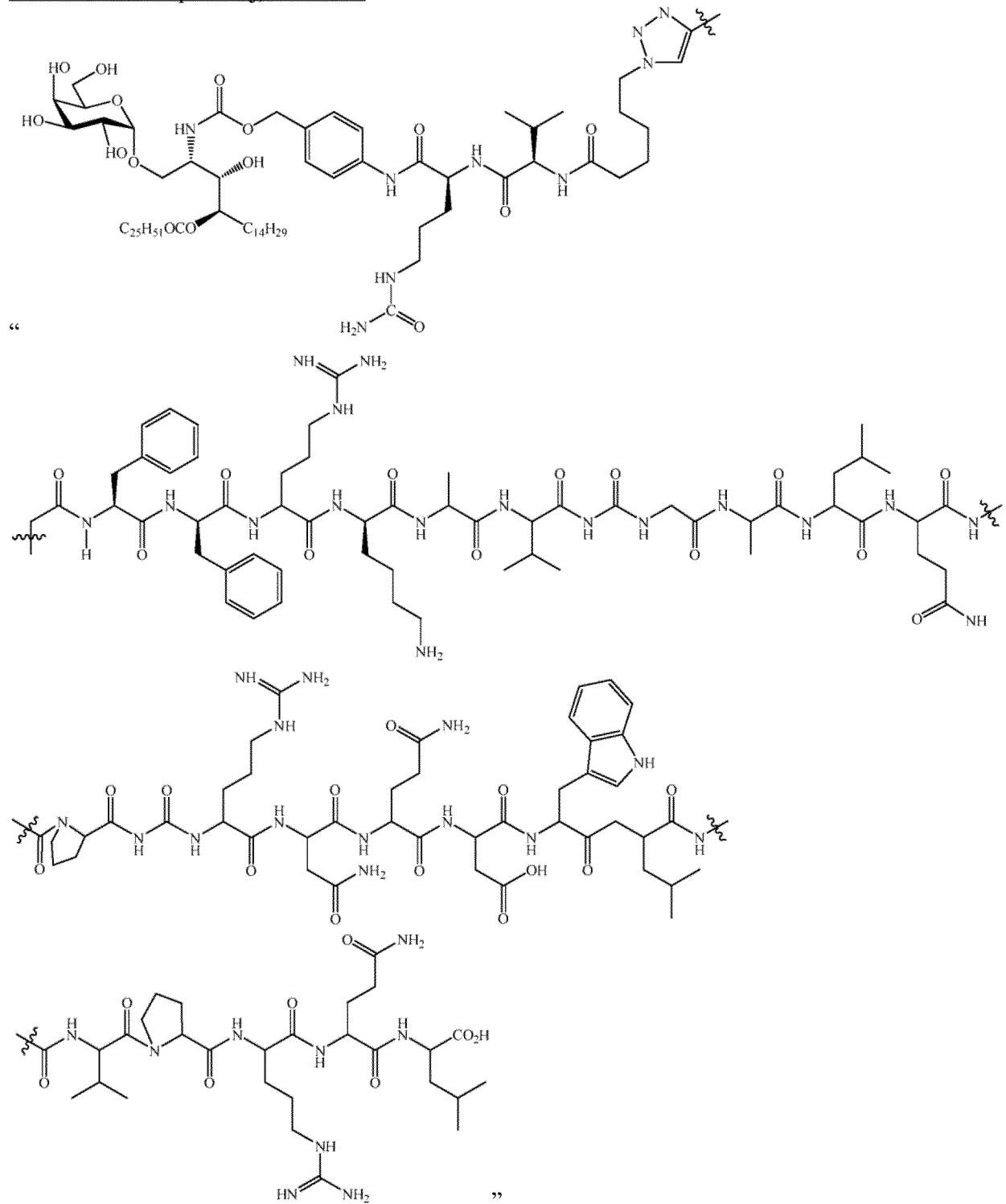
"

Should read:

CERTIFICATE OF CORRECTION (continued)
U.S. Pat. No. 9,764,037 B2

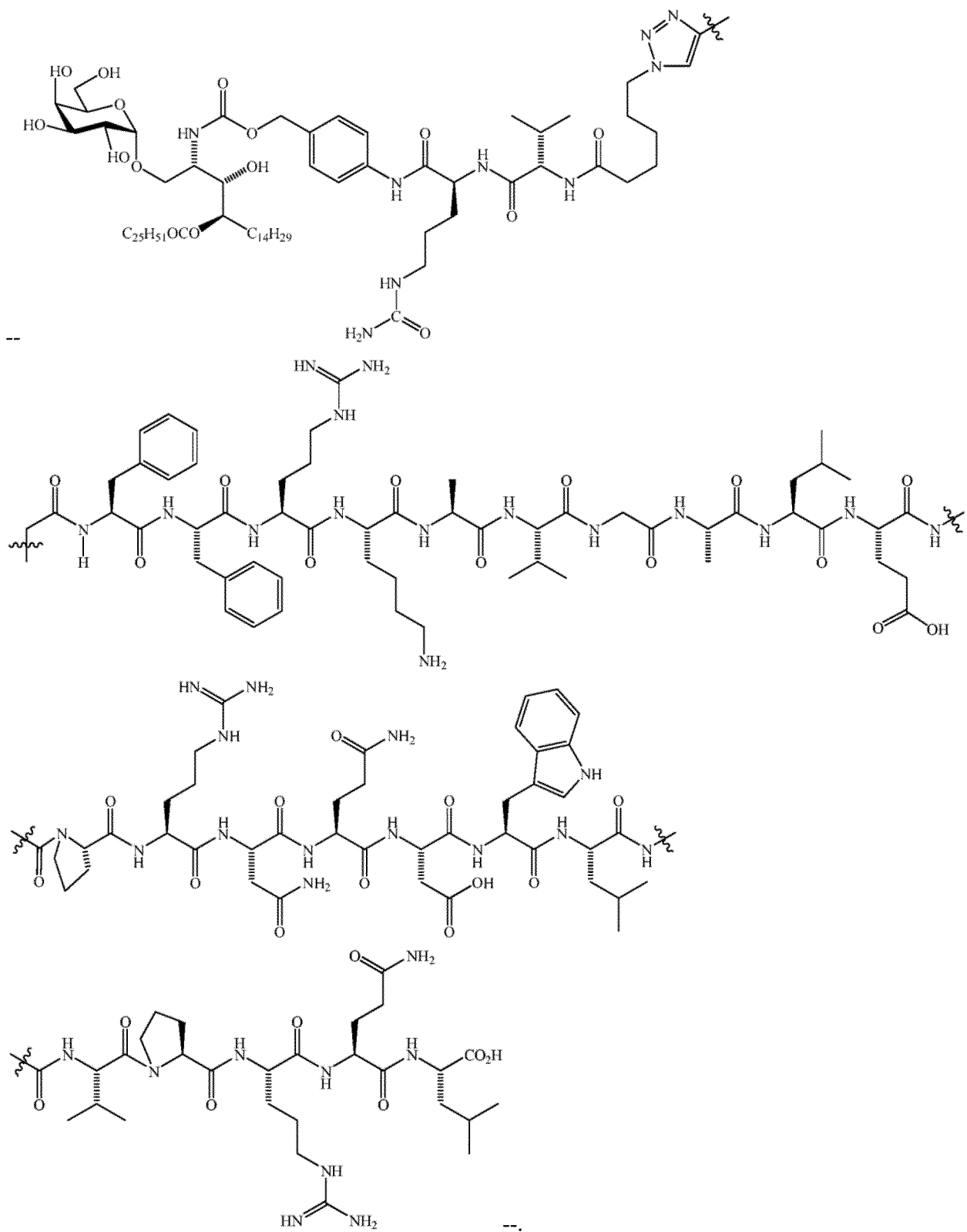

Columns 375-376, compound (k) Claim 16:

CERTIFICATE OF CORRECTION (continued)
U.S. Pat. No. 9,764,037 B2

"

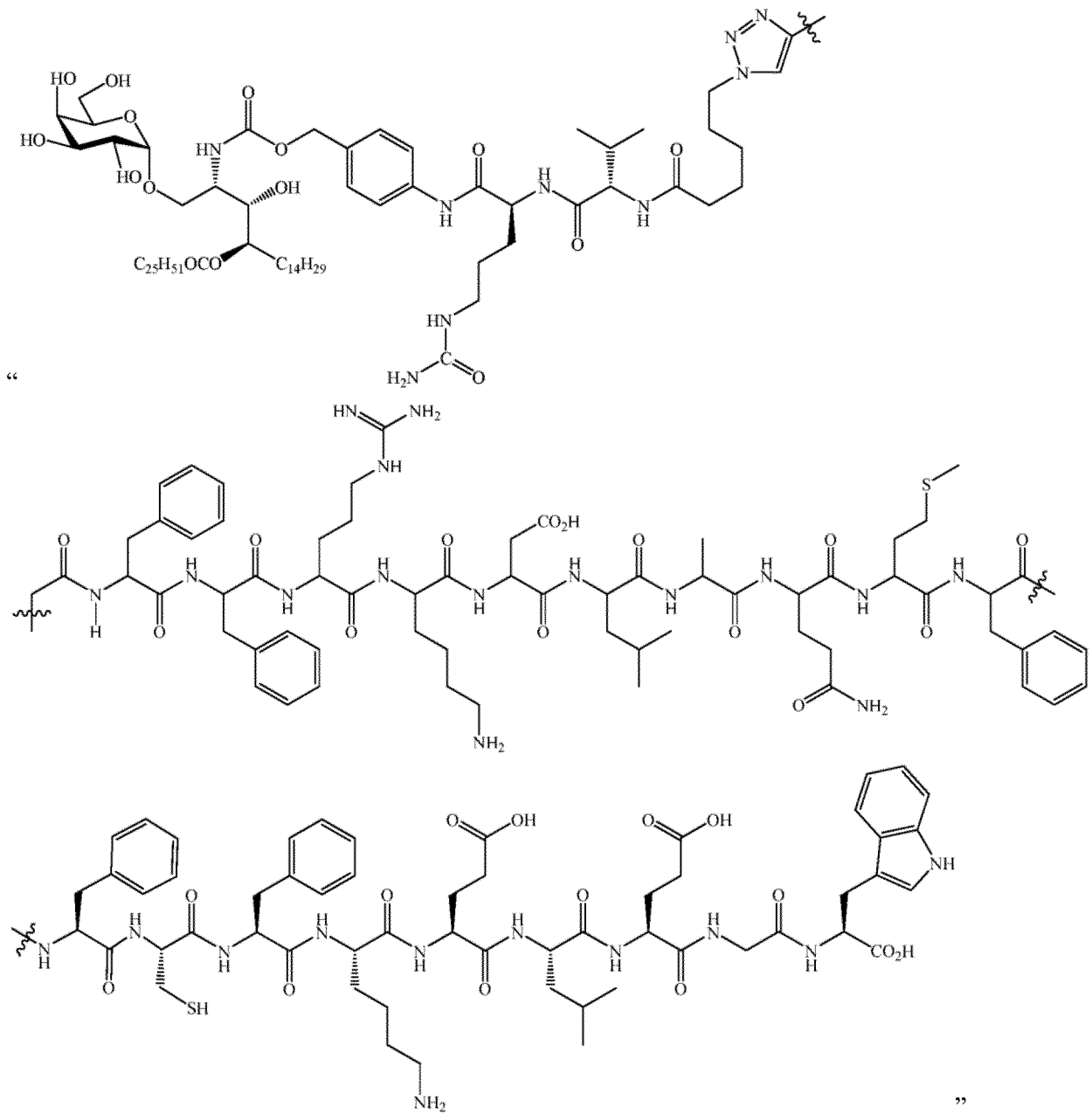

"

Should read:

CERTIFICATE OF CORRECTION (continued)
U.S. Pat. No. 9,764,037 B2

--

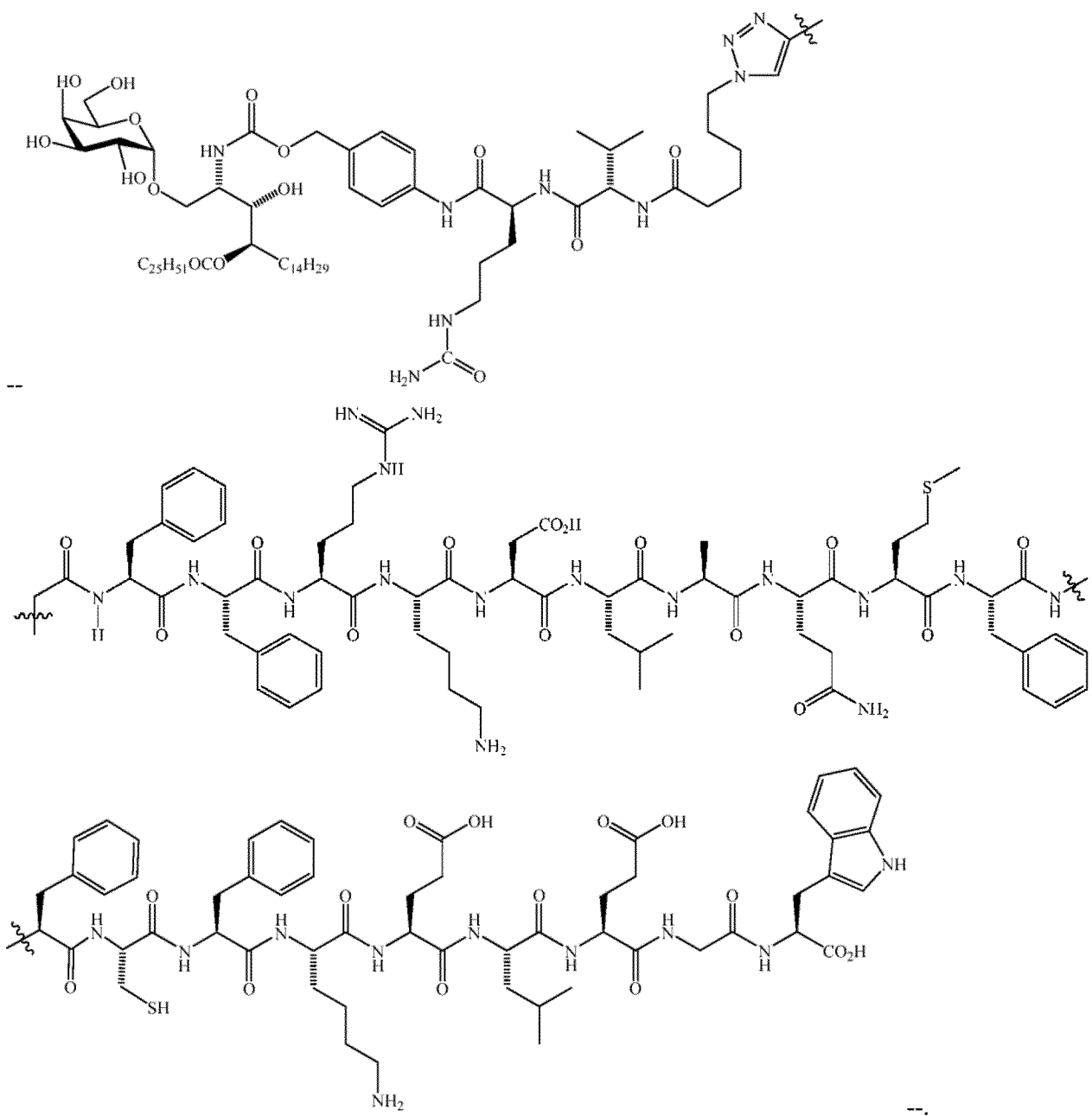

--.

CERTIFICATE OF CORRECTION (continued)
U.S. Pat. No. 9,764,037 B2

Columns 377-378, compound (l) Claim 16:

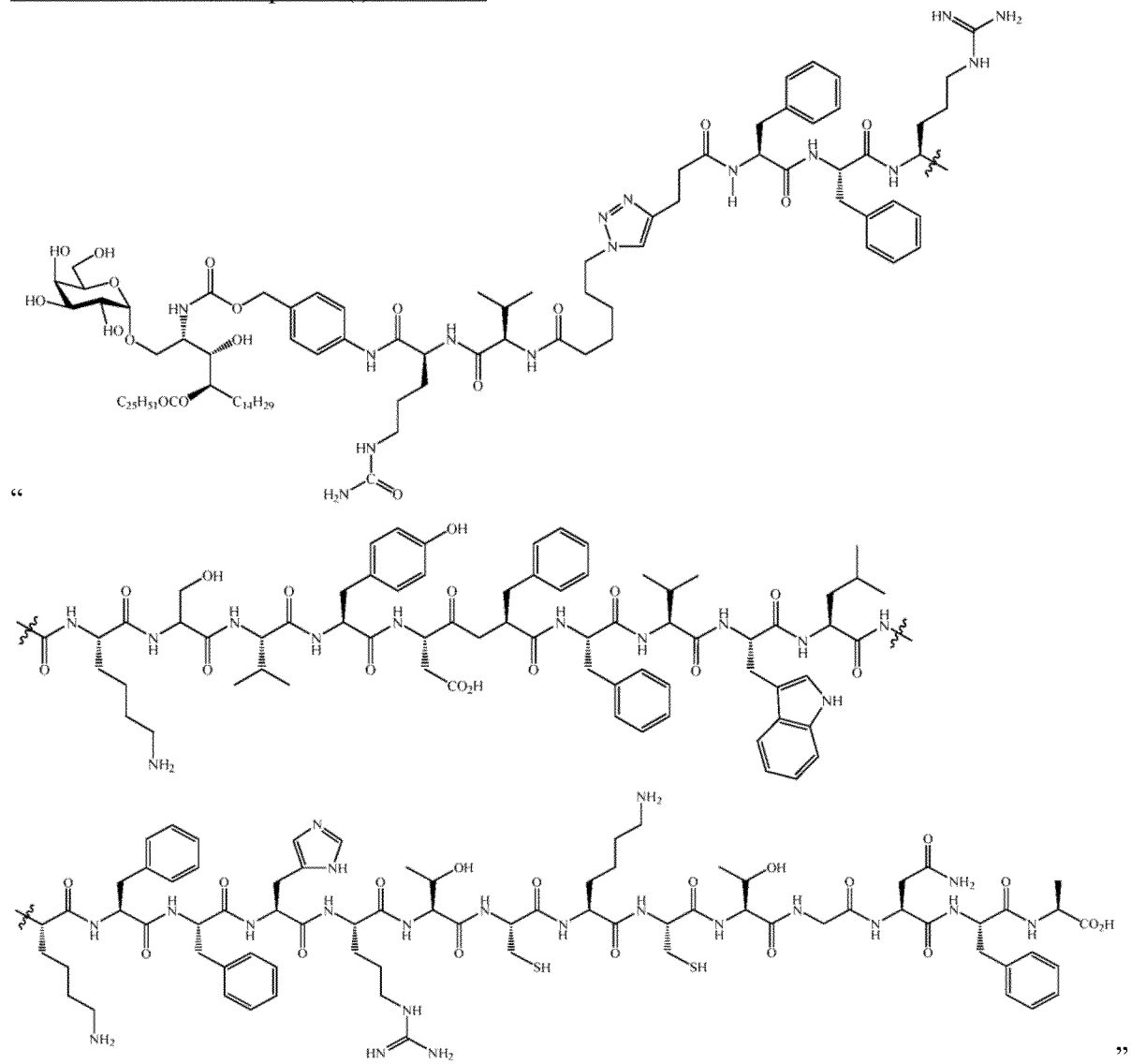

Should read:

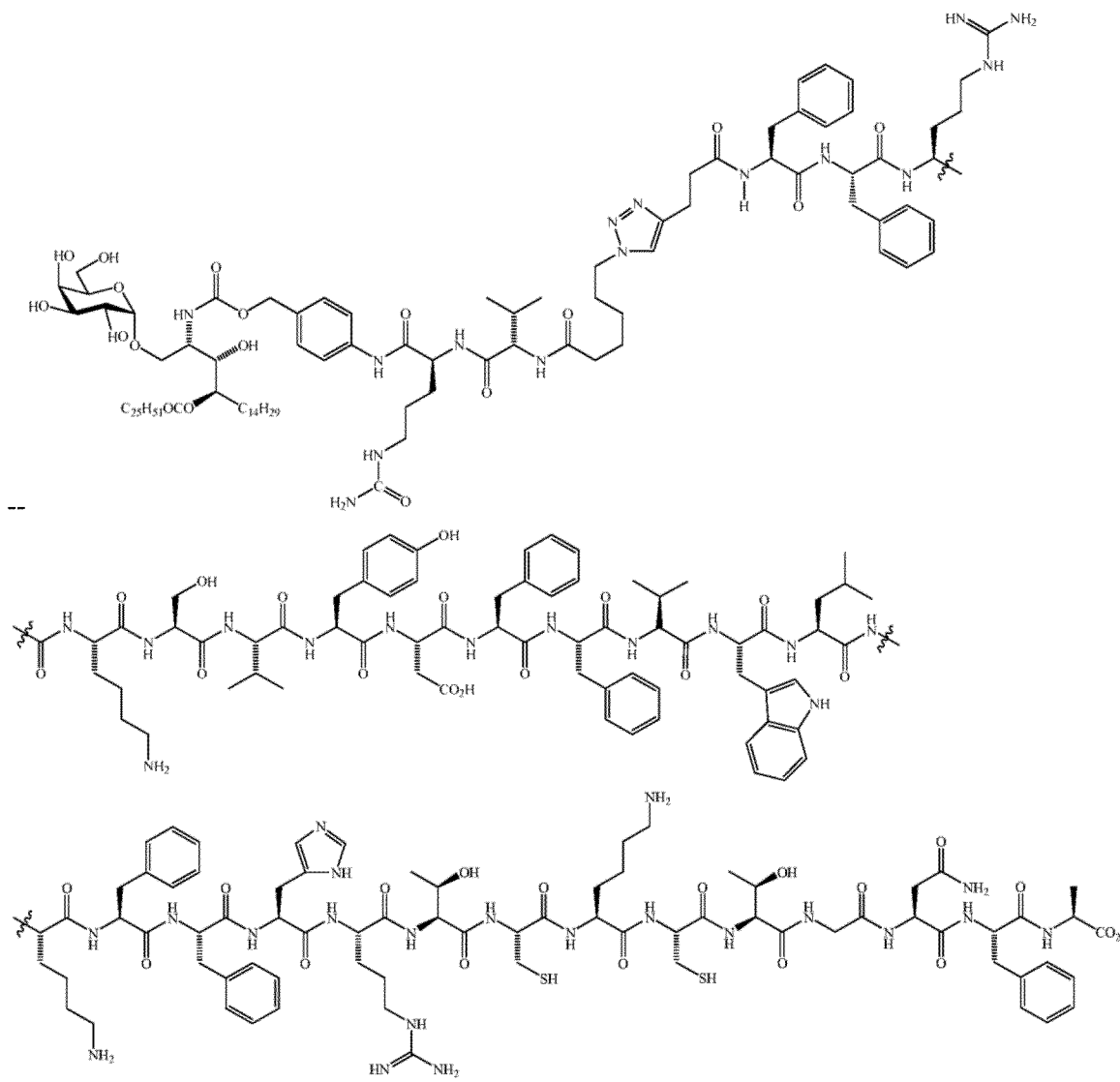
Columns 379-380, compound (m) Claim 16:

CERTIFICATE OF CORRECTION (continued)
U.S. Pat. No. 9,764,037 B2

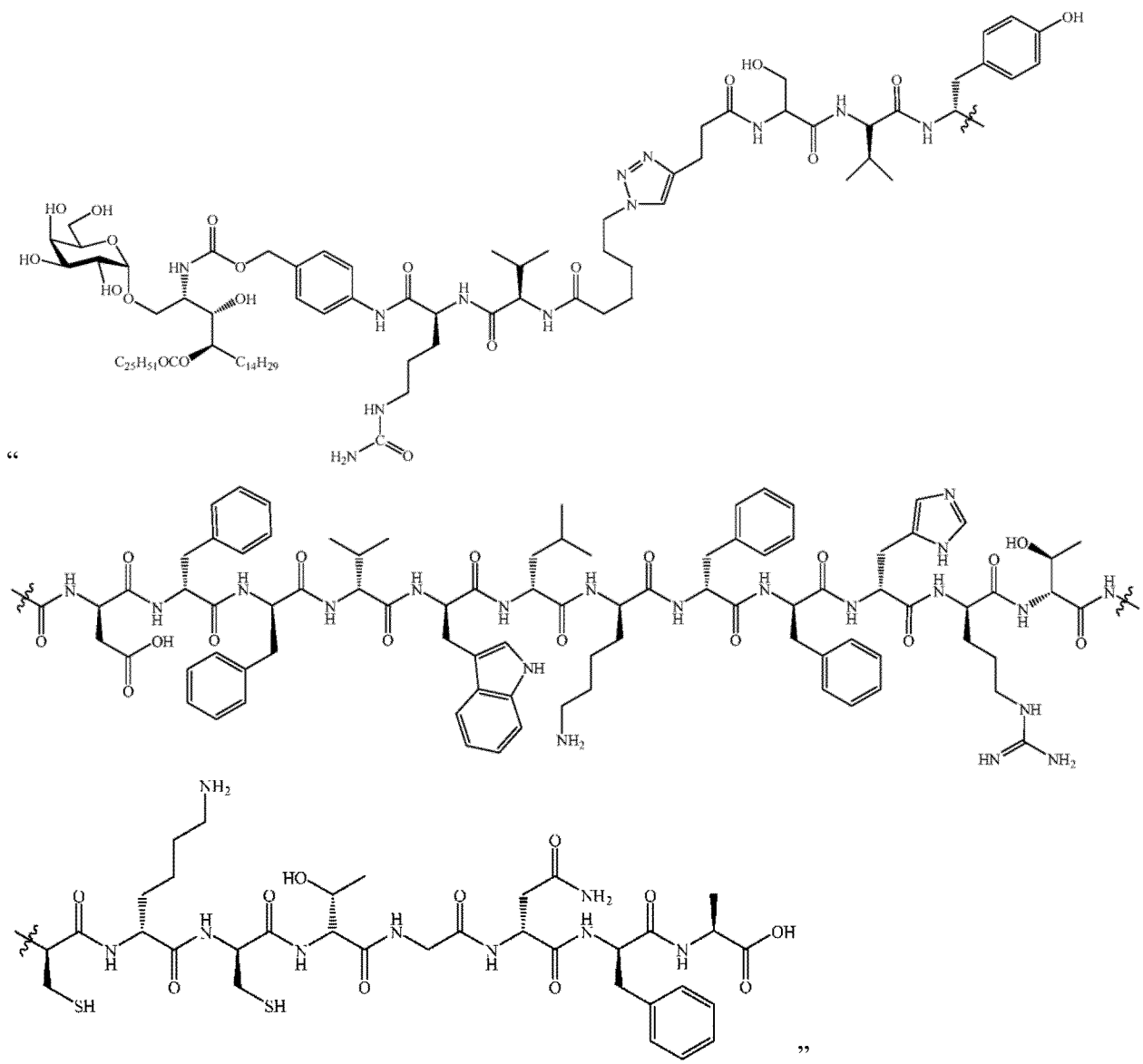

Should read:

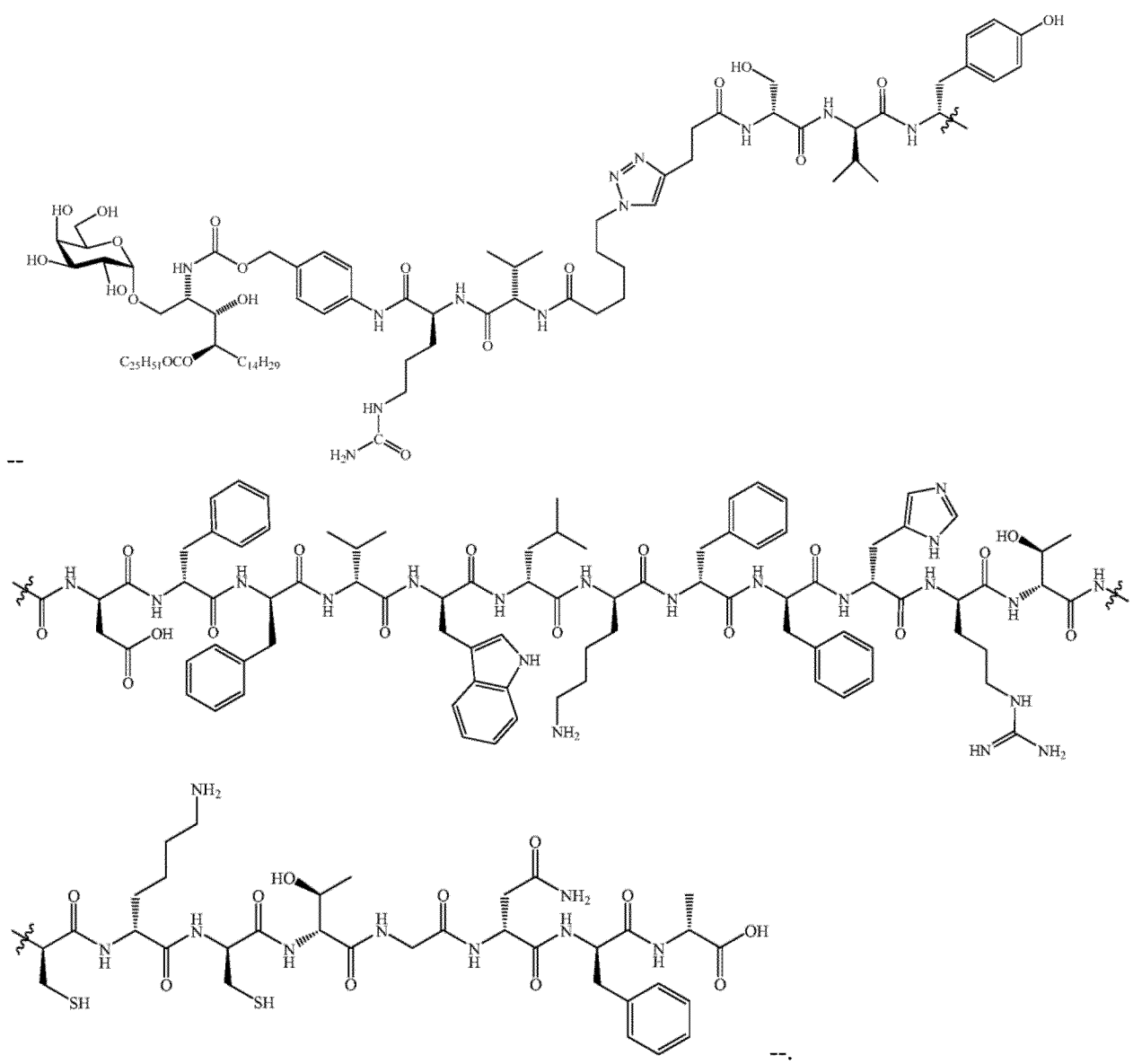

CERTIFICATE OF CORRECTION (continued)
U.S. Pat. No. 9,764,037 B2

Columns 381, compound (n) Claim 16:

"
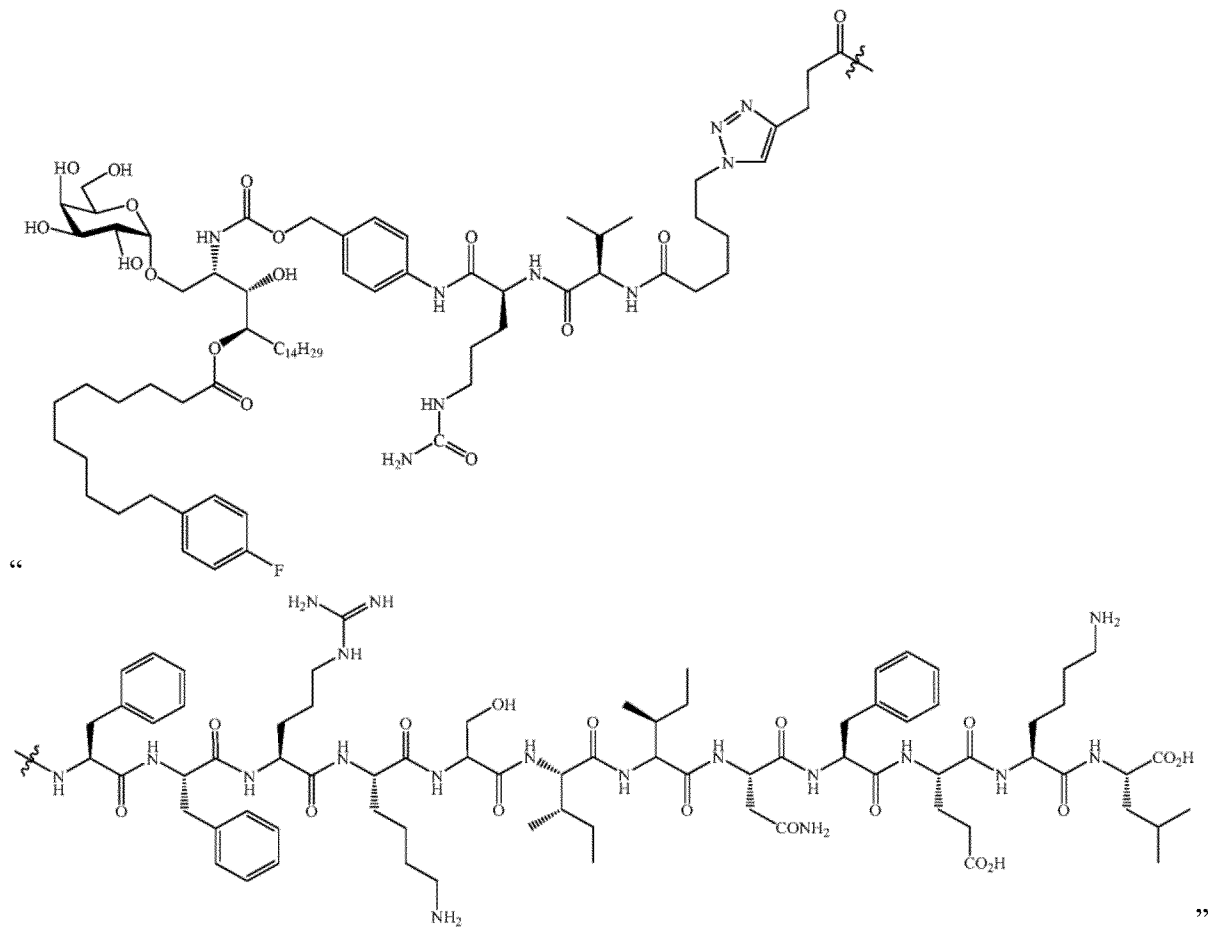
"

Should read:

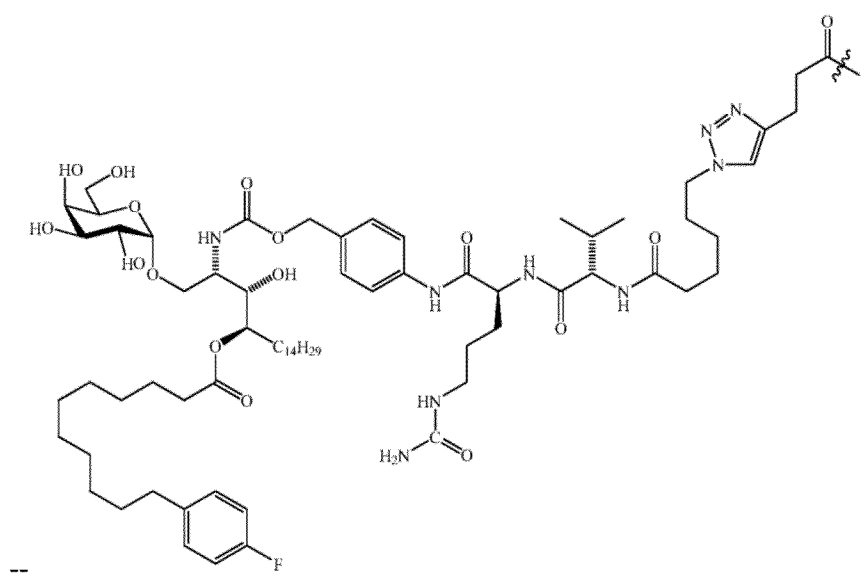

--

CERTIFICATE OF CORRECTION (continued)
U.S. Pat. No. 9,764,037 B2

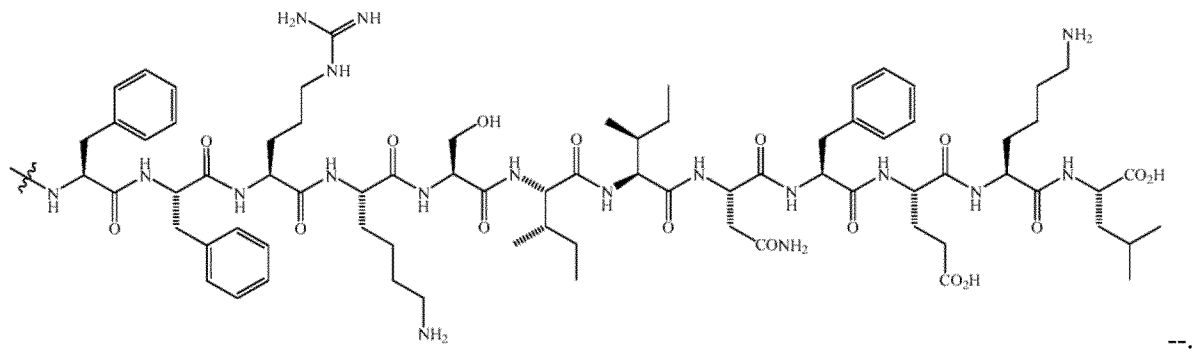

Column 382, compound (o) Claim 16:

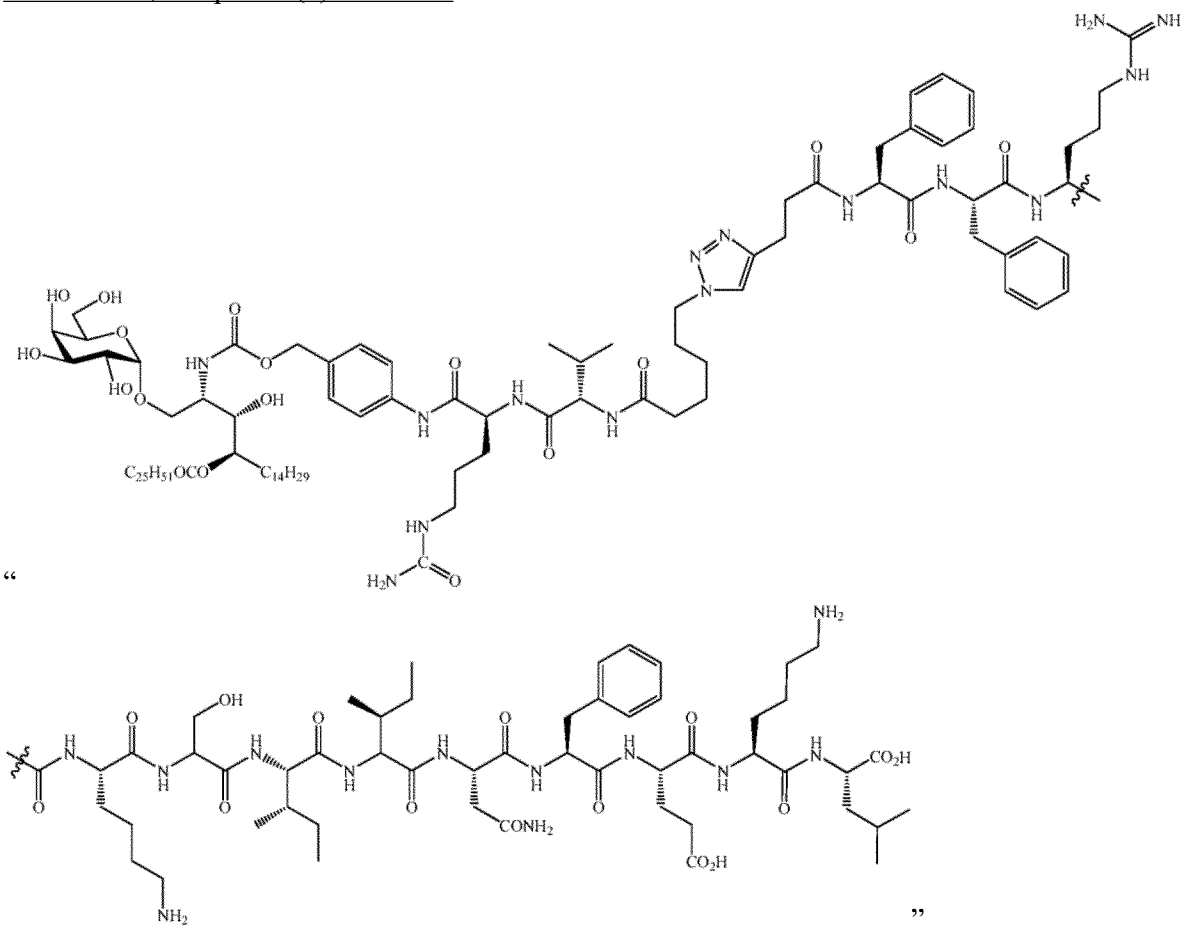

Should read:

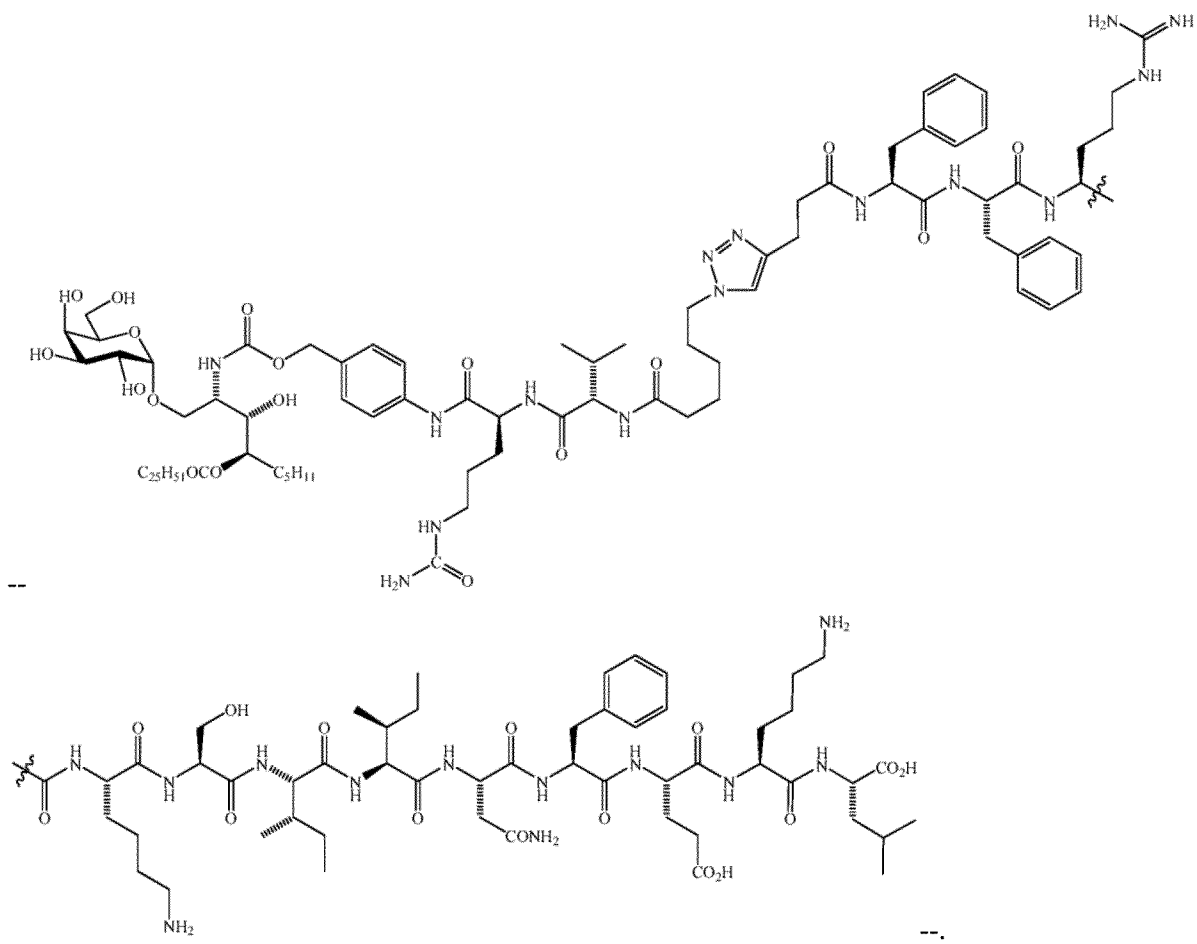
--
--.
Column 383, compound (p) Claim 16:
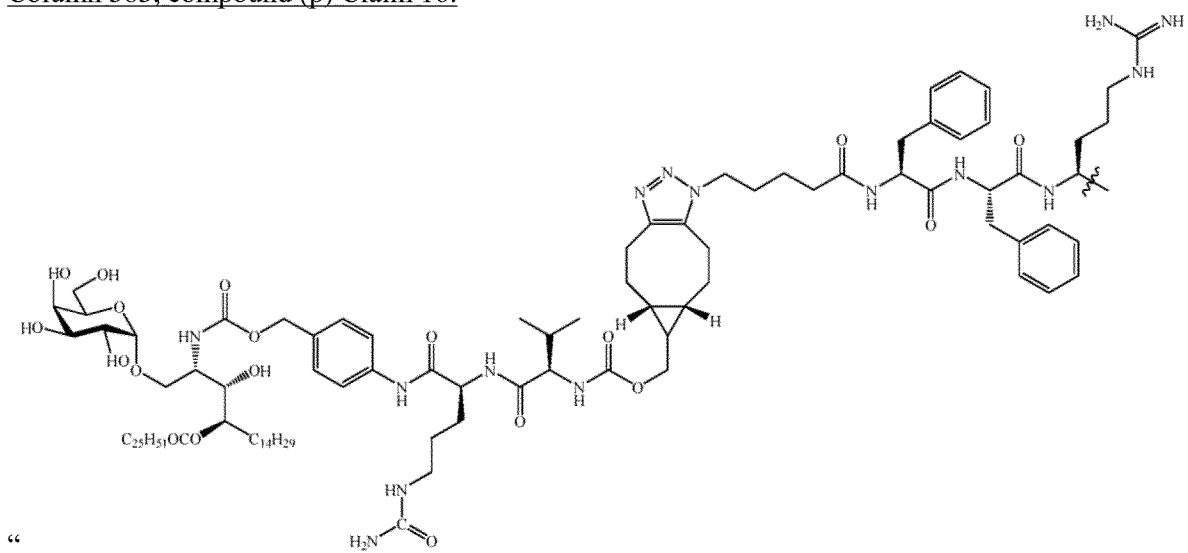
"

CERTIFICATE OF CORRECTION (continued)
U.S. Pat. No. 9,764,037 B2

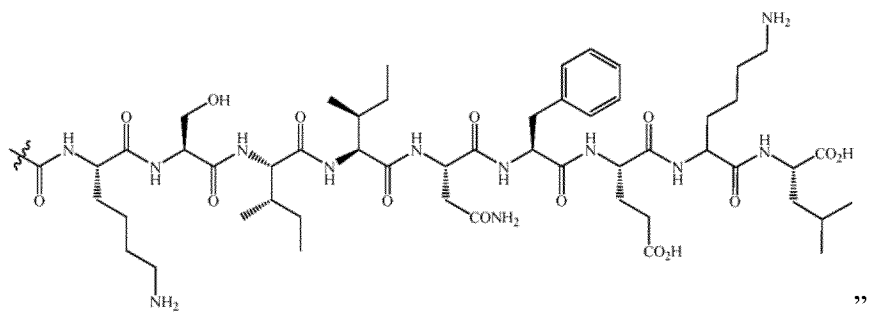

"

Should read:

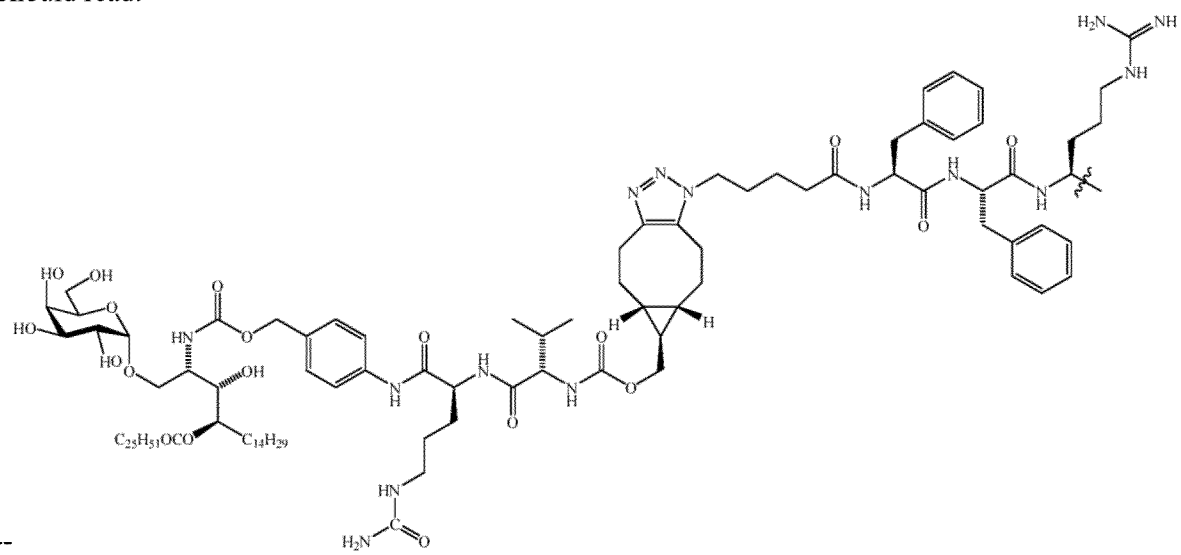

--

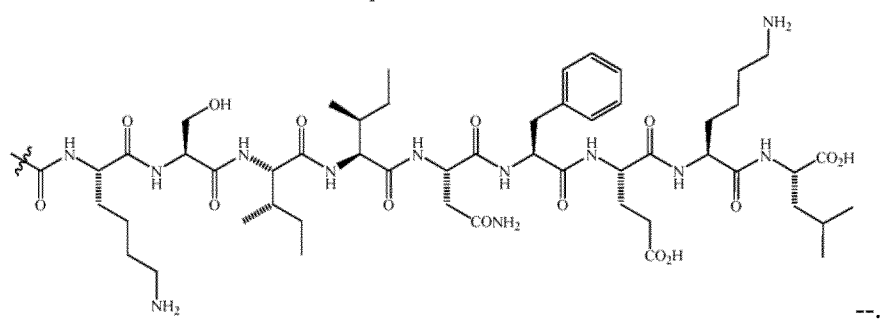

--.

CERTIFICATE OF CORRECTION (continued)
U.S. Pat. No. 9,764,037 B2

Column 384, compound (q) Claim 16:

"

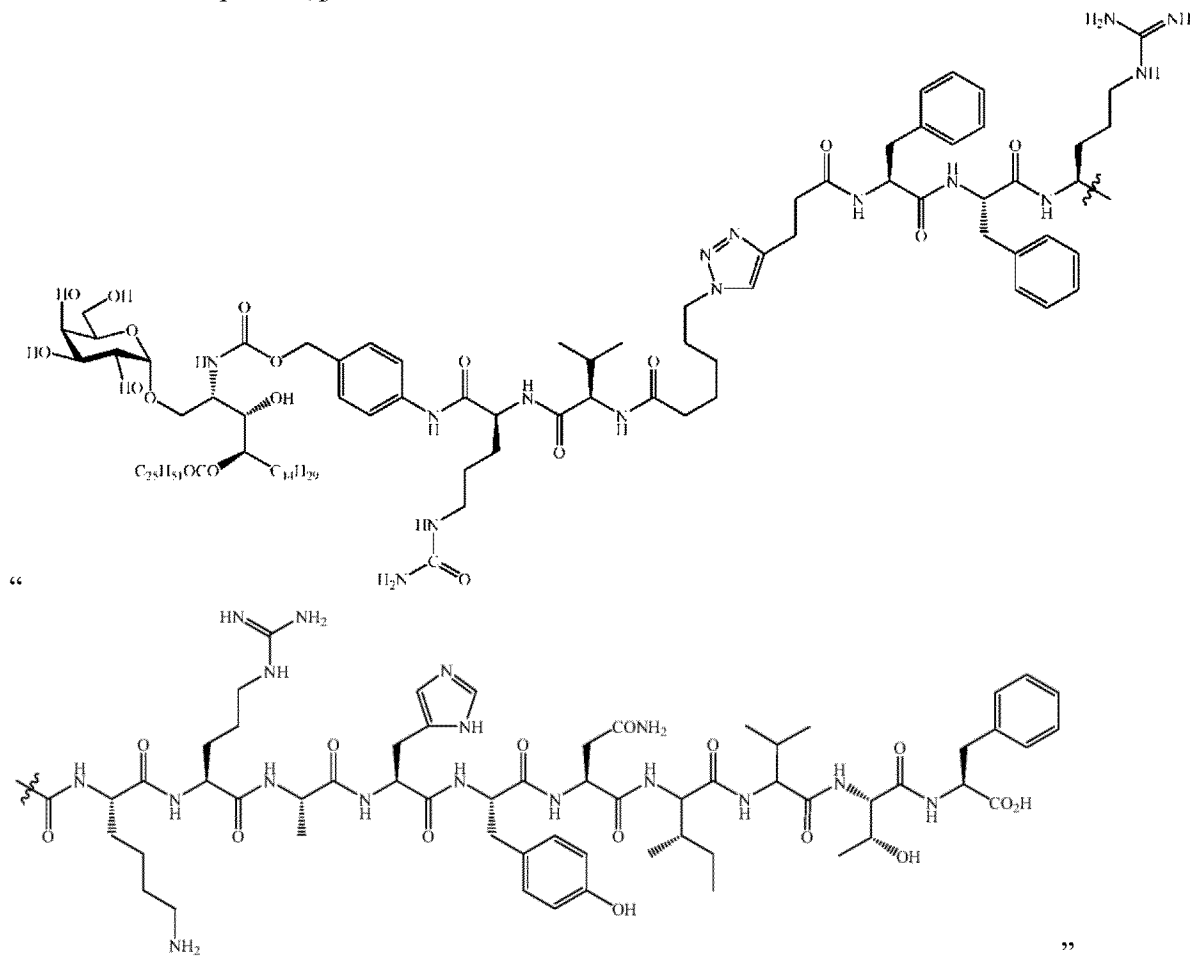

"

Should read:

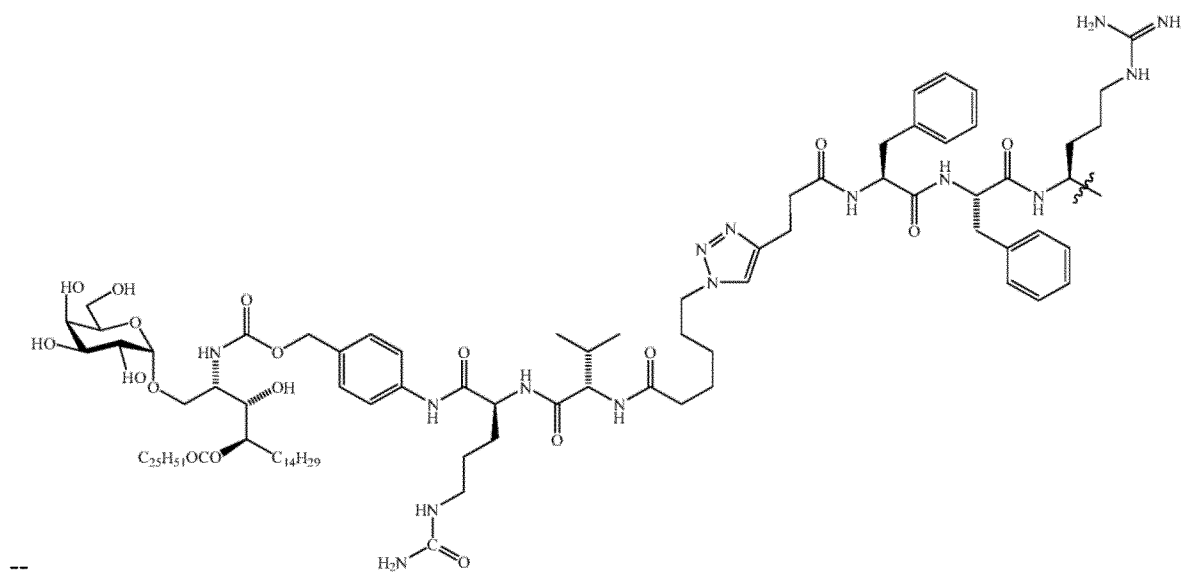

--

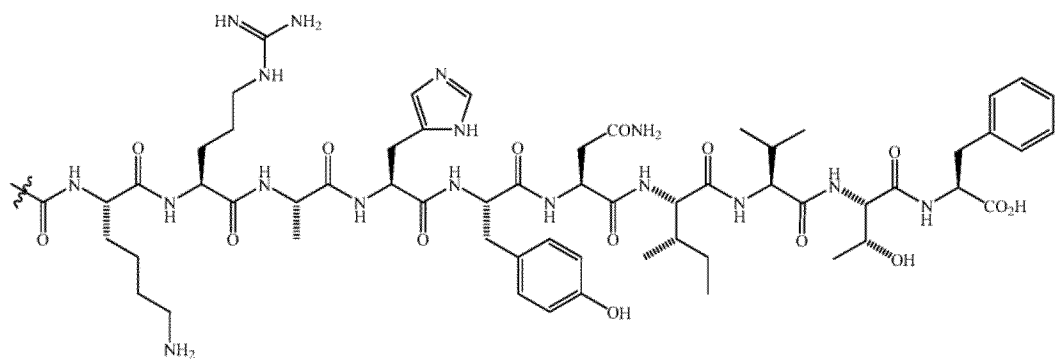
Columns 385-386, compound (r) Claim 16:
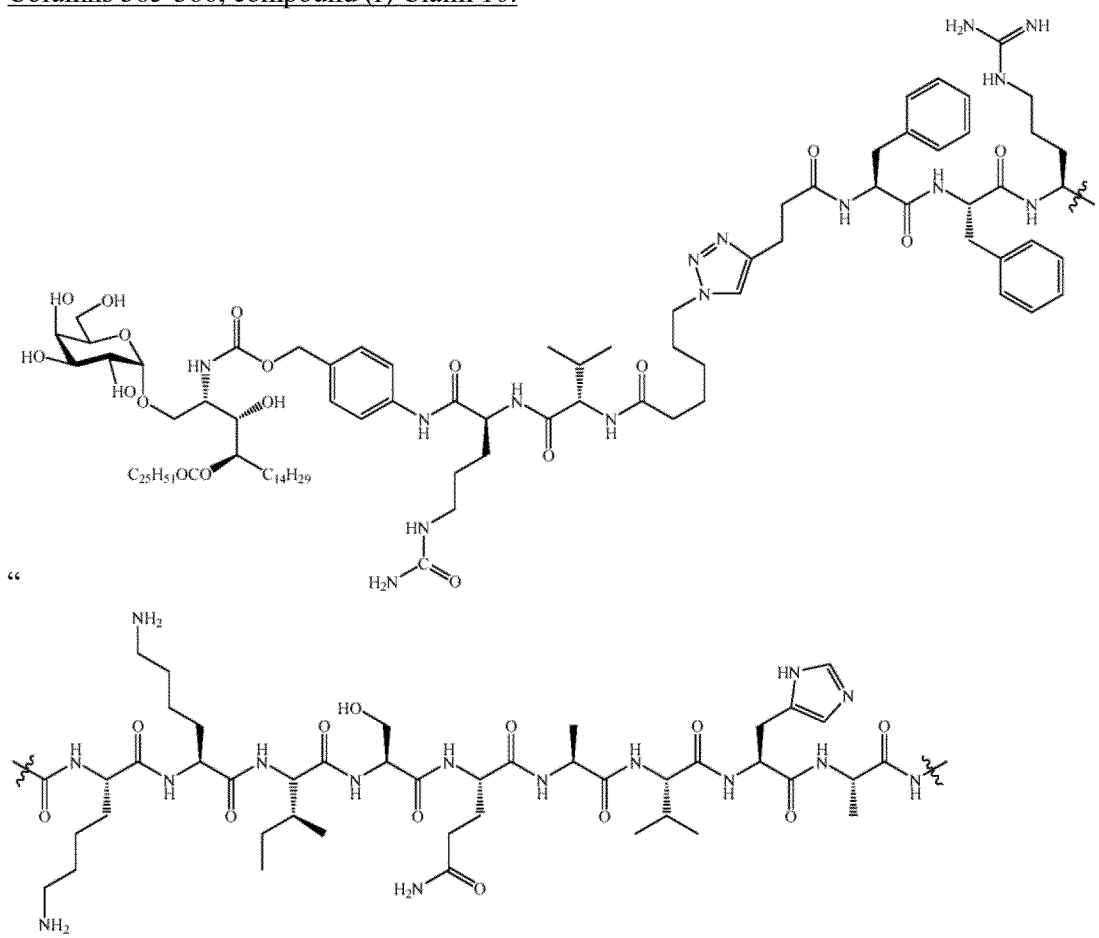

CERTIFICATE OF CORRECTION (continued)
U.S. Pat. No. 9,764,037 B2

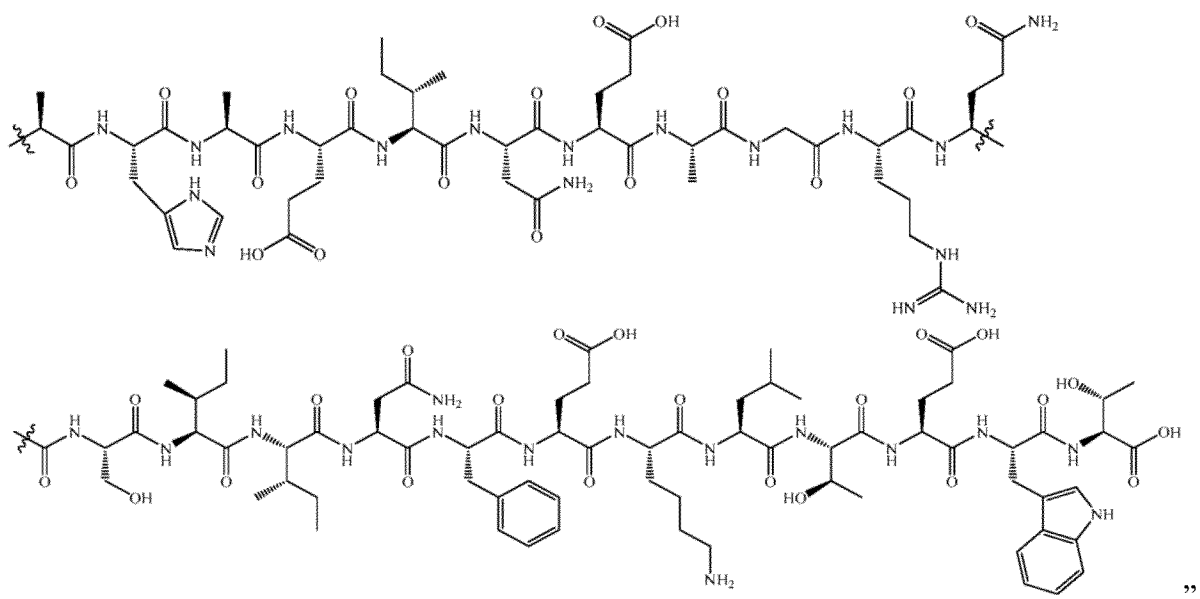

Should read:

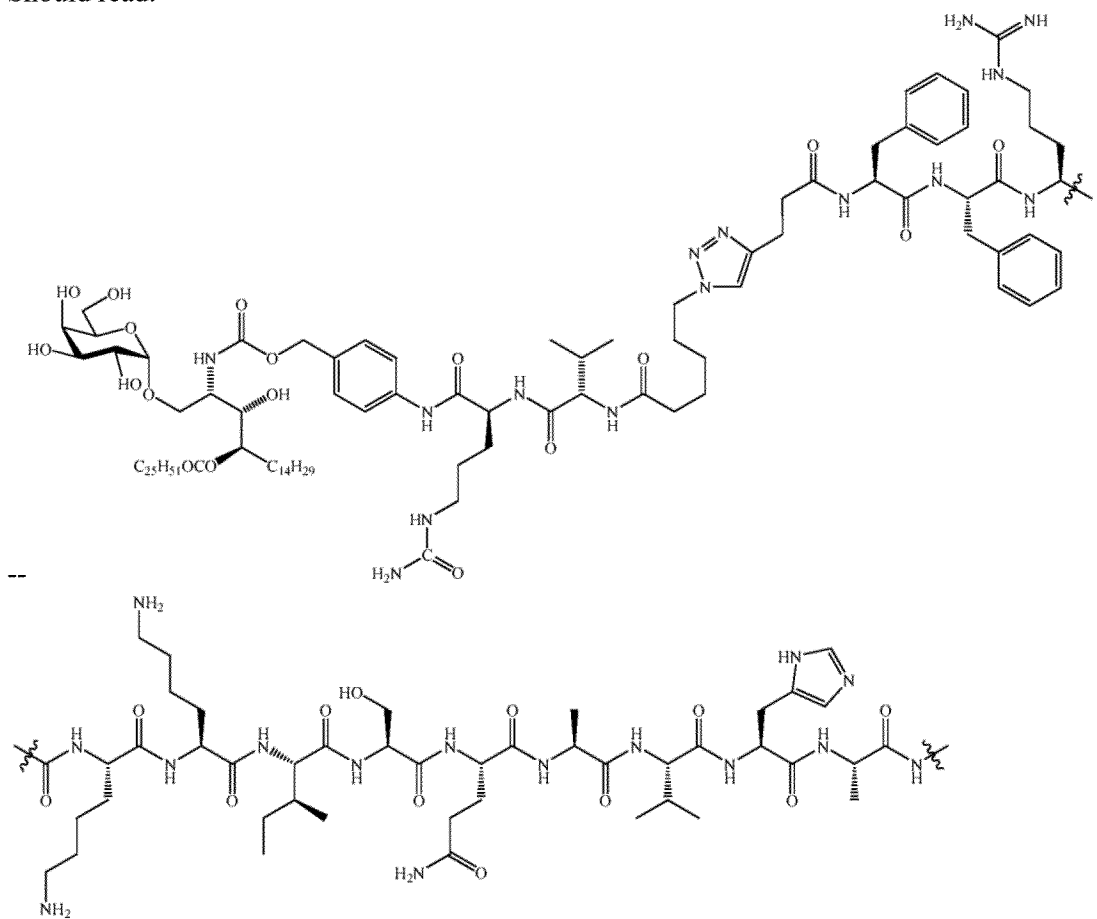

--

CERTIFICATE OF CORRECTION (continued)
U.S. Pat. No. 9,764,037 B2

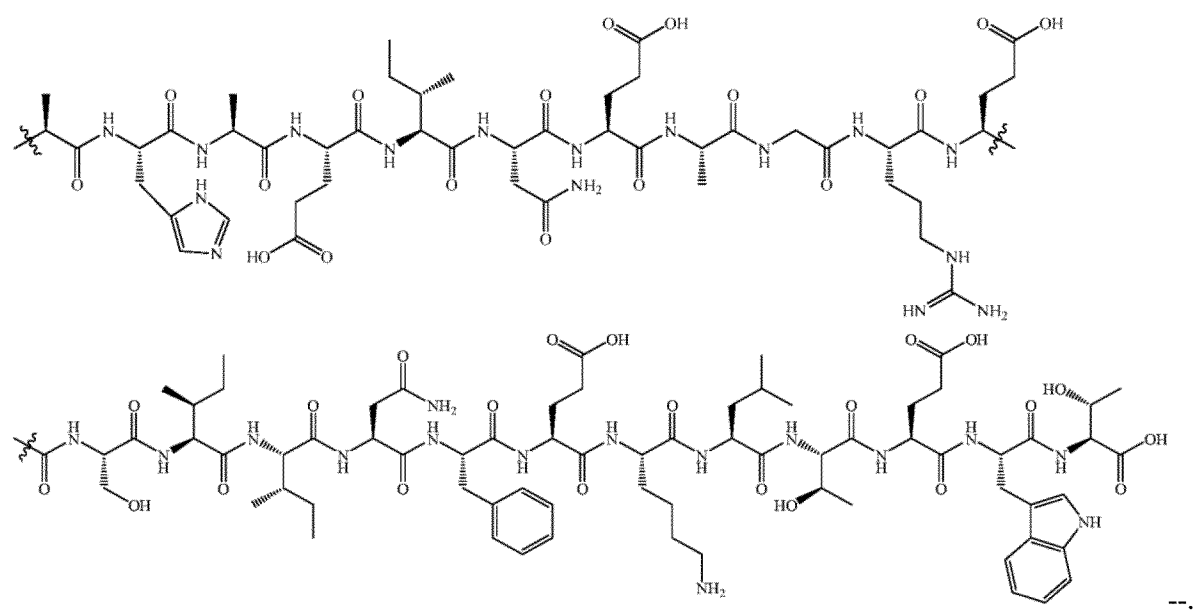

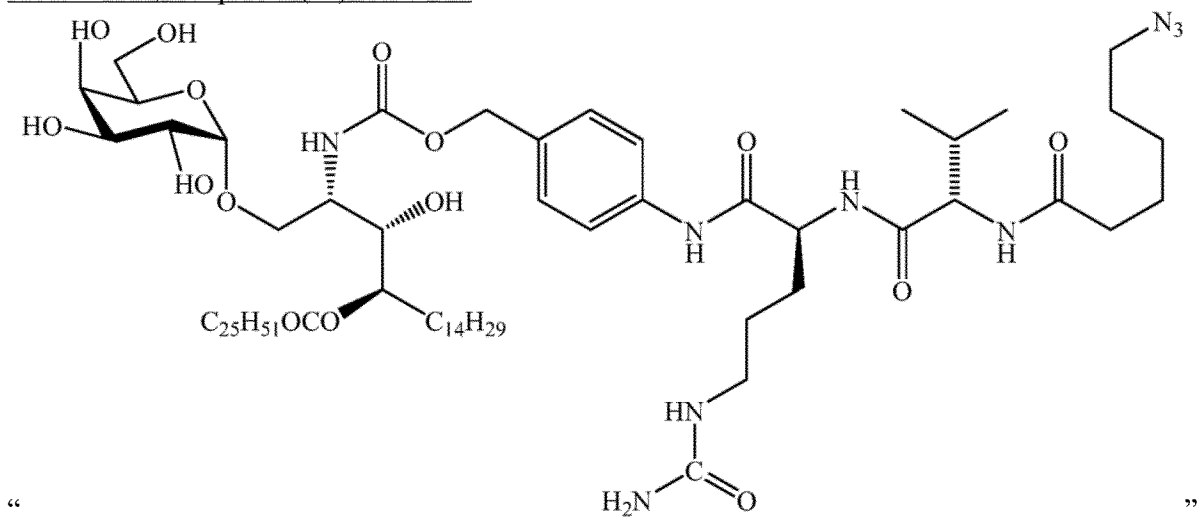

Column 393, compound (nn) Claim 17:

" "

Should read:

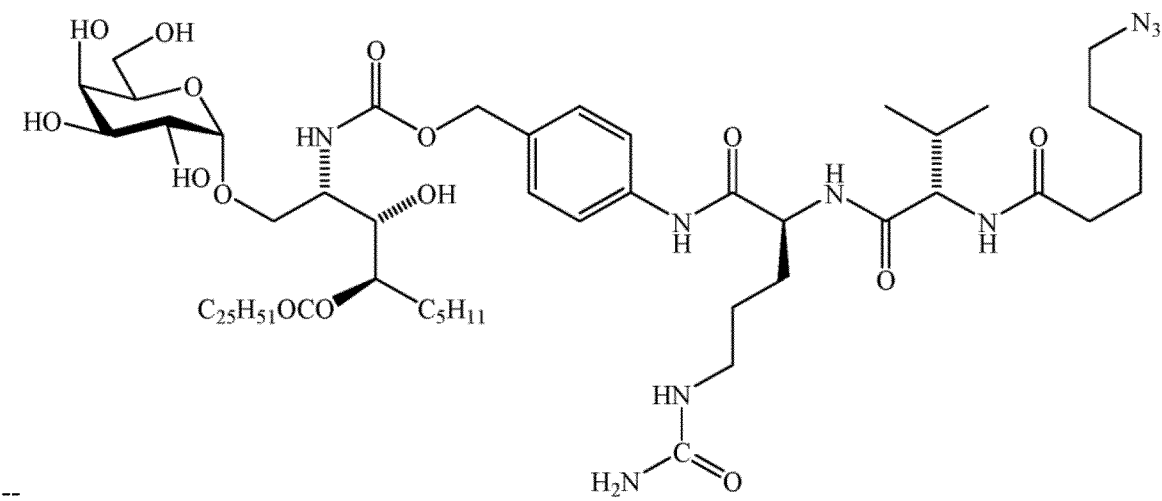
--                                                                                                          --.
Columns 399-402, Claim 21:
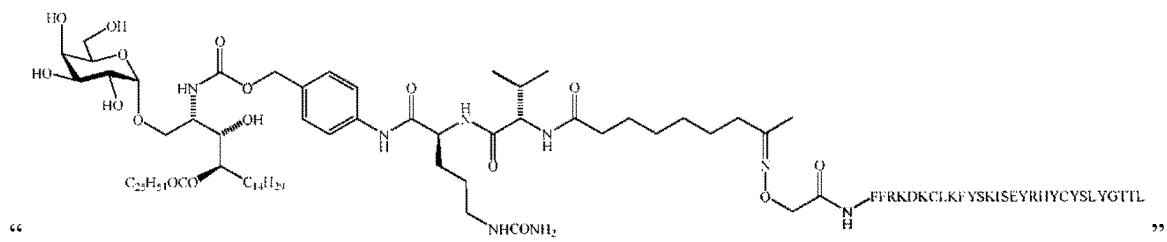
"                                                                                                          "
Should read:
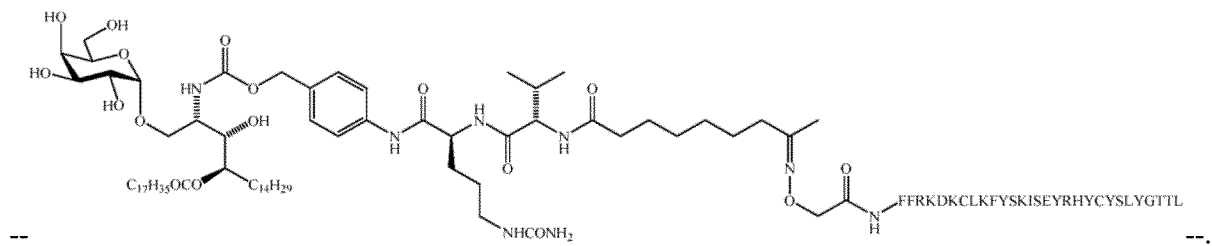
--                                                                                                          --.
Columns 401-402, Claim 21:
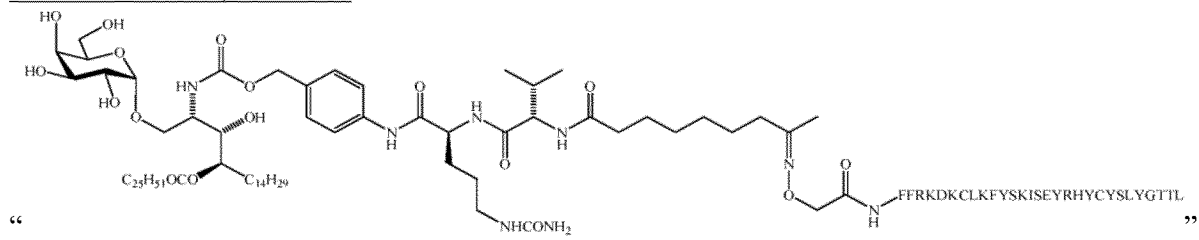
"                                                                                                          "
Should read:
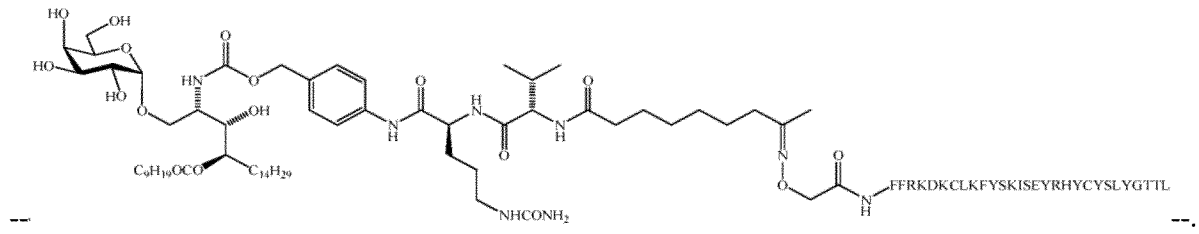
--                                                                                                          --.